US006806289B1

(12) United States Patent
Lippard et al.

(10) Patent No.: US 6,806,289 B1
(45) Date of Patent: Oct. 19, 2004

(54) COORDINATION COMPLEXES, AND METHODS FOR PREPARING BY COMBINATORIAL METHODS, ASSAYING AND USING THE SAME

(76) Inventors: Stephen J. Lippard, 15 Humboldt St., Cambridge, MA (US) 02140; Christopher J. Ziegler, 347 Warren St., #1, Waltham, MA (US) 02154

( * ) Notice: Subject to any disclaimer, the term of this patent is extended or adjusted under 35 U.S.C. 154(b) by 0 days.

(21) Appl. No.: 09/907,515

(22) Filed: Jul. 16, 2001

Related U.S. Application Data

(60) Provisional application No. 60/218,335, filed on Jul. 14, 2000.

(51) Int. Cl.$^7$ .......................... A61K 31/28; C07F 15/00
(52) U.S. Cl. ............................ 514/492; 546/2; 546/11; 546/12
(58) Field of Search .............................. 546/2, 11, 12; 514/492

(56) References Cited

U.S. PATENT DOCUMENTS

| | | | | |
|---|---|---|---|---|
| 4,902,797 A | * | 2/1990 | Totani et al. .................. | 546/11 |
| 4,921,963 A | * | 5/1990 | Skov et al. .................. | 548/101 |
| 4,939,256 A | * | 7/1990 | Takamatsu et al. ............ | 546/11 |
| 5,359,047 A | | 10/1994 | Donahue et al. ........... | 536/23.5 |
| 5,625,048 A | | 4/1997 | Tsien et al. ................. | 536/23.4 |
| 5,955,604 A | | 9/1999 | Tsien et al. .................. | 540/222 |
| 6,350,740 B1 | * | 2/2002 | Farrell ......................... | 514/185 |
| 6,413,953 B1 | * | 7/2002 | Gianomenico et al. ..... | 514/188 |
| 6,518,428 B1 | * | 2/2003 | Wong et al. .................... | 546/2 |

FOREIGN PATENT DOCUMENTS

WO     WO 96/30540     10/1996     ......... C07D/471/04

OTHER PUBLICATIONS

Trevor G. Appleton et al., "Reactions of Platinum (II) Aqua Complexes. 2. $^{195}$Pt NMR Study of Reactions between the Tetraaquaplatinum (II) Cation and Chloride, Hydrozide, Percholarate, Nitrate, Sulfate, Phosphate, and Acetate", *Inorganic Chemistry*, vol. 2, No. 22, pp. 3521–3525 (1984).

Robert W. Armstrong et al., "Multiple–Component Condensation Strategies for Combinatorial Library Synthesis", *Acc., Chem. Res. American Chemical Society*, vol. 29, No. 3, pp 123–131 (1996).

R. Bakhtiar et al., "Pharmacological applications of inorganic complexes", *General Pharmacology*, vol. 32, pp 525–540 (1999).

Friedhelm Balkenhohl et al., "Combinatorial Synthesis of Small Organic Molecules", *Angew. Chem. Int. Ed. Engl.*, 35, pp. 2289–2337 (1996).

Steven F. Bellon et al., "Bending studies of DNA site–specifically modified by cisplatin, *trans*–diamminedichloroplatinum(II) and *cis*–[Pt(NH$_3$)$_2$(N3–cytosine) C1]" *Biophysical Chemistry*,vol. 35, pp. 179–188 (1990).

Erich E. Blatter et al., "Interaction of the Antitumor Agents cis, cis, trans–Pt$^{IV}$(NH$_3$)$_2$CL$_2$(OH)$_2$ and cis, cis, tran–Pt$^{IV}$[(CH$_3$)$_2$CHNH$_2$]$_2$CL$_2$(OH)$_2$ and Their Reduction Products with PM2 DNA", *American Chemical Society*, vol. 23, No. 21, pp. 4817–4820 (1984).

P.D. Braddock et al., "Structure and Activity Relationships of Platinum Complexes with Anti–Tumour Activity" *Chem.– Biol. Interactions*, vol. 11, pp. 145–161 (1975).

Gabriel Bricefio et al., "A Class of Cobalt Oxide Magnetoresistance Materials Discovered with Combinatorial Synthesis", *Science*, vol. 270, pp. 273–275 (1995).

Matthew T. Burger et al., "Synthetic Ionophores. Encoded Combinatorial Libraries of Cyclen–based Receptors for Cu$^{2+}$Co$^{2+}$", *J. Org. Chem.*, vol. 60, No. 23, pp. 7382–7383 (1999).

Kevin Burgess et al., "New Catalysts and Conditions for A C–H Insertion Reaction Identified by High Throughput Catalyst Screening" *Andew. Chem. Int. Ed. Engl.*, vol. 35, No. 2, pp. 220–222 (1996).

Dominique Burnouf et al., "Spectrum of Cisplatin–induced Mutations In *Escherichia coli*", *Proc. Natl. Afad. Sci USA*, vol. 84, pp. 3758–3762 (1987).

Burton et al., "Florescien Dyes Derived From 2–Methylresocinol", *J.S.C.I.*, vol. 67, pp. 345–347 (1948).

David A. Campbell et al., "A Transition State Analogue Inhibitor Combinatorial Library", *J. Am. Chem. Soc.*, vol. 117, pp. 5381–5382 (1995).

Yu Chen et al., "Sterospecific and Kinetic Control over the Hydrolysis of a Sterically Hindered Platinum Picoline Anticancer Complex", *Chem. Eur. J.*, vol. 4, pp. 672–676 (1998).

Annalisa Chiocchetti et al., "Green Fluorescent protein as a reporter of gene expression in transgenic mice", *Biochimica et Biophsica Acta*, vol. 1352, pp. 193–202 (1997).

Takashi Chishima et al., "Cancer Invasion and Micrometastasis Visualized in Live Tissue by Green Fluorescent Protein Expression", *Cancer Research*, 57, 2042–2047 (1997).

Andrew P. Combs et al., "Protein Structure–Based Combinatorial Chemistry: Discovery of Non–Peptide Binding Elements to Src SH3 Domain", *J. Am. Chem. Soc.*, 118 pp 287–288 (1996).

P. M. Cowley et al., "Applications of Solid–Phase Synthesis to Drug Discovery", *Current Medicinal Chemistry*, vol. 4, pp 211–227 (1997).

(List continued on next page.)

*Primary Examiner*—Porfirio Nazario-Gonzalez

(57) ABSTRACT

The present invention provides novel coordination complexes, methods for synthesizing and identifying coordination complexes using combinatorial techniques, and assaying for their activity. In certain embodiments, the subject coordination complexes contain platinum,

25 Claims, 11 Drawing Sheets

OTHER PUBLICATIONS

Andrew B. Cubitt et al., Understanding, improving and using green fluorescent proteins:, *Techniques TiBS*, 20, pp. 448–455 (1995).

S. C. Dhara, A Rapid Method for the Synthesis of cis–[Pt(NH$_3$)$_2$CL$_2$]:, *Indian Journal of Chemistry*, vol. 8, No. 2, pp. 193–194 (1970).

S.G. Dixit et al., "Combinatorial Chemistry—Principles and Practices", *Journal of Scientific & Industrial Research*, vol. 57, pp. 173–183 (1988).

David J. Ecker et al., "Combinatorial Drug Discovery: Which Methods Will Produce the Greatest Value?", *Bio/Technology*, vol. 13, pp. 351–360 (1995).

H.N.A. Fraval et al., "Increased Sensitivity of UV–Repair–Deficient Human Cells To DNA Bound Platinum Products Which Unlike Thymine Dimers Are Not Recognized By An Endonuclease Extracted From *Micrococcus Luteus*", *Mutation Research*, vol. 51, pp. 121–132 (1978).

C. J. Frederickson, "Neurobiology of Zinc and Zinc–containing Neurons", *International Review of Neurobiology*, vol. 31, pp 145–238 (1989).

Hans–Hermann Gerdes et al., "Green fluorescent protein: applications in cell biology", *Federation of European Bichemical Societies, FEBS Letters*, 389, pp. 44–47 (1996).

Christen M. Giandomenico et al., "Carboxylation of Kinetically Inert Platinum(IV) Complexes. An Entrée into Orally Active Platinum(IV) Antitumor Agents", *Inorganic Chemistry*, vol. 34, No. 5, pp. 1015–1021 (1995).

Marisa Gariglio et al., "The High–Mobility Group Protein T160 Binds to both Linear and Cruciform DNA and Mediates DNA Bending as Determined by Ring Closure" *Experimental Cell Research*, vol. 236, Article No. EX973742, pp. 472–481 (1997).

Harold C. Harder et al., "Inhibitory Effects of Anti–Tumor Platinum Compounds on DNA, RNA and Protein Syntheses in Mammalian Cells In Vitro", *Int. J. Cancer*, 6, pp. 207–216 (1970).

Jerry A. Howle et al., "CIS–Dichlorodiammineplatinum (II) Persistent And Selective Inhibition of Deoxyribonucleic Acid Synthesis In Vivo", *Biochemical Pharmacology*, vol. 19, pp. 2757–2762 (1970).

Elizabeth R. Jamieson et al., "Structure, Recognition, and Processing of Cisplatin—DNA Adducts", *American Chemical Society, Chem. Rev*, vol. 99, No. 9, pp. 2467–2498 (1999).

Thomas W. Jones et al., "Cis–Diamminedichloroplatinum (II)–Induced Acute Renal Failure in the Rat—Correlation of Structural and Functional Alterations", *Laboratory Investigation*, vol. 52, No. 4, pp. 363–374 (1985).

S. R. Kain et al., "Green Fluorescent Protein as a Reporter of Gene Expression and Protein Localization", *BioTechniques*, vol. 19, No. 4, pp. 650–655 (1995).

Jana Kašpárková et al., "Effect of Geometric Isomerism in Dinucler Platinum Antitumor Complexes on DNA Interstrand Cross–Linking", *Biochemistry*, vol. 38, No. 34, pp. 10997–11005 (1999).

Miriam B.G. Kloster et al., "Consequences of Nucleic Acid Conformation on the Binding of a Trinuclear Platinum Drug" *Biochemistry*, vol. 38, No. 45, pp. 14731–14737 (1999).

K. W. Lee et al., Cis–dichlorodiammineplatinum(II). Aquation Equilibria and Isotopic Exchange of Chloride Ligands with Free Choloride and Tetrachloroplatinate(II), *Inorganica Chimica Acta*, vol. 17, pp.. 105–110 (1976).

Gary LeRoy et al., "Requirement of RSF and FACT for Transcription of Chromatin Templates in Vitro", *Science*, vol. 282, pp. 1900–1904 (1998).

Shuang Liu et al., "$^{99m}$Tc–Labeled Small Peptides as Diagnositc Radiopharmaceuticals", *American Chemical Society, Chemical Reviews*, vol. 99, No. 9, pp. 2235–2268 (1999).

Colin James Lyne Lock et al., "Crystal and Molecular Structures of cis–and trans–Dichlorobis (cyclobutylamine–N) platinum (II), PtCl$_2$(C$_4$H$_7$NH$_2$)$_2$, and some Comments on the Conversion of Cis to Trans" *Inorg. Chem*, vol. 20, No. 6, pp. 1817–1823 (1981).

Patrick J. Loehrer, M.D., et al., "Diagnosis and Treatment—Drugs Five Years Later", *Annals of Internal Medicine*, vol. 100, No. 5, pp 704–713 (1984).

Reinhard Malin et al., "Identification of Technetium–99m Binding Peptides Using Combinatorial Cellulose–Bound Peptide Libraries", *J. Am. Chem. Soc.*, vol. 117, No. 47, pp. 11821–11822 (1995).

Jill A. Mello et al., "The mismatch–repair protein hMSH2 binds slectively to DNA adducts of the anticancer drug cisplatin", *Chemistry & Biology*, vol. 3, No. 7, pp. 579–589 (1996).

D. D. Mosser et al., "Use of a Dicistronic Expression Cassette Encoding the Green Fluorescent Protein for the Screening and Selection of Cells Expressing Inducible Gene Products", *Bio Techniques*, vol. 22, No. 1, pp. 150–161 (1997).

Micheal C. Needels et al., "Generation and screening of an oligonucleotide–encoded synthetic peptide library", *Proc. Natl. Acad. Sci*, vol. 90, pp. 10700–10704 (1993).

Michael H.J. Ohlymeyer et al., "Complex synthetic chemical libraries indexed with molecular tags", *Proc. Natl. Acad. Sci, USA.*, vol. 90, pp. 10922–10926 (1993).

George Orphanides et al., "FACT, a Factor that Facilitates Transcript Elongation through Nucleosomes", *Cell*, vol. 92, pp. 105–116 (1998).

George Orphanides et al., "The chromatin–specific transcription elongation factor FACT comprises human SPT16 and SSRP1 proteins", *Nature*, vol. 400, pp. 284–288 (1999).

Kevin G. Peters et al., "Green Fluorescent Fusion Proteins: Powerful Tools for Monitoring Protein Expression in Live Zebrafish Embryos" *Developmental Biology*, vol. 171, pp. 252–257 (1995).

Ann L. Pinto et al., "Sequence–dependent termination of in vitro DNA sythesis by cis– and trans–diamminedichloroplatinum (II)", *Proc. Natl. Acad. Sci.*, vol. 82, pp. 4616–4619 (1985).

Yun Qu et al., "Dinuclear Platinum Complexes Form a Novel Intrastrand Adduct with d(GpG), an anti–syn Conformation of the Marochelate As Observed by NMR and Molecular Modeling" *J. Am. Chem. Soc.*, vol. 118, No. 39, pp. 9307–9313 (1996).

Janet A. Rice et al., "The major adduct of the antitumor drug cis–diamminedichloro–platinum(II) with DNA bends the duplex by = 40' toward the major groove", *Proc. Natl. Acad. Sci*, vol. 85, pp. 4158–4161 (1998).

F.D. Rochon et al., "Structure of an Antitumor Platinum(II) Compound cis–[PtCl$_2$(Cyclobutylamine)(NH$_3$)]", *Acta Crystallographica*, C42, pp. 1291–1294 (1986).

Karen E. Sandman et al., "A mechanism–based, solution–phase method for screening combinatorial mixtures of potential platinum anticancer drugs", *JBIC*, vol. 3, pp. 74–80 (1998).

Karen E. Sandman et al., "Rapid fluorescence–based reporter–gene assays to evaluate the cytotoxicity and antitumor drug potential of platinum complexes", *Chemistry & Biology*, vol. 6, No. 8, pp. 541–551 (1999).

Suzanne E. Sherman et al., "Structural Aspects of Platinum Anticancer Drug Interactions with DNA", *Chemical Reviews*, vol. 87, No. 5, pp. 1153–1181 (1987).

Ken D. Shimizu et al., "Search for Chiral Catalysts Through Ligand Diversity: Substrate–Specific Cataysts and Ligand Screening on Solid Phase", *Angew. Chem. Int. Ed. Engl.*, vol. 36, No. 16, pp. 1704–1707 (1997).

Christine M. Sorenson et al., "Mechanism of cis–Diamminedichloroplatinum(II)–induced Cytotoxicity: Role of $G_2$ Arrest and DNA Double–Strand Breaks" *Cancer Research*, vol. 48, pp. 4484–4488 (1988).

W. Clark Still, "Discovery of Sequence–Selective Peptide Binding by Synthetic Receptors Using Encoded Combinatorial Libraries", *Acc. Chem. Res.*, vol. 29, No. 3, pp. 155–163 (1996).

Wesley I. Sundquist et al., "Binding of cis– and trans–Diamminedichloroplatinum(II) to Deoxyribonucleic Acid Exposes Nucleosides As Measured Immunochemically with Anti–Nucleoside Antibodies", *Biochemistry*, vol. 25, No. 7, pp. 1520–1524 (1986).

Hans J. Tanke et al., "Use of Platinum Coproporphyrin and Delayed Luminescence Imaging to Extend the Number of Targets FISH Karyotypingp" *Cytometry*, vol. 33, pp. 453–459 (1998).

Lorin A. Thompson et al., "Synthesis and Applications of Small Molecule Libraries", *Chemical Reviews*, vol. 96, No. 1, pp. 555–600 (1996).

Gary T. Wang et al., "Synthetic Chemical Diversity: Solid Phase Synthesis of Libraries of $C_2$ Symmetric Inhibitors of HIV Protease Containing Diamino Diol and Diamino Alcohol Cores", *Journal of Medicinal Chemistry*, vol. 38, No. 16, pp. 2995–3002 (1995).

Julia Yaneva et al., "The major chromatin protein histone H1 binds preferentially to cis–platinum–damgaged DNA", *Proc. Natl. Acad. Sci.*, vol. 94, pp. 13448–13451 (1997).

Motofumi Yoshida et al., "Circumvention of platinum resistance: structure–activity relationship for homologous series of ammine/amine platinum(II) complexes in L1210 cell lines" *Anti–Cancer Drug Design*, vol. 9, pp. 425–434 (1994).

Hongtao Yu et al., "Structural Basis for the Binding of Proline–Rich Peptides to SH3 Domains", *Cell*, vol. 76, pp. 933–945 (1994).

Deborah B. Zamble et al., "Cisplatin and DNA repair in cancer chemotherapy", *TiBS*, vol. 20, pp. 435–439 (1995).

Xiaoquan Zhai et al., "Cisplatin–DNA Adducts Inhibit Ribosomal RNA Synthesis by Hijacking the Transcription Factor Human Upstream Binding Factor", *Biochemistry*, vol. 37, No. 46, pp. 16307–16315 (1998).

Christopher J. Ziegler et al., "High–throughput synthesis and screening of platinum drug candidates", *J. Biol Inorg Chem*, vol. 5, pp. 774–783 (2000).

Christopher J. Ziegler et al., "Toxicity of platinum(II) amino acid ($N_3O$) complexes parallels their binding to DNA as measured in a new solid phase assay involving a fluorescent HMG1 protein construct readout", *JBIC*, vol. 4., pp. 402–411 (1999).

Gregor Zlokarnik, "Fluorescent Molecular Sensor for Drug Discovery", *Analytical Chemistry News & Features*, pp. 322A–328A (1999).

Ronald N. Zuckermann et al., "Discovery of Nanomolar Ligands for 7–Transmembrane G–Protein–Coupled Receptors from a Diverse N–(Substituted)glycine Peptoid Library", *Journal of Medicinal Chemistry*, vol. 37, No. 17, pp. 2678–2685 (1994).

F. Zunino et al., "Current Approaches to New Drug Development in Cancer Chemotherapy", *Il Farmaco*, vol. 47, No. 9., pp 1115–1232 (1992).

* cited by examiner

ZD0473

*cis*-ammine(2-amino-3-picoline)
dichloroplatinum(II)

COORDINATION COMPLEXES, AND METHODS FOR PREPARING BY COMBINATORIAL METHODS, ASSAYING AND USING THE SAME

1. RELATED APPLICATION INFORMATION

This application claims the benefit of priority under 35 U.S.C. section 119(e) to Provisional Patent Application 60/218,335, filed July 14, 2000. This application is hereby incorporated by reference in its entirety.

2. GOVERNMENT SUPPORT

The subject invention was made in part with support from the U.S. Government under a grant from the National Cancer Institute and a National Cancer Institute National Research Service Award. Accordingly, the U.S. Government has certain rights in this invention.

3. INTRODUCTION

Cancer arises in many instances in which a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor (also referred to as a neoplasm). When a tumor is found, the clinical objective is to destroy malignant cells selectively while mitigating any harm caused to normal cells in the individual undergoing treatment.

Currently, three major approaches are generally followed for the clinical management of cancer in humans and other animals. Surgical resection of solid tumors, malignant nodules and or entire organs may be appropriate for certain types of neoplasia. For other types, e.g., those manifested as soluble (ascites) tumors, hematopoeitic malignancies such as leukemia, or where metastasis of a primary tumor to another site in the body is suspected, radiation or chemotherapy may be appropriate. Either of these techniques may also be used as an adjunct to surgery.

Chemotherapy is often based on the use of drugs that are selectively toxic (cytotoxic) to cancer cells. Several general classes of chemotherapeutic drugs have been developed. A first class, antimetabolite drugs, includes drugs that interfere with nucleic acid synthesis, protein synthesis, and other vital metabolic processes. Another class, genotoxic drugs, inflicts damage on cellular nucleic acids, including DNA. Two widely used genotoxic anticancer drugs that have been shown to damage cellular DNA by producing crosslinks therein are cisplatin [cis-diamminedichloroplatinum(II)] and carboplatin [diammine(1,1-cyclobutanedicarboxylato)-platinum(II)]. Cisplatin and carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin currently is preferred for the management of testicular carcinoma and in many instances produces a lasting remission. In cisplatin chemistry, one of the significant areas of research has involved the clinical difference, as exemplified in a variety of in vitro assays, indicating that trans-diamminedichloroplatinum(II) (trans-DDP) a regioisomer of cisplatin, is not an effective chemotherapeutic.

The repair of damage to cellular DNA is an important biological process carried out by a cell's enzymatic DNA repair machinery. Unrepaired lesions in a cell's genome may impede DNA replication, impair the replication fidelity of newly synthesized DNA or hinder the expression of genes needed for cell survival. Thus, genotoxic drugs generally are considered more toxic to actively dividing cells that engage in DNA synthesis than to quiescent, nondividing cells. Indeed, cells carrying a genetic defect in one or more elements of the enzymatic DNA repair machinery have been observed to be extremely sensitive to cisplatin. Normal cells of many body tissues, however, are quiescent and commit infrequently to reenter the cell cycle and divide. Greater time between rounds of cell division generally is afforded for the repair of DNA damage in normal cells inflected by chemotherapeutic genotoxins. As a result, some selectivity is achieved for the killing of cancer cells. Many treatment regimes reflect attempts to improve selectivity for cancer cells by co-administering chemotherapeutic drugs belonging to two or more of these general classes.

In some tissues, however, normal cells divide continuously. Thus, skin, hair follicles, buccal mucosa and other tissues of the gut lining, sperm and blood-forming tissues of the bone marrow remain vulnerable to the action of genotoxic drugs, including cisplatin. These and other classes of chemotherapeutic drugs can also cause severe adverse side effects in drug-sensitive organs, such as the liver and kidneys. These and other adverse side effects seriously constrain the dosage levels and lengths of treatment regimens that can be prescribed for individuals in need of cancer chemotherapy. Such constraints can prejudice the effectiveness of clinical treatment. For example, the drug or drug combination administered must contact and affect cancer cells at times appropriate to impair cell survival. Genotoxic drugs are most effective for killing cancer cells that are actively dividing when chemotherapeutic treatment is applied. Conversely, such drugs are relatively ineffective for the treatment of slow growing tumors. Carcinoma cells of the breast, lung and colorectal tissues, for example, typically double as slowly as once every 100 days. Such slowly growing tumors present difficult chemotherapeutic targets.

Moreover, cancer cells may acquire resistance to genotoxic drugs through diminished uptake or other changes in drug metabolism, such as those that occur upon drug-induced gene amplification or expression of a cellular gene for multiple drug resistance (MDR). Resistance to genotoxic drugs may also be acquired by activation or enhanced expression of enzymes in the cancer cell's enzymatic DNA repair machinery. Therapies that employ combinations of drugs, or drugs and radiation, attempt to overcome these limitations. The pharmacokinetic profile of each chemotherapeutic drug in such a combinatorial regime, however, will in all likelihood differ. In particular, permeability of neoplastic tissue for each drug may be different. Thus, it may be difficult to achieve genotoxically effective concentrations of multiple chemotherapeutic drugs in target tissues.

In part, there remain a variety of needs to address many of the concerns discussed above. Some exemplary needs include: additional therapeutic agents with, for example, improved selectivity for destroying transformed cells in situ without significantly impairing viability of untransformed cells; enhancing effectiveness of therapeutic agents, such that satisfactory cell killing may be achieved with lower doses thereof; and therapeutic agents with improved selectivity for destroying transformed cells. The present invention provides therapeutic agents, and methods of making and using the same, that may address such concerns in certain embodiments. In certain embodiments of the subject invention, the therapeutic agents are coordination complexes that may be synthesized in a combinatorial fashion (in addition to other means). In addition to the foregoing embodiments, the coordination complexes of the present invention may be used for catalysis and other uses customary to coordination complexes.

4. SUMMARY OF THE INVENTION

In one aspect, the present invention provides methods for synthesizing a number of compounds of interest, such as transition metal-containing compounds and other coordination complexes. In certain embodiments, a library of coordination complexes may be prepared by combinatorial means that provides coordination complexes that exhibit diversity of structure and properties (e.g., chemical and biological). Utilizing combinatorial chemistry techniques, such as direct characterization, encoding, spatially addressing and deconvolution, the molecular identity of individual members of subject libraries may be ascertained in a screening format. In still other embodiments, the synthesis of compositions and libraries of them is partially or wholly automated.

In certain embodiments, the present invention provides methods for the production of coordination complexes and libraries of coordination complexes. In certain embodiments, the present invention provides synthetic strategies that allow production of large collections of coordination complexes. In still other embodiments, the coordination complexes of an inventive library are reminiscent of cisplatin in that they contain one or more atoms of platinum (II). In yet other embodiments, the subject coordination complexes may contain platinum(IV). The coordination complexes of such inventive libraries may possess the capability of acting as a therapeutic agent in a fashion similar to cisplatin.

In addition to providing coordination complexes, combinatorial libraries thereof, and methods of their production, the present invention also contemplates linkers and supports, which may be used in the preparation of support-bound coordination complexes and libraries.

In one subject method, coordination complexes of the present invention containing a metal may be prepared as follows using a method for identifying one or more coordination complexes comprising platinum in a library, comprising:

(a) chemically synthesizing a library, wherein a plurality of members of said library comprise coordination complexes comprising platinum;

(b) subjecting said members of said library to an assay; and (c) comparing the response observed for any member of said library in said assay with the response of trans-DDP in said assay and the response of cisplatin in said assay.

Other exemplary embodiments of the subject invention are presented in the appended claims, which are incorporated by this reference in their entirety in this Summary of the Invention.

In another aspect, the present invention provides methods for identifying coordination complexes or other compositions that exhibit desirable properties. In certain embodiments of the present invention, a number of screening assays for the activity (e.g., biological, chemical, or catalytic) of subject coordination complexes may be determined and subsequently evaluated. Activities observed for subject coordination complexes may be compared to coordination complexes and other compositions having either desirable or undesirable properties in like assays.

For example, the present invention provides a method for determining one or more biological activities of a library member. In certain embodiments, the method for determining one or more biological activities of the inventive coordination complexes comprises contacting the inventive complexes with a biological target, such as a cell based assay, and determining a statistically significant change in a biochemical activity relative to the level of biochemical activity in the absence of the complex. One example of such a biochemical activity is the therapeutic index and other parameters relating to the efficacy and toxicity of any of the subject coordination complexes.

In one aspect, the present invention contemplates a variety of transcription-based assays to determine the biological activity of the subject compositions. In one embodiment, termed the CCF2/AM assay, the transcription of β-lactamase is monitored by the use of the CCF2/AM dye and its fluorescence upon treatment with the agent of interest, usually a platinum-containing complex. Changes in fluorescence as compared to the background and control compounds indicate some form of biological activity on the part of the agent so as to disrupt transcription. In certain embodiments, the results of the assay for any subject coordination complex are compared to agents that are known chemotherapeutics, such as cisplatin, and those that are not, such as trans-DDP.

Another particular embodiment of the present inventive assays involves a method to assess whether a subject coordination complex, such as a platinum-containing coordination complex, forms lesions in DNA that are bound or otherwise recognized by a DNA structure specific recognition protein ("SSRP"). In certain embodiments, the present invention provides an in vitro assay for predicting whether a suspected genotoxic agent forms persistent genoric lesions in eukaryotic cellular DNA. In still other embodiments, the present invention provides a method of screening new coordination complexes for the ability to form DNA lesions that are bound by a SSRP. For example, the present invention provides a screening method for the rational design of new genotoxic agents that form persistent genomic lesions in eukaryotic cells. Methods such as these allow for high-throughput, in vitro assessment of drug candidate libraries produced by combinatorial chemistry.

Furthermore, the methods contemplated by the present invention may involve two or more assays, either the same assay or different assays, to identify coordination complexes that may produce "false positives" in any single assay. In addition, the present inventive methods provide for positive and negative controls.

The present invention further provides a kit comprising a library of coordination complexes and reagents for determining one or more biological activities of a compound. To give but one example, the biological activity may be determined by providing a kit containing an appropriate assay and a library of coordination complexes. Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, diagnosis, therapy, vaccination and other applications.

In still another aspect, the present invention provides compositions including one or more of the coordination complexes identified by the subject method. The present invention additionally provides pharmaceutical compositions containing one or more library members. In certain embodiments, the pharmaceutical composition preferably comprises one or more of the inventive coordination complexes and a pharmaceutically acceptable carrier. In other embodiments, the present invention provides new therapeutic agents prepared by the inventive methods or identified by the inventive screening methods. In certain embodiments, those agents are coordination complexes. In still other embodiments, those agents contain the transition metal platinum.

In still another aspect, the compositions of the present invention, and methods of making and using the same, may be used in diagnostic applications, such as those embodiments in which the metal ion is suitable for imaging.

In another aspect, the compositions of the present invention may be used in the manufacture of a medicament for any number of uses, including for example treating any disease or other treatable condition of a patient. In still other aspects, the present invention is directed to a method for formulating coordination complexes of the present invention in a pharmaceutically acceptable carrier.

These embodiments of the present invention, other embodiments, and their features and characteristics, will be apparent from the description, drawings and claims that follow.

5. BRIEF DESCRIPTION OF THE DRAWINGS

FIGS. 1, 2 and 3 show embodiments of the present invention, whereby coordination complexes of the present invention are prepared by the reaction scheme shown using tetrachloroplatinate, amminetrichloroplatinate and trans-DDP as the metal precursor, respectively. The numbers for each step in the reaction scheme indicate where in the well structure of the reaction block each step occurs. As a general note, the chemical species shown for each step are believed to be the predominant species in the reaction mixture, but there may be other, even a majority, of other species present. In addition, the ligands (e.g., Cl, I, A, L) may be generalized as discussed further below.

6. DETAILED DESCRIPTION OF THE INVENTION

6.1. Introduction

Figure 1:
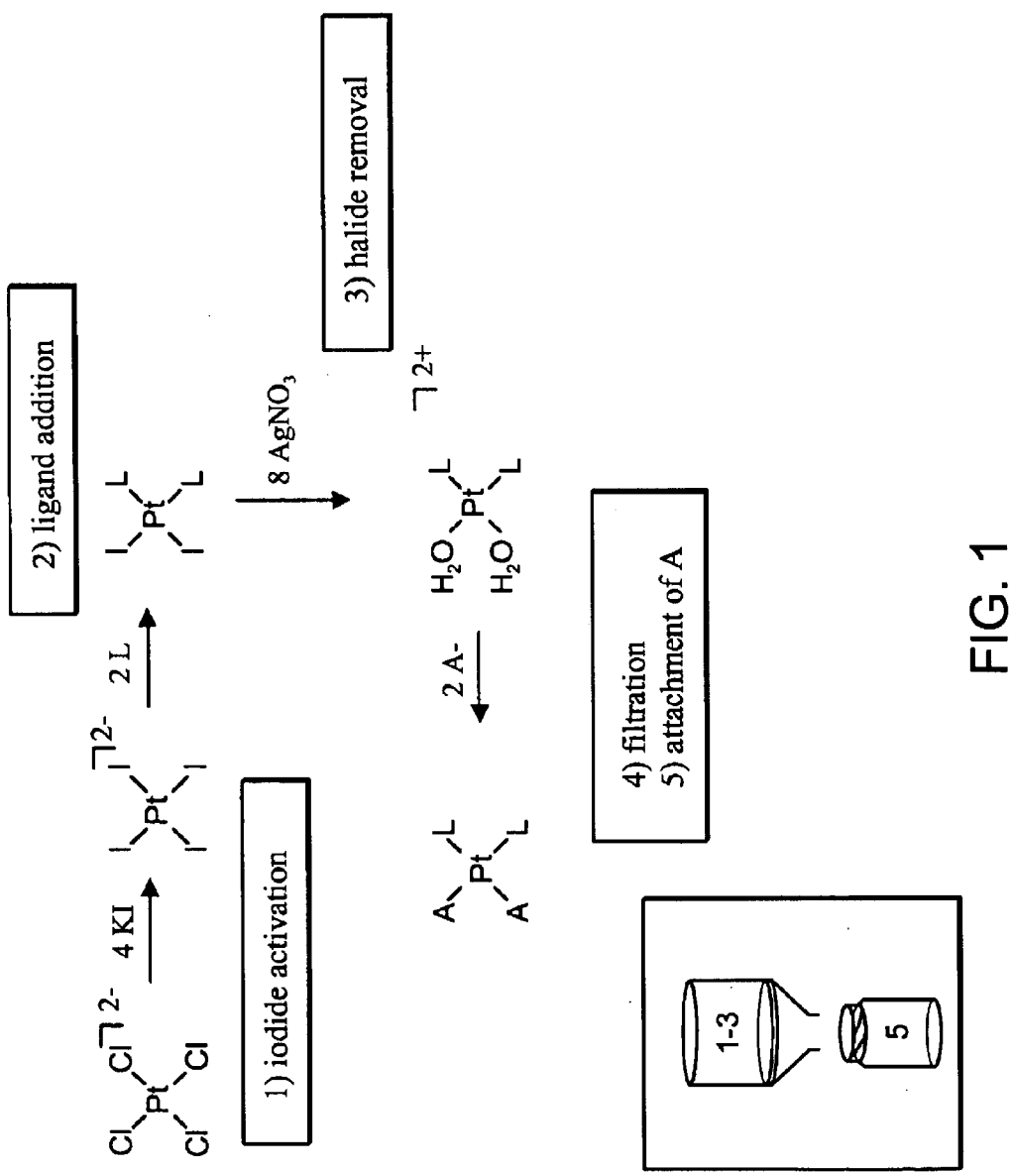

One challenge in the development of therapeutic agents lies in efficiently identifying potential coordination complexes of interest, through both an understanding of their mechanisms of action as well as the more rapid synthesis and screening of suitable candidates. In part, the present invention provides combinatorial chemistry methods for producing therapeutic agents of interest, and libraries thereof, and screening methodologies for the rapid evaluation of such agents. In particular embodiments, the therapeutic agents of the present invention are coordination complexes. In still other embodiments, the coordination complexes that may be of interest as genotoxic agents or are chemotoxic contain platinum. In yet other embodiments, the coordination complexes of the subject invention may be used as catalysts.

In part, the present invention is concerned with the relationship of ligand structure to the chemical and physical properties of metal complexes, for that relationship is fundamental to the properties observed for coordination complexes, including their toxicity and therapeutic, efficacy. In this context, a systematic method for the expedient generation of new classes of coordination complexes would clearly be of great value. Moreover, the rational design of such complexes may be possible by using the teachings of the present invention, which should allow for the preparation and identification of therapeutic agents exhibiting novel physical and chemical properties.

As described herein, the present invention provides coordination complexes and libraries of coordination complexes, and methods for making such libraries. In certain embodiments, the present invention provides synthetic strategies that allow production of coordination complexes and large collections of coordination complexes that are reminiscent of any number of therapeutic agents, such as the chemotherapeutic and genotoxic agent cisplatin. For this invention, chemical diversity may be defined as varying a specific characteristic or set of characteristics of the coordination complexes of the present invention including, but not limited to, atomic identity, topology, size, charge, hydrophilicity, hydrophobicity, and reactivity. Such variations may include, for example, the metal component, the ligand component, the counter-ion, the amount and type of solvation, and the like.

For those embodiments directed to analogs of cisplatin and the like, coordination complexes of the present invention contain at least one platinum atom, usually in a four-coordinate, square planar configuration, and a diversity of ligands coordinated thereto. In those embodiments in which analogs of cisplatin are synthesized, examples of diversity include, but are not limited to, variations in either the shape or chain length of a particular collection of atoms or variations in the particular atoms present in any ligands coordinated to the platinum.

In still other embodiments, the present invention also provides coordination complexes and libraries of coordination complexes that, although not based on an already known therapeutic agent, may achieve a therapeutic effect or produce positive assay results. Whether the coordination complexes are entirely novel or are based on an already known therapeutic agent, such as cisplatin, the coordination complexes and libraries of coordination complexes are expected to be useful as therapeutics and biological probes because of their ability to interact with biomolecules and other targets, such as proteins, carbohydrates, nucleic acids and the like.

The compounds of the present invention have a variety of uses. In one aspect, compounds may be used as a therapeutic agent to treat a host. In certain embodiments, the compound is a coordination complex, the host is a human, and the compound is formulated in a pharmaceutically acceptable carrier. In certain embodiments, a medicament may be formulated for the treatment of variety of diseases or conditions, including for example, neoplasms and other cancers.

In another aspect, compounds of the present invention may be used as imaging agents. For certain of those embodiments, the metal ion of a coordination complex may be critical if such ion is intended to render the complex subject to imaging. In still other aspects, the compounds of the present invention may be used as catalysts in organic transformations, to target a target cell, or for diagnostic purposes.

6.2. Definitions

For convenience, before further description of the present invention, certain terms employed in the specification, examples and appended claims are collected here. These definitions should be read in light of the remainder of the disclosure and understood as by a person of skill in the art.

The terms "Lewis base" and "Lewis basic" are art-recognized and generally refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O^{2-}$). In certain circumstances, a Lewis base or ligand may be positively charged. A Lewis base, when coordinated to a metal ion, is often referred to as a ligand. Further description of ligands relevant to the present invention is presented herein.

The term "ligand" is art-recognized and refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The term "coordinate bond" is art-recognized and refers to an interaction between an electron pair donor and a coordination site on a metal ion leading to an attractive force between the electron pair donor and the metal ion. The use of this term is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and refers to a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. For example, cisplatin is a coordination complex. A transition metal complex is a coordination complex in which the metal ion is a transition metal ion. In general, the terms "compound," "composition," "agent" and the like discussed herein include complexes, coordination complexes and transition metal complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a transitional metal complex is charged, in that the transition metal ion and any Lewis bases, in the aggregate, are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetrafluoroborate, hexafluorophosphate, and monocarboxylates having the general formula $RCOO^-$, and dianions such as sulfate. In some cases, coordination complexes themselves may serve as counterions to another coordination complex, as in Magnus (green) salt $[Pt(NH_3)_4]^{2+}[PtCl_4]^{2-}$.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors, including theoretical considerations, such as kinetic versus thermodynamic effects, and the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. In general, the members of any library show at least some structural diversity, which often results in chemical and biological diversity. Such structural diversity in preparing libraries of coordination compounds may include, by way of example, metal ion diversity, ligand diversity, solvation diversity or counter-ion diversity. A library may contain any number of members from two different members to about $10^8$ members or more. In certain embodiments, libraries of the present invention have more than about 12, 50 and 90 members. In certain embodiments of the present invention, the starting materials and certain of the reactants are the same, and chemical diversity in such libraries is achieved by varying at least one of the reactants or reaction conditions during the preparation of the library. Combinatorial libraries of the present invention may be prepared in solution or on the solid phase. Further details regarding the libraries of the present invention are described below.

The term "identifier tag" is art-recognized and refers to a means for recording a step in a series of reactions used in the synthesis of a chemical library. For the purposes of this application, the terms encoded chemical library and tagged chemical library both refer to libraries containing a means for recording each step in the reaction sequence for the synthesis of the chemical library.

The term "immobilized" is art-recognized and, when used with respect to a species, refers to a condition in which the species is attached to a surface with an attractive force stronger than attractive forces that are present in the intended environment of use of the surface, and that act on the species. For example, a chelating agent immobilized at a surface, the surface being used to capture a biological molecule from a fluid medium, is attracted to the surface with a force stronger than forces acting on the chelating agent in the fluid medium, for example solvating and turbulent forces.

The term "solid support" is art-recognized and refers to a material which is an insoluble matrix, and may (optionally) have a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "linker" is art-recognized and refers to a molecule or group of molecules connecting a support, including a solid support or polymeric support, and a combinatorial library member. The linker may be comprised of a single linking molecule or may comprise a linking molecule and a spacer molecule, intended to separate the linking molecule and the library member by a specific distance.

The term "polymeric support" is art-recognized and refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support may be soluble under certain conditions and insoluble under other conditions.

The term "functional group of a polymeric support" is art-recognized and refers to a chemical moiety of a polymeric support that can react with an chemical moiety to form a polymer-supported amino ester. Exemplary functional groups of a polymeric support include hydroxyl and sulfhydryl, and the like. In certain embodiments, functional groups of a polymeric support will form polymer-supported amino esters that are covalently bound to the polymeric support under mild conditions that do not adversely affect the polymer or the amino ester, and that are sufficiently stable to be isolated.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized and refers to the dose of a drug or other compound or coordination complex which produces 50% of its maximum response or effect, or alternatively, the dose which produces a pre-determined response in 50% of test subjects or preparations.

The term "$LD_{50}$" is art-recognized and refers to the dose of a drug or other compound or coordination complex which is lethal in 50% of test subjects.

The term "therapeutic index" is art-recognized and refers to the therapeutic index of a drug or other compound or coordination complex defined as $LD_{50}/ED_{50}$.

The term "structure-activity relationship" or "(SAR)" is art-recognized and refers to the way in which altering the molecular structure of a drug or other compound or coordination complex alters its interaction with a receptor, enzyme, nucleic acid or other target and the like.

The term "agonist" is art-recognized and refers to a compound or coordination complex that mimics the action of natural transmitter or, when the natural transmitter is not known, causes changes at the receptor complex in the absence of other receptor ligands.

The term "antagonist" is art-recognized and refers to a compound or coordination complex that binds to a receptor site, but does not cause any physiological changes unless another receptor ligand is present.

The term "competitive antagonist" is art-recognized and refers to a compound or coordination complex that binds to a receptor site; its effects may be overcome by increased concentration of the agonist.

The term "partial agonist" is art-recognized and refers to a compound or coordination complex that binds to a receptor site but does not produce the maximal effect regardless of its concentration.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxyls, alkylthios, aminoalkyls, carbonyl-substituted alkyls, —$CF_3$, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognzed and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3 to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO. "Halide" designates the corresponding anion of the halogens, and "pseudohalide" has the definition set forth on 560 of *Advanced Inorganic Chemistry* by Cotton and Wilkinson.

The terms "amine" and "amino" are art-recognized and refer to both unsubstituted and substituted amines, e.g., a moiety that may be represented by the general formulas:

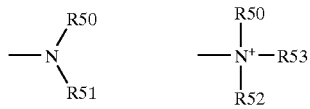

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "ammine" is art-recognized are refers to a compound containing an ammonia moiety or moieties coordinated to a metal ion. The term "ammonia" is art-recognized an refers to an amine group substituted with hydrogens.

The term "acylamino" is art-recognized and refers to a moiety that may be represented by the general formula:

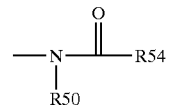

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

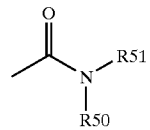

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

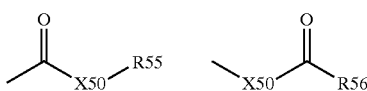

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

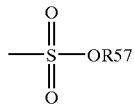

in which R57 is an electron pair, hydrogen, alkyl, cycloalkyl, or aryl.

The term "sulfate" is art recognized and includes a moiety that may be represented by the general formula:

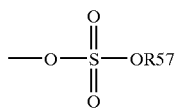

in which R57 is as defined above.

The term "sulfonamido" is art recognized and includes a moiety that may be represented by the general formula:

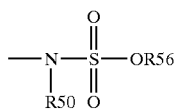

in which R50 and R56 are as defined above.

The term "sulfamoyl" is art-recognized and refers to a moiety that may be represented by the general formula:

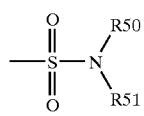

in which R50 and R51 are as defined above.

The term "sulfonyl" is art-recognized and refers to a moiety that may be represented by the general formula:

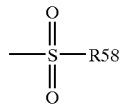

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

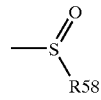

in which R58 is defined above.

The term "phosphoryl" is art-recognized and may in general be represented by the formula:

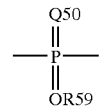

wherein Q50 represents S or O, and R59 represents hydrogen, a lower alkyl or an aryl. When used to substitute, e.g., an alkyl, the phosphoryl group of the phosphorylalkyl may be represented by the general formulas:

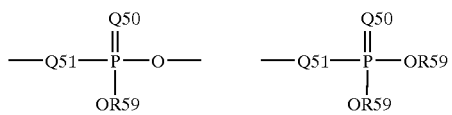

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

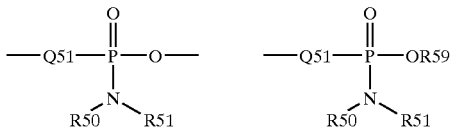

wherein Q51, R50, R51 and R59 are as defined above.

The term "phosphonamidite" is art-recognized and may be represented in the general formulas:

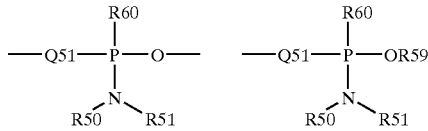

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "protecting group" is art-recognizes and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an aminno group from participating in a reaction carried out on some other functional group, but which can be removed from the amine when desired Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$–$C_4$ alkyl, halomethyl, or 2-halo-substituted-($C_2$–$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251–59 (McGraw Hill Book Company; New York, 1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The terms "amino acid residue" and "peptide residue" are art-recognized and refer to an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding $\alpha$-amino acid by eliminating the OH portion of the carboxyl group and the H portion of the $\alpha$-amino group. The term "amino acid side chain" is that part of an amino acid exclusive of the —$CH(NH_2)COOH$ portion, as defined by Kopple, *Peptides and Amino Acids* 2, 33 (W. A. Benjamin Inc., New York and Amsterdam, 1966); examples of such side chains of the common amino acids are —$CH_2CH_2SCH_3$ (the side chain of methionine), —$CH_2CH(CH_3)_2$ (the side chain of leucine) or —H (the side chain of glycine).

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compounds may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pure form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively.

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, decoy molecules, recombinant genes (including transgenes) and the like.

The terms "gene" or "recombinant gene" are art-recognized and refer to a nucleic acid comprising an open reading frame encoding a polypeptide, including both exonic and (optionally) intronic sequences.

The term "gene construct" is art-recognized and refers to a vector, plasmid, viral genome or the like which includes an "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct. The gene construct may include one or more regulatory elements operably linked to the coding sequence, as well as intronic sequences, poly adenylation sites, origins of replication, marker genes, etc.

The term "homology" is art-recognized and refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "operably linked" is art-recognized and refers to the relationship between two nucleic acid regions, means that they are functionally related to each other. For example, a promoter or other regulatory element is operably linked to a coding sequence of DNA if it controls the transcription of the coding sequence.

The terms "protein," "polypeptide" and "peptide" are art-recognized and are used interchangeably when referring to a gene product.

The term "antisense" nucleic acid is art-recognized and refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarily, or, for example, in the case of binding to DNA duplexes, through specific interactions in the major groove of the double helix.

The term "host cell" is art-recognized and refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are art-recognized and are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "regulatory element" is art-recognized and refers to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; Methods in Enzymology 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

Other examples of regulatory elements include the following: the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast $\alpha$-mating factors, the polyhedron promoter of the baculovirus system and other sequences known to control the expression of genes of prokaryotic or eukaryotic cells or their viruses, and various combinations thereof.

The term "ribozyme sequence" is art-recognized and refers to a catalytic RNA sequence capable of cleaving a target RNA, such as a hairpin or hammerhead ribozyme. The term also encompasses a nucleic acid sequence in an expression cassette from which the RNA is transcribed.

The term "transfection" is art-recognized and refers to the introduction of a nucleic acid, e.g., an expression vector, into a recipient cell, which in certain embodiments may be by nucleic acid-mediated gene transfer. "Transformation," as used with respect to transfected nucleic acid, is an art-recognized term and refers to a process in which a cell's genotype is changed as a result of the cellular uptake of exogenous nucleic acid.

The term "transfer vector" is art-recognized and refers to a first nucleic acid molecule to which a second nucleic acid has been linked, and includes for example plasmids, cosmids or phages (as discussed in grater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

Transfer vectors derived from viruses, which may be referred to as "viral vectors", may be employed in certain embodiments of the present invention. Some examples include retroviruses, adenoviruses and the like. Viral vectors are their uses in the present invention are discussed in more detail below. As for expression vectors, viral vectors may include regulatory elements.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

Some examples of expression vectors that may be used in certain embodiments of the present invention include the following. Suitable vectors for expression of a polypeptides include plasmids of the types: pBR322-derived plasmids, pEMBL-derived plasmids, pEX-derived plasmids, pBTac-derived plasmids and pUC-derived plasmids for expression in prokaryotic cells, such as E. coli. In some instances, it may be desirable to express the protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The term "transgenic animal" is art-recognized and refers to any animal, often a non-human mammal, a bird or an amphibian, in which one or more of the cells of the animal contain nucleic acid introduced by way of human intervention, such as by transgenic techniques well known in the art. Such nucleic acid may be referred to as a "transgene." The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA.

A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "antibody" is art-recognized and refers to whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

"Human monoclonal antibodies" or "humanized" murine antibodies, as the terms are used herein, refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

An "imaging agent" shall mean a composition capable of generating a detectable image upon binding with a target and shall include radionuclides (e.g., In-111, Tc-99m, I-123, I-125 F-18, Ga-67, Ga-680); for Positron Emission Tomography (PET) and Single Photon Emission Tomography (SPECT), unpair spin atoms and free radicals (e.g., Fe, lanthanides, and Gd); and contrast agents (e.g., chelated (DTPA) manganese) for Magnetic Resonance Imaging (MRI). Imaging agents are discussed in greater detail below.

The term "small molecule" is art-recognized and refers to a composition which has a molecular weight of less than about 2000 amu, or less than about 1000 amnu, and even less than about 500 amu.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). Certain target infectious organisms include those that are drug resistant (e.g., *Enterobacteriaceae, Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

"Target cells", which may serve as the target for the method or coordination complexes of the present invention, include prokaryotes and eukaryotes, including yeasts, plant cells and animal cells. The present method may be used to modify cellular function of living cells in vitro, i.e., in cell culture, or in vivo, in which the cells form part of or otherwise exist in plant tissue or animal tissue. Thus the cells may form, for example, the roots, stalks or leaves of growing plants and the present method may be performed on such plant cells in any manner which promotes contact of the targeted construct with the targeted cells. Alternatively, the target cells may form part of the tissue in an animal. Thus the target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "therapeutic agent" is art-recognized and refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Cisplatin and certain other platinum-containing drugs known in the art are examples of therapeutic agents. Coordination complexes of the present invention may be therapeutic agents.

A variety of therapeutic agents are known and may be identified by their effects. Certain therapeutic agents are capable of preventing the establishment or growth (systemic or local) of a tumor or infection. Examples include boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals. In certain embodiments for treating or preventing the establishment or growth of a tumor, the therapeutic agent may be a radionuclide, toxin, hormone antagonist, heavy metal complex, oligonucleotide, chemotherapeutic nucleotide, peptide, non-specific (non-antibody) protein, a boron compound or an enediyne. In other embodiments for treating or preventing the establishment or growth of a bacterial infection, the therapeutic agent may be an antibiotic, radionuclide or oligonucleotide. In still other embodiments for treating or preventing the establishment or growth of a viral infection, the therapeutic agent may be an antiviral compound, radionuclide or oligonucleotide. In yet other embodiments for treating or preventing the establishment or growth of a fungal infection, the therapeutic agent may be an antifingal compound, radionuclide or oligonucleotide.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds of the present invention, such as the subject coordination complex, may be administered in a sufficient amount to produce a at a reasonable benefit/risk ratio applicable to such treatment.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, coordination complexes of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject supplement, composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compounds described herein include compounds which otherwise correspond thereto, and which have the same general properties thereof (such as other genotoxic agents containing platinum(II) or platinum (IV)), wherein one or more simple variations of substituents are made which do not adversely affect the characteristics of the compounds of interest. In general, the compounds of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

6.3. Subject Compositions and Methods

A variety of complexes, and libraries thereof, are contemplated by the present invention. In certain embodiments, the subject complexes are coordination complexes, and more particularly, transition metal complexes, and even more particularly, the transition metal ion is platinum(B) or platinum(IV). A variety of methods of preparing such compositions, of assaying for the activity of such compositions, and of using such compositions are also taught by the subject invention. In addition, the present invention teaches using combinatorial libraries to prepare coordination complexes of interest. A number of different ligands and metal ions are contemplated for the subject coordination complexes, as set out in more detail below.

6.3.1. Ligands

Numerous ligands having a variety of structural, chemical and other characteristics are contemplated as components of the complexes of the present invention. For example, ligands for binding metal ions will generally include functional groups capable of interaction with a metal center, e.g., heteroatoms such as nitrogen, oxygen, suflir, and phosphorus.

More specifically, ligands of the present invention will usually include organic electron donor moieties. Large metal cations that necessarily (by definition) are Lewis acidic are able to bind various Lewis basic entities, including those that are negatively charged. Accordingly, in certain embodiments, the subject libraries are generated with ligands including one or more functional groups having an electron pair donor (Lewis base) capable of coordination with the transition metal. In general, the functional group will be a strongly acidic group, e.g., with a pKa less than about 7, and more preferably less than 5, which can produce a conjugate base that, under the reaction conditions, is a strong enough Lewis base to donate an electron pair to a metal atom to form a coordinate bond with the cationic form of the metal. However, the degree of this Lewis acid-to-Lewis base interaction is a function not only of the particular metal center coordinated to a functional group, but also of the Lewis base itself, because the latter may vary in the degree of basicity as well as in size and steric accessibility.

As set out above, the term "Lewis base" generally refers to any chemical species which has an electron pair donor. Two-electron Lewis bases are those bases which may donate a single pair of electrons. The types of Lewis base functional groups capable of forming coordinate complexes with metal ions are too numerous to categorize here, and are known to those of skill in the art. In many embodiments, ligands will include bases which bear atoms from Periodic Groups 15 and 16. Lewis bases from Group 15 contain nitrogen, phosphorous, arsenic, antimony or bismuth atoms as electron pair donors. Lewis bases from Group 16 contain oxygen, sulfur, or selenium atoms as electron pair donors.

Exemplary Lewis basic moieties which may be used as ligands include amines (primary, secondary, and tertiary) and aromatic amines, amino groups, amido groups, nitro groups, nitroso groups, amino alcohols, nitrites, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolfornyl groups), thioethers, mercaptans, sulfonic acids, sulfoxides, sulfates, sulfonates, sulfones, sulfonamides, sulfamoyls, and sulfinyls.

Illustrative of suitable ligands are those organic compounds containing at least one Lewis basic nitrogen, sulfur, phosphorous or oxygen atom or a combination of such nitrogen, sulfur, phosphorous and oxygen atoms. The carbon atoms of the ligands may be part of an aliphatic, cycloaliphatic or aromatic moiety. Typically, the ligands of the present invention will contain at least 2 carbon atoms. In addition to the organic Lewis base(s), ligands may also contain other atoms and/or groups as substituents, such as alkyl, aryl and halogen substituents. Useful ligands in the present invention include linear and branched functional compounds having at least one functional terminal reactive group which can act as a Lewis base. Examples of Lewis bases are: amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine , N,N-dibutylisopropanolamine, N-methyldiethaolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trmethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

In yet other embodiments, the functional group may be an aryl group, alkenyl group, alkynyl group or other moiety which may bind the metal atom in either a σ- or π-coordinated fashion.

As a further illustration, exemplary ligands include bifunctional compounds such as amino acids, hydroxy acids, hydroxy thiols, mercapto amines, and the like. Other exemplary modular components include nucleic acids and nucleic acid analogs and derivatives, diacids, diamines, and the like.

If desired, one functionality of a ligand may be selectively protected or blocked to permit reaction of an unblocked functional group. Thus, for example, amino acid ligands may be blocked and deblocked according to known procedures for selective peptide synthesis. After coordination to the metal ion, the ligand may be modified, e.g., capped or blocked to prevent further reaction. Alternatively, a ligand may be so modified in vivo.

6.3.2. Metal Ions

The metal atom may be selected from those that have usually at least two, three, four, five six, seven coordination sites or more. In certain embodiments, the subject methods may be used to identify ligands for any transition metal, e.g., a metal selected from one of Groups 3–12 of the Periodic Table or from the lanthanide series. A non-limiting list of metal ions for which the present invention may be employed (including exemplary and non-limiting oxidation states for them) includes $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, Tc, $Au^{3+}$, $Au^+$, $Ag^+$, $Cu^+$, $MoO_2^{2+}$, $Ti^{3+}$, $Ti^{4+}$, $Bi3+$, $CH_3Hg^+$, $Al^{3+}$, $Ga^{3+}$, $Ce^{3+}$, $UO_2^{2+}$, $Y^{+3}$ Eu, Gd and $La^{3+}$.

The metal ion to be used in the subject invention depends in part on the use to which the resulting coordination complex may be put. For example, platinum(II) may be used in those coordination complexes that may be used as therapeutics to treat neoplasms and other diseases or conditions. Alternatively, other metal ions may be used for those coordination complexes that may be used for imaging purposes, or as catalysts.

A variety of starting coordination complexes, or precursor metal reagents, may be used to prepare the libraries of the present invention, and will generally include the metal ions of the desired product and optionally one or more ligands of the desired product.

6.3.3. Exemplary Platinum-containing Coordination Complexes

Using the methods of the present invention, a significant number of novel platinum-containing coordination complexes have been prepared. Certain of these complexes exhibit desirable assay reactivities, as described in greater detail below.

In general, many of the platinum-containing coordination complexes are represented by the general formula comprising $[PtL_nL'_m]$, wherein: (a) L and L' are each independently a neutral ligand; and (b) n or m may each independently be 0, 1 or 2 as long as the sum of the coordination bonds formed between Pt and $L_n$ and $L'_m$ is 1 or 2.

In certain embodiments, a library comprising coordination complexes comprising platinum is constructed wherein a plurality of said members of said library are represented by the general formula comprising $\{PtL_nA_{(4-n)}\}$, wherein: (a) each L independently is a non-labile ligand, and n is equal to 1, 2 or 3; and (b) each A independently is a labile ligand.

In certain embodiments, an inventive coordination complex comprises a structure represented by the following Formula I:

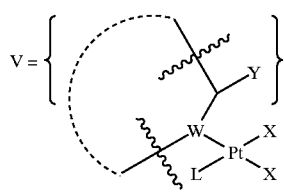

Formula I wherein, independently for each occurrence:
X represents halogen or other labile ligand;
W represents S, N, or P;
Y represents —OR7, —SR7, a halogen or —N(R9)R10;
R9 and R10, each independently, represent —H, alkyl, alkenyl, —(CH2)$_n$—R7, or R9 and
R10 taken together with the N atom to which they are attached complete a heterocycle having from 4 to about 8 atoms in the ring structure, all optionally substituted;
L represents a non-labile ligand; and
R7 represents —H, alkyl, aryl, cycloalkyl, cycloalkenyl, heterocycle or polycycle; wherein the ligand V comprises W, Y, and a heterocycle having from 4 to about 8 atoms in the ring structure, optionally aromatic and optionally substituted.

In certain embodiments, the central platinum atom of the above formula is Pt(II). In other embodiments, the platinum atom is Pt(IV), and optionally two additional ligands in the trans axial positions of the formula depicted are present. In certain embodiments, both of X are —Cl.

In certain embodiments, the above formula is directed to the trans configuration as opposed to the depicted cis configuration.

In certain embodiments, the non-labile ligand L is an amine having the structure NR2(R3). Other non-labile ligands are described herein.

In certain embodiments, of V, n is 0, 1 or 2 so V comprises a 5-, 6- or 7-membered heteroaromatic, respectively. Non-limiting examples of V include pyrrole, furan, thiophene, imidazole, thiazole, triazole, pyrazole, pyridine, pyrazine, pyridazine and pyrimidine, and the like. V may include in the ring structure heteroatoms in addition to W.

The aromatic ring V may be substituted at one or more ring positions, addition to the substituent Y, with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

One example of such a compound is cis-am mine(2-amino-3-picoline)dichloro-platinum(II).

6.63.4. Combinatorial Chemistry

The synthesis and screening of combinatorial libraries is a validated strategy for the identification and study of organic compounds of interest. Because the stability and activity of coordination complexes are similarly dependent on numerous interrelated variables, such as the coordination geometry required by the metal and the steric and electronic characteristics of the ligand, combinatorial chemistry may provide a powerful approach for discovering new types of coordination complexes of interest.

According to the present invention, the synthesis of libraries containing coordination complexes may be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", *Chemical and Engineering News*, Feb. 24, 1997, p. 43; Thompson et al., *Chem. Rev.* 1996, 96, 555). One of ordinary skill in the art will realize that the choice of method for any particular embodiments will depend upon the specific number of coordination complexes to be synthesized, the specific reaction chemistry, and the availability of specific instrumentation, such as robotic instrumentation for the preparation and analysis of the inventive libraries. In certain embodiments, the reactions to be performed to generate the libraries are selected for their ability to proceed in high yield, and in a stereoselective and regioselective fashion, if applicable.

In regard to automation of the present subject methods, a variety of instrumentation may be used to allow for the facile and efficient preparation of chemical libraries of the present invention, and methods of assaying members of such libraries. In general, automation, as used in reference to the synthesis and preparation of the subject chemical libraries, involves having instrumentation complete one or more of the operative steps that must be repeated a multitude of times because a library instead of a single compound is being prepared. Examples of automation include, without limitation, having instrumentation complete the addition of reagents, the mixing and reaction of them, filtering of reaction mixtures, washing of solids with solvents, removal and addition of solvents, and the like. Automation may be applied to any steps in a reaction scheme, like those set forth in FIGS. 1, 2, and 3, including those to prepare, purify and assay coordination complexes of the present invention.

There is a range of automation possible. For example, the synthesis of the subject libraries may be wholly automated or only partially automated. If wholly automated, the subject library may be prepared by the instrumentation without any human intervention after initiating the synthetic process, other than refilling reagent bottles or monitoring or programming the instrumentation as necessary. Although synthesis of a subject library may be wholly automated, it may be necessary for there to be human intervention for purification, identification, or the like of the library members.

In contrast, partial automation of the synthesis of a subject library involves some robotic assistance with the physical steps of the reaction schema that gives rise to the library, such as mixing, stirring, filtering and the like, but still requires some human intervention other than just refilling reagent bottles or monitoring or programming the instrumentation. This type of robotic automation is distinguished from assistance provided by convention organic synthetic and biological techniques because in partial automation, instrumentation still completes one or more of the steps of any schema that is required to be completed a multitude of times because a library of compounds is being prepared.

In certain embodiments, the subject library may be prepared in multiple reaction vessels (e.g., microtitre plates and the like), and the identity of particular members of the library may be determined by the location of each vessel. In other embodiments, the subject library may be synthesized in solution, and by the use of deconvolution techniques, the identity of particular members may be determined.

Coordination complexes of the present invention may be prepared using solid support chemistry known in the art as well. For example, polypeptides having up to twenty amino acids or more may be generated using standard solid phase technology on commercially available equipment (such as Advanced Chemtech multiple organic synthesizers). In certain embodiments, the chief requirement is that the supported species have at least one Lewis base available as a ligand for the metal center of the resultant coordination complex. In certain embodiments, it may be the case that the supported species (or a portion thereof) ultimately remains as a ligand to the metal center upon cleavage of the resultant coordination complex from the solid support, whereas in other cases, the supported species may not be incorporated into the resultant coordination complex.

In the prophetic example, after generation of the appropriate species on the solid support, an equivalent amount of a platinum precursor in aqueous solution may be added to the supported species, which will serve as a ligand thereto. The precursor could be, for example, $K_2PtCl_4$ or $K[(NH_3)PtCl_3]$ or a number of platinum compounds with at least one liable coordination site. The resultant resin/water slurry could then be agitated by vortex for 24 hours to allow for coordination of the support bound sidechain to the platinum metal center.

After this 24 hour period, the resin could be collected by filtration, washed, and the desired platinum species cleaved from the solid support using standard methodologies, which usually would depend on the nature of the solid support used.

In one aspect of the invention, the subject screening method may be carried out utilizing immobilized libraries. In certain embodiments, the immobilized library will have the ability to coordinate to metal precursors as a ligand as described above. In other embodiments, the components of the immobilized library will contain coordination complexes as monomers. The choice of a suitable support will be routine to the skilled artisan. Important criteria may include that the reactivity of the support not interfere with the reactions required to prepare the library. Insoluble polymeric supports include functionalized polymers based on polystyrene, polystyrene/divinylbenzene copolymers, and the like. It will be understood that the polymeric support may be coated, grafted or otherwise bonded to other solid supports.

In another embodiment, the polymeric support may be provided by reversibly soluble polymers. Such polymeric supports include functionalized polymers based on polyvinyl alcohol or polyethylene glycol (PEG). A soluble support may be made insoluble (e.g., may be made to precipitate) by addition of a suitable inert nonsolvent. One advantage of reactions performed using soluble polymeric supports is that reactions in solution may be more rapid, higher yielding, and more complete than reactions that are performed on insoluble polymeric supports.

Once the synthesis of either a desired solution phase or solid support bound template has been completed, the template is then available for further reaction to yield the desired solution phase or solid support bound structure. The use of solid support bound templates enables the use of more rapid split and pool techniques.

The coordination complexes of the present invention may be attached directly to the solid support or may be attached to the solid support through a linking reagent, an example of which is shown directly below for a Pt(II) coordination complex:

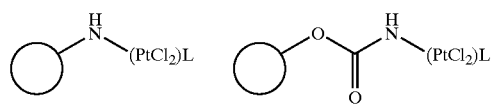

Direct attachment to the solid support may be useful if it is desired not to detach the library member from the solid support. For example, for direct on-bead analysis of biological activity or analysis of the coordination complex structure, a stronger interaction between the library member and the solid support may be desirable. Alternatively, the use of a linking reagent may be useful if more facile cleavage of the inventive library members from the solid support is desired.

Furthermore, any linking reagent used in the present invention may comprise a single linking molecule, or alternatively may comprise a linking molecule and one or more spacer molecules, an example of which is shown directly below for a Pt(II) coordination complex:

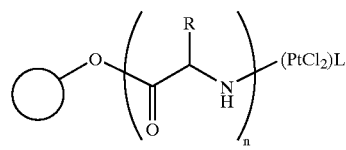

A spacer molecule is particularly useful when the particular reaction conditions require that the linking molecule be separated from the library member, or if additional distance between the solid support/linking unit and the library member is desired.

In certain embodiments, photocleavable linkers may be employed to attach the solid support to the desired coordination complex, an example of which is shown directly below for a Pt(II) coordination complex:

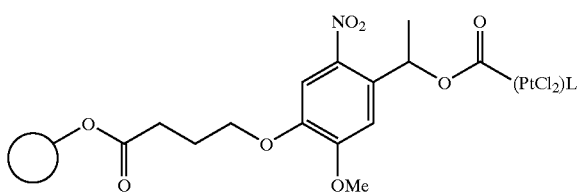

Photocleavable linkers may be suitable for use in in vivo screening strategies. Once the template is released from the solid support via photocleavage, the complex small molecule is able to enter the cell. One of ordinary skill in the art will also realize that this photolinker as well as other photolinkers may be employed with the limitation that they will not degrade in the presence of the reaction steps employed in the synthesis of the coordination complexes and combinatorial libraries.

Furthermore, in certain embodiments, a spacer unit is utilized to ensure that the photolinker or other linker is sufficiently distanced from the coordination complex. Representative spacer units include but are not limited to aminocaproic acid (Aca), glycine, and any other amino acid that does not contain a functionality incompatible with the reaction scheme require to prepare the library members.

In certain embodiments, a starting material or later reactant may be attached to the solid phase, through a linking unit, or directly, and subsequently used in the synthesis of desired coordination complexes. The choice of linkage will depend upon the reactivity of the coordination complexes and the solid support units and the stability of these linkages.

Figure 4:
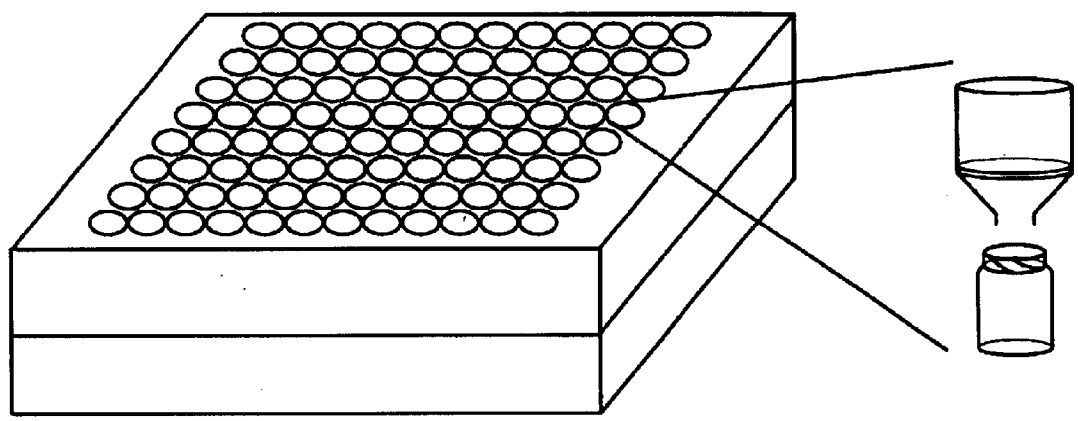
FIG. 4 shows a 96-well reaction block with a magnified view of the well structure that is used in the embodiment of the present invention described in the Examples to prepare subject coordination complexes and libraries thereof.

In one aspect of the present invention, the inventive libraries are generated using a solution phase technique. Traditional advantages of solution phase techniques for the synthesis of combinatorial libraries include the availability of a much wider range of reactions, and the relative ease with which products may be characterized, and ready identification of library members, as discussed below. For example, in certain embodiments, for the generation of a solution phase combinatorial library, a parallel synthesis technique is utilized, in which all of the products are assembled separately in their own reaction vessels. In a particular parallel synthesis procedure, a microtitre plate containing n rows and m columns of tiny wells which are capable of holding a few milliliters of the solvent in which the reaction will occur, is utilized. It is possible to then use n variants of reactant A, such as a ligand, and m variants of reactant B, such as a second ligand, to obtain n×m variants, in n×m wells. One of ordinary skill in the art will realize that this particular procedure is most useful when smaller libraries are desired, and the specific wells may provide a ready means to identify the library members in a particular well. An example of such a reaction plate is shown in FIG. 4.

In other embodiments of the present invention, a solid phase synthesis technique is utilized. Solid phase techniques allow reactions to be driven to completion because excess reagents may be utilized and the unreacted reagent washed away. Solid phase synthesis also allows the use a technique called "split and pool", in addition to the parallel synthesis technique, developed by Furka. See, e.g., Furka et al., *Abstr. 14th Int. Congr. Biochem.*, (Prague, Czechoslovakia) 5:47 (1988); Furka et al., *Int. J. Pept. Protein Res.* 37:487 (1991); Sebestyen et al., *Bioorg. Med. Chem. Lett.* 3:413 (1993). In this technique, a mixture of related coordination complexes may be made in the same reaction vessel, thus substantially reducing the number of containers required for the synthesis of very large libraries, such as those containing as many as or more than one million library members. As an example, the solid support with the starting material attached may be divided into n vessels, where n represents the number species of reagent A to be reacted with the such starting material. After reaction, the contents from n vessels are combined and then split into m vessels, where m represents the number of species of reagent B to be reacted with the now modified starting materials. This procedure is repeated until the desired number of reagents is reacted with the starting materials to yield the inventive library.

The use of solid phase techniques in the present invention may also include the use of a specific encoding technique. Specific encoding techniques have been reviewed by Czarnik in *Current Opinion in Chemical Biology* 1:60 (1997). One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. In other embodiments, an encoding technique involves the use of a particular "identifying agent" attached to the solid support, which enables the determination of the structure of a specific library member without reference to its spatial coordinates. Examples of such encoding techniques include, but are not limited to, spatial encoding techniques, graphical encoding techniques, including the "tea bag" method, chemical encoding methods, and spectrophotometric encoding methods. One of ordinary skill in the art will realize that the particular encoding method to be used in the present invention must be selected based upon the number of library members desired, and the reaction chemistry employed.

Characterization of the library members may be performed using standard analytical techniques, such as mass spectrometry, Nuclear Magnetic Resonance Spectroscopy, including $^{195}$Pt and $^{1}$H NMR, chromatography (e.g, liquid etc.) and infra-red spectroscopy. One of ordinary skill in the art will realize that the selection of a particular analytical technique will depend upon whether the inventive library members are in the solution phase or on the solid phase. In addition to such characterization, the library member may be synthesized separately to allow for more ready identification. The Examples provide examples of such characterization methods.

6.3.5. Examples of Subject Libraries

A. Libraries of Coordination Complexes Containing Platinum, and Assays and Uses Thereof.

In certain embodiments, the present invention contemplates coordination complexes containing platinum, and libraries thereof. The interest in such complexes is derived, at least in part, from the therapeutic effects observed for the genotoxic agent cisplatin. The teachings of the following embodiments of the subject invention apply equally well to coordination complexes containing transition metal ions other than platinum.

Cisplatin and several of the clinically effective platinum coordination drugs developed subsequently usually comprise a pair of cis-configured, substitutionally labile chloride moieties. Cisplatin-like drugs most likely form DNA adducts that are similar to the well-characterized adducts of cisplatin itself. Typically, such coordination complexes comprise a platinum atom linked to a pair of cis-configured substitutionally moieties that are labile in vivo and a pair of cis-configured Lewis base moieties. Binding of the coordination complexes to nucleic acids occurs upon substitution of the cis-configured labile moieties with atoms of the nucleotide bases, usually adenosine (A) or guanine (G) residues. This produces a crosslink, bridged by the metal atom (e.g., platinum) between two vicinal, adjacent or paired nucleotide bases. Platinum-bridged crosslinks between adjacent adenosine and/or guanine residues within a single nucleotide strand (1,2-intrastrand dinucleotide adducts or lesions) of double stranded DNA are abbreviated herein as 1,2-d(A^G) and 1,2-d(G^G) lesions. The adduct or lesion formed most frequently by the binding of cisplatin to cellular DNA is the 1,2-intrastrand dinucleotide adduct, in, which adjacent nucleotide bases become crosslinked directly through a platinum bridge. 1,2-d(A^G) and 1,2-d (G^G) adducts account together for approximately 90% of the DNA lesions produced in vivo by cisplatin and cisplatin-type drugs.

The class of genotoxic coordination complexes related to cisplatin include carboplatin (diammine(1,1-cyclobutane-dicarboxylato)platinum(II), cis-diamminetetrachloroplatinum(IV), iproplatin (CHIP), DACCP, malonatoplatin, cis-dichloro(ethylenediamine) platinum(II), cis-dichloro(1,2-diaminocyclohexyl)platinum (II), and the like. In contrast, platinum compounds lacking the cis-configured labile moieties, including the tnans stereoisomer of cisplatin, trans-DDP, are generally thought to be largely biologically ineffective. There are, however, exceptions to this general observation, including some of the compounds described in the following articles: Kloster et al. (1999), 38 *Biochemistry* 14731–37; Kapárková et al. (1999), 38 *Biochemistry* 10997–11005; Yun et al. (1996), 118 *Journal of the American Chemical Society* 9307–13. As indicated in the Examples described below and the general discussion, the present invention is directed, in part, to preparing, and methods of making and using, platinum-containing complexes in a variety of oxidation states and geometries. The known compounds provide one useful measure by which the activity of the subject coordination complexes may be compared in certain of the assays described below.

1. Libraries

Figure 2:
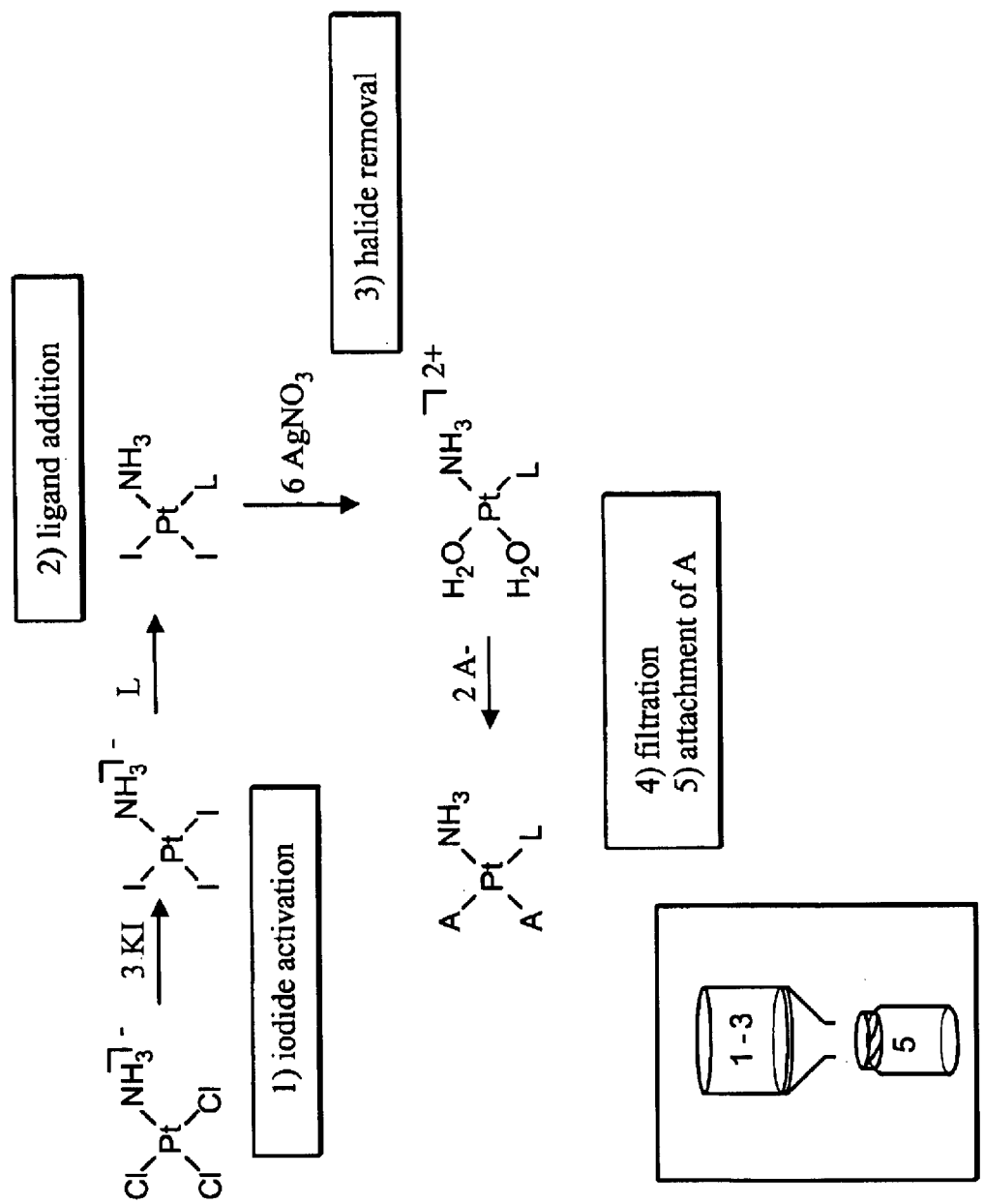
Figure 3:
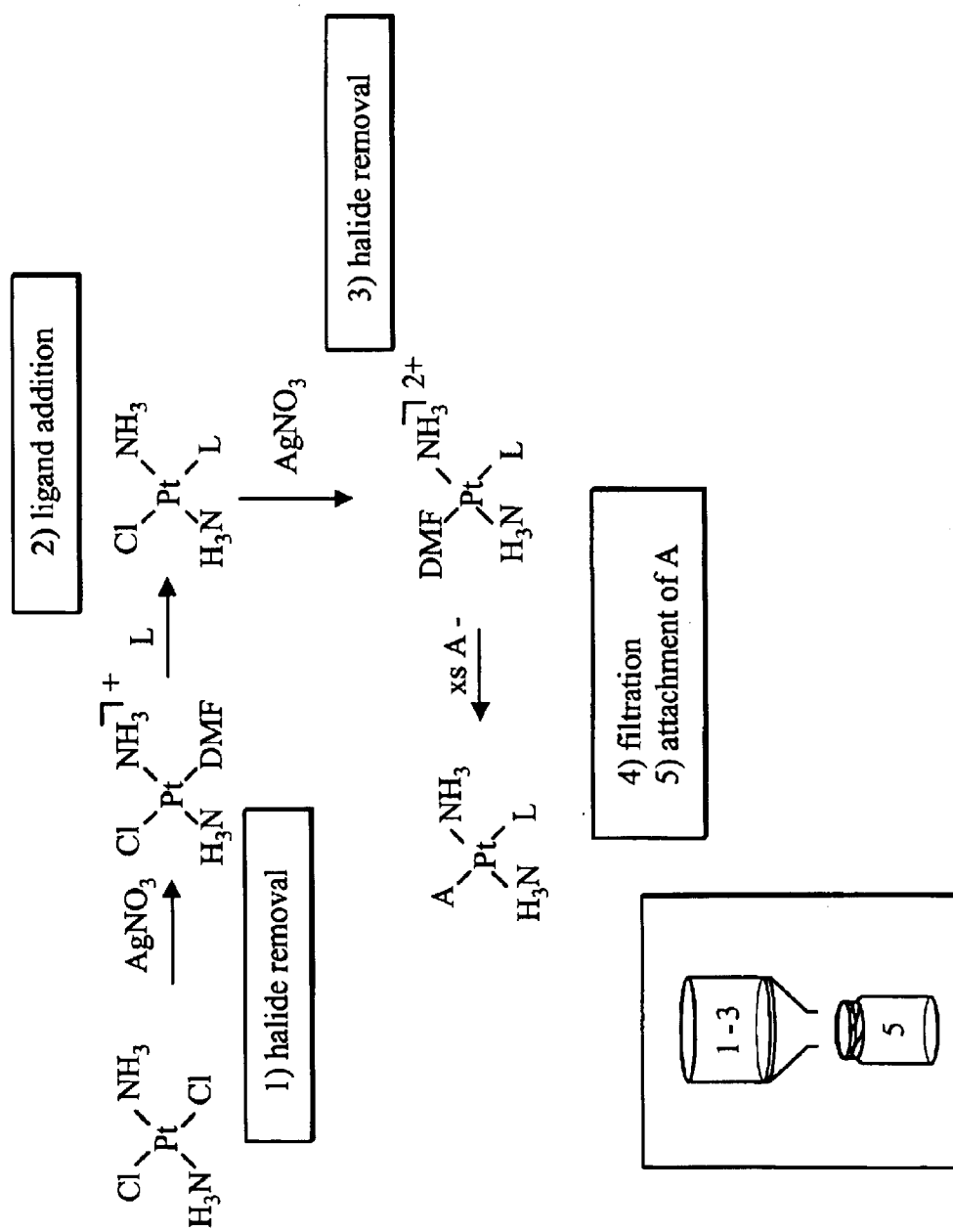

FIGS. 1, 2 and 3 show reaction schema whereby libraries of coordination complexes containing platinum may be prepared. The following discussion explains certain features of such chemistry. These reaction schema and libraries are intended to be exemplary and non-limiting examples of the present invention. The reaction scheme of FIGS. 1 and 2 result in coordination complexes of platinum having a cis configuration of ligands, whereas the reaction scheme of FIG. 3 produces a coordination complex in a trans configuration. The different coordination complexes prepared by these schema are shown in Table 1. Formation of the subject complexes is based in part on the strategic use of the trans effect in the schema presented in FIGS. 1 and 2. By taking advantage of the trans effect in platinum substitution reactions, platinum complexes may be prepared in which the resulting regiochemistry may be predicted with appreciable success. The trans affect may be defined as the labilization of ligands trans to other, trans-directing ligands. By way of example, a ligand that has a strong trans effect, such as cyanide ($CN^-$), will labilize a ligand trans to it more readily than a ligand that does not have as strong a trans effect, such as chloride. A ligand that is labilized will be readily replaced by another ligand in a substitution reaction.

The present invention allows the use of a variety of platinum starting coordination complexes, including, for example, $[PtX4]^{2-}$, $[Pt(L)X3]^+$ and trans-DDP, where X is an anionic ligand, often a halogen, and L is any neutral ligand. The number of ligands used in the synthetic scheme depends on the number of available coordination sites as well as the desired number of coordinated ligands other than X in the resulting product. Thus, this method may generate species from one to three non-labile ligands, identified as L, bound to the metal ion, with three to one, respectively, ligands that are generally more labile, identified as X.

In the first steps of the generic reaction schema shown in FIGS. 1 and 2, the platinum-containing precursor may be activated for further reaction with ligands. In addition to iodine, used in the examples presented below, bromide, carbon monoxide, cyanide, ethylene, thiocyanate, and phosphines ($PR_3$) and other agents known to those of skill in the art may be used as the activating agent. In the embodiments shown in FIGS. 1 and 2, the activating agent should have a strong trans effect and should be removable after reaction to form a cis complex by some synthetic means, some examples of which are described below.

In the examples of FIGS. 1 and 2, tetrachloroplatinate or amminetrichloroplatinate, respectively, is reacted with the appropriate number of equivalents or an excess of potassium iodine to give the soluble tetraiodate or triiodate species, respectively. Although chloride or other halogens may be used, the use of iodide is preferred over chloride in part because formation of the cis product after two ligand substitution reactions is more favored in the case of iodide as compared to chloride because iodide has a stronger trans effect than chloride. In addition, a stronger trans ligand is favored in the embodiments shown in the aforementioned figures because the greater the trans effect of the activating ligand, the more labile the ligand trans to such activator, which encourages stoichiometric substitiution reactions.

As a general matter, a number of the ligands discussed above may be used in the present scheme. Depending on the reaction scheme observed, the same ligand or two or more different ligands may be used. Ligands suitable in platinum-containing coordination complexes include the following: NH3, primary amines, secondary amines, heterocyclic amines, amides, sulfoxides, thiols, monohydroxylic alcohols, polyhydroxylic alcohols, phosphines, ethers, thioethers, ester of phosphoric acid, ester of boric acid, ester of carboxylic acid, esters of carbonic acidnitriles, thioesters, atkenes, arsines, selenides, halides, pseudohalides, carboxylates and negatively charged and neutral variants thereof. In certain embodiments, the primary and secondary amines will comprise lower primary and secondary alkyl amines; heterocyclic amines will comprise pyridine, quinoline, isoquinoline, imidazole, thiazole, substituted pyridine, substituted quinoline, substituted isoquinoline, substituted thiazole, piperidine, pyrrolidine, morpholine, and N-alkyl or N-acyl-piperazine; anionic ligands will comprise halides, pseudohalides, carboxylates and other mono- and divalent anions. Typical examples of carboxylate groups which may be utilized in the subject coordination complexes comprise acetate, propionate, butyrate, chloroacetate, hydroxyacetate, benzoate and chelating dicarboxylate groups such as oxalate, malonate, substituted malonate, succinate, glutarate, and phthalate.

After the reaction of the coordination complexes with the desired ligands, the activating groups are removed through some method. Examples of such methods include ion exchange, halide removal or exposure to mineral or organic acids. For example, an ion exchange method would employ an ion exchange resin of an appropriate type for the leaving group, and would involve, for example, either mixing of a solution of the platinum compound with a slurry of the ion exchange resin, or the use of a column packed with the ion exchange resin. By way of another example, a mineral or organic acid would facilitate a change in leaving group upon dissolution of the platinum complex in either a neat or highly concentrated solution of the mineral acid. In other embodiments, the desired complex could then be isolated by crystallization from the acid solution. In certain embodiments, a reagent for halide removal results in formation of a by-product that precipitates, which facilitates isolation of the desired compound. Precipitation of the by-product is dependent on a number of factors, including, for example, the identity of the by-product, the solubility of the by-product in the reaction solvent (if any), the concentration of the by-product, and the temperature of the reaction. In such embodiments, the halide removal reagent may be termed a precipitating reagent.

In the examples set forth in FIGS. 1 and 2, iodide ligands are removed through halide removal with silver nitrate. By adding at least as many equivalents of silver nitrate as there are of chloride and iodide in the reaction well for this example, the formation of an aquated platinum compound is favored. This presence of silver nitrate promotes the decomposition of unreacted starting material prior to filtration. If ligation of an amine does not occur after the activation step (as might be the case with very sterically hindered amines), reaction with silver nitrate will form highly aquated platinum species, such as $[Pt(H_2O)_4]^{2+}$. These highly aquated platinum compounds usually disproportionate in basic solution (generated by the unreacted amine) to form an insoluble mixture of platinum metal and platinum oxide, which will remain in the reaction well after filtration. Thus, only reactions where some of the ligands have attached to the metal center will usually survive the halide removal process.

After halide removal, additional ligands A may be added, if appropriate, to produce the final subject compound. In certain embodiments, such ligands are intended to be labile and allow for substitution reactions at the metal ion in those coordination complexes upon use, such as those observed for cisplatin. Often such ligands are anionic. Examples of suitable ligands include without limitation, carboxylates, halides, sulfates, nitrates, and other counter-ions known to those of skill in the art. The identity of such ligands may affect the solubility, bioavailability and other physical characteristics of the resulting complex.

In contrast to the reaction schema shown in FIGS. 1 and 2, the reaction scheme in FIG. 3 shows the preparation of trans platinum-containing coordination complexes by using the metal precursor trans-DDP. In the example show in FIG. 3, no activating agent (at least as explained above) is used; instead halides are selectively removed and ligand substitution of the solvated species follows. Otherwise, the principles discussed above for the reaction schema of FIGS. 1 and 2 also apply to FIG. 3.

The reaction schema shown in FIGS. 1, 2 and 3 may be conducted in a single reaction vessel. Without limiting the particulars of any embodiment of the present invention, the methods employed in this scheme afford generally high yields of platinum products when reactions occur, while preventing starting materials from entering the product vial. Although the products produced from these reactions may be impure (contaminated at least with nitrate salts), the impurities do not necessarily affect adversely any screening process or other subsequent process or processes to which these platinum-containing complexes may be subjected. By judicious choice of the activating group and ligands used for substitution, it is possible to design a synthetic scheme that will favor certain products, a result that simplifies any subsequent screening of the resulting library and allows for ready automation for preparation of the subject libraries.

2. Assays

In the subject invention, libraries of platinum-containing coordination complexes may be assayed by a variety of methods. Library members which exhibit a desired biological effect may be selected for further evaluation of their therapeutic effect, e.g., antitumor efficacy, by using other assays such as transformed cell lines, primary cells in culture or animal models. For all the assays described herein, a single coordination complex, a mixture of them, or even an entire library may be assayed at once as appropriate. Also, more than one type of assay (or the same assay in series conducted under the same or different conditions) may be used to determine the therapeutic effect or other characteristics of a compound of interest.

As a general matter, one or more inventive coordination complexes may contacted with a target, often of biological origin. Biological targets include, for example, enzymes, receptors, peptides, nucleic acid and the like. The biological target may be provided in the form of a purified or semi-purified composition, a cell lysate, a whole cell or tissue, or even a whole organism. The level of biochemical activity is detected in the presence of the coordination complex, and a statistically significant change in the biochemical activity, relative to the level of biochemical activity in the absence of the coordination complex, identifies the coordination complex as a modulator, e.g. inhibitor or potentiator of the biological activity of the target protein. In some cases, particularly where assays are done on whole cells or organisms, the effect of the chemical coordination complex may be to alter the amount, in addition to or instead of the activity, of the particular biological target.

To further refine any of the subject assays, a variety of techniques may be used. For example, two or more assays, either the same assay or different assays, may be used to identify coordination complexes that may produce "false positives" in any single assay. Alternatively, the present inventive methods provide for positive and negative controls.

In certain of the subject assays, to evaluate the results using the subject compositions, comparisons may be made to known agents, such as cisplatin and trans-DDP. For example, cisplatin, trans-DDP and a coordination complex of interest may be assayed. The result of the assay for the subject complex will be of a type and of a magnitude that may be compared to cisplatin and trans-DDP. In general, the response observed for trans-DDP in the assay will be deemed a negative result, whereas the response observed for cisplatin will be deemed a positive response. To the extent that the subject complex exhibits a type of response in the assay that is quantifiably different from that of trans-DDP and of the type, if not of the same magnitude, of the response observed for cisplatin, then the result for such complex in the assay would be deemed a positive or favorable result. In addition, the magnitude of the response observed for the subject complex may be compared to that observed for cisplatin. In certain assays, the magnitude of the response may be expressed as a percentage response with trans-DDP set as the baseline and the response observed for cisplatin being 100%, with such percentage exceeding about 10% or less, 25%, 50%, 75% 100% or 150% or more for any subject complex.

The following subsections present a more detailed description of assays which may be suitable for subject libraries and coordination complexes containing platinum. Any of the following assays may be provided in kit format and may be automated. Many of the following particularized assays rely on general principles, such as blockage or prevention of transcription, that may apply to other particular assays. These teachings will also apply to assays of subject coordination complexes and libraries thereof containing a metal ion other than platinum.

(A) GFP Assays

In one aspect, libraries of platinum complexes may be screened, in human cancer cells, for the ability to block transcription and translation upon binding to DNA. In an example of such an assay, stable HeLa cell lines may be chemically induced to produce green fluorescent protein (GFP) (or wavelength shifted mutant thereof) as a marker such as described in U.S. Pat. No. 5,625,048 to Tsien et al.; Gerdes et al., *FEBS Lett*. 389:44–47 (1996); Chiocchetti et al., *BioChim. Biophys. Acta* 1352:193–202 (1997); Chishima et al., *Cancer Res*. 57:10:2042–47 (1997); Mosser et al., *Biotechniques* 22:150–61 (1997); Kain et al., *Biotechniques* 19:650–55 (1995); Peters et al., *Dev. Biol*. 171:252–57 (1995); Cubitt et al., *Trends Biochem. Sci*. 20:11:445–55 (1995); Sandman et al., *Chem. Bio*. 8:541–551 (1999).

When using platinum-containing coordination complexes in such an assay, for example, the fluorescence of the treated cells is measured to identify platinum complexes that form persistent nucleic acid lesions within the cells. Active platinum complexes should enter the cells and block the transcription and translation of the GFP. Thus, a decrease in fluorescence activity of the cells should be indicative of the presence of platinum-lesioned nucleic acids within the cells. In contrast, observation of no significant changes in GFP fluorescence should be indicative of inactive platinum complexes that are therapeutically ineffective, at least on this basis of this assay. In contrast, toxic agents that produce a general mammalian stress response generally upregulate expression of GFP. A number of reasons may explain why a platinum complex shows no activity, including the following: it does not enter the cell, it does not form any substantial amount of DNA adducts, or it does form a nontrivial amount of DNA adducts that are rapidly repaired.

Sandman et al. showed that the TRE-EGFP 27 cells effectively differentiate between different cytotoxic agents, such as between cisplatin and trans-DDP. See Sandman et al., Chem. Bio. 6:541–51 (1999). In addition, the assay has been shown to be mechanism based, because Northern analysis showed that transcription of the EGFP gene is inhibited by cisplatin treatment and lower overall production of RNA. Therefore, this assay may provide useful information on the clinical potential of transition metal drug candidates, including those containing platinum.

(B) CCF2/AM Assay

Figure 10:
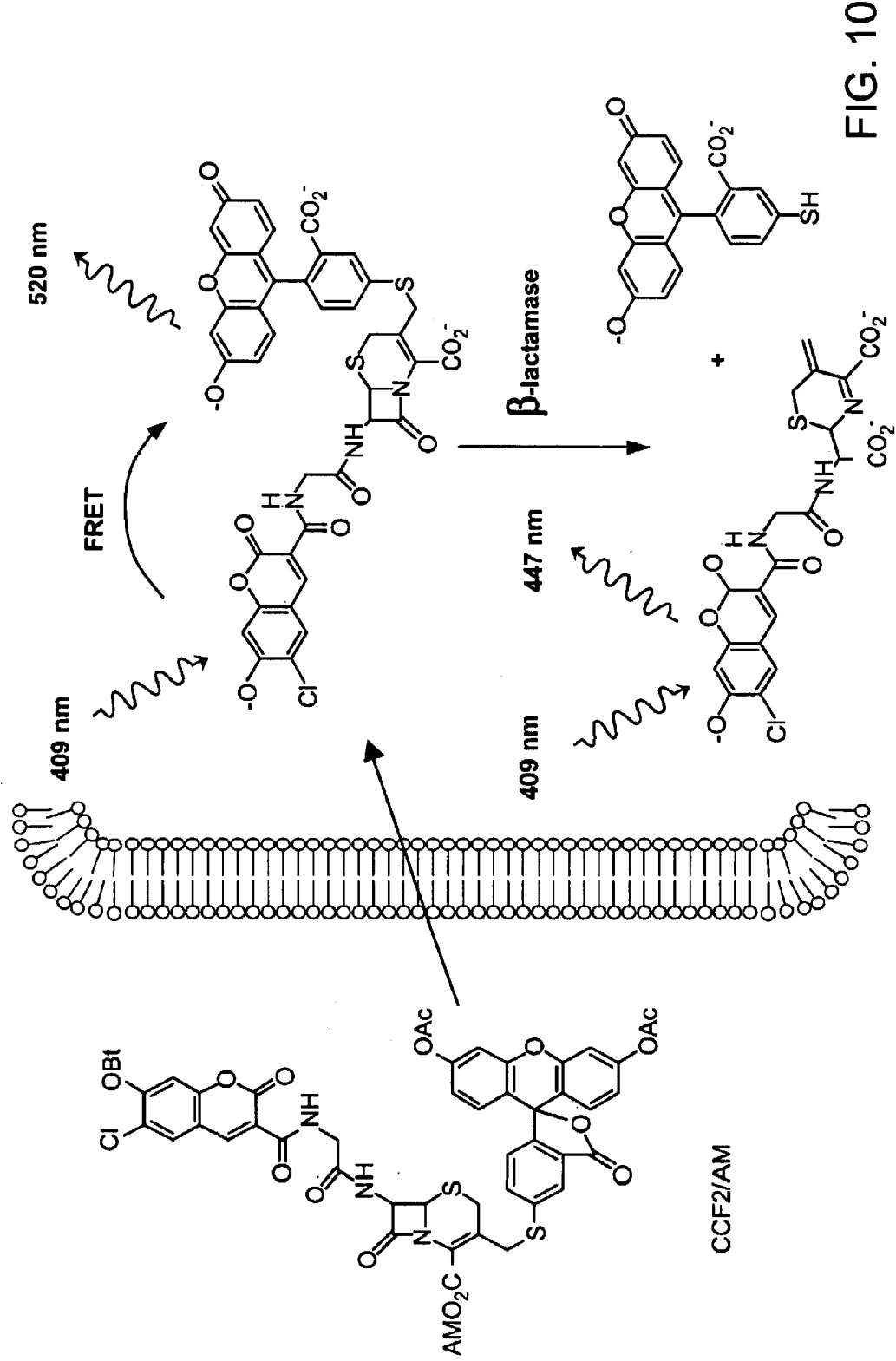
FIG. 10 shows schematically what is believed to be the mechanism of action of CCF2/AM in vitro.

Another example of a subject assay is termed the CCF2/AM assay. The CCF2/AM dye is an effective assay for the presence of 62-actamase, and thus may be used as a sensor for its transcription. See, for example, U.S. Pat. No. 5,955,604 and WO 9630540. The proposed mechanism of the assay's action is shown in FIG. 10. This screen in based on a cellular response that is relatively unique to cisplatin. Other cytotoxic events and agents, such as heat shock and methylating compounds, or inactive platinum compounds, like trans-DDP, do not generate an inhibition response and actually have been shown to generate an increase in transcription. This behavior has been demonstrated for Jurkat cells expressing the BlaM vector using the CMV promoter. See Sandman et al., Chem. Bio. 6:541–51 (1999). In the subject invention, HeLa cells may be employed, and control experiments (Northern blot and microscopy) demonstrate identical behavior to that of the Jurkat cells. In addition, the rapid inhibition of transcription, which occurs prior to apoptosis, may be evaluated over a short period of time. In the BlaM HeLa cell line used herein, the inhibition of transcription coupled with the half-life of ambient β-lactamase results in a one-day screening protocol.

(C) SSRP-Based Assays

One means of assessing suitable subject libraries involves in vitro screening procedure for assessing whether coordination complexes form DNA lesions that are recognized by SSRP family members. New coordination complexes, tested singly or as a group, may be selected and further refined for their ability to form lesions that are bound with high affinity by a preferred SSRP, or that are bound by a panel of HMG domain SSRPs.

This assay relies on the discovery, recounted in U.S. Pat. No. 5,359,047 and other patents claiming priority thereto, that eukaryotic cells contain one or more SSRPs that bind to 1,2-dinucleotide intrastrand adducts of genotoxic metal coordination complexes currently used as chemotherapeutic agents in the clinical management of cancer, such as cisplatin. Genotoxic agents or genotoxins bind to or otherwise physically or chemically interact with cellular DNA, causing injury thereto. A site of injury (a lesion) in cellular DNA is referred to herein as a genomic lesion. DNA lesions may include disruptions of the nucleotide sequence, nucleotide base pairing or distortions of the structure of the DNA double helix. Structural distortion lesions produce three-dimensional DNA structural motifs (e.g., bends, kinks, unwinding, overwinding, non-B helical forms such as A- or Z-DNA, junctions between different helical forms, stem-loop structures, cruciforms, local melting, crossover junctions, and the like). Genomic lesions in cellular DNA that are not repaired before the cell commits itself to the cycle of cell division in all likelihood contribute to cell death. Thus, one determinant of a genotoxic agent's cytotoxicity (propensity for contributing to cell death) may be the resistance of genomic lesions formed therefrom to cellular repair. Genotoxic agents that form persistent genomic lesions, e.g., lesions that remain in the genome at least until the cell commits to the cell cycle, are therefore believed to be more effective cytotoxins than agents that form transient, easily repaired genomic lesions.

SSRPs thus far reported to bind to 1,2-intrastrand cisplatin-type lesions in DNA comprise at least one structural domain generally referred to as an HMG domain. Exemplary SSRP HMG domains include the HMG domains of human and Drosophilae SSRP1. Other useful SSRP HMG domains are encoded by nucleic acids that hybridize specifically, at least under low stringency hybridization conditions such as described in U.S. Pat. No. 5,359,047, to nucleic acid encoding the HMG domain of human or Drosophilae SSRP1. SSRPs comprising such HMG domains and occurring in non-human or non-Drosophilae eukaryotes are considered homologues of human or Drosophilae SSRP1. SSRP-encoding homologous nucleic acids have been detected in diverse eukaryotes, including arthropods (represented by the fruit fly Drosophilae melanogaster) and vertebrates including mammals (e.g., human, chimpanzee, monkey, elephant, pig, dog, rabbit, mouse and opossum), aves (e.g., chicken) and fish. It is deduced that homologues of the human and/or Drosophilae SSRP occur in numerous eukaryotes, including at least arthropods and vertebrates. SSRP variants occurring within a given eukaryotic species (e.g., humans) that are encoded by nucleic acids comprising sequences similar but not identical to are understood to be polymorphic or allelic SSRP1 variants. Homologous and polymorphic SSRP1 variants also are useful in this assay.

Proteins comprising still other useful SSRP HMG domains may be identified empirically, based upon their ability to form detectable cisplatin-lesioned DNA/protein complexes. Such other useful SSRP HMG domains need not be encoded by nucleic acid that hybridizes specifically to nucleic acid encoding the HMG domain of human or Drosophila SSRP. At least one such empirically identified, useful SSRP is fractional yeast SSRP (fySSRP), also identified as DCR-I (intrastrand crosslink recognition protein 1). Additional useful SSRP HMG domains occur in such known HMG proteins as HMG-1, HMG-2, UBF, LEF-1, SRY, mtTFA, ABF2 and the like. These and other known HMG domain SSRPs have been isolated, variously, from diverse eukaryotes, including human, rodent, Xenopus, Drosophila and yeast.

A variety of hypotheses have been advanced to explain the role of SSRPs in curtailing unwanted cell proliferation; and in no way is this assay or the subject invention intended to be delimited by them. The first such hypothesis provides as follows. The consequence of SSRP binding to a genomic lesion is that the sterically large SSRP (or a fragment thereof comprising an HMG domain) becomes localized in the immediate vicinity of the genomic lesion. The SSRP is large enough to sterically obscure (cover) a region of cellular DNA extending from the lesion site in either the 5' and 3' direction. As a result, it is believed that lesion-bound SSRP shields the genomic lesion from repair by the cell's enzymatic DNA repair machinery. SSRP-shielded lesions would therefore appear to be more effective for prejudicing the fidelity of DNA replication, hindering the expression of genes relevant to cell survival, and otherwise contributing to disarray of the cell's nuclear architecture.

The second hypothesis postulates the following. Certain HMG domain proteins useful herein as SSRPs have been characterized in the literature as transcription factors that control or modulate the expression of one or more cellular genes, including genes that are relevant to cell metabolism or cell secretory function. One such transcription factor is upstream binding factor (UBF), which controls the expression of ribosomal RNA genes and thus is pivotal to the function of the cell's protein synthesis machinery. It is thought that cisplatin-type lesions to which such transcription factors bind as SSRPs mimic or resemble the factor's natural genomic binding site. Binding of such transcription factors to cisplatin-type genomic lesions in effect sequesters the transcription factors at sites other than the natural genomic binding site. Titration of the transcription factors away from their natural genomic binding sites contributes to deregulation of the controlled genes and therefore contributes to disarray of cellular processes and functions directed by the products (generally proteins, e.g., enzymes) of the controlled genes. For example, sequestration or "hijacking" of the HMG domain transcription factor UBF by cisplatin-type lesions may contribute to disarray of cellular protein synthesis, a process needed for cell survival.

In one example of this assay, a sample of double-stranded DNA bearing a lesion formed by the genotoxic agent is contacted with a DNA structure-specific recognition protein, such that a lesioned DNA/SSRP complex forms. This complex is detected or visualized, and optionally quantitated, e.g., relative to a standard genotoxic agent known to form a DNA lesion bound by the SSRP. Capacity of the genotoxic agent to form SSRP-shielded DNA lesions in vitro may be predictive of competence of the agent to form persistent genomic lesions in cellular DNA, which should signal a more effective genotoxic agent.

In another example of this assay, the susceptibility of any coordination complex known to cause DNA lesions may be examined. A sample comprising eukaryotic cells is treated so as to release intracellular proteins. The released intracellular proteins are assessed for the presence of one or more DNA SSRPs that bind to DNA lesioned by the coordination complex being examined. Thus, released intracellular proteins are contacted with probe DNA which has one or more lesions formed by the genotoxin, such that a lesioned probe DNA/cellular SSRP complex is formed. This complex is detected or visualized, and optionally quantitated e.g., relative to a standard SSRP known to bind DNA lesions formed by the genotoxic agent. Presence within the eukaryotic cells of one or more SSRPs that bind to the lesioned probe DNA may be predictive of formation of persistent genomic lesions in cellular DNA. Accordingly, the presence and amount of SSRPs within the eukaryotic cells may be used to confirm whether a particular coordination complex will be cytotoxic to the cells. Such information may also assist in calculating the appropriate dose of any coordination complex for treatment.

In yet another form, the assay allows novel coordination complexes that bind to DNA to form genomic lesions to be readily identified. That is, the invention features a screening method for assessing new candidates for the ability to form SSRP-recognizable and thus persistent genomic lesions. This method involves contacting a sample of DNA, optionally comprising a detectable moiety, with one or more candidate coordination complexes, then incubating the DNA with the candidate under conditions sufficient for DNA binding of genotoxic agents. The DNA bearing a genomic lesion formed by a candidate genotoxin is separated from the incubation mixture comprising unlesioned DNA and unbound candidate. Successfully lesioned DNA is contacted to an SSRP under conditions sufficient for the formation of a lesioned DNA/SSRP complex, which is thereupon detected. Optionally, SSRP may be used as an affinity separation agent to isolate successfully lesioned DNA from the incubation mixture. This rational drug screening method may be automated for high-throughput screening of libraries, and members thereof. For one example of such a method, see Ziegler et al. (1999), 4 *JBIC* 402–11.

SSRP shielding in the foregoing assays may be assessed using any appropriate detection method known to one of skill in the art for visualizing biomolecular interactions. Generally, some examples include techniques described in U.S. Pat. No. 5,359,047, modified Western (Southwestern) blotting, electrophoretic mobility shift analysis (EMSA, also known as bardshift analysis), and techniques involving GFP-based assays.

More specifically, suitable methods for detecting lesioned DNA/SSRP complexes formed in the above aspects of the present invention include EMSA and Southwestern blotting. In these and other methods described herein, detection may optionally be facilitated through the use of lesioned probe DNA-Probe DNA is a fragment (e.g., a restriction fragment) of naturally occurring or recombinant DNA, or is a synthetically constructed DNA, of a size suitable for use in standard analytical procedures. For example, the probe DNA may be at least about 60, 80 or 100 basepairs (bp). Lesioned probe DNA contains at least one structural motif (lesion) produced by the binding thereto of a genotoxic agent. Optionally, the probe DNA also comprises a detectable moiety, such as a radioisotope, chromophore, fluorophore, hapten or other high affinity ligand (e.g., biotin).

Other methods for detecting lesioned DNA/SSRP complexes, optionally involving the use of a suitable probe DNA, include nitrocellulose filter retention assay and excinuclease protection assay, both described herein. The nitrocellulose filter retention assay is based upon the selective retention or filter-binding of proteins such as SSRPs. Lesioned probe DNA binds to the SSRP and thus is retained by the filter, whereas unlesioned probe DNA (or probe DNA bearing an unrecognized lesion) flows through or is not retained by the filter. If desired, the filter may be blocked or treated to reduce nonspecific retention. Nitrocellulose filter retention assays may be carried out, e.g., using a standard dot blotting apparatus. The selective retention principle of the nitrocellulose filter retention assay may be enlarged to other affinity based separation or analytical systems, including affinity chromatography systems and the like, through no more than routine experimentation.

The excinuclease protection assay is based directly on the steric hindrance, by bound SSRP, of DNA lesion repair by a eukaryotic DNA repair enzyme. In this assay, the lesioned DNA/SSRP complex is contacted with excinuclease and incubated therewith under conditions sufficient for the excinuclease-catalyzed removal of lesions from DNA. If a DNA lesion is accessible to the excinuclease, a single-stranded nucleic acid fragment comprising the lesion is removed from the double-stranded DNA. Typically, the fragment is less than 30 bp long. The resulting gap is filled with a patch of newly synthesized DNA complementary to the sequence of the unlesioned strand. Using appropriate nucleic acid labeling techniques, one or more of the nucleic acid products of successful excinuclease repair can be detected. Failure to excise a lesion from DNA, or the degree (e.g., percent) of inhibition thereof indicates SSRP shielding and thus is reasonably correlated with persistence of lesions in the genome.

Still other methods for detecting lesioned DNA/SSRP complexes formed according to the present invention include GFP-based assays. In some aspect, platinum complexes may be screened for the ability to form DNA adducts that specifically bind to HMG domain proteins using a fusion protein consisting of HMG-1 and GFP. Such fusion protein is first expressed in E. coli and purified. Libraries of subject coordination complexes may be allowed to react with nucleic acid covalently linked to microscopic beads. The beads are then washed with a solution of the HMG-1-GFP fusion protein. The beads containing platinum complexes whose DNA adducts bind to HMG-1-GFP should appear green under a fluorescence microscope. The green beads may then be selected and the platinum complexes they contain be ultimately identified by several iterations of sublibrary synthesis and screening.

(D) Other Assays

A number of biological activities may be assayed for activity of platinum-containing compounds with reference to cisplatin. These include (some of which are discussed in greater detail above): binding to purines on DNA or other nucleic acid; recognition and binding of HMG domain proteins to platinum-DNA lesions; excision repair inhibition; transcription inhibition; telomere shortening; colony counting assays; whole animal xenograft studies; and the like.

6.3.6. Some Exemplary Uses of Coordination Complexes Containing Platinum

In one aspect, coordination complexes containing platinum may be used as therapeutic agents to treat a host. In certain embodiments, the host is a human, and/or the coordination complex is formulated in a pharmaceutically acceptable carrier. In certain embodiments, a medicament may be formulated for the treatment of variety of diseases or conditions, including neoplasms and other malignancies.

In another aspect, the invention features a method of forming genomic lesions in cellular nucleic acids. This method involves contacting eukaryotic cells with a genotoxic agent or a pharmacological composition thereof. In certain embodiments, the agent of interest is a library member that is identified with the subject methods and assays.

In still another aspect, the invention features a method of killing eukaryotic cells. This method also includes contacting eukaryotic cells with an effective amount of a genotoxic agent or a pharmacologically acceptable composition thereof. In certain embodiments, the therapeutic activity of the agent is identified using the subject methods and assays.

In some embodiments, these methods also include expression within the cell of a SSRP having at least one HMG domain according to the present invention These methods may be applied to transformed cells, such as carcinoma or sarcoma cells, for example. Alternatively, these methods may be applied to cells of mammalian origin. In certain embodiments, these methods concern cells of human origin, and more specifically transformed cells of the nervous system, mammary cells, cutaneous cell, cells of the respiratory tract, gastrointestinal tract, or urogenital tract.

For example, in a particular method for killing eukaryotic cells, the method involves contacting the cells to be killed with nucleic acid encoding an SSRP that binds to lesions in DNA produced by a selected genotoxic agent, under conditions sufficient for the internalization and expression or overexpression of the SSRP-encoding nucleic acid within the cells.

In other embodiments, the method involves contacting the cells with a genotoxic coordination complex. The method further may further involve contacting the cells expressing the encoded SSRP with the selected genotoxic agent, under conditions sufficient for the formation of persistent and therefore cytotoxic lesions in the cell genome. Advantageously, then, in certain instances, the invention may allow the use of low doses of the genotoxic agent and thereby improve its therapeutic index. The invention also may enhance the effectiveness of additional genotoxins, including genotoxins formerly considered poorly effective or ineffective as cytotoxins. Further, the invention may reconstitute the cytotoxic susceptibility of cells that are refractory to killing by genotoxins, including cells that express a gene for multiple drug resistance.

Eukaryotic cells with which the methods of the present invention may be practiced may be cells of a unicellular or multi-cellular organism. The cells may be maintained in or adapted to culture ex vivo, or may be cells withdrawn from a multi-cellular organism (e.g., a body fluid sample or tissue biopsy). Alternatively, the cells may be present in vivo in tissue or organs of a multi-cellular eukaryotic organism. The term, multi-cellular eukaryotic organism, embraces at least arthropods and vertebrates, including fish, amphibians, birds and mammals, particularly humans.

The eukaryotic cells may exhibit either normal or transformed phenotypes. Thus, the eukaryotic cells may be transformed (neoplastic or malignant) cells, including carcinoma cells and sarcoma cells. Transformed mammalian cells with which the present invention may be practiced include transformed cells arising within any body tissue or body compartment, including transformed cells of central or peripheral nervous system, mammary, lymphoid, myeloid, cutaneous, respiratory tract, gastrointestinal tract, and urogenital tract origin.

To assess susceptibility of transformed cells to killing by a desired chemotherapeutic agent, a sample comprising the transformed cells may be withdrawn from an individual to be treated with the chemotherapeutic agent by standard biopsy techniques and processed for the release of intracellular proteins comprising endogenous SSRPs as described above.

If desired, transformed cells may be sensitized to cell killing in situ by the genotoxic agent by causing them to internalize foreign nucleic acid encoding SSRP. Nucleic acid encoding SSRP may be administered to the individual using standard techniques or modifications thereof, appropriate to deliver the nucleic acid to the body compartment, organ or tissue harboring transformed cells. Preferably, the SSRP encoding nucleic acid is internalized by dividing cells, including transformed cells that have escaped normal physiologic and molecular restraints on cell proliferation and cell differentiation. Subsequent exposure of the SSRP-expressing transformed cells to a genotoxic agent according to accepted chemotherapeutic protocols or routine modifications thereof results in preferential killing in situ of the transformed cells.

6.3.7. Libraries of Other Coordination Complexes, and Assays Thereof

The present invention contemplates varieties of libraries involving coordination complexes in addition to those described containing platinum. Exemplary targets of such libraries are those identified in the following articles: Liu et al., Chem. Rev. 99:2235–68 (1999) (discussing Tc); and Caravan et al., Gadolinium(III) Chelates as MRI Contrast Agents: Structure, Dynamics, and Applications 2293–352.

Figure 11:
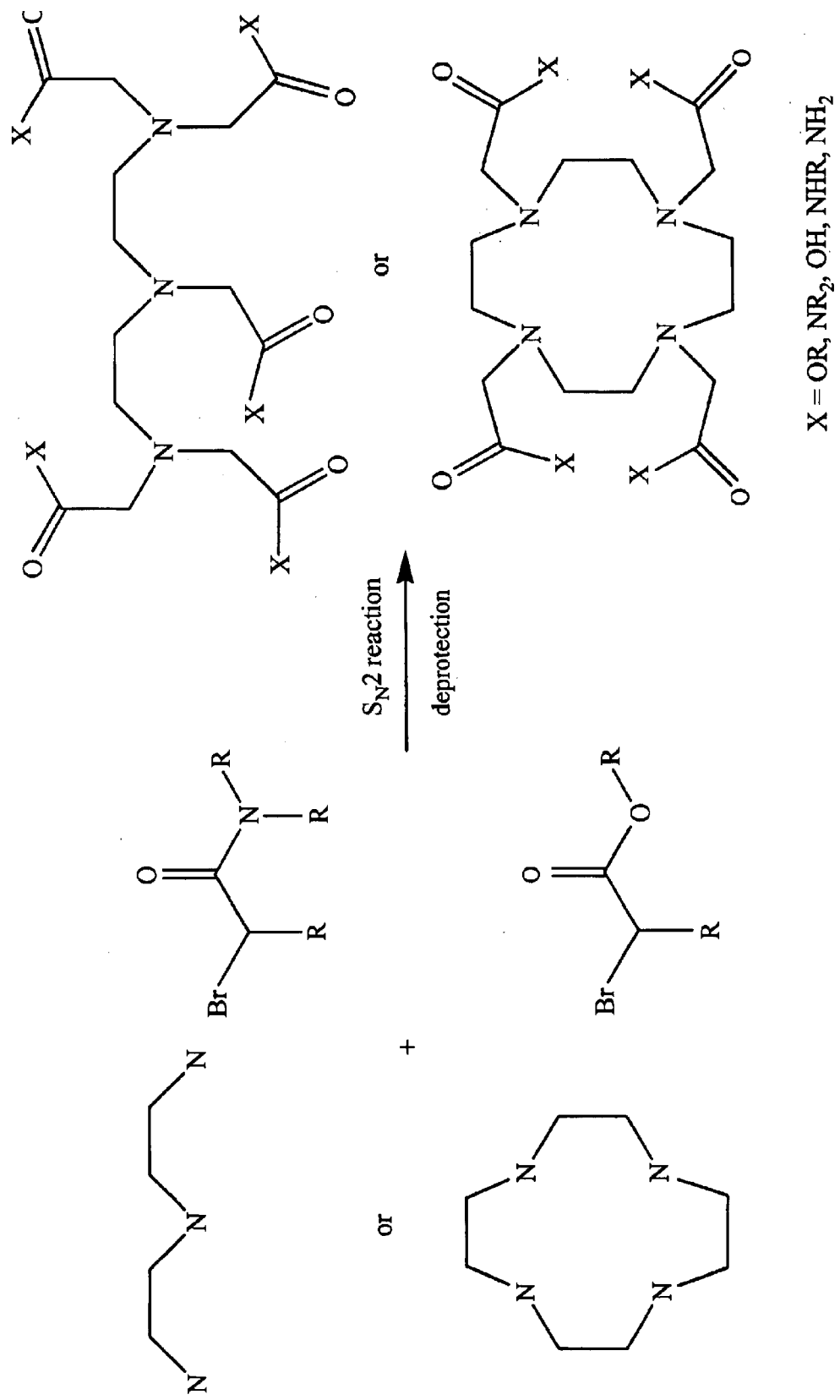
FIG. 11 shows a reaction scheme for preparing ligands for coordination complexes containing gadolinium, and libraries thereof.

As shown by a prophetic example set forth in FIG. 11, libraries of such coordination complexes and libraries thereof may be prepared in accordance with the teachings of the present invention. In that example, gadolinium contrast agents may be generated by using a combinatorial protocol similar to the one described herein. DPTA and DOPA ligand analogs may be synthesized from mixtures of diethylenetriamine or tetraazacyclododecane and bromoacetate esters or bromoacetamides. Once the ligand analogs have been produced in the reaction wells, a metal precursor such as $Gd(NO_3)_3$ or similar salt may be added to the wells to generate the drug candidate. The ligand analogs will coordinate to the gadolinium to form octacoordinate compounds with an open site for water coordination. The resultant candidates may then be screened for activity and compared to existing gadolinium drugs.

In addition, suitable assays known to those of skill in the art may be used to assess for desired activities of the subject coordination complexes and libraries thereof.

6.3.8. Dosages

The dosage of any compound of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention contemplates mixtures of more than one subject compound, as well as other therapeutic agents.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular compound of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

6.3.9. Formulations

The compounds of the present invention may be administered by various means, depending on their intended use, as is well known in the art. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eyedrops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound thereof as an active ingredient. Compounds of the present invention may also be administered as a bolus, electuary, or paste.

In solid dosage forms for oral administration (capsules, tablets, pills, dragees, powders, granules and the like), the coordination complex thereof is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a coordination complex of the present invention with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a supplement or component includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compound.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

6. EXEMPLIFICATIONS

The present invention now being generally described, it may be more readily understood by reference to the following examples which are included merely for purposes of illustration of certain aspects and embodiments of the present invention, and are not intended to limit the invention.

Example 1

Experimental Methods a) Methods and Materials

Potassium tetrachloroplatinate, $K_2PtCl_4$, was provided by Johnson-Matthey. All other chemical reagents were supplied by Sigma-Aldrich, and solvents were purchased from EM Scientific. The combinatorial reactions were carried out on an Advanced Chemtech Labtech organic synthesizer as well as a robotic 348 Omega synthesizer. Platinum atomic absorption measurements were made on a Varian AA-1475 instrument. Infrared spectra of the platinum complexes were obtained on a Biorad FTS-7 FTIR 3200 spectrometer. $^{195}Pt$ NMR measurements were made with a Varian VXR-500 instrument.

b) Synthesis of $K[Pt(NH_3)Cl_3]$

This coordination complex was synthesized using a previously reported procedure (Giandomenico et al., *Inorg. Chem.* 34:1015–21 (1995)). A solution of cisplatin (2.34 g) and tetraethylamrmonium chloride (1.66 g) in fresh dimethylacetamide (200 mL) was heated to 100 C with stirring while purging with argon. The temperature was maintained for 7 h, and the solution volume was allowed to reduce to approximately 50 mL by the end of the reaction time. Care was made to prevent prolonged heating above 100° C. to avoid decomposition of the platinum reagent. After completion of the reaction, the reaction solution was allowed to cool to room temperature, 450 mL of a 1:1 hexane:ethyl acetate mixture was added, and the resultant solution cooled at −20 C overnight. This cooling precipitates out an orange product oil, which was easily separated from the supernatant solution. The orange product contains the tetraethylammonium salt of the desired platinum complex, $(Et_4N)[Pt(NH_3)Cl_3]$. This oil was dissolved in 20 mL of water, and the solution allowed to sit for 30 min to allow for precipitation of unreacted cisplatin. This solution was filtered, and mixed with 50 mL of rinsed acidic Dowex 50W-X8 to affect ion exchange. The solution was again filtered to remove the resin, and the volume of the resultant solution was reduced to 1–2 mL by rotary evaporation. Crystals of $K[Pt(NH_3)Cl_3]$ were isolated through the addition of a 3 mL of a saturated KCl solution to the ion exchanged $[Pt(NH_3)Cl_3]$ solution. The resultant mixture was chilled at 5 C for several hours, and afforded orange crystalline $K[Pt(NH_3)Cl_3]$. Yield: 2.01 g (69%), $^{195}Pt$ NMR($H_2O$): −1743 ppm $[Pt(NH_3)Cl_3]^+$, FTIR ($cm^{-1}$, KBr pellet): 3529, 3475, 1626, 1545, 1324, 544, 520.

c) Synthesis of Cisplatin

This reaction was based on the rapid synthesis of cisplatin developed by Dhara (Dhara, S. C. *Indian J Chem.* 8:193–94 (1970)). A solution of the precursor complex, $K_2PtCl_4$ (10 Mg) in 300 μL water, was mixed with four equivalents of potassium iodide (16 mg) in 200 μL water. The red solution turned dark brown after about ten minutes, indicating formation of the activated species, $[PtI_4]^{2-}$. At this point, 2.2 equivalents of ammonia (30 μl, of a 3% aqueous solution) were added to the dark solution, and a yellow precipitate formed immediately. This yellow species is the iodide form of cisplatin, $Pt(NH_3)_2I_2$. In the same pot, eight equivalents of $AgNO_3$ (32 mg in 100 μL $H_2O$) were added to the reaction mixture, forming a slurry of AgI, AgCl, and aquated cisplatin, $[Pt(NH_3)_2(H2O)_2](NO_3)_2$. The solution was filtered, and two equivalents of KCl (3.5 mg) were added. Yellow crystals of cisplatin formed, which could be isolated by filtration. Yield: 6.3 mg (84%), $^{195}Pt$ NMR($H_2O$): −2139 ppm ($Pt(NH_3)2)Cl_2$), −1825 PPM ($Pt(NH_3)_2(H_2O)_2$ Cl+), FTIR ($cm^{-1}$, KBr pellet): 3293, 3196, 1624, 1538, 1319, 1296, 795. Synthesis of trans-DDP. $K_2PtCl_4$ (1 g) was dissolved in 10 mL of $H_2O$ with 2 mL concentrated HCl. 10 mL aliquots of concentrated $NH_4OH$ were added to this solution with mixing and heating until all of the $PtCl_4^{2-}$ had converted into $Pt(NH_3)_4^{2+}$, which is colorless. During the reaction, the color of the solution changed from red to yellow, producing a yellow precipitate, and finally formed a green precipitate in a clear solution. Once this green product (Magnus green salt) had been completely dissolved, the volume of the solution was reduced to ~3 mL, and 10 mL of concentrated HCl was then added to the cooled solution. The resultant solution was then set aside in the refrigerator overnight, and the yellow trans-DDP product was collected by filtration. The product was recrystallized from 0.1 M HCl. Yield: 525 mg (73%).

d) The combinatorial Synthesis of Cisplatin Analogs and Other Coordination Complexes Although the exact protocol for the combinatorial synthesis of platinum drugs differed between the two instruments used in these investigations, the fundamental chemical sequence remained substantially the same. Both devices used an identical Teflon reaction block, pictured in FIG. 4. For these embodiments, the process may be divided into five steps: activation of a platinum precursor with iodide, mixture of the resultant iodo species with a ligand or ligand solution, removal of halide through addition of $AgNO_3$, filtration, and addition of the ligand A. A description of the basic reaction protocol may be seen in FIGS. 1, 2 and 3, depending on the metal precursor used.

In the Labtech device, reagents were added manually to the reaction block by pipet. A platinum compound precursor ($K_2PtCl_4$ or $K[Pt(L)Cl_3]$, 24 μmoles) in 300 μL $H_2O$ was activated with a 200 μL solution of KI (4 or 3 equivalents) in several or all of the wells on the synthesizer device. After formation of the reactive activated intermediate (probably $PtI_4^{2-}$ or $Pt(NH_3)I_3^-$) after a 10 min mixing period at 650 rpm, 2.2 or 1.1 equivalents of ligand were added to the solution. Different ligands or combinations of ligands were added to each well to generate an array of compounds on the synthesizer. The reagents reacted to form compounds immediately. At this point, a number of equivalents of AgNO$_3$ equal to the equivalents of chloride and iodide in solution (8 or 6) in 100 μL H$_2$O were added to each well, rapidly forming a precipitate. To help solubilize the resulting platinum compounds, 400 μL of DMF were added to each reaction well, and the resulting solutions were mixed for 10 min at 650 rpm at room temperature. After mixing, the solutions were filtered through 1 micron Teflon frits at the bottom of the reaction wells into the separate vials below the reaction block. Each of these vials contains at least 3 equivalents (72 μmol) of KCl or potassium carboxylate salt, which provides chloride ligands for the solvated complexes, although a larger excess may be used. The reaction wells are washed with 400 μL of DMF, mixed for 10 min at 650 rpm, and filtered again into the collection vials below the reaction block.

An analogous sequence of events took place in the wholly automated 348 Omega synthesizer. In this device, a robotic arm dispenses reagents one at a time as directed by a PC workstation. The linear transfer of liquids prevents the simultaneous addition of ligands to the [PtI$_4^{2-}$] solution; therefore, in the synthesizer device the ligands were dispensed to the reaction wells prior to the addition of the activated platinum solution.

These samples were then lyophilized and analyzed for platinum concentration. A summary of the of platinum-containing coordination complexes prepared is shown in Table 1. The coordination complexes listed in Table 1 were prepared using the different reaction schema shown in FIGS. 1, 2 and 3, with each reaction scheme used readily identified by the metal precursor listed in Table 1. Almost all of these coordination complexes were prepared as libraries of 96 complexes. In many libraries, certain ligands were used through the block and diversity was obtained by varying the other ligands and counterions (if any) of the subject coordination complexes. Reactions are once again lyophilized for storage until they can be screened using the BlaM HeLa assay. Maximum throughput achieved typically attained for the robotic 348 Omega system was approximately four 96-well reactions per week (384 reactions).

e) The Combinatorial Synthesis of Trans-DDP Analogs and Other Coordination Complexes The general teachings of the previous examples apply to the preparation of such analogs. The reaction scheme for the preparation of trans configured platinum-containing compounds is shown in FIG. 3, and the resulting coordination complexes are also listed in Table 1. They are readily identified in the table by the metal precursor trans-DDP. For these reactions and libraries, the following chemistry was pursued: a solution of 2.5 mmoles of trans-diamminedichloroplatinum(II) is reacted with 1.1 equivalents of silver nitrate, AgNO$_3$ for ten minutes in 400 μL of water, protected from light. This solution is filtered, and one equivalent of the desired ligand in 50 μL water is added to the resultant solution. The mixture is allowed to react for ten minutes with vortexing at 600 rpm, followed by addition of 400 μL of DMF to increase solubility. Then, another equivalent of silver nitrate is added to the solution, precipitating out the second chloride as AgCl. The solution is then filtered into a vial containing an excess (3 equivalents) of the desired leaving group. The reactions are then lyophilized and stored for later analysis and screening.

f) Assay using BlaM HeLa

To screen drug candidates for transcription inhibition activity, genetically modified HeLa cells developed by Aurora Biosciences were exposed to the products from the above parallel reactions. BlaM HeLa cells have been permanently transfected with a vector encoding the 29-kD plasmid encoded TEM-1 β-lactamase from $E.$ $coli$. This enzyme is the product of the ampicillin resistance gene Amp$^r$, and is not normally expressed in mammalian cells.

BlaM HeLa cells were grown up from stock provided by Aurora Biosciences using standard cell culture techniques. This cell line was grown in 10 cm plates by using a modified Dulbecco's Modified Eagle Medium supplemented with 10% fetal bovine serum, 2 mM L-glutamine, 1.0 mM sodium pyruvate, and 0.1 mM non-essential amino acids. Bacterial growth was inhibited through intermittent exposure to 100 μg/mL penicillin, 100 U/mL streptomycin, and selection of the BlaM cells was maintained through the weekly administration of 800 μg/mL G418 (geneticin).

For plate reader-based experiments, HeLa cells were distributed into black, clear-bottom, 96-well plates (Corning). Nearly confluent 10 cm plates (60–70%) were trypsinized and distributed (100 μL) into the 96-well plates, and allowed to adhere and grow for approximately 18 h. Cells were then washed with 100 μL PBS and provided with fresh media prior to treatment. After treatment, the cells were exposed to the CCF2/AM dye for one hour, and measured for fluorescence on the fmax plate reader. The cellular response to platinum compounds was determined by taking the ratio of the absolute value of measured fluorescence at 530 nm (green) over the absolute value of measured fluorescence at 460 nm (blue). This response is corrected for the background of the microplate.

Concentration and time-dependent studies were conducted with cisplatin and other pure platinum compounds to determine the response of the cells to platinum chemotherapeutics. For the library screen, cells were exposed to 30 μM of platinum product from the reactions for 28 hours. 72 reactions were screened manually per day, with each compound measured in triplicate. Reactions that had little or no platinum yield were screened at a standard dilution of 20,000 from a 1 mL solution of the reaction products. After the exposure period the cells were worked up using the CCF2/AM dye protocol, and hits were determined by their response related to that of a cisplatin standard at the same concentration. Initial hits were then rescreened for dose dependent toxicity, over a range from 0 to 75 μM concentrations. Compounds that exhibited a positive response in this second round of screening were then examined by electrospray mass spectrometry to determine the nature of the platinum species in solution.

g) Northern Blotting of RNA from BlaM HeLa Cells

Figure 5:
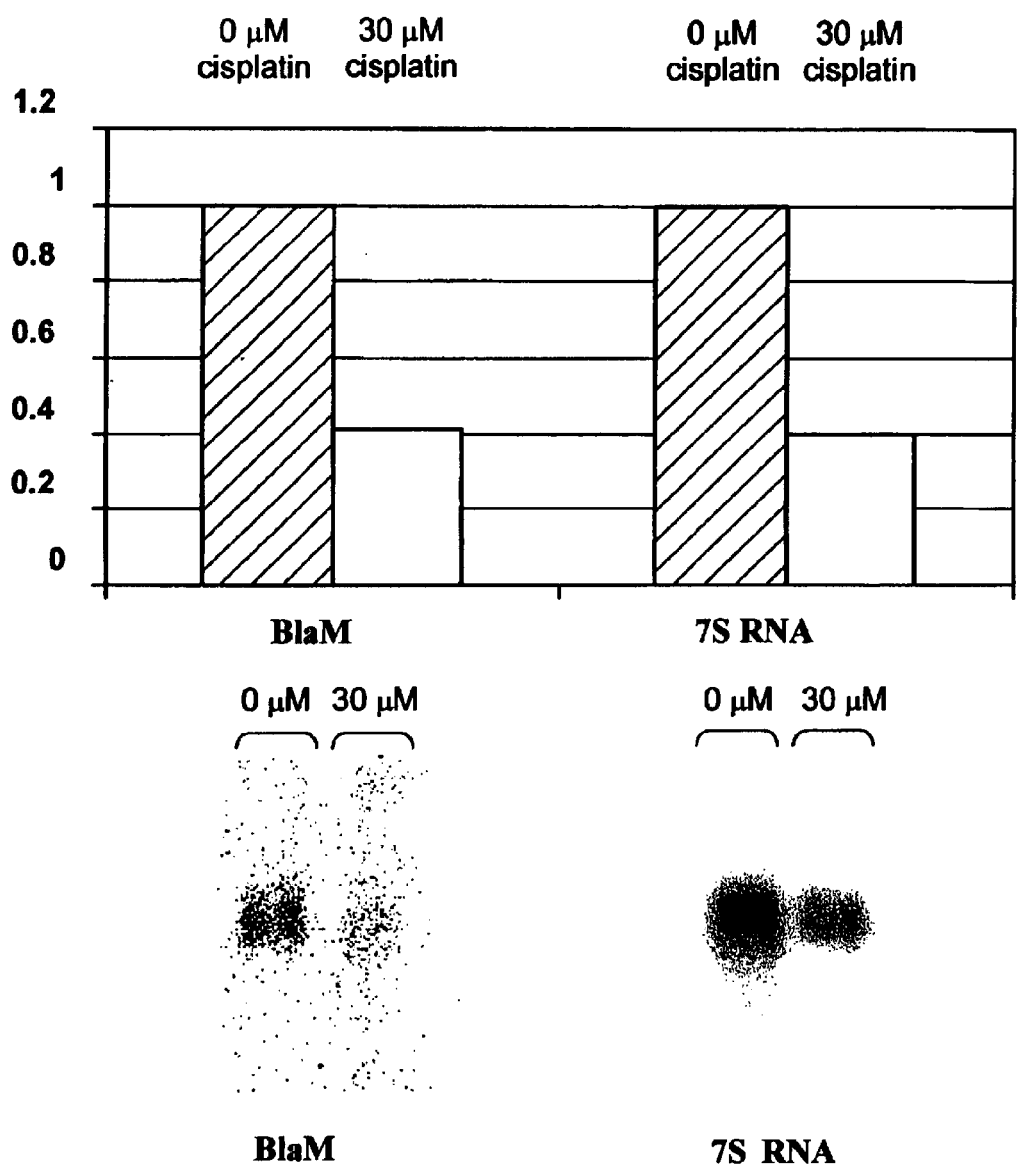
FIG. 5 shows the decrease in transcription as demonstrated by a Northern blot analysis for treatment of two cell types with cisplatin.

Two 10 cm plates of BlaM HeLa cells were grown to 60–70% confluence, and one treated with 30 μM cisplatin for twelve hours. After this treatment, RNA was extracted from the cells on each plate using an Ambion kit and quantified by UV-visible spectroscopy. The RNA was electrophoresed on an agarose-formaldehyde gel, transferred to a nylon membrane, and crosslinked with a Stratalinker UV device by using standard procedures. This blot was probed with $^{32}$P labeled BlaM fragment from pcDNA-3 (Aurora Biosciences) and 7S RNA from pUC(Amp), and quantified by a Biorad phosphorimager apparatus. The results of this experiment are shown in FIG. 5.

h) Microscopy of BlaM HeLa Cells

Nearly confluent 10 cm plates of BlaM HeLa and wt HeLa cells were distributed to 6-well plates containing cover slips. After attachment, these cells were exposed to the agent (cisplatin and trans-DDP) for 24 hours, followed by a CCF2/AM dye work-up as described previously. After the dye exposure, cells on the cover slips were fixed using a 3% paraformaldehyde solution, immersed in an anti-fade glycerol buffer, and sealed to slides by using nail polish. Pictures were taken using a fluorescent microscope at 40×magnification.

i) Synthesis of Subject Coordination Complexes by Non-combinatorial Means 1. cis-(isopropylamine)$_2$PtCl$_2$: This compound has been previously synthesized as described in Braddock et al. (1975) 11 Chem.-Biol. Interact. 145–61. To a solution of K$_2$PtCl$_4$ (100 mg, 2.4×10$^{-4}$ moles) in 3 mL H$_2$O was added an excess of isopropylamine (10 equivalents, 340 μL) and buffered to pH~9.0 with HCl. The reaction solution was allowed to sit overnight, and afforded 45 mg of the desired product. Yield: 48% In an alternative route to this product, 4 equivalents of KI (160 mg, 9.6×10$^{-4}$ moles) was added to an above described aqueous solution of K$_2$PtCl$_4$ and allowed to react for ten minutes, after which the red solution turned a dark brown color indicative of the PtI$_4^{2-}$ anion. Two equivalents of isopropylamine, (68 μL) were then mixed with this solution, resulting in a dark yellow precipitate, ((CH$_3$)$_2$CHNH$_2$)$_2$PtI$_2$. This product was isolated, dried and reacted with two equivalents of AgNO$_3$ in 5 mL H$_2$O. The resultant mixture was protected from light and allowed to react with stirring overnight. The reaction solution was then filtered, and to the filtrate was added three equivalents of KCl (55 mg) which resulted in the formation of the desired product. Yield: 57 mg (61%); $^1$H NMR: 1.32 (CH$_3$), 3.30 (CH), 4.87 (NH$_2$) ppm; $^{195}$Pt NMR: -2218 ppm.

2. cis-(cyclobutylamine)$_2$PtCl$_2$: This compound has been generated previously and was synthesized in an analogous manner to that of the isopropylamine species. See, e.g., Lock et al. (1981), 20 Inorg. Chem. 1817–23; Rochon et al. (1986), C42 Acta Crystallogr., Sect. C 1291–94. Yield (from iodide reaction) 72 mg (73%). $^1$H NMR: 1.63 (CH$_2$), 2.09 (CH$_2$), 2.28 (CH$_2$), 3.71 (CH), 3.98 (NH$_2$) ppm; $^{195}$Pt NMR: -2225 ppm. Single crystals suitable for x-ray diffraction may be grown from DMF, and a structural analysis of the compound confirmed the structure.

3. cis-ammine(cyclobutylamine)PtCl$_2$: The synthesis of this species was taken from a synthesis by Giandomenico et al. (1995) Inorg. Chem. 1015–1021. Yield: 54 mg (55%); $^1$H NMR: 1.61 (CH$_2$), 2.10 (CH$_2$), 2.31 (CH$_2$), 3.70 (NH$_2$), 4.30 (NH$_3$) ppm; $^{195}$Pt NMR: -2175 ppm.

4. cis-ammine(2-amino-3-picoline)dichloroplatinum(II: The synthesis of this species was based on a synthesis by Giandomenico et al. (1995) Inorg. Chem. 1015–1021. A solution of K[Pt(NH$_3$)Cl$_3$] (150 mg) in 1 mL H$_2$O was mixed with a solution of KI (120 mg) in 0.5 mL H$_2$O, which immediately turned from an orange to a darker red color. 2-amino-3-picoline (100 μL) was then added to the solution with mixing, and a yellow precipitate formed immediately. The reaction solution was allowed to mix for an hour, and the solid was collected, washed with water and ethanol, and air-dried. The product, cis-ammine(2-amino-3-picoline)chloroiodoplatinum(II), was collected, weighed, and reacted with 1.6 equivalents of AgNO$_3$ in 4 mL of H$_2$O while protected from light. After one hour of mixing, the filtrate was collected and mixed with 200 μL of a saturated KCl solution in H$_2$O. A yellow precipitate formed immediately, and the water was then removed by rotary evaporator. The dry product was then dissolved in acetone, filtered, and precipitated through the addition of ethanol. Yield: 65 mg (40%). $^1$H NMR: 8.23 (d) 7.45 (d) 6.56 (t) (aromatic H's), 7.28 (NH2), 4.40 (NH3), 2.22 (CH$_3$) ppm; $^{195}$Pt NMR: -2115 ppm. IR: 3457(m), 3386(m), 3343(m), 3269(m), 3176(m), 1621(s), 1589(s), 1480(s), 1382(s), 1317(s), 12039m), 1134(w), 1076(w), 1005(w), 825(m), 777(m), 751 (m) cm$^{-1}$.

j) The Screening of Metal Drug Candidates by the TRE-EGFP 27 Assay

The TRE-EGFP 27 HeLa cells were provided by Sandman (Sandman et al. (1999), 6 Chem. & Biol. 541–51). The cells were maintained in low glucose Dulbecco's Modified Eagle Medium (D-MEM) supplemented with 10% fetal bovine serum, 100 μg/mL penicillin, 100 U/mL streptomycin, 0.4 μg/ML geneticin, and 0.2 μg/mL hygromycin. One day prior to the experiment, cells were distributed into 6-well plates (1 mL per well) such that they would be nearly confluent (60–70%) upon induction. Prior to cotreatment, the 6-well plated cells were washed with PBS and placed in fresh media.

Subject complexes and cisplatin solutions were generated less than 2 hours prior to use. Aqueous solutions were made for the platinum complexes, and 5% DMF in water solutions were used for the ruthenium species, due to their limited solubility. Cells were cotreated with the metal complexes and 10 μg/mL doxycycline and the resulting 6 -well plates were incubated for 13.5 hours. All samples were prepared in triplicate. After incubation, the cells were washed with PBS and lysed by vigorous shaking in 126 μL of a 0.5% solution of SDS in PBS.

The lysates were transferred to a black 96-well plate for fluorescence measurement. Fluorescence measurement of induced GFP was made by exciting at 390 nm and monitoring emission at 510 nm. To normalize each well for net protein, a 4 μL aliquot from each well was quantified for total protein using the Nan-Orange assay (Molecular Probes). Each fluorescence measurement was divided by the protein assay reading, and normalized to the unexposed control sample.

Example 2

Results

The reactions run on the Labtech and 348 Omega devices the yields in grams atoms platinum from the reactions determined by graphite furnace atomic absorption spectrometry are summarized in Table 1.

Figure 6:
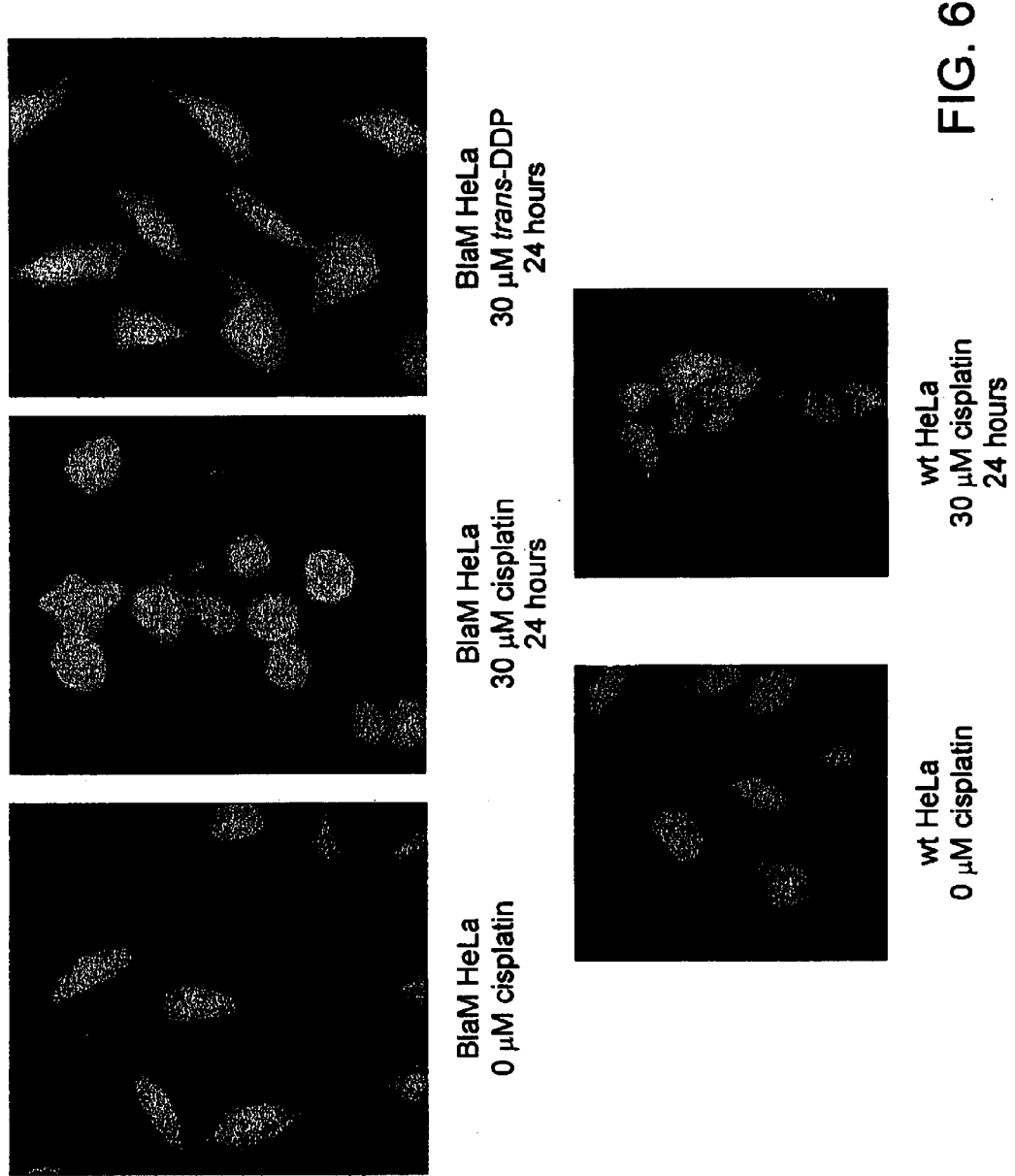
FIG. 6 shows microscopy of wt and BlaM HeLa cells treated with CCF2/AM and different amounts of cisplatin and trans-DDP.

Prior to examining the activity of any of the subject complexes, the BlaM HeLa cell line was evaluated for its response to cisplatin and trans-DDP. Changes in transcription in response to various cytotoxic agents including cisplatin has been examined in detail previously using a CMV-Bla Jurkat cell line (Sandman et al., Chem. Biol. 6:541–51 (1999)). Two control experiments were conducted to demonstrate that analogous behavior is observed in the HeLa variant used herein. In both cell lines, the CMV promoter regulates the expression of β-lactamase. In a Northern blot experiment, described in detail below, treatment of BlaM HeLa cells with cisplatin for 12 hours resulted in a decrease in transcription of both the BlaM vector as well as control 7S RNA. This response was demonstrated in EGFP HeLa C27 cells for the EGFP vector and global transcription of GAPDH. In addition, images of dye treated BlaM HeLa and wt HeLa exhibit identical behavior as that observed in similarly treated CMV-bla Jurkat cells. See FIG. 6 and the experimental description below.

Using 96-well clear bottom microplates and a Fmax microplate reader, concentration and time dependence were determined to maximize response to cisplatin relative to trans-DDP. For time-response experiments, various time points were measured using a fresh DMSO solution of CCF2/AM as well as a three week old solution of CCF2/AM to determine the best response time over the lifetime of the dye. These experiments demonstrate that a response time greater than 24 hours is needed, as well as the fact that a fresh dye sample is needed for optimum response. For the purpose of the sample screening, a treatment time of 28 hours was chosen to allow for both the formation of platinum adducts on the genomic DNA as well as the decay of ambient β-lactamase constitutively expressed by the BlaM HeLa cells.

Figure 7:
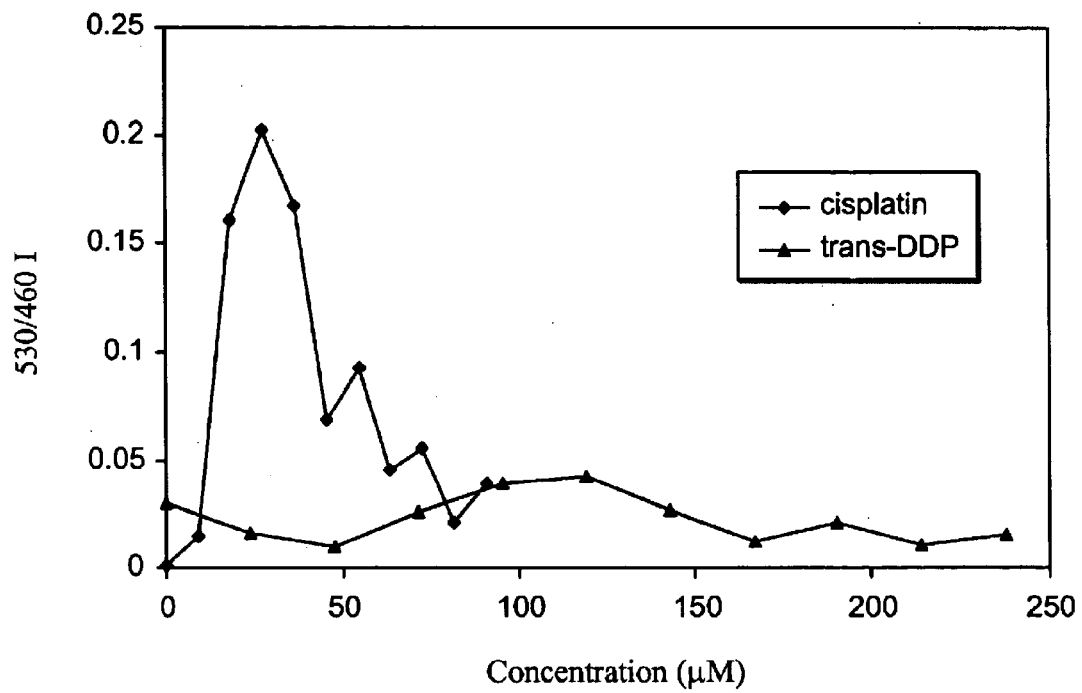
FIG. 7 shows concentration dependency of BlaM HeLa cell response to treatment with cisplatin and trans-DDP after twenty-eight hours as measured by the CCF2/AM assay.
Figure 8:
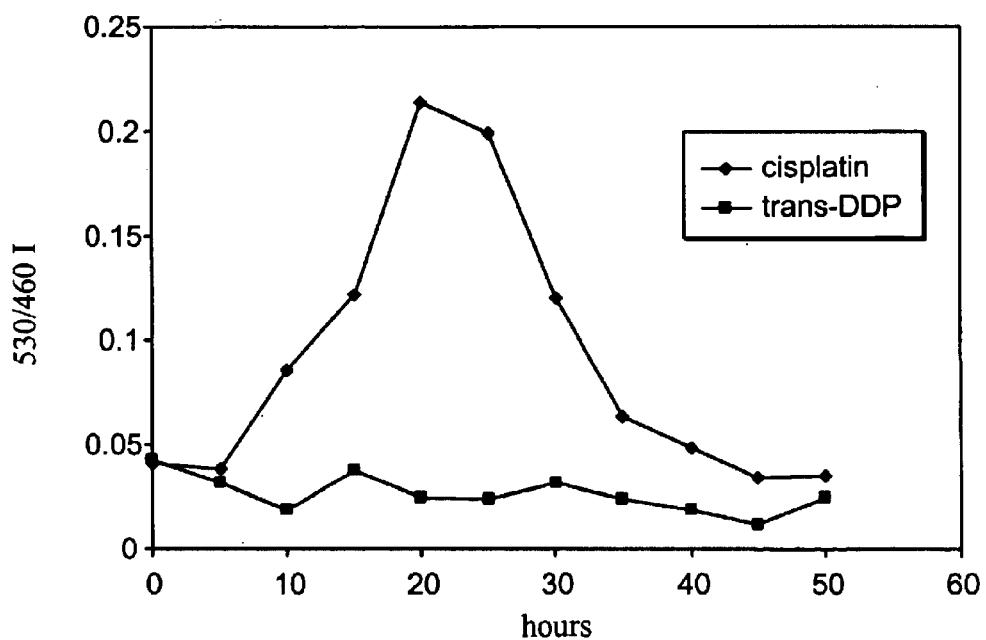
FIG. 8 shows time dependence of BlaM HeLa cell response upon treatment of cisplatin and trans-DDP as measured by the CCF2/AM assay.

BlaM HeLa cell responses to differing platinum compound concentrations were also examined to determine the optimum concentration for the screening of the candidate library. BlaM HeLa cells were exposed to increasing concentrations of cisplatin and trans-DDP and exposed to dye, which can be seen in FIG. 6. With increasing concentration, cisplatin shows a definite increase in the ratio of green to blue fluorescence, whereas trans-DDP shows no increase over the same range (FIG. 7). For the purpose of the screen, a concentration of 30 μM was chosen for the initial evaluation of the library. Cisplatin's behavior at this point may be readily distinguished from that of trans-DDP. The time dependence of the cell response was also measured using this assay. The cell reponse to cisplatin peaked after approximately 20 hours, while trans-DDP evoked no cell response at any of the times measured (FIG. 8).

Figure 12:
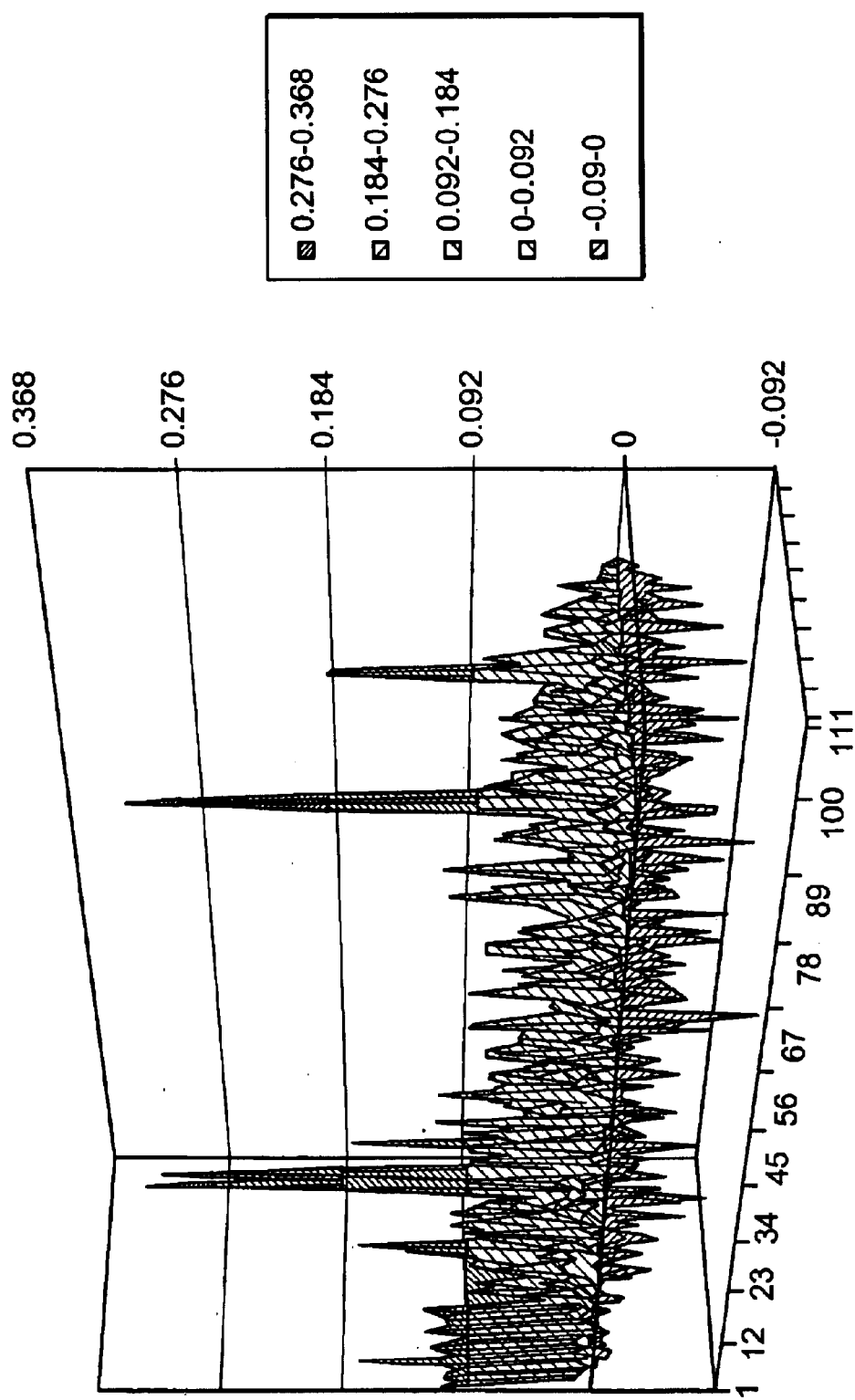
FIG. 12 shows results of the assay of libraries of coordination complexes containing platinum(II) described in the examples.

In order to evaluate the compounds generated by the combinatorial synthetic method, an initial assessment was made using the BlaM HeLa assay using a single concentration evaluation measured in triplicate. The results from the initial screen with the BlaM HeLa cells at 30 μM concentration of the first 3611 combinatorial reactions are shown in FIG. 12. The reactions that gave a response above 0.092 (the average response for cisplatin controls in the screens) were considered hits in the assay. Fourteen hits came out from this initial screen when compared to the response observed for the same concentration of cisplatin, excluding controls where cisplatin was generated by the synthesizer (reactions 1–16, 32, 48, 144, 239, 254, 445, 541, 637, and 685, wherein these reaction numbers correspond to row numbers set forth in Table I). The second round of screening, involving a dose dependent comparison of the hits from the first round, was able to differentiate true hits from false leads. Of the fourteen reactions that were hits in the first screen, three reaction products were found to be toxic by the secondary dose-dependent screen. These reaction products (numbers 52, 302, and 3207) were then analyzed by electrospray mass spectroscopy to determine the identity of the species within these reactions. Each of these solutions contained platinum species that resulted from the reaction of the ligand combinations with the platinum precursor. In reaction number 52, where isopropylamine was the ligand, cis(isopropylamine)$_2$PtCl$_2$ was found to be the predominate species present. Reaction 302 contained a mixture of cis-(cyclobutylamine)$_2$PtCl$_2$ and cis-ammine(cyclobutylamine)PtCl$_2$ resulting from the iodide mediated reaction between K[Pt(NH$_3$)Cl$_3$] and cyclobutylamine. The final hit, number 3207, contained a number of platinum-2-amino-3-picoline products.

In order to corroborate the toxicity of these reaction products, we independently synthesized several platinum compounds. For reaction number 52, we generated cis-(isopropylamine)PtCl$_2$, and for reaction number 302 we synthesized both the bis-cyclobutylamine species as well as the amine-cyclobutylamine complex. Because reaction number 3207 contained a number of compounds of unclear structure, we synthesized a new complex, cis-amine(2-amino-3-picoline)dichloroplatinum(II) as a preliminary experiment to determine if the family of compounds would be toxic. These compounds were then evaluated with the BlaM HeLa cell line, and all four compounds exhibited a positive response on the assay.

Three of these compounds have been previously elucidated as highly cytotoxic platinum drug candidates. An isopropylamine platinum(IV) compound, CHIP or iproplatin, was one of the 27 compounds that entered clinical trials in the 1980s. See Weiss et al., *Drugs* 46:360–77 (1993). Although this compound is a Pt(IV) species, it is reduced in vivo to form the cis-(isopropylamine)$_2$PtCl$_2$ compound. See Blatter et al., *Biochemistry* 23:4817–20 (1984). Cyclobutylamine platinum compounds have also been assessed as potential anti-tumor agents since early investigations into structure/activity relationships. See Braddock et al., *Chem.-Biol. Interact.* 11:145–61 (1975),; Rochon et al., *Acta Crystallogr., Sect.* C42:1291–94 (1986); Yoshida et al., *Anti Cancer Drug Des.* 9:425–34 (1994).

Figure 13:
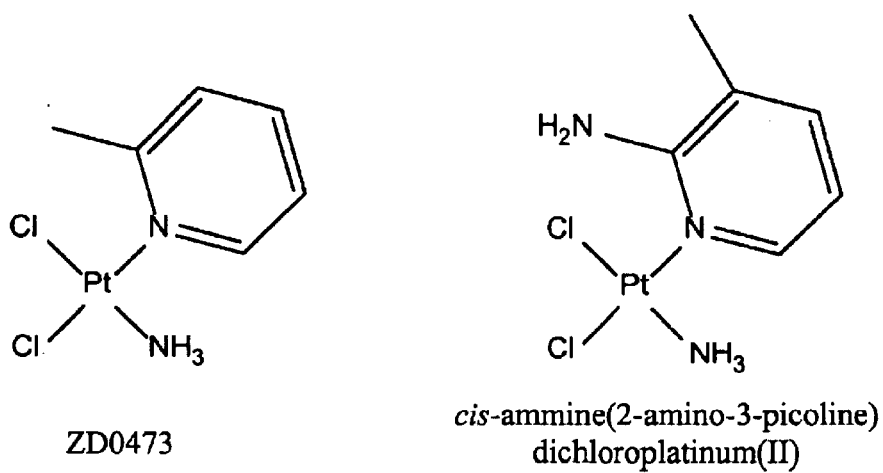
FIG. 13 shows the structure of the subject coordination complex amine(2-amino-3-picoline)dichloroplatinum(II) as compared to the drug candidate ZD0473.

The fourth compound is very similar to several new compounds that have been examined for cytotoxic activity. The sterically hindered picoline species ZD0473 is very similar in structure to the ammine(2-amino-3-picoline) dichloroplatinum(II) species prepared in this report (FIG. 13), as described in Chen et al., *Chem. Eur. J.* 4:672 (1998). One possible hypothesis for the observed activity is that the steric bulk of the picoline inhibits efforts for cellular detoxicification while the complex retains its ability to bind to DNA.

Figure 9:
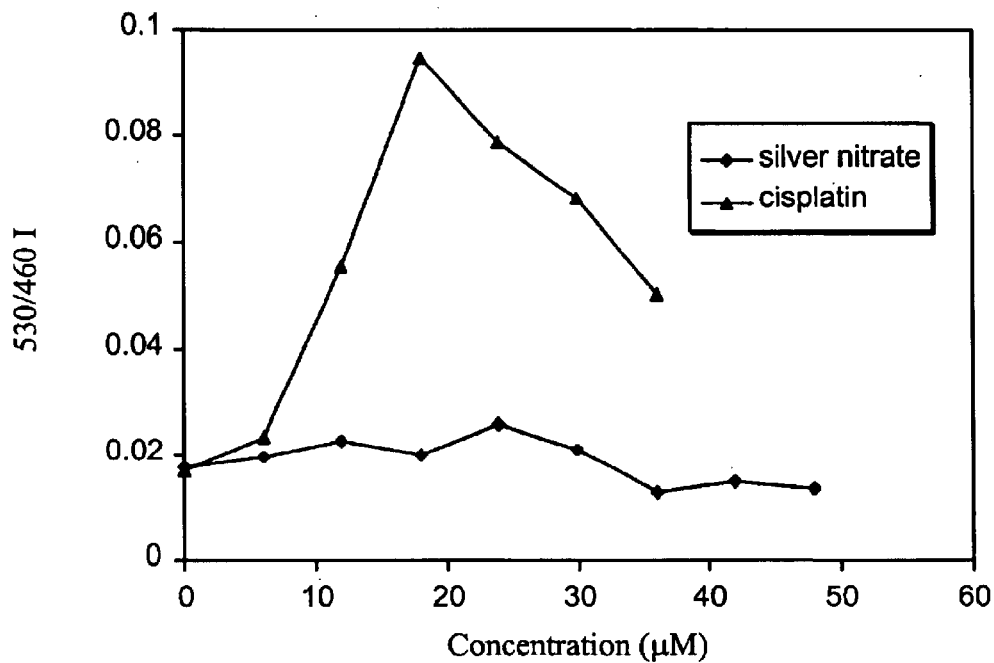
FIG. 9 shows the BlaM HeLa cell response to AgNO$_3$ as compared to cisplatin.

There is a concern that silver salts might have a similar effect as cisplatin in the screens and assays, but it is unlikely that silver salts are generating false positives in the BlaM screen described herein. First, we believe that silver nitrate will only enter the product vial if the halide removal step does not reach completion. Furthermore, if any silver salts are entering the product vial, they will quickly complex with the excess leaving group present to generate silver salts, which are nontoxic as a result of their lack of solubility. Finally, any soluble silver ions that are present in the cell-based screen will be precipitated by chloride in the media, which is at ~130 mM. Although soluble silver may be toxic to cells, silver nitrate administered to BlaM HeLa cells in media at the same concentration as that of cisplatin (~30 μM) does not give a transcription inhibition response, as shown in FIG. 9.

7. REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Appleton et al., *Inorg. Chem.* 23:3521–25 (1984); Armstrong et al., *Acc. Chem. Res.* 29:123 (1994); Bakhtiar R, Ochiai, *Gen Pharmacol* 32: (5) 525–540 (1999); Balkenhohl, et al., *Angew. Chem. Int. Ed. Eng*, 35:2289–2337 (1996); Beck et al., *J. Bacteriol* 116:1247 (1973); Bellon et al., *Biophys. Chem.* 35:179 (1990); Brice no et al., *Science* 270:273 (1995); Bruhn et al., *Proc. Inorg. Chem.* 38:477 (1990); Burger et al., *J. Org. Chem.* 60:7382 (1995); Burgess et al., *Angew. Chem. Int. Ed. Engl.* 35:220 (1996); Burnouf et al., *Proc. Natl. Acad. Sci. USA* 84:3758 (1987); Campbell et al., *J. Am. Chem. Soc.* 117:5381 (1995); Combs et al., *J. Am. Chem. Soc.* 118:287 (1996); Cowley et al., *C. Curr. Med. Chem.* 4:211–227 (1997); Dixit et al., *J Sci. Ind. Res.* (1998); Ecker et al., *Bio-Technology*, 13:351–360 (1995); Fraval et al., *Mutat. Res.* 51:121 (1978); Gariglio et al., *Exp. Cell. Res.* 236:472–81 (1997); Gordon et al., *Combinatorial Chemistry and Molecular Diversity in Drug Discovery* (1998); Harder et al., *Int. J. Cancer* 6:207 ((1970); *Harrison's Principles of Internal Medicine*, Part 11

Hematology and Oncology, Ch. 296, 297 and 300–08 (1991); Howle et al., *Biochem. Pharmacol* 19:2757 (1970); Jamieson et al., *Chem. Rev.* 99:2467–98 (1999); Jones et al., *Lab. Invest.* 52:363–74 (1985); Lee et al., *Inorg. Chim. Acta* 17:105 (1976); LeRoy et al., *Science* 282:1900–04 (1998); Lim et al., *J. Inorg. Nucl. Chem.* 38:119 (1984); Lippard et al., *Principles of Bioinorganic Chemistry* (1994); Loehrer et al., *Ann. Int. Med.* 100:704–14 (1984); Malin et al., *J. Am. Chem. Soc.* 117:11821 (1995); Mello et al., *Chem. Biol.* 3:579–89 (1996); Needels et al., *Proc. Natl. Acad. Sci. USA* 90:10700 (1993); Ohlmeyer et al., *Proc. Natl. Acad. Sci. USA* 90:10922 (1993); Orphanides et al., *Nature* 400:284–88 (1999); Orphanides et al., *Cell* 92:105–16 (1998); Pil et al., *Cisplatin and Related Drugs* 1 ed., Vol. 1 (1997); Pinto et al., *Proc. Natl. Acad. Sci. USA* 82:4616 (1985); Rice et al., *Proc. Natl. Acad. Sci. USA* 85:4158 (1988); Sandman et al., *Chem. Biol.* 6:541–51 (1999); Sandman et al., *J Biol Inorg Chem* 3: (1) 74–80 (1998); Schimizu et al., *Angewandte Chemie* 36:1704 (1997); Sherman and Lippard, *Chem. Rev.* 87:1153 (1987); Sorenson et al., *Cancer Res.* 48:4484 and 6703 (1987); Still et al., *Acc. Chem. Res.* 29:155 (1996); Sundquist et al., *Biochemistry* 25:1520 (1986); Tanke et al., *Cytometry* 33: (4) 453–459 (1998); Thompson et al., *Chem Rev.* 96:555 (1996); Wang et al., *J. Med. Chem.* 38:2995 (1995); Yaneva et al., *Proc. Natl. Acad. Sci.* 13448–51 (1997); Yu et al., *Cell* 76:933 (1994); Zamble et al., *TIBS* 20:435–39 (1995); Zhai et al., *Biochemistry* 37:16307–15 (1998); Zlokamik, G. *Anal. Chem.* 71: (9) 322A-328A (1999); Zuckermann et al., *J. Med. Chem.* 37:2678 (1994); Zunino et al., *Farmaco*, 47:1115–1132 (1992); Ziegler, et al. *J. Biol. Inorg. Chem.*, 5(6):774–783 (2000).

8. EQUIVALENTS

The invention now being fully described, it will be apparent to one of ordinary skill in the art that many changes and modifications may be made thereto without requiring more than routine experimentation or departing from the spirit or scope of the appended claims.

The specification and examples should be considered examplary only with the true scope and spirit of the invention suggested by the following claims.

TABLE 1

| No. | Ligand(s) | Equiv. | Precursor | Leaving Group | Yld, g atm Pt |
|---|---|---|---|---|---|
| 1 | ammonia | 2 | K2PtCl4 | KCl | 1.73E-03 |
| 2 | ammonia | 2 | K2PtCl4 | KCl | 2.24E-03 |
| 3 | ammonia | 2 | K2PtCl4 | KCl | 1.97E-03 |
| 4 | ammonia | 2 | K2PtCl4 | KCl | 2.13E-03 |
| 5 | ammonia | 2 | K2PtCl4 | KCl | 2.44E-03 |
| 6 | ammonia | 2 | K2PtCl4 | KCl | 4.31E-03 |
| 7 | ammonia | 2 | K2PtCl4 | KCl | 3.89E-03 |
| 8 | ammonia | 2 | KtPtCl4 | KCl | 2.22E-03 |
| 9 | ammonia | 2 | K2PtCl4 | KCl | 3.52E-03 |
| 10 | ammonia | 2 | K2PtCl4 | KCl | 4.12E-03 |
| 11 | ammonia | 2 | K2PtCl4 | KCl | 3.46E-03 |
| 12 | ammonia | 2 | K2PtCl4 | KCl | 3.08E-03 |
| 13 | ammonia | 2 | K2PtCl4 | KCl | 3.10E-03 |
| 14 | ammonia | 2 | K2PtCl4 | KCl | 3.61E-03 |
| 15 | ammonia | 2 | K2PtCl4 | KCl | 4.40E-03 |
| 16 | ammonia | 2 | K2PtCl4 | KCl | 3.59E-03 |
| 17 | ammonia | 2 | K2PtCl4 | KCl | 1.34E-03 |
| 18 | methylamine | 2 | K2PtCl4 | KCl | 2.29E-03 |
| 19 | ethylamine | 2 | K2PtCl4 | KCl | 2.61E-03 |
| 20 | propylamine | 2 | K2PtCl4 | KCl | 3.80E-03 |
| 21 | isopropylamine | 2 | K2PtCl4 | KCl | 2.22E-03 |
| 22 | butylamine | 2 | K2PtCl4 | KCl | 2.68E-03 |
| 23 | t-butylamine | 2 | K2PtCl4 | KCl | 2.14E-03 |
| 24 | cyclopentylamine | 2 | K2PtCl4 | KCl | 1.74E-03 |
|  | cyclohexylamine |  | KtPtCl4 | KCl | 7.99E-04 |
| 25 | diethylamine | 2 | K2PtCl4 | KCl | 2.65E-03 |
| 26 | diisopropylamine | 2 | K2PtCl4 | KCl | 1.64E-04 |
| 27 | triethylamine | 2 | K2PtCl4 | KCl | 3.02E-05 |
| 28 | N,N diisopropylethylamine | 2 | K2PtCl4 | KCl | 0.00E+00 |
| 29 | ethylenediamine | 2 | K2PtCl4 | KCl | 3.09E-03 |
| 30 | N,N dimethylethylenediamine | 2 | K2PtCl4 | KCl | 3.71E-03 |
| 31 | 1,3 diaminopropane | 2 | K2PtCl4 | KCl | 2.14E-03 |
| 32 | ammonia | 2 | K2PtCl4 | KCl | 3.16E-03 |
| 33 | methylamine | 2 | K2PtCl4 | KCl | 3.44E-03 |
| 34 | ethylamine | 2 | K2PtCl4 | KCl | 4.17E-03 |
| 35 | propylamine | 2 | K2PtCl4 | KCl | 3.66E-03 |
| 36 | isopropylamine | 2 | K2PtCl4 | KCl | 3.78E-03 |
| 37 | butylamine | 2 | K2PtCl4 | KCl | 3.74E-03 |
| 38 | t-butylamine | 2 | K2PtCl4 | KCl | 1.97E-03 |
| 39 | cyclopentylamine | 2 | K2PtCl4 | KCl | 3.67E-03 |
| 40 | cyclohexylamine | 2 | K2PtCl4 | KCl | 1.16E-03 |
| 41 | diethylamine | 2 | K2PtCl4 | KCl | 2.55E-03 |
| 42 | diisopropylamine | 2 | K2PtCl4 | KCl | 8.05E-04 |
| 43 | triethylamine | 2 | K2PtCl4 | KCl | 1.41E-04 |
| 44 | N,N diisopropylethylamine | 2 | K2PtCl4 | KCl | 1.34E-04 |
| 45 | ethylenediamine | 2 | K2PtCl4 | KCl | 4.75E-03 |
| 46 | N,N dimethylethylenediamine | 2 | K2PtCl4 | KCl | 4.73E-03 |
| 47 | 1,3 diaminopropane | 2 | K2PtCl4 | KCl | 2.84E-03 |

TABLE 1-continued

| No. | Ligand(s) | Equiv. | Precursor | Leaving Group | Yld, g atm Pt |
|---|---|---|---|---|---|
| 48 | ammonia | 2 | K2PtCl4 | KCl | 2.63E−03 |
| 49 | methylamine | 2 | K2PtCl4 | KCl | 3.14E−03 |
| 50 | ethylamine | 2 | K2PtCl4 | KCl | 4.75E−03 |
| 51 | propylamine | 2 | K2PtCl4 | KCl | 2.98E−05 |
| 52 | isopropylamine | 2 | K2PtCl4 | KCl | 1.25E−04 |
| 53 | ISOBUTYLAMINE | 2 | K2PtCl4 | KCl | 4.76E−03 |
| 55 | t-butylamine | 2 | K2PtCl4 | KCl | 4.27E−03 |
| 54 | sec-butylamine | 2 | K2PtCl4 | KCl | 3.03E−03 |
| 57 | 1-2-DIMETHYLPROPYLAMINE | 2 | K2PtCl4 | KCl | 2.26E−03 |
| 56 | 1-ETHYLPROPYLAMINE | 2 | K2PtCl4 | KCl | 2.88E−03 |
| 58 | 1-methylbutylamine | 2 | K2PtCl4 | KCl | 1.48E−03 |
| 59 | 2-methylbutylamine | 2 | K2PtCl4 | KCl | 2.19E−04 |
| 60 | hexylamine | 2 | K2PtCl4 | KCl | 3.12E−03 |
| 61 | heptylamine | 2 | K2PtCl4 | KCl | 1.48E−03 |
| 62 | octylamine | 2 | K2PtCl4 | KCl | 1.31E−03 |
| 63 | 1-METHYLHEPTYLAMINE | 2 | K2PtCl4 | KCl | 1.66E−03 |
| 64 | 1,5-DIMETHYLHEXYLAMINE | 2 | K2PtCl4 | KCl | 1.70E−03 |
| 65 | 2-ETHYLHEXYLAMINE | 2 | K2PtCl4 | KCl | 1.18E−03 |
| 66 | decylamine | 2 | K2PtCl4 | KCl | 1.35E−03 |
| 67 | TERT-OCTYLAMINE | 2 | K2PtCl4 | KCl | 1.27E−03 |
| 68 | UNDECYLAMINE | 2 | K2PtCl4 | KCl | 1.18E−03 |
| 69 | allylamine | 2 | K2PtCl4 | KCl | 2.74E−03 |
| 70 | diethylamine | 2 | K2PtCl4 | KCl | 1.34E−03 |
| 71 | dipropylamine | 2 | K2PtCl4 | KCl | 1.45E−03 |
| 72 | diisopropylamine | 2 | K2PtCl4 | KCl | 1.10E−03 |
| 73 | dibutylamine | 2 | K2PtCl4 | KCl | 1.49E−03 |
| 74 | dipentylamine | 2 | K2PtCl4 | KCl | 4.79E−04 |
| 75 | DIHEXYLAMINE | 2 | K2PtCl4 | KCl | 1.97E−04 |
| 76 | DIOCTYLAMINE | 2 | K2PtCl4 | KCl | 3.67E−04 |
| 77 | N-METHYLPROPYLAMINE | 2 | K2PtCl4 | KCl | 1.30E−03 |
| 78 | N-METHYLISOPROPYLAMINE | 2 | K2PtCl4 | KCl | 1.19E−03 |
| 79 | N-METHYLBUTYLAMINE | 2 | K2PtCl4 | KCl | 2.09E−03 |
| 80 | N-METHYL-TERT-BUTYLAMINE | 2 | K2PtCl4 | KCl | 1.29E−03 |
| 81 | N-METHYLHEXYLAMINE | 2 | K2PtCl4 | KCl | 1.13E−03 |
| 82 | N-ETHYLMETHYLAMINE | 2 | K2PtCl4 | KCl | 1.38E−03 |
| 83 | N-ETHYLISOPROPYLAMINE | 2 | K2PtCl4 | KCl | 6.62E−04 |
| 84 | N-ETHYLBUTYLAMINE | 2 | K2PtCl4 | KCl | 1.48E−03 |
| 85 | N-TERT-BUTYLISOPROPYLAMINE | 2 | K2PtCl4 | KCl | 5.91E−04 |
| 86 | TRIETHYLAMINE | 2 | K2PtCl4 | KCl | 5.85E−04 |
| 87 | TRIPROPYLAMINE | 2 | K2PtCl4 | KCl | 0.00E+00 |
| 88 | TRIISOPROPYLAMINE | 2 | K2PtCl4 | KCl | 1.48E−03 |
| 89 | TRIISOBUTYLAMINE | 2 | K2PtCl4 | KCl | 9.13E−04 |
| 90 | TRIHEXYLAMINE | 2 | K2PtCl4 | KCl | 7.72E−04 |
| 91 | TRIOCTYLAMINE | 2 | K2PtCl4 | KCl | 1.67E−03 |
| 92 | TRIISOOCTYLAMINE | 2 | K2PtCl4 | KCl | 2.83E−03 |
| 93 | TRIDECYLAMINE | 2 | K2PtCl4 | KCl | 1.56E−03 |
| 94 | N,N diisopropyl ethylamine | 2 | K2PtCl4 | KCl | 2.72E−05 |
| 95 | cyclopropylamine | 2 | K2PtCl4 | KCl | 4.17E−03 |
| 96 | cyclobutylamine | 2 | K2PtCl4 | KCl | 2.93E−03 |
| 97 | CYCLOPENTYLAMINE | 2 | K2PtCl4 | KCl | 1.07E−03 |
| 98 | CYCLOHEXYLAMINE | 2 | K2PtCl4 | KCl | 3.15E−04 |
| 99 | CYCLOHEPTYLAMINE | 2 | K2PtCl4 | KCl | 3.76E−04 |
| 100 | CYCLOOCTYLAMINE | 2 | K2PtCl4 | KCl | 2.36E−04 |
| 101 | CYCLODODECYLAMINE | 2 | K2PtCl4 | KCl | 1.25E−04 |
| 102 | 2-METHYLCYCLOHEXYLAMINE | 2 | K2PtCl4 | KCl | 3.65E−04 |
| 103 | 2,3-DIMETHYLCYCLOHEXYLAMINE | 2 | K2PtCl4 | KCl | 5.81E−04 |
| 104 | ALLYLCYCLOHEXYLAMINE | 2 | K2PtCl4 | KCl | 9.59E−04 |
| 105 | N-ALLYLCYCLOPENTYLAMINE | 2 | K2PtCl4 | KCl | 1.19E−03 |
| 106 | N-METHYLCYCLOHEXYLAMINE | 2 | K2PtCl4 | KCl | 1.57E−04 |
| 107 | N-ETHYLCYCLOHEXYLAMINE | 2 | K2PtCl4 | KCl | 2.45E−04 |
| 108 | N-ISOPROPYLCYCLOHEXYLAMINE | 2 | K2PtCl4 | KCl | 1.33E−03 |
| 109 | N-TERT-BUTYLCYCLOHEXYLAMINE | 2 | K2PtCl4 | KCl | 6.31E−04 |
| 110 | (R)-(−)-1-CYCLOHEXYLETHYLAMINE | 2 | K2PtCl4 | KCl | 8.78E−04 |
| 111 | (S)-(+)-1-CYCLOHEXYLETHYLAMINE | 2 | K2PtCl4 | KCl | 1.48E−03 |
| 112 | DICYCLOHEXYLAMINE | 2 | K2PtCl4 | KCl | 6.20E−04 |
| 113 | 1-AMINO-2-PROPANOL | 2 | K2PtCl4 | KCl | 3.54E−03 |
| 114 | DL-2-AMINO-1-PROPANOL | 2 | K2PtCl4 | KCl | 3.07E−03 |
| 115 | (R)-(−)-1-AMINO-2-PROPANOL | 2 | K2PtCl4 | KCl | 1.33E−03 |
| 116 | (S)-(+)-1-AMINO-2-PROPANOL | 2 | K2PtCl4 | KCl | 4.28E−03 |
| 117 | (R)-(−)-2-AMINO-1-PROPANOL | 2 | K2PtCl4 | KCl | 3.98E−03 |
| 118 | (S)-(+)-2-AMINO-1-PROPANOL | 2 | K2PtCl4 | KCl | 4.49E−03 |
| 119 | 3-AMINO-1-PROPANOL | 2 | K2PtCl4 | KCl | 4.86E−03 |
| 121 | 2-AMINO-1-BUTANOL | 2 | K2PtCl4 | KCl | 4.76E−03 |
| 120 | (R)-(−)-2-AMINO-1-BUTANOL | 2 | K2PtCl4 | KCl | 2.49E−03 |
| 122 | (S)-(+)-2-AMINO-1-BUTANOL | 2 | K2PtCl4 | KCl | 3.22E−03 |
| 123 | 4-AMINO-1-BUTANOL | 2 | K2PtCl4 | KCl | 3.65E−03 |
| 124 | 5-AMINO-1-PENTANOL | 2 | K2PtCl4 | KCl | 4.57E−04 |

TABLE 1-continued

| No. | Ligand(s) | Equiv. | Precursor | Leaving Group | Yld, g atm Pt |
|---|---|---|---|---|---|
| 125 | DL-2-AMINO-1-PENTANOL | 2 | K2PtCl4 | KCl | 2.76E−03 |
| 126 | 6-AMINO-1-HEXANOL | 2 | K2PtCl4 | KCl | 2.04E−03 |
| 127 | DL-2-AMINO-1-HEXANOL | 2 | K2PtCl4 | KCl | 1.21E−03 |
| 128 | 2-AMINO-2-METHYL-1-PROPANOL | 2 | K2PtCl4 | KCl | 2.36E−03 |
| 129 | 2-AMINO-3-METHYL-1-BUTANOL | 2 | K2PtCl4 | KCl | 3.10E−03 |
| 130 | (R)-(−)-2-AMINO-3-METHYL-1-BUTANOL | 2 | K2PtCl4 | KCl | 2.03E−03 |
| 131 | (S)-(+)-2-AMINO-3-METHYL-1-BUTANOL | 2 | K2PtCl4 | KCl | 2.45E−03 |
| 132 | 6-AMINO-2-METHYL-2-HEPTANOL | 2 | K2PtCl4 | KCl | 4.39E−04 |
| 133 | 2-(2-AMINOETHYOXY)ETHANOL | 2 | K2PtCl4 | KCl | 1.77E−03 |
| 134 | 2-(METHYLAMINO)ETHANOL | 2 | K2PtCl4 | KCl | 3.09E−03 |
| 135 | 2-(PROPYLAMINO)ETHANOL | 2 | K2PtCl4 | KCl | 2.10E−03 |
| 136 | 2-(TERT-BUTYLAMINO)ETHANOL | 2 | K2PtCl4 | KCl | 4.32E−03 |
| 137 | 1-AMINOMETHYL-1-CYCLOHEXANOL | 2 | K2PtCl4 | KCl | 5.98E−04 |
| 138 | TRANS-4-AMINOCYCLOHEXANOL | 2 | K2PtCl4 | KCl | 4.32E−03 |
| 139 | diethanolamine | 2 | K2PtCl4 | KCl | 2.63E−03 |
| 140 | 3-AMINO-1,2-PROPANEDIOL | 2 | K2PtCl4 | KCl | 2.57E−03 |
| 141 | 2-AMINO-2-METHYL-1,3-PROPANEDIOL | 2 | K2PtCl4 | KCl | 1.89E−03 |
| 142 | 2-AMINO-2-ETHYL-1,3-PROPANEDIOL | 2 | K2PtCl4 | KCl | 1.80E−03 |
| 143 | 3-AMINO-1-PROPANOL VINYL ETHER | 2 | K2PtCl4 | KCl | 9.81E−04 |
| 144 | ammonia | 2 | K2PtCl4 | KCl | 2.99E−03 |
| 145 | methylamine | 2 | K2PtCl4 | KCl | 4.17E−03 |
| 146 | ethylamine | 2 | K2PtCl4 | KCl | 2.66E−03 |
| 147 | propylamine | 2 | K2PtCl4 | KCl | 2.21E−03 |
| 148 | isopropylamine | 2 | K2PtCl4 | KCl | 2.58E−03 |
| 149 | ISOBUTYLAMINE | 2 | K2PtCl4 | KCl | 1.15E−03 |
| 150 | t-butylamine | 2 | K2PtCl4 | KCl | 1.79E−03 |
| 151 | sec-butylamine | 2 | K2PtCl4 | KCl | 2.04E−03 |
| 152 | 1,2-DIMETHYLPROPYLAMINE | 2 | K2PtCl4 | KCl | 1.74E−03 |
| 153 | 1-ETHYLPROPYLAMINE | 2 | K2PtCl4 | KCl | 1.39E−03 |
| 154 | 1-methylbutylamine | 2 | K2PtCl4 | KCl | 1.30E−03 |
| 155 | 2-methylbutylamine | 2 | K2PtCl4 | KCl | 1.33E−03 |
| 156 | hexylamine | 2 | K2PtCl4 | KCl | 1.11E−03 |
| 157 | heptylamine | 2 | K2PtCl4 | KCl | 8.38E−04 |
| 158 | octylamine | 2 | K2PtCl4 | KCl | 1.14E−03 |
| 159 | 1-METHYLHEPTYLAMINE | 2 | K2PtCl4 | KCl | 1.01E−03 |
| 160 | 1,5-DIMETHYLHEXYLAMINE | 2 | K2PtCl4 | KCl | 1.12E−03 |
| 161 | 2-ETHYLHEXYLAMINE | 2 | K2PtCl4 | KCl | 1.26E−03 |
| 162 | decylamine | 2 | K2PtCl4 | KCl | 1.53E−03 |
| 163 | TERT-OCTYLAMINE | 2 | K2PtCl4 | KCl | 1.19E−03 |
| 164 | UNDECYLAMINE | 2 | K2PtCl4 | KCl | 1.44E−03 |
| 165 | allylamine | 2 | K2PtCl4 | KCl | 9.64E−04 |
| 166 | diethylamine | 2 | K2PtCl4 | KCl | 1.96E−03 |
| 167 | dipropylamine | 2 | K2PtCl4 | KCl | 8.22E−04 |
| 168 | diisopropylamine | 2 | K2PtCl4 | KCl | 1.38E−03 |
| 169 | dipentylamine | 2 | K2PtCl4 | KCl | 8.22E−04 |
| 170 | DIHEXYLAMINE | 2 | K2PtCl4 | KCl | 9.17E−04 |
| 171 | DIOCTYLAMINE | 2 | K2PtCl4 | KCl | 1.07E−03 |
| 172 | N-METHYLPROPYLAMINE | 2 | K2PtCl4 | KCl | 1.91E−03 |
| 173 | N-METHYLISOPROPYLAMINE | 2 | K2PtCl4 | KCl | 1.22E−03 |
| 174 | N-METHYLBUTYLAMINE | 2 | K2PtCl4 | KCl | 1.82E−03 |
| 175 | N-METHYL-TERT-BUTYLAMINE | 2 | K2PtCl4 | KCl | 8.38E−04 |
| 176 | N-METHYLHEXYLAMINE | 2 | K2PtCl4 | KCl | 1.64E−03 |
| 177 | N-ETHYLMETHYLAMINE | 2 | K2PtCl4 | KCl | 2.36E−03 |
| 178 | N-ETHYLISOPROPYLAMINE | 2 | K2PtCl4 | KCl | 4.90E−04 |
| 179 | N-ETHYLBUTYLAMINE | 2 | K2PtCl4 | KCl | 2.06E−03 |
| 180 | N-TERT-BUTYLISOPROPYLAMINE | 2 | K2PtCl4 | KCl | 2.69E−03 |
| 181 | TRIETHYLAMINE | 2 | K2PtCl4 | KCl | 1.28E−03 |
| 182 | TRIPROPYLAMINE | 2 | K2PtCl4 | KCl | 4.43E−04 |
| 183 | TRIISOPROPYLAMINE | 2 | K2PtCl4 | KCl | 5.53E−04 |
| 184 | TRIISOBUTYLAMINE | 2 | K2PtCl4 | KCl | 4.90E−04 |
| 185 | TRIHEXYLAMINE | 2 | K2PtCl4 | KCl | 9.01E−04 |
| 186 | TRIOCTYLAMINE | 2 | K2PtCl4 | KCl | 9.80E−04 |
| 187 | TRIISOOCTYLAMINE | 2 | K2PtCl4 | KCl | 1.23E−03 |
| 188 | TRIDECYLAMINE | 2 | K2PtCl4 | KCl | 4.71E−04 |
| 189 | N,N diisopropyl ethylamine | 2 | K2PtCl4 | KCl | 0.00E+00 |
| 190 | cyclopropylamine | 2 | K2PtCl4 | KCl | 9.10E−04 |
| 191 | cyclobutylamine | 2 | K2PtCl4 | KCl | 1.31E−03 |
| 192 | CYClOPENTYLAMINE | 2 | K2PtCl4 | KCl | 1.80E−03 |
| 193 | CYClOHEXYLAMINE | 2 | K2PtCl4 | KCl | 1.65E−03 |
| 194 | CYClOHEPTYLAMINE | 2 | K2PtCl4 | KCl | 1.42E−03 |
| 195 | CYCLOOCTYLAMINE | 2 | K2PtCl4 | KCl | 1.63E−03 |
| 196 | CYCLODODECYLAMINE | 2 | K2PtCl4 | KCl | 1.87E−03 |
| 197 | 2-METHYLCYCLOHEXYLAMINE | 2 | K2PtCl4 | KCl | 1.48E−03 |
| 198 | 2,3-DIMETHYLCYCLOHEXYLAMINE | 2 | K2PtCl4 | KCl | 1.30E−03 |
| 199 | ALLYLCYCLOHEXYLAMINE | 2 | K2PtCl4 | KCl | 1.43E−03 |
| 200 | N-ALLYLCYCLOPENTYLAMINE | 2 | K2PtCl4 | KCl | 9.52E−04 |
| 201 | N-METHYLCYCLOHEXYLAMINE | 2 | K2PtCl4 | KCl | 1.44E−03 |

TABLE 1-continued

| No. | Ligand(s) | Equiv. | Precursor | Leaving Group | Yld, g atm Pt |
|---|---|---|---|---|---|
| 202 | N-ETHYLCYCLOHEXYLAMINE | 2 | K2PtCl4 | KCl | 7.45E−04 |
| 203 | N-ISOPROPYLCYCLOHEXYLAMINE | 2 | K2PtCl4 | KCl | 6.98E−04 |
| 204 | N-TERT-BUTYLCYCLOHEXYLAMINE | 2 | K2PtCl4 | KCl | 2.38E−04 |
| 205 | (R)-(−)-1-CYCLOHEXYLETHYLAMINE | 2 | K2PtCl4 | KCl | 1.32E−03 |
| 206 | (S)-(+)-1-CYCLOHEXYLETHYLAMINE | 2 | K2PtCl4 | KCl | 2.22E−04 |
| 207 | DICYCLOHEXYLAMINE | 2 | K2PtCl4 | KCl | 9.36E−04 |
| 208 | 1-AMINO-2-PROPANOL | 2 | K2PtCl4 | KCl | 2.27E−03 |
| 209 | DL-2-AMINO-1-PROPANOL | 2 | K2PtCl4 | KCl | 2.68E−03 |
| 210 | (R)-(−)-1-AMINO-2-PROPANOL | 2 | K2PtCl4 | KCl | 3.25E−03 |
| 211 | (S)-(+)-1-AMINO-2-PROPANOL | 2 | K2PtCl4 | KCl | 3.95E−03 |
| 212 | (R)-(−)-2-AMINO-1-PROPANOL | 2 | K2PtCl4 | KCl | 2.39E−03 |
| 213 | (S)-(+)-2-AMINO-1-PROPANOL | 2 | K2PtCl4 | KCl | 3.57E−03 |
| 214 | 3-AMINO-1-PROPANOL | 2 | K2PtCl4 | KCl | 2.46E−03 |
| 215 | 2-AMINO-1-BUTANOL | 2 | K2PtCl4 | KCl | 2.35E−03 |
| 216 | (R)-(−)-2-AMINO-1-BUTANOL | 2 | K2PtCl4 | KCl | 3.33E−03 |
| 217 | (S)-(+)-2-AMINO-1-BUTANOL | 2 | K2PtCl4 | KCl | 2.85E−03 |
| 218 | 4-AMINO-1-BUTANOL | 2 | K2PtCl4 | KCl | 1.97E−03 |
| 219 | 5-AMINO-1-PENTANOL | 2 | K2PtCl4 | KCl | 2.66E−03 |
| 220 | DL-2-AMINO-1-PENTANOL | 2 | K2PtCl4 | KCl | 2.09E−03 |
| 221 | 6-AMINO-1-HEXANOL | 2 | K2PtCl4 | KCl | 2.66E−03 |
| 222 | DL-2-AMINO-1-HEXANOL | 2 | K2PtCl4 | KCl | 1.52E−03 |
| 223 | 2-AMINO-2-METHYL-1-PROPANOL | 2 | K2PtCl4 | KCl | 2.79E−03 |
| 224 | 2-AMINO-3-METHYL-1-BUTANOL | 2 | K2PtCl4 | KCl | 2.84E−03 |
| 225 | (R)-(−)-2-AMINO-3-METHYL-1-BUTANOL | 2 | K2PtCl4 | KCl | 2.46E−03 |
| 226 | (S)-(+)-2-AMINO-3-METHYL-1-BUTANOL | 2 | K2PtCl4 | KCl | 3.33E−03 |
| 227 | 6-AMINO-2-METHYL-2-HEPTANOL | 2 | K2PtCl4 | KCl | 7.14E−04 |
| 228 | 2-(2-AMINOETHYOXY)ETHANOL | 2 | K2PtCl4 | KCl | 3.35E−03 |
| 229 | 2-(METHYLAMINO)ETHANOL | 2 | K2PtCl4 | KCl | 2.52E−03 |
| 230 | 2-(PROPYLAMINO)ETHANOL | 2 | K2PtCl4 | KCl | 2.06E−03 |
| 231 | 2-(TERT-BUTYLAMINO)ETHANOL | 2 | K2PtCl4 | KCl | 1.28E−03 |
| 232 | 1-AMINOMETHYL-1-CYCLOHEXANOL | 2 | K2PtCl4 | KCl | 1.49E−03 |
| 233 | TRANS-4-AMINOCYCLOHEXANOL | 2 | K2PtCl4 | KCl | 1.62E−03 |
| 234 | diethanolamine | 2 | K2PtCl4 | KCl | 2.71E−03 |
| 235 | 3-AMINO-1,2-PROPANEDIOL | 2 | K2PtCl4 | KCl | 3.49E−03 |
| 236 | 2-AMINO-2-METHYL-1,3-PROPANEDIOL | 2 | K2PtCl4 | KCl | 3.38E−03 |
| 237 | 2-AMINO-2-ETHYL-1,3-PROPANEDIOL | 2 | K2PtCl4 | KCl | 2.38E−03 |
| 238 | 3-AMINO-1-PROPANOL VINYL ETHER | 2 | K2PtCl4 | KCl | 2.25E−03 |
| 239 | ammonia | 1 | KPt(NH3)Cl3 | KCl | 3.35E−03 |
| 240 | methylamine | 1 | KPt(NH3)Cl3 | KCl | 2.78E−03 |
| 241 | ethylamine | 1 | KPt(NH3)Cl3 | KCl | 2.44E−03 |
| 242 | propylamine | 1 | KPt(NH3)Cl3 | KCl | 1.63E−03 |
| 243 | isopropylamine | 1 | KPt(NH3)Cl3 | KCl | 1.81E−03 |
| 244 | t-butylamine | 1 | KPt(NH3)Cl3 | KCl | 3.16E−03 |
| 245 | cyclopentylamine | 1 | KPt(NH3)Cl3 | KCl | 5.04E−03 |
| 246 | cyclohexylamine | 1 | KPt(NH3)Cl3 | KCl | 3.35E−03 |
| 247 | diethylamine | 1 | KPt(NH3)Cl3 | KCl | 2.76E−03 |
| 248 | diisopropylamine | 1 | KPt(NH3)Cl3 | KCl | 6.57E−04 |
| 249 | triethylamine | 1 | KPt(NH3)Cl3 | KCl | 1.31E−03 |
| 250 | N,N diisopropylethylamine | 1 | KPt(NH3)Cl3 | KCl | 2.17E−03 |
| 251 | ethylenediamine | 1 | KPt(NH3)Cl3 | KCl | 2.90E−03 |
| 252 | N,N dimethylethylenediamine | 1 | KPt(NH3)Cl3 | KCl | 2.22E−03 |
| 253 | 1,3 diaminopropane | 1 | KPt(NH3)Cl3 | KCl | 2.98E−03 |
| 254 | ammonia | 1 | KPt(NH3)Cl3 | KCl | 2.57E−03 |
| 255 | methylamine | 1 | KPt(NH3)Cl3 | KCl | 3.62E−03 |
| 256 | ethylamine | 1 | KPt(NH3)Cl3 | KCl | 2.95E−03 |
| 257 | propylamine | 1 | KPt(NH3)Cl3 | KCl | 2.59E−03 |
| 258 | isopropylamine | 1 | KPt(NH3)Cl3 | KCl | 3.02E−03 |
| 259 | ISOBUTYLAMINE | 1 | KPt(NH3)Cl3 | KCl | 3.04E−03 |
| 260 | t-butylamine | 1 | KPt(NH3)Cl3 | KCl | 1.95E−03 |
| 261 | sec-butylamine | 1 | KPt(NH3)Cl3 | KCl | 2.73E−03 |
| 262 | 1,2-DIMETHYLPROPYLAMINE | 1 | KPt(NH3)Cl3 | KCl | 3.20E−03 |
| 263 | 1-ETHYLPROPYLAMINE | 1 | KPt(NH3)Cl3 | KCl | 2.68E−03 |
| 264 | 1-methylbutylamine | 1 | KPt(NH3)Cl3 | KCl | 1.23E−03 |
| 265 | 2-methylbutylamine | 1 | KPt(NH3)Cl3 | KCl | 3.85E−03 |
| 266 | hexylamine | 1 | KPt(NH3)Cl3 | KCl | 2.68E−03 |
| 267 | heptylamine | 1 | KPt(NH3)Cl3 | KCl | 2.23E−03 |
| 268 | octylamine | 1 | KPt(NH3)Cl3 | KCl | 2.15E−03 |
| 269 | 1-METHYLHEPTYLAMINE | 1 | KPt(NH3)Cl3 | KCl | 2.41E−03 |
| 270 | 1,5-DIMETHYLHEXYLAMINE | 1 | KPt(NH3)Cl3 | KCl | 2.39E−03 |
| 271 | 2-ETHYLHEXYLAMINE | 1 | KPt(NH3)Cl3 | KCl | 2.21E−03 |
| 272 | decylamine | 1 | KPt(NH3)Cl3 | KCl | 1.32E−03 |
| 273 | TERT-OCTYLAMINE | 1 | KPt(NH3)Cl3 | KCl | 2.35E−03 |
| 274 | UNDECYLAMINE | 1 | KPt(NH3)Cl3 | KCl | 6.87E−04 |
| 275 | allylamine | 1 | KPt(NH3)Cl3 | KCl | 1.10E−03 |
| 276 | diethylamine | 1 | KPt(NH3)Cl3 | KCl | 2.14E−03 |
| 277 | dipropylamine | 1 | KPt(NH3)Cl3 | KCl | 1.99E−03 |
| 278 | diisopropylamine | 1 | KPt(NH3)Cl3 | KCl | 1.48E−03 |

TABLE 1-continued

| No. | Ligand(s) | Equiv. | Precursor | Leaving Group | Yld, g atm Pt |
|---|---|---|---|---|---|
| 279 | dibutylamine | 1 | KPt(NH3)Cl3 | KCl | 2.90E−03 |
| 280 | dipentylamine | 1 | KPt(NH3)Cl3 | KCl | 2.30E−03 |
| 281 | DIHEXYLAMINE | 1 | KPt(NH3)Cl3 | KCl | 1.38E−03 |
| 282 | DIOCTYLAMINE | 1 | KPt(NH3)Cl3 | KCl | 1.34E−03 |
| 283 | N-METHYLPROPYLAMINE | 1 | KPt(NH3)Cl3 | KCl | 2.19E−03 |
| 284 | N-METHYLISOPROPYLAMINE | 1 | KPt(NH3)Cl3 | KCl | 2.24E−03 |
| 285 | N-METHYLBUTYLAMINE | 1 | KPt(NH3)Cl3 | KCl | 2.80E−03 |
| 286 | N-METHYL-TERT-BUTYLAMINE | 1 | KPt(NH3)Cl3 | KCl | 1.41E−03 |
| 287 | N-METHYLHEXYLAMINE | 1 | KPt(NH3)Cl3 | KCl | 2.33E−03 |
| 288 | N-ETHYLMETHYLAMINE | 1 | KPt(NH3)Cl3 | KCl | 2.55E−03 |
| 289 | N-ETHYLISOPROPYLAMINE | 1 | KPt(NH3)Cl3 | KCl | 1.59E−03 |
| 290 | N-ETHYLBUTYLAMINE | 1 | KPt(NH3)Cl3 | KCl | 1.76E−03 |
| 291 | N-TERT-BUTYLISOPROPYLAMINE | 1 | KPt(NH3)Cl3 | KCl | 1.70E−03 |
| 292 | TRIETHYLAMINE | 1 | KPt(NH3)Cl3 | KCl | 2.35E−03 |
| 293 | TRIPROPYLAMINE | 1 | KPt(NH3)Cl3 | KCl | 2.55E−03 |
| 294 | TRIISOPROPYLAMINE | 1 | KPt(NH3)Cl3 | KCl | 2.77E−03 |
| 295 | TRIISOBUTYLAMINE | 1 | KPt(NH3)Cl3 | KCl | 1.71E−03 |
| 296 | TRIHEXYLAMINE | 1 | KPt(NH3)Cl3 | KCl | 1.30E−03 |
| 297 | TRIOCTYLAMINE | 1 | KPt(NH3)Cl3 | KCl | 1.49E−03 |
| 298 | TRIISOOCTYLAMINE | 1 | KPt(NH3)Cl3 | KCl | 2.08E−03 |
| 299 | TRIDECYLAMINE | 1 | KPt(NH3)Cl3 | KCl | 1.37E−03 |
| 300 | N,N diisopropyl ethylamine | 1 | KPt(NH3)Cl3 | KCl | 1.73E−03 |
| 301 | cyclopropylamine | 1 | KPt(NH3)Cl3 | KCl | 2.43E−03 |
| 302 | cyclobutylamine | 1 | KPt(NH3)Cl3 | KCl | 2.99E−03 |
| 303 | CYCLOPENTYLAMINE | 1 | KPt(NH3)Cl3 | KCl | 2.71E−03 |
| 304 | CYCLOHEXYLAMINE | 1 | KPt(NH3)Cl3 | KCl | 2.77E−03 |
| 305 | CYCLOHEPTYLAMINE | 1 | KPt(NH3)Cl3 | KCl | 2.99E−03 |
| 306 | CYCLOOCTYLAMINE | 1 | KPt(NH3)Cl3 | KCl | 2.36E−03 |
| 307 | CYCLODODECYLAMINE | 1 | KPt(NH3)Cl3 | KCl | 1.47E−03 |
| 308 | 2-METHYLCYCLOHEXYLAMINE | 1 | KPt(NH3)Cl3 | KCl | 1.80E−03 |
| 309 | 2,3-DIMETHYLCYCLOHEXYLAMINE | 1 | KPt(NH3)Cl3 | KCl | 1.76E−03 |
| 310 | ALLYLCYCLOHEXYLAMINE | 1 | KPt(NH3)Cl3 | KCl | 1.65E−03 |
| 311 | N-ALLYLCYCLOPENTYLAMINE | 1 | KPt(NH3)Cl3 | KCl | 1.83E−03 |
| 312 | N-METHYLCYCLOHEXYLAMINE | 1 | KPt(NH3)Cl3 | KCl | 2.31E−03 |
| 313 | N-ETHYLCYCLOHEXYLAMINE | 1 | KPt(NH3)Cl3 | KCl | 2.04E−03 |
| 314 | N-ISOPROPYLCYCLOHEXYLAMINE | 1 | KPt(NH3)Cl3 | KCl | 5.95E−04 |
| 315 | N-TERT-BUTYLCYCLOHEXYLAMINE | 1 | KPt(NH3)Cl3 | KCl | 1.74E−03 |
| 316 | (R)-(−)-1-CYCLOHEXYLETHYLAMINE | 1 | KPt(NH3)Cl3 | KCl | 3.25E−03 |
| 317 | (S)-(+)-1-CYCLOHEXYLETHYLAMINE | 1 | KPt(NH3)Cl3 | KCl | 2.54E−03 |
| 318 | DICYCLOHEXYLAMINE | 1 | KPt(NH3)Cl3 | KCl | 1.44E−03 |
| 319 | 1-AMINO-2-PROPANOL | 1 | KPt(NH3)Cl3 | KCl | 3.48E−03 |
| 320 | DL-2-AMINO-1-PROPANOL | 1 | KPt(NH3)Cl3 | KCl | 2.84E−03 |
| 321 | (R)-(−)-1-AMINO-2-PROPANOL | 1 | KPt(NH3)Cl3 | KCl | 3.23E−03 |
| 322 | (S)-(+)-1-AMINO-2-PROPANOL | 1 | KPt(NH3)Cl3 | KCl | 2.98E−03 |
| 323 | (R)-(−)-2-AMINO-1-PROPANOL | 1 | KPt(NH3)Cl3 | KCl | 5.93E−03 |
| 324 | (S)-(+)-2-AMINO-1-PROPANOL | 1 | KPt(NH3)Cl3 | KCl | 4.40E−03 |
| 325 | 3-AMINO-1-PROPANOL | 1 | KPt(NH3)Cl3 | KCl | 3.09E−03 |
| 326 | 2-AMINO-1-BUTANOL | 1 | KPt(NH3)Cl3 | KCl | 6.39E−03 |
| 327 | (R)-(−)-2-AMINO-1-BUTANOL | 1 | KPt(NH3)Cl3 | KCl | 3.59E−03 |
| 328 | (S)-(+)-2-AMINO-1-BUTANOL | 1 | KPt(NH3)Cl3 | KCl | 3.64E−03 |
| 329 | 4-AMINO-1-BUTANOL | 1 | KPt(NH3)Cl3 | KCl | 4.08E−03 |
| 330 | 5-AMINO-1-PENTANOL | 1 | KPt(NH3)Cl3 | KCl | 3.27E−03 |
| 331 | DL-2-AMINO-1-PENTANOL | 1 | KPt(NH3)Cl3 | KCl | 2.86E−03 |
| 332 | 6-AMINO-1-HEXANOL | 1 | KPt(NH3)Cl3 | KCl | 3.48E−03 |
| 333 | DL-2-AMINO-1-HEXANOL | 1 | KPt(NH3)Cl3 | KCl | 3.62E−03 |
| 334 | 2-AMINO-2-METHYL-1-PROPANOL | 1 | KPt(NH3)Cl3 | KCl | 3.85E−03 |
| 335 | 2-AMINO-3-METHYL-1-BUTANOL | 1 | KPt(NH3)Cl3 | KCl | 2.88E−03 |
| 336 | (R)-(−)-2-AMINO-3-METHYL-1-BUTANOL | 1 | KPt(NH3)Cl3 | KCl | 3.62E−03 |
| 337 | (S)-(+)-2-AMINO-3-METHYL-1-BUTANOL | 1 | KPt(NH3)Cl3 | KCl | 3.05E−03 |
| 338 | 6-AMINO-2-METHYL-2-HEPTANOL | 1 | KPt(NH3)Cl3 | KCl | 3.00E−03 |
| 339 | 2-(2-AMINOETHOXY)ETHANOL | 1 | KPt(NH3)Cl3 | KCl | 3.23E−03 |
| 340 | 2-(METHYLAMINO)ETHANOL | 1 | KPt(NH3)Cl3 | KCl | 3.34E−03 |
| 341 | 2-(PROPYLAMINO)ETHANOL | 1 | KPt(NH3)Cl3 | KCl | 2.95E−03 |
| 342 | 2-(TERT-BUTYLAMINO)ETHANOL | 1 | KPt(NH3)Cl3 | KCl | 5.95E−04 |
| 343 | 1-AMINOMETHYL-1-CYCLOHEXANOL | 1 | KPt(NH3)Cl3 | KCl | 2.36E−03 |
| 344 | TRANS-4-AMINOCYCLOHEXANOL | 1 | KPt(NH3)Cl3 | KCl | 2.40E−03 |
| 345 | diethanolamine | 1 | KPt(NH3)Cl3 | KCl | 2.77E−03 |
| 346 | 3-AMINO-1,2-PROPANEDIOL | 1 | KPt(NH3)Cl3 | KCl | 2.63E−03 |
| 347 | 2-AMINO-2-METHYL-1,3-PROPANEDIOL | 1 | KPt(NH3)Cl3 | KCl | 3.48E−03 |
| 348 | 2-AMINO-2-ETHYL-1,3-PROPANEDIOL | 1 | KPt(NH3)Cl3 | KCl | 3.43E−03 |
| 349 | 3-AMINO-1-PROPANOL VINYL ETHER | 1 | KPt(NH3)Cl3 | KCl | 2.93E−03 |
| 350 | ammonia + methylamine | 1 each | K2PtCl4 | KCl | 1.87E−03 |
| 351 | methylamine + methylamine | 1 each | K2PtCl4 | KCl | 2.76E−03 |
| 352 | ethylamine + methylamine | 1 each | K2PtCl4 | KCl | 2.24E−03 |
| 353 | propylamine + methylamine | 1 each | K2PtCl4 | KCl | 1.69E−03 |
| 354 | isopropylamine + methylamine | 1 each | K2PtCl4 | KCl | 1.42E−03 |
| 355 | ISOBUTYLAMINE+methylamine | 1 each | K2PtCl4 | KCl | 1.18E−03 |

TABLE 1-continued

| No. | Ligand(s) | Equiv. | Precursor | Leaving Group | Yld, g atm Pt |
|---|---|---|---|---|---|
| 356 | t-butylamine + methylamine | 1 each | K2PtCl4 | KCl | 1.38E−03 |
| 357 | sec-butylamine + methylamine | 1 each | K2PtCl4 | KCl | 1.69E−03 |
| 358 | 1,2-DIMETHYLPROPYLAMINE + methylamine | 1 each | K2PtCl4 | KCl | 1.87E−03 |
| 359 | 1-ETHYLPROPYLAMINE+methylamine | 1 each | K2PtCl4 | KCl | 2.05E−03 |
| 360 | 1-methylbutylamine + methylamine | 1 each | K2PtCl4 | KCl | 1.38E−03 |
| 361 | 2-methytbutylamine + methylamine | 1 each | K2PtCl4 | KCl | 1.46E−03 |
| 362 | hexylamine + methylamine | 1 each | K2PtCl4 | KCl | 1.04E−03 |
| 363 | heptylamine + methylamine | 1 each | K2PtCl4 | KCl | 1.34E−03 |
| 364 | octylamine + methylamine | 1 each | K2PtCl4 | KCl | 1.67E−03 |
| 365 | 1-METHYLHEPTYLAMINE+methylamine | 1 each | K2PtCl4 | KCl | 9.75E−04 |
| 366 | 1,5-DIMETHYLHEXYLAMINE + methylamine | 1 each | K2PtCl4 | KCl | 2.17E−03 |
| 367 | 2-ETHYLHEXYLAMINE+methylamine | 1 each | K2PtCl4 | KCl | 3.03E−03 |
| 368 | decylamine + methylamine | 1 each | K2PtCl4 | KCl | 1.44E−03 |
| 369 | TERT-OCTYLAMINE+methylamine | 1 each | K2PtCl4 | KCl | 2.07E−03 |
| 370 | UNDECYLAMINE+methylamine | 1 each | K2PtCl4 | KCl | 1.48E−03 |
| 371 | allylamine + methylamine | 1 each | K2PtCl4 | KCl | 1.63E−04 |
| 372 | diethylamine + methylamine | 1 each | K2PtCl4 | KCl | 2.05E−03 |
| 373 | dipropylamine + methylamine | 1 each | K2PtCl4 | KCl | 2.68E−03 |
| 374 | diisopropylamine + methylamine | 1 each | K2PtCl4 | KCl | 2.26E−03 |
| 375 | dibutylamine + methylamine | 1 each | K2PtCl4 | KCl | 2.11E−03 |
| 376 | dipentylamine + methylamine | 1 each | K2PtCl4 | KCl | 2.21E−03 |
| 377 | DIHEXYLAMINE+methylamine | 1 each | K2PtCl4 | KCl | 1.26E−03 |
| 378 | DIOCTYLAMINE+methylamine | 1 each | K2PtCl4 | KCl | 6.71E−04 |
| 379 | N-METHYLPROPYLAMINE+methylamine | 1 each | K2PtCl4 | KCl | 2.56E−03 |
| 380 | N-METHYLISOPROPYLAMINE + methylamine | 1 each | K2PtCl4 | KCl | 2.32E−03 |
| 381 | N-METHYLBUTYLAMINE+methylamine | 1 each | K2PtCl4 | KCl | 1.85E−03 |
| 382 | N-METHYL-TERT-BUTYLAMINE + methylamine | 1 each | K2PtCl4 | KCl | 2.66E−03 |
| 383 | N-METHYLHEXYLAMINE+methylamine | 1 each | K2PtCl4 | KCl | 3.31E−03 |
| 384 | N-ETHYLMETHYLAMINE+methylamine | 1 each | K2PtCl4 | KCl | 2.28E−03 |
| 385 | N-ETHYLISOPROPYLAMINE+methylamine | 1 each | K2PtCl4 | KCl | 2.11E−03 |
| 386 | N-ETHYLBUTYLAMINE+methylamine | 1 each | K2PtCl4 | KCl | 2.95E−03 |
| 387 | N-TERT-BUTYLISOPROPYLAMINE + methylamine | 1 each | K2PtCl4 | KCl | 3.11E−03 |
| 388 | TRIETHYLAMINE+methylamine | 1 each | K2PtCl4 | KCl | 1.79E−03 |
| 389 | TRIPROPYLAMINE+methylamine | 1 each | K2PtCl4 | KCl | 2.34E−03 |
| 390 | TRIISOPROPYLAMINE+methylamine | 1 each | K2PtCl4 | KCl | 2.34E−03 |
| 391 | TRIISOBUTYLAMINE+methylamine | 1 each | K2PtCl4 | KCl | 2.64E−03 |
| 392 | TRIHEXYLAMINE+methylamine | 1 each | K2PtCl4 | KCl | 3.35E−03 |
| 393 | TRIOCTYLAMINE+methylamine | 1 each | K2PtCl4 | KCl | 2.82E−03 |
| 394 | TRIISOOCTYLAMINE+methylamine | 1 each | K2PtCl4 | KCl | 3.01E−03 |
| 395 | TRIDECYLAMINE+methylamine | 1 each | K2PtCl4 | KCl | 1.71E−03 |
| 396 | N,N diisopropyl ethylamine + methylamine | 1 each | K2PtCl4 | KCl | 3.70E−03 |
| 397 | cyclopropylamine + methylamine | 1 each | K2PtCl4 | KCl | 2.99E−03 |
| 398 | cyclobutylamine + methylamine | 1 each | K2PtCl4 | KCl | 4.36E−03 |
| 399 | CYCLOPENTYLAMINE+methylamine | 1 each | K2PtCl4 | KCl | 4.16E−03 |
| 400 | CYCLOHEXYLAMINE+methylamine | 1 each | K2PtCl4 | KCl | 3.98E−03 |
| 401 | CYCLOHEPTYLAMINE+methylamine | 1 each | K2PtCl4 | KCl | 3.52E−03 |
| 402 | CYCLOOCTYLAMINE+methylamine | 1 each | K2PtCl4 | KCl | 2.83E−03 |
| 403 | CYCLODODECYLAMINE+methylamine | 1 each | K2PtCl4 | KCl | 3.17E−03 |
| 404 | 2-METHYLCYCLOHEXYLAMINE + methylamine | 1 each | K2PtCl4 | KCl | 3.40E−03 |
| 405 | 2,3-DIMETHYLCYCLOHEXYLAMINE + methylamine | 1 each | K2PtCl4 | KCl | 4.18E−03 |
| 406 | ALLYLCYCLOHEXYLAMINE+methylamine | 1 each | K2PtCl4 | KCl | 3.58E−03 |
| 407 | N-ALLYLCYCLOPENTYLAMINE + methylamine | 1 each | K2PtCl4 | KCl | 2.71E−03 |
| 408 | N-METHYLCYCLOHEXYLAMINE + methylamine | 1 each | K2PtCl4 | KCl | 2.35E−03 |
| 409 | N-ETHYLCYCLOHEXYLAMINE + methylamine | 1 each | K2PtCl4 | KCl | 3.18E−03 |
| 410 | N-ISOPROPYLCYCLOHEXYLAMINE + methylamine | 1 each | K2PtCl4 | KCl | 2.39E−03 |
| 411 | N-TERT-BUTYLCYCLOHEXYLAMINE + methylamine | 1 each | K2PtCl4 | KCl | 1.39E−03 |
| 412 | (R(-(−)-1-CYCLOHEXYLETHYLAMINE + methylamine | 1 each | K2PtCl4 | KCl | 3.28E−03 |
| 413 | (S)-(+)-1-CYCLOHEXYLETHYLAMINE + methylamine | 1 each | K2PtCl4 | KCl | 2.29E−03 |
| 414 | DICYCLOHEXYLAMINE+methylamine | 1 each | K2PtCl4 | KCl | 2.45E−03 |
| 415 | 1-AMINO-2-PROPANOL + methylamine | 1 each | K2PtCl4 | KCl | 4.02E−03 |
| 416 | DL-2-AMINO-1-PROPANOL + methylamine | 1 each | K2PtCl4 | KCl | 2.85E−03 |
| 417 | (R)-(−)-1-AMINO-2-PROPANOL + methylamine | 1 each | K2PtCl4 | KCl | 4.12E−03 |

TABLE 1-continued

| No. | Ligand(s) | Equiv. | Precursor | Leaving Group | Yld, g atm Pt |
|---|---|---|---|---|---|
| 418 | (S)-(+)-1-AMINO-2-PROPANOL + methylamine | 1 each | K2PtCl4 | KCl | 2.29E−03 |
| 419 | (R)-(−)-2-AMINO-1-PROPANOL + methylamine | 1 each | K2PtCl4 | KCl | 3.74E−03 |
| 420 | (S)-(+)-2-AMINO-1-PROPANOL + methylamine | 1 each | K2PtCl4 | KCl | 4.92E−03 |
| 421 | 3-AMINO-1-PROPANOL + methylamine | 1 each | K2PtCl4 | KCl | 4.50E−03 |
| 422 | 2-AMINO-1-BUTANOL + methylamine | 1 each | K2PtCl4 | KCl | 3.56E−03 |
| 423 | (R)-(−)-2-AMINO-1-BUTANOL + methylamine | 1 each | K2PtCl4 | KCl | 3.84E−03 |
| 424 | (S)-(+)-2-AMINO-1-BUTANOL + methylamine | 1 each | K2PtCl4 | KCl | 4.24E−03 |
| 425 | 4-AMINO-1-BUTANOL + methylamine | 1 each | K2PtCl4 | KCl | 3.50E−03 |
| 426 | 5-AMINO-1-PENTANOL + methylamine | 1 each | K2PtCl4 | KCl | 4.62E−03 |
| 427 | DL-2-AMINO-1-PENTANOL + methylamine | 1 each | K2PtCl4 | KCl | 3.15E−03 |
| 428 | 6-AMINO-1-HEXANOL + methylamine | 1 each | K2PtCl4 | KCl | 4.50E−03 |
| 429 | DL-2-AMINO-1-HEXANOL + methylamine | 1 each | K2PtCl4 | KCl | 4.52E−03 |
| 430 | 2-AMINO-2-METHYL-1-PROPANOL + methylamine | 1 each | K2PtCl4 | KCl | 3.98E−03 |
| 431 | 2-AMINO-3-METHYL-1-BUTANOL + methylamine | 1 each | K2PtCl4 | KCl | 3.82E−03 |
| 432 | (R)-(−)-2-AMINO-3-METHYL-1-BUTANOL + methylamine | 1 each | K2PtCl4 | KCl | 3.62E−03 |
| 433 | (S)-(+)-2-AMINO-3-METHYL-1-BUTANOL + methylamine | 1 each | K2PtCl4 | KCl | 3.88E−03 |
| 434 | 6-AMINO-2-METHYL-2-HEPTANOL + methylamine | 1 each | K2PtCl4 | KCl | 3.38E−03 |
| 435 | 2-(2-AMINOETHOXY)ETHANOL + methylamine | 1 each | K2PtCl4 | KCl | 4.06E−03 |
| 436 | 2-(METHYLAMINO)ETHANOL + methylamine | 1 each | K2PtCl4 | KCl | 3.24E−03 |
| 437 | 2-(PROPYLAMINO)ETHANOL + methylamine | 1 each | K2PtCl4 | KCl | 3.36E−03 |
| 438 | 2-(TERT-BUTYLAMINO)ETHANOL + methylamine | 1 each | K2PtCl4 | KCl | 2.73E−03 |
| 439 | TRANS-4-AMINOCYCLOHEXANOL + methylamine | 1 each | K2PtCl4 | KCl | 2.79E−03 |
| 440 | diethanolamine + methylamine | 1 each | K2PtCl4 | KCl | 3.72E−03 |
| 441 | 3-AMINO-1,2-PROPANEDIOL + methylamine | 1 each | K2PtCl4 | KCl | 2.34E−03 |
| 442 | 2-AMINO-2-METHYL-1,3-PROPANEDIOL + methylamine | 1 each | K2PtCl4 | KCl | 2.20E−03 |
| 443 | 2-AMINO-2-ETHYL-1,3-PROPANEDIOL + methylamine | 1 each | K2PtCl4 | KCl | 2.10E−03 |
| 444 | 3-AMINO-1-PROPANOL VINYL ETHER + methylamine | 1 each | K2PtCl4 | KCl | 2.10E−03 |
| 445 | ammonia | 2 | K2PtCl4 | KCl | 1.73E−03 |
| 446 | pyridine | 2 | K2PtCl4 | KCl | 2.04E−03 |
| 447 | 2-propylpyridine | 2 | K2PtCl4 | KCl | 2.22E−03 |
| 448 | 2-ethylpyridine | 2 | K2PtCl4 | KCl | 1.13E−03 |
| 449 | 2-(2-aminoethylamino)-5-nitropyridine | 2 | K2PtCl4 | KCl | 1.63E−03 |
| 450 | 2-amino-3-nitropyridine | 2 | K2PtCl4 | KCl | 7.32E−04 |
| 451 | 2,3-dihydroxypyridine | 2 | K2PtCl4 | KCl | 1.25E−04 |
| 452 | 2-amino-3-hydroxypyridine | 2 | K2PtCl4 | KCl | 3.93E−04 |
| 453 | 2-amino-5-bromopyridine | 2 | K2PtCl4 | KCl | 5.00E−03 |
| 454 | 2-amino-4-picoline | 2 | K2PtCl4 | KCl | 1.27E−03 |
| 455 | 2,3-diaminopyridine | 2 | KtPtCl4 | KCl | 1.29E−03 |
| 456 | 2-(2-hydroxyethyl)pyridine | 2 | K2PtCl4 | KCl | 1.41E−03 |
| 457 | 2-iminopiperidine HCl | 2 | K2PtCl4 | KCl | 3.75E−04 |
| 458 | 2-pyridine aldoxime methochloride | 2 | K2PtCl4 | KCl | 7.15E−05 |
| 459 | 1,2,3,6-tetrahydropyridine | 2 | K2PtCl4 | KCl | 3.39E−04 |
| 460 | 2-amino-3,5-dichloropyridine | 2 | K2PtCl4 | KCl | 2.29E−03 |
| 461 | 2,4,6-collidine | 2 | K2PtCl4 | KCl | 3.93E−03 |
| 462 | 2,6-pyridine dicarbonyl dichloride | 2 | K2PtCl4 | KCl | 1.61E−03 |
| 463 | 2,6-lutidine alpha-2,3-diol | 2 | K2PtCl4 | KCl | 7.15E−05 |
| 464 | 2-amino-3-bentyloxypyridine | 2 | K2PtCl4 | KCl | 3.93E−04 |
| 465 | 2-butoxypyridine | 2 | K2PtCl4 | KCl | 1.82E−03 |
| 466 | 2,5-lutidine | 2 | K2PtCl4 | KCl | 1.57E−03 |
| 467 | 2-chloro-6-methoxypyridine | 2 | K2PtCl4 | KCl | 1.43E−04 |
| 468 | 2,6-pyridine dimethanol | 2 | K2PtCl4 | KCl | 5.36E−05 |
| 469 | 2-picolyl chloride HCl | 2 | K2PtCl4 | KCl | 3.77E−03 |
| 470 | 2,4-dihydroxypyridine | 2 | K2PtCl4 | KCl | 1.07E−04 |
| 471 | 2-amino-3,5-dibromopyridine | 2 | K2PtCl4 | KCl | 1.54E−03 |
| 472 | 2-hydroxy-3-nitropyridine | 2 | K2PtCl4 | KCl | 2.32E−04 |
| 473 | 2,6-dichloro-3-nitropyridine | 2 | K2PtCl4 | KCl | 1.61E−03 |
| 474 | 2,5-dichloropyridine | 2 | K2PtCl4 | KCl | 1.09E−03 |
| 475 | 2-benzyl aminopyridine | 2 | K2PtCl4 | KCl | 3.39E−04 |
| 476 | 2,3-cyclododecenopyridine | 2 | K2PtCl4 | KCl | 7.68E−04 |
| 477 | 2,3-cycloheptenopyridine | 2 | K2PtCl4 | KCl | 1.41E−03 |
| 478 | 2-(methylamino)pyridine | 2 | K2PtCl4 | KCl | 2.11E−03 |

TABLE 1-continued

| No. | Ligand(s) | Equiv. | Precursor | Leaving Group | Yld, g atm Pt |
|---|---|---|---|---|---|
| 479 | 2,6-di-t-butylpyridine | 2 | K2PtCl4 | KCl | 1.07E−04 |
| 480 | 2-chloro3,5-dinitropyridine | 2 | K2PtCl4 | KCl | 2.86E−04 |
| 481 | 2,6-difluoropyridine | 2 | K2PtCl4 | KCl | 7.15E−05 |
| 482 | 2,4,6-tri-t-butylpyridine | 2 | K2PtCl4 | KCl | 3.57E−05 |
| 483 | 2,6-di-t-butyl-4-methylpyridine | 2 | K2PtCl4 | KCl | 5.36E−05 |
| 484 | 2,6-pyridine dicarboxaldehyde | 2 | K2PtCl4 | KCl | 9.47E−05 |
| 485 | 2-bromo-5-methylpyridine | 2 | K2PtCl4 | KCl | 9.83E−04 |
| 486 | 2,4,6-collidine p-toluenesulfonate | 2 | K2PtCl4 | KCl | 1.07E−04 |
| 487 | 2-amino-4-methyl-3-nitropyridine | 2 | K2PtCl4 | KCl | 4.47E−04 |
| 488 | 2-amino-4-methyl-5-nitropyridine | 2 | K2PtCl4 | KCl | 2.50E−04 |
| 489 | 2-hydroxy-4-methyl-5-nitropyridine | 2 | K2PtCl4 | KCl | 8.93E−05 |
| 490 | 2-chloro-4-methyl-5-nitropyridine | 2 | K2PtCl4 | KCl | 9.94E−04 |
| 491 | 2,4-bis(5,6-biphenyl-1,2,4-triaziN-3-yl)pyridine | 2 | K2PtCl4 | KCl | 5.52E−05 |
| 492 | 2,3,5,6-tetrafluoro-4-methylpyridine | 2 | K2PtCl4 | KCl | 9.20E−05 |
| 493 | 2-pyridineethane sulfonic acid | 2 | K2PtCl4 | KCl | 2.94E−04 |
| 494 | 2-chloro-4-methyl-3-nitropyridine | 2 | K2PtCl4 | KCl | 5.34E−04 |
| 495 | 2,3,5,6-tetrafluoropyridine | 2 | K2PtCl4 | KCl | 7.36E−05 |
| 496 | 2-(2-isopropoxyethyl)pyridine | 2 | K2PtCl4 | KCl | 2.19E−03 |
| 497 | 2-bromo-5-nitropyridine | 2 | K2PtCl4 | KCl | 1.10E−04 |
| 498 | 2,3,5,6-tetrafluoro-4-pyridine carbonitrile | 2 | K2PtCl4 | KCl | 1.10E−04 |
| 499 | 2-benzylamino-6-methylpyridine | 2 | K2PtCl4 | KCl | 1.29E−04 |
| 500 | 2-bromo-4-methylpyridine | 2 | K2PtCl4 | KCl | 2.74E−03 |
| 501 | 2-chloro-6-methyl nicotinic acid | 2 | K2PtCl4 | KCl | 5.15E−04 |
| 502 | 1H-1,2,3-triazolo(4,5-b)pyridine | 2 | K2PtCl4 | KCl | 1.10E−04 |
| 503 | 2-chloro-6-methyl-3-pyridine carbonitrile | 2 | K2PtCl4 | KCl | 2.21E−04 |
| 504 | 2-hydroxy-4-methylpyridine | 2 | K2PtCl4 | KCl | 5.34E−04 |
| 505 | 2-amino-3-chloro-5-(trifluoromethyl)pyridine | 2 | K2PtCl4 | KCl | 1.38E−03 |
| 506 | 2-chloro-5-(trifluoromethyl)pyridine | 2 | K2PtCl4 | KCl | 9.39E−04 |
| 507 | 2,3-dichloro-5-(trifluoromethyl)pyridine | 2 | K2PtCl4 | KCl | 3.86E−04 |
| 508 | 2-amino-5-bromo-3-nitropyridine | 2 | K2PtCl4 | KCl | 3.86E−04 |
| 509 | 2,6-bis(2-benzimidazolyl)pyridine | 2 | K2PtCl4 | KCl | 3.13E−04 |
| 510 | 2,6-dihydroxy-4-methyl-3-pyridine carbonitrile | 2 | K2PtCl4 | KCl | 1.66E−04 |
| 511 | 2,3,5-trichloropyridine | 2 | K2PtCl4 | KCl | 4.97E−04 |
| 512 | 2,6-dimethyl-3,5-pyridine | 2 | K2PtCl4 | KCl | 3.68E−04 |
| 513 | 2-(4-(dimethylamino)styryl)pyridine | 2 | K2PtCl4 | KCl | 1.07E−03 |
| 514 | 2-(trifluoroacetoxy)pyridine | 2 | K2PtCl4 | KCl | 5.52E−04 |
| 515 | 2-amino-5-oxo-5H-(1)benzopyrano(2,3-b)pyridine-3-carbonitrile | 2 | K2PtCl4 | KCl | 3.31E−04 |
| 516 | 2-amino-7-methyl-5-oxo-5H-(1)benzopyrano(2,3-b)pyridine-3-carbonitrile | 2 | K2PtCl4 | KCl | 2.21E−04 |
| 517 | 2-amino-7-ethyl-5-oxo-5H-(1)benzopyrano(2,3-b)pyridine-3-carbonitrile | 2 | K2PtCl4 | KCl | 3.50E−04 |
| 518 | 2-amino-7-isopropyl-5-oxo-5H-(1)benzopyrano(2,3-b)pyridine-3-carbonitrile | 2 | K2PtCl4 | KCl | 2.94E−04 |
| 519 | 2-amino-7-chloro-5-oxo-5H-(1)benzopyrano(2,3-b)pyridine-3-carbonitrile | 2 | K2PtCl4 | KCl | 2.21E−04 |
| 520 | 2-amino-7-bromo-5-oxo-5H-(1)benzopyrano(2,3-b)pyridine-3-carbonitrile | 2 | K2PtCl4 | KCl | 2.76E−04 |
| 521 | 2-amino-7,9-dimethyl-5-oxo-5H-(1)benzopyrano(2,3-b)pyridine-3-carbonitrile | 2 | K2PtCl4 | KCl | 3.50E−04 |
| 522 | 2(N,N-bis(trifluoromethylsulfonyl)amino)pyridine | 2 | K2PtCl4 | KCl | 3.50E−04 |
| 523 | 2(N,N-bis(trifluoromethylsulfonyl)amino)-5-chloropyridine | 2 | K2PtCl4 | KCl | 4.23E−04 |
| 524 | 2,6-bis(chloromethyl)pyridine | 2 | K2PtCl4 | KCl | 3.31E−04 |
| 525 | 2,6-bis(bromomethyl)pyridine | 2 | K2PtCl4 | KCl | 5.34E−04 |
| 526 | 2,6-bis((4s)-ispropyl-2-oxazoliN-2-yl)pyridine | 2 | K2PtCl4 | KCl | 1.09E−03 |
| 527 | 1',3'-dihydrospiro(cyclohexane-1',2'-(2H)imidazo(4,5-b)pyridine) | 2 | K2PtCl4 | KCl | 5.52E−04 |
| 528 | 2-bromo-6-methylpyridine | 2 | K2PtCl4 | KCl | 6.07E−04 |
| 529 | 2,6-diamino-3-nitrosopyridine | 2 | K2PtCl4 | KCl | 7.18E−04 |
| 530 | 2-bromo-3-methylpyridine | 2 | K2PtCl4 | KCl | 1.58E−03 |
| 531 | (R)-(+)-alpha-methyl-4-pyridine methanol | 2 | K2PtCl4 | KCl | 3.59E−03 |
| 532 | 2-(3-sulfobenzoyl)pyridine 2-pyridyl hydrazone | 2 | K2PtCl4 | KCl | 6.26E−04 |
| 533 | 2-acetylpyridine | 2 | K2PtCl4 | KCl | 6.07E−04 |
| 534 | 2-amino-5-chloropyridine | 2 | K2PtCl4 | KCl | 2.06E−03 |
| 535 | 2-amine-4,6-dimethylpyridine | 2 | K2PtCl4 | KCl | 1.87E−03 |
| 536 | 2-(2-aminomethyl)pyridine | 2 | K2PtCl4 | KCl | 3.08E−03 |
| 537 | 2-(2-aminoethyl)pyridine | 2 | K2PtCl4 | KCl | 2.74E−03 |
| 538 | 2-amino-5-nitropyridine | 2 | K2PtCl4 | KCl | 2.05E−04 |
| 539 | 2-amino-3-picoline | 2 | K2PtCl4 | KCl | 2.45E−03 |
| 540 | 2-(5,6-bis(4-sulfophenyl)-1,2,4-triaziN-3-3yl)-4-(4-sulfophenyl)pyridine | 2 | K2PtCl4 | KCl | 5.13E−04 |
| 541 | ammonia | 1 | KPt(NH3)Cl3 | KCl | 2.08E−04 |
| 542 | pyridine | 1 | KPt(NH3)Cl3 | KCl | 2.20E−03 |
| 543 | 2-propylpyridine | 1 | KPt(NH3)Cl3 | KCl | 3.60E−03 |
| 544 | 2-ethylpyridine | 1 | KPt(NH3)Cl3 | KCl | 3.22E−03 |

TABLE 1-continued

| No. | Ligand(s) | Equiv. | Precursor | Leaving Group | Yld, g atm Pt |
|---|---|---|---|---|---|
| 545 | 2-(2-aminoethylamino)-5-nitropyridine | 1 | KPt(NH3)Cl3 | KCl | 3.22E–03 |
| 546 | 2-amino-3-nitropyridine | 1 | KPt(NH3)Cl3 | KCl | 1.73E–03 |
| 547 | 2,3-dihydroxypyridine | 1 | KPt(NH3)Cl3 | KCl | 2.79E–03 |
| 548 | 2-amino-3-hydroxypyridine | 1 | KPt(NH3)Cl3 | KCl | 3.43E–03 |
| 549 | 2-amino-5-bromopyridine | 1 | KPt(NH3)Cl3 | KCl | 3.39E–03 |
| 550 | 2-amino-4-picoline | 1 | KPt(NH3)Cl3 | KCl | 2.87E–03 |
| 551 | 2,3-diaminopyridine | 1 | KPt(NH3)Cl3 | KCl | 2.00E–03 |
| 552 | 2-(2-hydroxyethyl)pyridine | 1 | KPt(NH3)Cl3 | KCl | 2.31E–03 |
| 553 | 2-iminopiperidine HCl | 1 | KPt(NH3)Cl3 | KCl | 1.52E–03 |
| 554 | 2-pyridine aldoxime methochloride | 1 | KPt(NH3)Cl3 | KCl | 3.18E–03 |
| 555 | 1,2,3,6-tetrahydropyridine | 1 | KPt(NH3)Cl3 | KCl | 3.18E–03 |
| 556 | 2-amino-3,5-dichloropyridine | 1 | KPt(NH3)Cl3 | KCl | 5.10E–03 |
| 557 | 2,4,6-collidine | 1 | KPt(NH3)Cl3 | KCl | 5.97E–03 |
| 558 | 2,6-pyridine dicarbonyl dichloride | 1 | KPt(NH3)Cl3 | KCl | 5.57E–03 |
| 559 | 2,6-lutidine alpha-2,3-diol | 1 | KPt(NH3)Cl3 | KCl | 5.53E–03 |
| 560 | 2-amino-3-benzyloxypyridine | 1 | KPt(NH3)Cl3 | KCl | 4.58E–03 |
| 561 | 2-butoxypyridine | 1 | KPt(NH3)Cl3 | KCl | 3.85E–03 |
| 562 | 2,5-lutidine | 1 | KPt(NH3)Cl3 | KCl | 2.97E–03 |
| 563 | 2-chloro-6-methoxypyridine | 1 | KPt(NH3)Cl3 | KCl | 3.18E–03 |
| 564 | 2,6-pyridine dimethanol | 1 | KPt(NH3)Cl3 | KCl | 1.52E–03 |
| 565 | 2-picolyl chloride HCl | 1 | KPt(NH3)Cl3 | KCl | 1.10E–03 |
| 566 | 2,4-dihydroxypyridine | 1 | KPt(NH3)Cl3 | KCl | 4.16E–05 |
| 567 | 2-amino-3,5-dibromopyridine | 1 | KPt(NH3)Cl3 | KCl | 6.24E–05 |
| 568 | 2-hydroxy-3-nitropyridine | 1 | KPt(NH3)Cl3 | KCl | 4.16E–05 |
| 569 | 2,6-dichloro-3-nitropyridine | 1 | KPt(NH3)Cl3 | KCl | 6.24E–05 |
| 570 | 2,5-dichloropyridine | 1 | KPt(NH3)Cl3 | KCl | 7.90E–04 |
| 571 | 2-benzyl aminopyridine | 1 | KPt(NH3)Cl3 | KCl | 3.43E–03 |
| 572 | 2,3-cyclododecenopyridine | 1 | KPt(NH3)Cl3 | KCl | 1.85E–03 |
| 573 | 2,3-cycloheptenopyridine | 1 | KPt(NH3)Cl3 | KCl | 3.45E–03 |
| 574 | 2-(methylamino)pyridine | 1 | KPt(NH3)Cl3 | KCl | 3.10E–03 |
| 575 | 2,6-di-t-butylpyridine | 1 | KPt(NH3)Cl3 | KCl | 2.08E–03 |
| 576 | 2-chloro3,5-dinitropyridine | 1 | KPt(NH3)Cl3 | KCl | 3.35E–03 |
| 577 | 2,6-Difluoropyridine | 1 | KPt(NH3)Cl3 | KCl | 2.68E–03 |
| 578 | 2,4,6-tri-t-butylpyridine | 1 | KPt(NH3)Cl3 | KCl | 1.06E–03 |
| 579 | 2,6-di-t-butyl-4-methylpyridine | 1 | KPt(NH3)Cl3 | KCl | 1.48E–03 |
| 580 | 2,6-pyridine dicarboxaldehyde | 1 | KPt(NH3)Cl3 | KCl | 3.49E–03 |
| 581 | 2-bromo-5-methylpyridine | 1 | KPt(NH3)Cl3 | KCl | 3.46E–03 |
| 582 | 2,4,6-collidine p-toluenesulfonate | 1 | KPt(NH3)Cl3 | KCl | 3.28E–03 |
| 583 | 2-amino-4-methyl-3-nitropyridine | 1 | KPt(NH3)Cl3 | KCl | 3.30E–03 |
| 584 | 2-amino-4-methyl-5-nitropyridine | 1 | KPt(NH3)Cl3 | KCl | 3.82E–03 |
| 585 | 2-hydroxy-4-methyl-5-nitropyridine | 1 | KPt(NH3)Cl3 | KCl | 3.97E–03 |
| 586 | 2-chloro-4-methyl-5-nitropyridine | 1 | KPt(NH3)Cl3 | KCl | 3.15E–03 |
| 587 | 2,4-bis(5,6-diphenyl-1,2,4-triaziN-3-yl)pyridine | 1 | KPt(NH3)Cl3 | KCl | 3.15E–03 |
| 588 | 2,3,5,6-tetrafluoro-4-methylpyridine | 1 | KPt(NH3)Cl3 | KCl | 1.53E–03 |
| 589 | 2-pyridineethane sulfonic acid | 1 | KPt(NH3)Cl3 | KCl | 3.62E–03 |
| 590 | 2-chloro-4-methyl-3-nitropyridine | 1 | KPt(NH3)Cl3 | KCl | 2.46E–03 |
| 591 | 2,3,5,6-tetrafluoropyridine | 1 | KPt(NH3)Cl3 | KCl | 3.46E–03 |
| 592 | 2-(2-isopropoxyethyl)pyridine | 1 | KPt(NH3)Cl3 | KCl | 3.38E–03 |
| 593 | 2-bromo-5-nitropyridine | 1 | KPt(NH3)Cl3 | KCl | 2.89E–03 |
| 594 | 2,3,5,6-tetrafluoro-4-pyridine carbonitrile | 1 | KPt(NH3)Cl3 | KCl | 3.03E–03 |
| 595 | 2-benzylamino-6-methylpyridine | 1 | KPt(NH3)Cl3 | KCl | 3.09E–03 |
| 596 | 2-bromo-4-methylpyridine | 1 | KPt(NH3)Cl3 | KCl | 2.40E–03 |
| 597 | 2-chloro-6-methyl nitotinic acid | 1 | KPt(NH3)Cl3 | KCl | 4.05E–03 |
| 598 | 1H-1,2,3-triazolo(4,5-b)pyridine | 1 | KPt(NH3)Cl3 | KCl | 1.95E–03 |
| 599 | 2-chloro-6-methyl-3-pyridine carbonitrile | 1 | KPt(NH3)Cl3 | KCl | 3.42E–03 |
| 600 | 2-hydroxy-4-methylpyridine | 1 | KPt(NH3)Cl3 | KCl | 3.36E–03 |
| 601 | 2-amino-3-chloro-5-(trifluoromethyl)pyridine | 1 | KPt(NH3)Cl3 | KCl | 3.72E–03 |
| 602 | 2-chloro-5-(trifluoromethyl)pyridine | 1 | KPt(NH3)Cl3 | KCl | 3.64E–03 |
| 603 | 2,3-dichloro-5-(trifluoromethyl)pyridine | 1 | KPt(NH3)Cl3 | KCl | 2.77E–03 |
| 604 | 2-amino-5-bromo-3-nitropyridine | 1 | KPt(NH3)Cl3 | KCl | 3.26E–03 |
| 605 | 2,6-bis(2-benzimidazolyl)pyridine | 1 | KPt(NH3)Cl3 | KCl | 2.38E–03 |
| 606 | 2,6-dihydroxy-4-methyl-3-pyridine carbonitrile | 1 | KPt(NH3)Cl3 | KCl | 2.40E–03 |
| 607 | 2,3,5-trichloropyridine | 1 | KPt(NH3)Cl3 | KCl | 1.87E–03 |
| 608 | 2,6-dimethyl-3,5-pyridine | 1 | KPt(NH3)Cl3 | KCl | 2.06E–03 |
| 609 | 2-(4-(dimethylamino)styryl)pyridine | 1 | KPt(NH3)Cl3 | KCl | 2.97E–03 |
| 610 | 2-(trifluoroacetoxy)pyridine | 1 | KPt(NH3)Cl3 | KCl | 5.90E–04 |
| 611 | 2-amino-5-oxo-5H-(1)benzopyrano(2,3-b)pyridine-3-carbonitrile | 1 | KPt(NH3)Cl3 | KCl | 2.56E–03 |
| 612 | 2-amino-7-methyl-5-oxo-5H-(I)benzopyrano(2,3-b)pyridine-3-carbonitrile | 1 | KPt(NH3)Cl3 | KCl | 2.58E–03 |
| 613 | 2-amino-7-ethyl-5-oxo-5H-(I)benzopyrano(2,3-b)pyridine-3-carbonitrile | 1 | KPt(NH3)Cl3 | KCl | 2.77E–03 |
| 614 | 2-amino-7-isopropyl-5-oxo-5H-(1)benzopyrano(2,3-b)pyridine-3-carbonitrile | 1 | KPt(NH3)Cl3 | KCl | 2.99E–03 |
| 615 | 2-amino-7-chloro-5-oxo-5H-(1)benzopyrano(2,3-b)pyridine-3-carbonitrile | 1 | KPt(NH3)Cl3 | KCl | 3.52E–03 |

TABLE 1-continued

| No. | Ligand(s) | Equiv. | Precursor | Leaving Group | Yld, g atm Pt |
|---|---|---|---|---|---|
| 616 | 2-amino-7-bromo-5-oxo-5H-(1)benzopyrano(2,3-b)pyridine-3-carbonitrile | 1 | KPt(NH3)Cl3 | KCl | 3.70E−03 |
| 617 | 2-amino-7,9-dimethyl-5-oxo-5H-(I)benzopyrano(2,3-b)pyridine-3-carbonitrile | 1 | KPt(NH3)Cl3 | KCl | 3.44E−03 |
| 618 | 2(N,N-bis(trifluoromethylsulfonyl)amino)pyridine | 1 | KPt(NH3)Cl3 | KCl | 3.85E−03 |
| 619 | 2(N,N-bis(trifluoromethylsulfonyl)amino)-5-chloropyridine | 1 | KPt(NH3)Cl3 | KCl | 3.15E−03 |
| 620 | 2,6-bis(chloromethyl)pyridine | 1 | KPt(NH3)Cl3 | KCl | 2.12E−03 |
| 621 | 2,6-bis(bromomethyl)pyridine | 1 | KPt(NH3)Cl3 | KCl | 2.54E−03 |
| 622 | 2,6-bis((4s)-isopropyl-2-oxazoliN-2-yl)pyridine | 1 | KPt(NH3)Cl3 | KCl | 3.01E−03 |
| 623 | 1',3'-dihydrospiro(cyclohexane-1',2'-(2H)imidazo(4,5-b)pyridine) | 1 | KPt(NH3)Cl3 | KCl | 3.50E−03 |
| 624 | 2-bromo-6-methylpyridine | 1 | KPt(NH3)Cl3 | KCl | 3.19E−03 |
| 625 | 2,6-diamino-3-nitrosopyridine | 1 | KPt(NH3)Cl3 | KCl | 3.54E−03 |
| 626 | 2-bromo-3-methylpyridine | 1 | KPt(NH3)Cl3 | KCl | 3.42E−03 |
| 627 | (R)-(+)-alpha-methyl-4-pyridine methanol | 1 | KPt(NH3)Cl3 | KCl | 3.55E−03 |
| 628 | 2-(3-sulfobenzoyl)pyridine 2-pyridyl hydrazone | 1 | KPt(NH3)Cl3 | KCl | 2.41E−03 |
| 629 | 2-acetylpyridine | 1 | KPt(NH3)Cl3 | KCl | 2.11E−03 |
| 630 | 2-amino-5-chloropyridine | 1 | KPt(NH3)Cl3 | KCl | 3.27E−03 |
| 631 | 2-amine-4,6-dimethylpyridine | 1 | KPt(NH3)Cl3 | KCl | 1.59E−03 |
| 632 | 2-(2-aminomethyl)pyridine | 1 | KPt(NH3)Cl3 | KCl | 2.15E−05 |
| 633 | 2-(2-aminoethyl)pyridine | 1 | KPt(NH3)Cl3 | KCl | 1.27E−03 |
| 634 | 2-amino-5-nitropyridine | 1 | KPt(NH3)Cl3 | KCl | 9.47E−04 |
| 635 | 2-amino-3-picoline | 1 | KPt(NH3)Cl3 | KCl | 1.21E−03 |
| 636 | 2-(5,6-bis(4-sulfophenyl)-1,2,4-triaziN-3-3yl)-4-(4-sulfophenyl)pyridine | 1 | KPt(NH3)Cl3 | KCl | 1.21E−03 |
| 637 | ammonia | 2 | K2PtCl4 | KCl | 1.83E−03 |
| 638 | pyridine | 2 | K2PtCl4 | KCl | 2.28E−03 |
| 639 | 2-bromopyridine | 2 | K2PtCl4 | KCl | 1.28E−03 |
| 640 | 2-chloro-6-methoxy-3-nitropyridine | 2 | K2PtCl4 | KCl | 8.52E−05 |
| 641 | 2-chloro-5-nitropyridine | 2 | K2PtCl4 | KCl | 2.77E−04 |
| 642 | 2-chloro-3-nitropyridine | 2 | K2PtCl4 | KCl | 2.77E−04 |
| 643 | 2-chloropyridine | 2 | K2PtCl4 | KCl | 1.49E−03 |
| 644 | 2-cyanopyridine | 2 | K2PtCl4 | KCl | 2.56E−03 |
| 645 | 2,6-dimethoxypyridine | 2 | K2PtCl4 | KCl | 2.34E−03 |
| 646 | 2,6 diaminopyridine | 2 | K2PtCl4 | KCl | 9.37E−04 |
| 647 | 2,5-dibromopyridine | 2 | K2PtCl4 | KCl | 4.47E−04 |
| 648 | 2,6-dibromopyridine | 2 | K2PtCl4 | KCl | 3.62E−04 |
| 649 | 2,3-dichloropyridine | 2 | K2PtCl4 | KCl | 1.06E−03 |
| 650 | 2,6-dichloropyridine | 2 | K2PtCl4 | KCl | 1.70E−04 |
| 651 | 2,6-diacetylpyridine | 2 | K2PtCl4 | KCl | 1.28E−04 |
| 652 | 2-amino-5-picoline | 2 | K2PtCl4 | KCl | 6.03E−03 |
| 653 | 2-hydrazinopyridine | 2 | K2PtCl4 | KCl | 1.32E−03 |
| 654 | 2-hydroxy-6-methyl pyridine carboxylic acid | 2 | K2PtCl4 | KCl | 3.83E−04 |
| 655 | 2-hydroxy-5-nitropyridine | 2 | K2PtCl4 | KCl | 4.26E−04 |
| 656 | 2-hydroxypyridine | 2 | K2PtCl4 | KCl | 3.83E−04 |
| 657 | 2,3-lutidine | 2 | K2PtCl4 | KCl | 1.62E−03 |
| 658 | 2,4-lutidine | 2 | K2PtCl4 | KCl | 1.11E−03 |
| 659 | 2-methoxxy-5-nitropyridine | 2 | K2PtCl4 | KCl | 4.47E−04 |
| 660 | 2-methoxypyridine | 2 | K2PtCl4 | KCl | 7.45E−04 |
| 661 | 2(2-methylaminoethyl)pyridine | 2 | K2PtCl4 | KCl | 1.32E−03 |
| 662 | 2-phenylpyridine | 2 | K2PtCl4 | KCl | 1.04E−03 |
| 663 | 2-pyridinealdoxime methiodide | 2 | K2PtCl4 | KCl | 2.77E−04 |
| 664 | 2-pyridinecarboxyaldehyde | 2 | K2PtCl4 | KCl | 1.24E−03 |
| 665 | 2,3-pyridine dicarboxylic acid | 2 | K2PtCl4 | KCl | 2.98E−04 |
| 666 | 2,5-pyridine dicarboxylic acid | 2 | K2PtCl4 | KCl | 4.47E−04 |
| 667 | 2,6-pyridine dicarboxylic acid | 2 | K2PtCl4 | KCl | 5.96E−04 |
| 668 | 2,3-pyridine dicarboxylic acid anhydride | 2 | K2PtCl4 | KCl | 1.24E−03 |
| 669 | 2-pyridylacetate | 2 | K2PtCl4 | KCl | 5.28E−03 |
| 670 | 2-pyridine propanol | 2 | K2PtCl4 | KCl | 1.49E−03 |
| 671 | 2-hydroxy-6-methyl pyridine | 2 | K2PtCl4 | KCl | 3.19E−04 |
| 672 | 2-benaylamino-4-methylpyridine | 2 | K2PtCl4 | KCl | 4.47E−04 |
| 673 | 2-hydroxy-4-methyl-5-nitropyridine | 2 | K2PtCl4 | KCl | 3.41E−04 |
| 674 | 2-pyridinecarboxyaldehyde-4-nitrophenyl hydrazone | 2 | K2PtCl4 | KCl | 4.05E−04 |
| 675 | (S)(−)alpha methyl-4-pyridine methanol | 2 | K2PtCl4 | KCl | 4.07E−03 |
| 676 | 2,6-pyridinedicarboxamide | 2 | K2PtCl4 | KCl | 2.77E−04 |
| 677 | 2(p-tolyl)pyridine | 2 | K2PtCl4 | KCl | 6.97E−04 |
| 678 | 2,6-dihydroxypyridine | 2 | K2PtCl4 | KCl | 2.26E−03 |
| 679 | 2-(dimethylaminomethyl)-3-hydroxypyridine | 2 | K2PtCl4 | KCl | 1.85E−03 |
| 680 | 2,6-lutidine | 2 | K2PtCl4 | KCl | 2.26E−04 |
| 681 | 2-benzylpyridine | 2 | KtPtCl4 | KCl | 2.54E−03 |
| 682 | 2-amino-6-picoline | 2 | K2PtCl4 | KCl | 6.21E−03 |
| 683 | 2-aminopyridine | 2 | K2PtCl4 | KCl | 2.39E−03 |
| 684 | 2-anilinopyridine | 2 | K2PtCl4 | KCl | 5.08E−04 |
| 685 | ammonia | 1 | KPt(NH3)Cl3 | KCl | 4.09E−03 |
| 686 | pyridine | 1 | KPt(NH3)Cl3 | KCl | 2.86E−03 |

TABLE 1-continued

| No. | Ligand(s) | Equiv. | Precursor | Leaving Group | Yld, g atm Pt |
|---|---|---|---|---|---|
| 687 | 2-bromopyridine | 1 | KPt(NH3)Cl3 | KCl | 3.73E−03 |
| 688 | 2-chloro-6-methoxy-3-nitropyridine | 1 | KPt(NH3)Cl3 | KCl | 2.60E−03 |
| 689 | 2-chloro-5-nitropyridine | 1 | KPt(NH3)Cl3 | KCl | 3.09E−03 |
| 690 | 2-chloro-3-nitropyridine | 1 | KPt(NH3)Cl3 | KCl | 2.92E−03 |
| 691 | 2-chloropyridine | 1 | KPt(NH3)Cl3 | KCl | 3.62E−03 |
| 692 | 2-cyanopyridine | 1 | KPt(NH3)Cl3 | KCl | 3.46E−03 |
| 693 | 2,6-dimethoxypyridine | 1 | KPt(NH3)Cl3 | KCl | 3.07E−03 |
| 694 | 2,6 diaminopyridine | 1 | KPt(NH3)Cl3 | KCl | 2.18E−03 |
| 695 | 2,5-dibromopyridine | 1 | KPt(NH3)Cl3 | KCl | 3.26E−03 |
| 696 | 2,6-dibromopyridine | 1 | KPt(NH3)Cl3 | KCl | 2.67E−03 |
| 697 | 2,3-dichloropyridine | 1 | KPt(NH3)Cl3 | KCl | 3.86E−03 |
| 698 | 2,6-dichloropyridine | 1 | KPt(NH3)Cl3 | KCl | 3.09E−03 |
| 699 | 2,6-diacetylpyridine | 1 | KPt(NH3)Cl3 | KCl | 2.98E−03 |
| 700 | 2-amino-5-picoline | 1 | KPt(NH3)Cl3 | KCl | 3.86E−03 |
| 701 | 2-hydrazinopyridine | 1 | KPt(NH3)Cl3 | KCl | 1.90E−03 |
| 702 | 2-hydroxy-6-methyl pyridine carboxylic acid | 1 | KPt(NH3)Cl3 | KCl | 3.09E−03 |
| 703 | 2-hydroxy-5-nitropyridine | 1 | KPt(NH3)Cl3 | KCl | 3.24E−03 |
| 704 | 2-hydroxypyridine | 1 | KPt(NH3)Cl3 | KCl | 2.92E−03 |
| 705 | 2,3-lutidine | 1 | KPt(NH3)Cl3 | KCl | 3.16E−03 |
| 706 | 2,4-lutidine | 1 | KPt(NH3)Cl3 | KCl | 3.54E−03 |
| 707 | 2-methoxy-5-nitropyridine | 1 | KPt(NH3)Cl3 | KCl | 2.98E−03 |
| 708 | 2-methoxypyridine | 1 | KPt(NH3)Cl3 | KCl | 3.11E−03 |
| 709 | 2(2-methylaminoethyl)pyridine | 1 | KPt(NH3)Cl3 | KCl | 3.03E−03 |
| 710 | 2-phenylpyridine | 1 | KPt(NH3)Cl3 | KCl | 2.79E−03 |
| 711 | 2-pyridinealdoxime methiodide | 1 | KPt(NH3)Cl3 | KCl | 3.07E−03 |
| 712 | 2-pyridinecarboxyaldehyde | 1 | KPt(NH3)Cl3 | KCl | 2.33E−03 |
| 713 | 2,3-pyridine dicarboxylic acid | 1 | KPt(NH3)Cl3 | KCl | 1.98E−03 |
| 714 | 2,5-pyridine dicarboxylic acid | 1 | KPt(NH3)Cl3 | KCl | 2.58E−03 |
| 715 | 2,6-pyridine dicarboxylic acid | 1 | KPt(NH3)Cl3 | KCl | 2.18E−03 |
| 716 | 2,3-pyridine dicarboxylic acid anhydride | 1 | KPt(NH3)Cl3 | KCl | 3.58E−03 |
| 717 | 2-pyridylacetate | 1 | KPt(NH3)Cl3 | KCl | 3.13E−03 |
| 718 | 2-pyridine propanol | 1 | KPt(NH3)Cl3 | KCl | 3.35E−03 |
| 719 | 2-hydroxy-6-methyl pyridine | 1 | KPt(NH3)Cl3 | KCl | 2.81E−03 |
| 720 | 2-benzylamino-4-methylpyridine | 1 | KPt(NH3)Cl3 | KCl | 2.22E−03 |
| 721 | 2-hydroxy-4-methyl-5-nitropyridine | 1 | KPt(NH3)Cl3 | KCl | 2.82E−03 |
| 722 | 2-pyridinecarboxyaldehyde-4-nitrophenyl hydrazone | 1 | KPt(NH3)Cl3 | KCl | 2.74E−03 |
| 723 | (S)(−) alpha methyl-4-pyridine methanol | 1 | KPt(NH3)Cl3 | KCl | 4.19E−03 |
| 724 | 2,6-pyridinedicarboxamide | 1 | KPt(NH3)Cl3 | KCl | 1.91E−03 |
| 725 | 2(p-tolyl)pyridine | 1 | KPt(NH3)Cl3 | KCl | 1.89E−03 |
| 726 | 2,6-dihyroxypyridine | 1 | KPt(NH3)Cl3 | KCl | 2.62E−03 |
| 727 | 2-(dimethylaminomethyl)-3-hydroxypyridine | 1 | KPt(NH3)Cl3 | KCl | 1.63E−03 |
| 728 | 2,6-lutidine | 1 | KPt(NH3)Cl3 | KCl | 1.91E−03 |
| 729 | 2-benzylpyridine | 1 | KPt(NH3)Cl3 | KCl | 2.09E−03 |
| 730 | 2-amino-6-picoline | 1 | KPt(NH3)Cl3 | KCl | 2.24E−03 |
| 731 | 2-aminopyridine | 1 | KPt(NH3)Cl3 | KCl | 3.09E−03 |
| 732 | 2-anilinopyridine | 1 | KPt(NH3)Cl3 | KCl | 2.11E−03 |
| 733 | ammonia + pyridine | 1 each | K2PtCl4 | KCl | 4.70E−03 |
| 734 | methylamine + pyridine | 1 each | K2PtCl4 | KCl | 3.20E−03 |
| 735 | ethylamine + pyridine | 1 each | K2PtCl4 | KCl | 3.48E−03 |
| 736 | propylamine + pyridine | 1 each | K2PtCl4 | KCl | 2.95E−03 |
| 737 | isopropylamine + pyridine | 1 each | K2PtCl4 | KCl | 2.47E−03 |
| 738 | ISOBUTYLAMINE+pyridine | 1 each | K2PtCl4 | KCl | 2.55E−03 |
| 739 | t-butylamine + pyridine | 1 each | K2PtCl4 | KCl | 2.55E−03 |
| 740 | sec-butylamine + pyridine | 1 each | K2PtCl4 | KCl | 2.41E−03 |
| 741 | 1,2-DIMETHYLPROPYLAMINE+pyridine | 1 each | K2PtCl4 | KCl | 2.95E−03 |
| 742 | 1-ETHYLPROPYLAMINE+pyridine | 1 each | K2PtCl4 | KCl | 2.73E−03 |
| 743 | 1-methylbutylamine + pyridine | 1 each | K2PtCl4 | KCl | 2.49E−03 |
| 744 | 2-methylbutylamine + pyridine | 1 each | K2PtCl4 | KCl | 2.53E−03 |
| 745 | hexylamine + pyridine | 1 each | K2PtCl4 | KCl | 2.41E−03 |
| 746 | heptylamine + pyridine | 1 each | K2PtCl4 | KCl | 3.09E−03 |
| 747 | octylamine + pyridine | 1 each | K2PtCl4 | KCl | 3.07E−03 |
| 748 | 1-METHYLHEPTYLAMINE+pyridine | 1 each | K2PtCl4 | KCl | 2.59E−03 |
| 749 | 1,5-DIMETHYLHEXYLAMINE+pyridine | 1 each | K2PtCl4 | KCl | 2.87E−03 |
| 750 | 2-ETHYLHEXYLAMINE+pyridine | 1 each | K2PtCl4 | KCl | 2.53E−03 |
| 751 | decylamine + pyridine | 1 each | K2PtCl4 | KCl | 3.80E−03 |
| 752 | TERT-OCTYLAMINE+pyridine | 1 each | K2PtCl4 | KCl | 2.61E−03 |
| 753 | UNDECYLAMINE+pyridine | 1 each | K2PtCl4 | KCl | 3.52E−03 |
| 754 | allylamine + pyridine | 1 each | K2PtCl4 | KCl | 1.39E−03 |
| 755 | diethylamine + pyridine | 1 each | K2PtCl4 | KCl | 3.05E−03 |
| 756 | dipropylamine + pyridine | 1 each | K2PtCl4 | KCl | 2.53E−03 |
| 757 | diisopropylamine + pyridine | 1 each | K2PtCl4 | KCl | 1.49E−03 |
| 758 | dibutylamine + pyridine | 1 each | K2PtCl4 | KCl | 2.15E−03 |
| 759 | dipentylamine + pyridine | 1 each | K2PtCl4 | KCl | 2.19E−03 |
| 760 | DIHEXYLAMINE+pyridine | 1 each | K2PtCl4 | KCl | 1.61E−03 |
| 761 | DIOCTYAMINE+pyridine | 1 each | K2PtCl4 | KCl | 2.13E−03 |
| 762 | N-METHYLPROPYLAMINE+pyridine | 1 each | K2PtCl4 | KCl | 1.63E−03 |

TABLE 1-continued

| No. | Ligand(s) | Equiv. | Precursor | Leaving Group | Yld, g atm Pt |
|---|---|---|---|---|---|
| 763 | N-METHYLISOPROPYLAMINE+pyridine | 1 each | K2PtCl4 | KCl | 2.09E-03 |
| 764 | N-METHYLBUTYLAMINE+pyridine | 1 each | K2PtCl4 | KCl | 2.29E-03 |
| 765 | N-METHYL-TERT-BUTYLAMINE+pyridine | 1 each | K2PtCl4 | KCl | 1.55E-03 |
| 766 | N-METHYLHEXYLAMINE+pyridine | 1 each | K2PtCl4 | KCl | 2.67E-03 |
| 767 | N-ETHYLMETHYLAMINE+pyridine | 1 each | K2PtCl4 | KCl | 2.11E-03 |
| 768 | N-ETHYLISOPROPYLAMINE+pyridine | 1 each | K2PtCl4 | KCl | 1.61E-03 |
| 769 | N-ETHYLBUTYLAMINE+pyridine | 1 each | K2PtCl4 | KCl | 2.93E-03 |
| 770 | N-TERT-BUTYLISOPROPYLAMINE+pyridine | 1 each | K2PtCl4 | KCl | 1.37E-03 |
| 771 | TRIETHYLAMINE+pyridine | 1 each | K2PtCl4 | KCl | 2.41E-03 |
| 772 | TRIPROPYLAMINE+pyridine | 1 each | K2PtCl4 | KCl | 2.39E-03 |
| 773 | TRIISOPROPYLAMINE+pyridine | 1 each | K2PtCl4 | KCl | 2.15E-03 |
| 774 | TRIISOBUTYLAMINE+pyridine | 1 each | K2PtCl4 | KCl | 2.03E-03 |
| 775 | TRIHEXYLAMINE+pyridine | 1 each | K2PtCl4 | KCl | 1.87E-03 |
| 776 | TRIOCTYLAMINE+pyridine | 1 each | K2PtCl4 | KCl | 1.87E-03 |
| 777 | TRIISOOCTYLAMINE+pyridine | 1 each | K2PtCl4 | KCl | 2.23E-03 |
| 778 | TRIDECYLAMINE+pyridine | 1 each | K2PtCl4 | KCl | 2.32E-03 |
| 779 | N,N diisopropyl ethylamine + pyridine | 1 each | K2PtCl4 | KCl | 3.77E-03 |
| 780 | cyclopropylamine + pyridine | 1 each | K2PtCl4 | KCl | 1.56E-03 |
| 781 | cyclobutylamine + pyridine | 1 each | K2PtCl4 | KCl | 2.25E-03 |
| 782 | CYCLOPENTYLAMINE+pyridine | 1 each | K2PtCl4 | KCl | 2.65E-03 |
| 783 | CYCLOHEXYLAMINE+pyridine | 1 each | K2PtCl4 | KCl | 1.95E-03 |
| 784 | CYCLOHEPTLAMINE+pyridine | 1 each | K2PtCl4 | KCl | 2.25E-03 |
| 785 | CYCLOOCTYLAMINE+pyridine | 1 each | K2PtCl4 | KCl | 2.26E-03 |
| 786 | CYCLODODECYLAMINE+pyridine | 1 each | K2PtCl4 | KCl | 1.91E-03 |
| 787 | 2-METHYLCYCLOHEXYLAMINE+pyridine | 1 each | K2PtCl4 | KCl | 2.71E-03 |
| 788 | 2,3-DIMETHYLCYCLOHEXYLAMINE+pyridine | 1 each | K2PtCl4 | KCl | 2.43E-03 |
| 789 | ALLYLCYCLOHEXYLAMINE+pyridine | 1 each | K2PtCl4 | KCl | 3.15E-03 |
| 790 | N-ALLYLCYCLOPENTYLAMINE+pyridine | 1 each | K2PtCl4 | KCl | 3.59E-03 |
| 791 | N-METHYLCYCLOHEXYLAMINE+pyridine | 1 each | K2PtCl4 | KCl | 2.21E-03 |
| 792 | N-ETHYLCYCLOHEXYLAMINE+pyridine | 1 each | K2PtCl4 | KCl | 2.37E-03 |
| 793 | N-ISOPROPYLCYCLOHEXYLAMINE+pyridine | 1 each | K2PtCl4 | KCl | 2.21E-03 |
| 794 | N-TERT-BUTYLCYCLOHEXYLAMINE+pyridine | 1 each | K2PtCl4 | KCl | 1.82E-03 |
| 795 | (R)-(−)-1-CYCLOHEXYLETHYLAMINE + pyridine | 1 each | K2PtCl4 | KCl | 2.08E-03 |
| 796 | (S)-(+)-1-CYCLOHEXYLETHYLAMINE + pyridine | 1 each | K2PtCl4 | KCl | 1.77E-03 |
| 797 | DICYCLOHEXYLAMINE+pyridine | 1 each | K2PtCl4 | KCl | 1.53E-03 |
| 798 | 1-AMINO-2-PROPANOL + pyridine | 1 each | K2PtCl4 | KCl | 2.61E-03 |
| 799 | DL-2-AMINO-1-PROPANOL + pyridine | 1 each | K2PtCl4 | KCl | 1.84E-03 |
| 800 | (R)-(−)-1-AMINO-2-PROPANOL + pyridine | 1 each | K2PtCl4 | KCl | 3.06E-03 |
| 801 | (S)-(+)-1-AMINO-2-PROPANOL + pyridine | 1 each | K2PtCl4 | KCl | 2.39E-03 |
| 802 | (R)-(−)-2-AMINO-1-PROPANOL + pyridine | 1 each | K2PtCl4 | KCl | 2.26E-03 |
| 803 | (S)-(+)-2-AMINO-1-PROPANOL + pyridine | 1 each | K2PtCl4 | KCl | 3.02E-03 |
| 804 | 3-AMINO-1-PROPANOL + pyridine | 1 each | K2PtCl4 | KCl | 3.42E-03 |
| 805 | 2-AMINO-1-BUTANOL + pyridine | 1 each | K2PtCl4 | KCl | 2.93E-03 |
| 806 | (R)-(−)-2-AMINO-1-BUTANOL + pyridine | 1 each | K2PtCl4 | KCl | 2.43E-03 |
| 807 | (S)-(+)-2-AMINO-1-BUTANOL + pyridine | 1 each | K2PtCl4 | KCl | 2.83E-03 |
| 808 | 4-AMINO-1-BUTANOL + pyridine | 1 each | K2PtCl4 | KCl | 3.06E-03 |
| 809 | 5-AMINO-1-PENTANOL + pyridine | 1 each | K2PtCl4 | KCl | 3.06E-03 |
| 810 | DL-2-AMINO-1-PENTANOL + pyridine | 1 each | K2PtCl4 | KCl | 3.42E-03 |
| 811 | 6-AMINO-1-HEXANOL + pyridine | 1 each | K2PtCl4 | KCl | 2.98E-03 |
| 812 | DL-2-AMINO-1-HEXANOL + pyridine | 1 each | K2PtCl4 | KCl | 2.67E-03 |
| 813 | 2-AMINO-2-METHYL-1-PROPANOL + pyridine | 1 each | K2PtCl4 | KCl | 2.32E-03 |
| 814 | 2-AMINO-3-METHYL-1-BUTANOL + pyridine | 1 each | K2PtCl4 | KCl | 2.87E-03 |
| 815 | (R)-(−)-2-AMINO-3-METHYL-1-BUTANOL + pyridine | 1 each | K2PtCl4 | KCl | 2.54E-03 |
| 816 | (S)-(+)-2-AMINO-3-METHYL-1-BUTANOL + pyridine | 1 each | K2PtCl4 | KCl | 2.45E-03 |
| 817 | 6-AMINO-2-METHYL-2-HEPTANOL + pyridine | 1 each | K2PtCl4 | KCl | 2.06E-03 |
| 818 | 2-(2-AMINOETHOXY)ETHANOL + pyridine | 1 each | K2PtCl4 | KCl | 3.46E-03 |
| 819 | 2-(METHYLAMINO)ETHANOL + pyridine | 1 each | K2PtCl4 | KCl | 2.59E-03 |
| 820 | 2-(PROPYLAMINO)ETHANOL + pyridine | 1 each | K2PtCl4 | KCl | 2.71E-03 |
| 821 | 2-(TERT-BUTYLAMINO)ETHANOL + pyridine | 1 each | K2PtCl4 | KCl | 1.90E-03 |
| 822 | 1-AMINOMETHYL-1-CYCLOHEXANOL + pyridine | 1 each | K2PtCl4 | KCl | 2.47E-03 |
| 823 | TRANS-4-AMINOCYCLOHEXANOL + pyridine | 1 each | K2PtCl4 | KCl | 2.54E-03 |
| 824 | diethanolamine + pyridine | 1 each | K2PtCl4 | KCl | 2.59E-03 |
| 825 | 3-AMINO-1,2-PROPANEDIOL + pyridine | 1 each | K2PtCl4 | KCl | 2.83E-03 |
| 826 | 2-AMINO-2-METHYL-1,3-PROPANEDIOL + pyridine | 1 each | K2PtCl4 | KCl | 2.30E-03 |
| 827 | 2-AMINO-2-ETHYL-1,3-PROPANEDIOL + pyridine | 1 each | K2PtCl4 | KCl | 2.23E-03 |
| 828 | 3-AMINO-1-PROPANOL VINYL ETHER + pyridine | 1 each | K2PtCl4 | KCl | 2.98E-03 |
| 829 | ammonia + imidazole | 1 each | K2PtCl4 | KCl | 8.75E-04 |
| 830 | methylamine + imidazole | 1 each | K2PtCl4 | KCl | 2.33E-03 |
| 831 | ethylamine + imidazole | 1 each | K2PtCl4 | KCl | 1.62E-03 |
| 832 | propylamine + imidazole | 1 each | K2PtCl4 | KCl | 1.56E-03 |
| 833 | isopropylamine + imidazole | 1 each | K2PtCl4 | KCl | 1.52E-03 |
| 834 | ISOBUTYLAMINE+imidazole | 1 each | K2PtCl4 | KCl | 1.73E-03 |
| 835 | t-butylamine + imidazole | 1 each | K2PtCl4 | KCl | 1.34E-03 |

TABLE 1-continued

| No. | Ligand(s) | Equiv. | Precursor | Leaving Group | Yld, g atm Pt |
|---|---|---|---|---|---|
| 836 | sec-butylamine + imidazole | 1 each | K2PtCl4 | KCl | 1.52E−03 |
| 837 | 1,2-DIMETHYLPROPYLAMINE+imidazole | 1 each | K2PtCl4 | KCl | 1.41E−03 |
| 838 | 1-ETHYLPROPYLAMINE+imidazole | 1 each | K2PtCl4 | KCl | 1.07E−03 |
| 839 | 1-methylbutylamine + imidazole | 1 each | K2PtCl4 | KCl | 3.09E−03 |
| 840 | 2-methylbutylamine + imidazole | 1 each | K2PtCl4 | KCl | 1.66E−03 |
| 841 | hexylamine + imidazole | 1 each | K2PtCl4 | KCl | 2.95E−03 |
| 842 | heptylamine + imidazole | 1 each | K2PtCl4 | KCl | 1.86E−03 |
| 843 | octylamine + imidazole | 1 each | K2PtCl4 | KCl | 1.28E−03 |
| 844 | 1-METHYLHEPTYLAMINE+imidazole | 1 each | K2PtCl4 | KCl | 1.71E−03 |
| 845 | 1,5-DIMETHYLHEXYLAMINE+imidazole | 1 each | K2PtCl4 | KCl | 1.07E−03 |
| 846 | 2-ETHYLHEXYLAMINE+imidazole | 1 each | K2PtCl4 | KCl | 1.52E−03 |
| 847 | decylamine + imidazole | 1 each | K2PtCl4 | KCl | 1.24E−03 |
| 848 | TERT-OCTYLAMINE+imidazole | 1 each | K2PtCl4 | KCl | 6.83E−04 |
| 849 | UNDECYLAMINE+imidazole | 1 each | K2PtCl4 | KCl | 1.32E−03 |
| 850 | allylamine + imidazole | 1 each | K2PtCl4 | KCl | 5.34E−04 |
| 851 | diethylamine + imidazole | 1 each | K2PtCl4 | KCl | 1.26E−03 |
| 852 | dipropylamine + imidazole | 1 each | K2PtCl4 | KCl | 2.48E−03 |
| 853 | diisopropylamine + imidazole | 1 each | K2PtCl4 | KCl | 6.83E−04 |
| 854 | dibutylamine + imidazole | 1 each | K2PtCl4 | KCl | 1.39E−03 |
| 855 | dipentylamine + imidazole | 1 each | K2PtCl4 | KCl | 4.70E−04 |
| 856 | DIHEXYLAMINE+imidazole | 1 each | K2PtCl4 | KCl | 1.88E−03 |
| 857 | DIOCTYLAMINE+imidazole | 1 each | K2PtCl4 | KCl | 1.56E−03 |
| 858 | N-METHYLPROPYLAMINE+imidazole | 1 each | K2PtCl4 | KCl | 4.27E−04 |
| 859 | N-METHYLISOPROPYLAMINE+imidazole | 1 each | K2PtCl4 | KCl | 1.39E−03 |
| 860 | N-METHYLBUTYLAMINE+imidazole | 1 each | K2PtCl4 | KCl | 2.41E−03 |
| 861 | N-METHYL-TERT-BUTYLAMINE+imidazole | 1 each | K2PtCl4 | KCl | 1.17E−03 |
| 862 | N-METHYLHEXYLAMINE+imidazole | 1 each | K2PtCl4 | KCl | 2.48E−03 |
| 863 | N-ETHYLMETHYLAMINE+imidazole | 1 each | K2PtCl4 | KCl | 1.22E−03 |
| 864 | N-ETHYLISOPROPYLAMINE+imidazole | 1 each | K2PtCl4 | KCl | 5.34E−04 |
| 865 | N-ETHYLBUTYLAMINE+imidazole | 1 each | K2PtCl4 | KCl | 1.13E−03 |
| 866 | N-TERT-BUTYLISOPROPYLAMINE+imidazole | 1 each | K2PtCl4 | KCl | 1.52E−03 |
| 867 | TRIETHYLAMINE+imidazole | 1 each | K2PtCl4 | KCl | 2.22E−03 |
| 868 | TRIPROPYLAMINE+imidazole | 1 each | K2PtCl4 | KCl | 5.98E−04 |
| 869 | TRIISOPROPYLAMINE+imidazole | 1 each | K2PtCl4 | KCl | 2.48E−04 |
| 870 | TRIISOBUTYLAMINE+imidazole | 1 each | K2PtCl4 | KCl | 2.94E−04 |
| 871 | TRIHEXYLAMINE+imidazole | 1 each | K2PtCl4 | KCl | 1.55E−05 |
| 872 | TRIOCTYLAMINE+imidazole | 1 each | K2PtCl4 | KCl | 1.08E−04 |
| 873 | TRIISOCCTYLAMINE+imidazole | 1 each | K2PtCl4 | KCl | 5.26E−04 |
| 874 | TRIDECYLAMINE+imidazole | 1 each | K2PtCl4 | KCl | 5.57E−04 |
| 875 | N,N diisopropyl ethylamine + imidazole | 1 each | K2PtCl4 | KCl | 2.32E−04 |
| 876 | cyclopropylamine + imidazole | 1 each | K2PtCl4 | KCl | 5.73E−04 |
| 877 | cyclobutylamine + imidazole | 1 each | K2PtCl4 | KCl | 9.60E−04 |
| 878 | CYCLOPENTYLAMINE+imidazole | 1 each | K2PtCl4 | KCl | 8.21E−04 |
| 879 | CYCLOHEXYLAMINE+imidazole | 1 each | K2PtCl4 | KCl | 5.57E−04 |
| 880 | CYCLOHEPTYLAMINE+imidazole | 1 each | K2PtCl4 | KCl | 1.04E−03 |
| 881 | CYCLOOCTYLAMINE+imidazole | 1 each | K2PtCl4 | KCl | 3.72E−04 |
| 882 | CYCLODODECYLAMINE+imidazole | 1 each | K2PtCl4 | KCl | 0.00E+00 |
| 883 | 2-METHYLCYCLOHEXYLAMINE+imidazole | 1 each | K2PtCl4 | KCl | 7.59E−04 |
| 884 | 2,3-DIMETHYLCYCLOHEXYLAMINE+imidazole | 1 each | K2PtCl4 | KCl | 3.87E−04 |
| 885 | ALLYLCYCLOHEXYLAMINE+imidazole | 1 each | K2PtCl4 | KCl | 8.21E−04 |
| 886 | N-ALLYLCYCLOPENTYLAMINE+imidazole | 1 each | K2PtCl4 | KCl | 9.44E−04 |
| 887 | N-METHYLCYCLOMEXYLAMINE+imidazole | 1 each | K2PtCl4 | KCl | 6.19E−05 |
| 888 | N-ETHYLCYCLOMEXYLAMINE+imidazole | 1 each | K2PtCl4 | KCl | 7.74E−05 |
| 889 | N-ISOPROPYLCYCLOHEXYLAMINE+imidazole | 1 each | K2PtCl4 | KCl | 0.00E+00 |
| 890 | N-TERT-BUTYLCYCLOHEXYLAMINE+imidazole | 1 each | K2PtCl4 | KCl | 9.29E−05 |
| 891 | (R)-(−)-1-CYCLOHEXYLETHYLAMINE+imidazole | 1 each | K2PtCl4 | KCl | 2.48E−04 |
| 892 | (S)-(+)-1-CYCLOHEXYLETHYLAMINE+imidazole | 1 each | K2PtCl4 | KCl | 1.07E−03 |
| 893 | DICYCLOHEXYLAMINE+imidazole | 1 each | K2PtCl4 | KCl | 2.94E−04 |
| 894 | 1-AMINO-2-PROPANOL + imidazole | 1 each | K2PtCl4 | KCl | 7.43E−04 |
| 895 | DL-2-AMINO-1-PROPANOL + imidazole | 1 each | K2PtCl4 | KCl | 2.94E−04 |
| 896 | (R)-(−)-1-AMINO-2-PROPANOL + imidazole | 1 each | K2PtCl4 | KCl | 8.98E−04 |
| 897 | (S)-(+)-1-AMINO-2-PROPANOL + imidazole | 1 each | K2PtCl4 | KCl | 5.42E−04 |
| 898 | (R)-(−)-2-AMINO-1-PROPANOL + imidazole | 1 each | K2PtCl4 | KCl | 1.72E−03 |
| 899 | (S)-(+)-2-AMINO-1-PROPANOL + imidazole | 1 each | K2PtCl4 | KCl | 3.25E−03 |
| 900 | 3-AMINO-1-PROPANOL + imidazole | 1 each | K2PtCl4 | KCl | 6.97E−04 |
| 901 | 2-AMINO-1-BUTANOL + imidazole | 1 each | K2PtCl4 | KCl | 0.00E+00 |
| 902 | (R)-(−)-2-AMINO-1-BUTANOL + imidazole | 1 each | K2PtCl4 | KCl | 9.91E−04 |
| 903 | (S)-(+)-2-AMINO-1-BUTANOL + imidazole | 1 each | K2PtCl4 | KCl | 8.21E−04 |
| 904 | 4-AMINO-1-BUTANOL + imidazole | 1 each | K2PtCl4 | KCl | 1.72E−03 |
| 905 | 5-AMINO-1-PENTANOL + imidazole | 1 each | K2PtCl4 | KCl | 5.42E−04 |
| 906 | DL-2-AMINO-1-PENTANOL + imidazole | 1 each | K2PtCl4 | KCl | 3.87E−04 |
| 907 | 6-AMINO-1-HEXANOL + imidazole | 1 each | K2PtCl4 | KCl | 1.32E−03 |
| 908 | DL-2-AMINO-1-HEXANOL + imidazole | 1 each | K2PtCl4 | KCl | 5.88E−04 |
| 909 | 2-AMINO-2-METHYL-1-PROPANOL + imidazole | 1 each | K2PtCl4 | KCl | 3.56E−04 |
| 910 | 2-AMINO-3-METHYL-1-BUTANOL + imidazole | 1 each | K2PtCl4 | KCl | 6.04E−04 |
| 911 | (R)-(−)-2-AMINO-3-METHYL-1-BUTANOL + imidazole | 1 each | K2PtCl4 | KCl | 1.70E−04 |

TABLE 1-continued

| No. | Ligand(s) | Equiv. | Precursor | Leaving Group | Yld, g atm Pt |
|---|---|---|---|---|---|
| 912 | (S)-(+)-2-AMINO-3-METHYL-1-BUTANOL + imidazole | 1 each | K2PtCl4 | KCl | 5.11E−04 |
| 913 | 6-AMINO-2-METHYL-2-HEPTANOL + imidazole | 1 each | K2PtCl4 | KCl | 9.29E−04 |
| 914 | 2-(2-AMINOETHOXY)ETHANOL + imidazole | 1 each | K2PtCl4 | KCl | 1.15E−03 |
| 915 | 2-(METHYLAMINO)ETHANOL + imidazole | 1 each | K2PtCl4 | KCl | 3.70E−05 |
| 916 | 2-(PROPYLAMINO)ETHANOL + imidazole | 1 each | K2PtCl4 | KCl | 5.74E−04 |
| 917 | 2-(TERT-BUTYLAMINO)ETHANOL + imidazole | 1 each | K2PtCl4 | KCl | 5.55E−05 |
| 918 | 1-AMINOMETHYL-1-CYCLOHEXANOL + imidazole | 1 each | K2PtCl4 | KCl | 7.03E−04 |
| 919 | TRANS-4-AMINOCYCLOHEXANOL + imidazole | 1 each | K2PtCl4 | KCl | 3.15E−04 |
| 920 | diethanolamine + imidazole | 1 each | K2PtCl4 | KCl | 3.70E−05 |
| 921 | 3-AMINO-1,2-PROPANEDIOL + imidazole | 1 each | K2PtCl4 | KCl | 1.44E−03 |
| 922 | 2-AMINO-2-METHYL-1,3-PROPANEDIOL + imidazole | 1 each | K2PtCl4 | KCl | 7.40E−05 |
| 923 | 2-AMINO-2-ETHYL-1,3-PROPANEDIOL + imidazole | 1 each | K2PtCl4 | KCl | 2.78E−04 |
| 924 | 3-AMINO-1-PROPANOL VINYL ETHER + imidazole | 1 each | K2PtCl4 | KCl | 5.18E−04 |
| 925 | ammonia + cyclohexylamine | 1 each | K2PtCl4 | KCl | 1.11E−03 |
| 926 | methylamine + cyclohexylamine | 1 each | K2PtCl4 | KCl | 2.06E−03 |
| 927 | ethylamine + cyclohexylamine | 1 each | K2PtCl4 | KCl | 3.59E−03 |
| 928 | propylamine + cyclohexylamine | 1 each | K2PtCl4 | KCl | 1.52E−03 |
| 929 | isopropylamine + cyclohexylamine | 1 each | K2PtCl4 | KCl | 2.02E−03 |
| 930 | ISOBUTYLAMINE+cyclohexylamine | 1 each | K2PtCl4 | KCl | 1.98E−03 |
| 931 | t-butylamine + cyclohexylamine | 1 each | K2PtCl4 | KCl | 3.15E−04 |
| 932 | sec-butylamine + cyclohexylamine | 1 each | K2PtCl4 | KCl | 2.12E−03 |
| 933 | 1,2-DIMETHYLPROPYLAMINE+cyclohexylamine | 1 each | K2PtCl4 | KCl | 1.42E−03 |
| 934 | 1-ETHYLPROPYLAMINE+cyclohexylamine | 1 each | K2PtCl4 | KCl | 1.50E−03 |
| 935 | 1-methylbutylamine + cyclohexylamine | 1 each | K2PtCl4 | KCl | 1.90E−03 |
| 936 | 2-methylhutylamine + cyclohexylamine | 1 each | K2PtCl4 | KCl | 1.46E−03 |
| 937 | hexylamine + cyclohexylamine | 1 each | K2PtCl4 | KCl | 1.80E−02 |
| 938 | heptylamine + cyclohexylamine | 1 each | K2PtCl4 | KCl | 1.70E−03 |
| 939 | octylamine + cyclohexylamine | 1 each | K2PtCl4 | KCl | 1.28E−03 |
| 940 | 1-METHYLHEPTYLAMINE+cyclohexylamine | 1 each | K2PtCl4 | KCl | 1.30E−03 |
| 941 | 1,5-DIMETHYLHEXYLAMINE+cyclohexylamine | 1 each | K2PtCl4 | KCl | 2.50E−03 |
| 942 | 2-ETHYLHEXYLAMINE+cyclohexylamine | 1 each | K2PtCl4 | KCl | 1.51E−03 |
| 943 | decylamine + cyclohexylamine | 1 each | K2PtCl4 | KCl | 1.32E−03 |
| 944 | TERT-OCTYLAMINE+cyclohexylamine | 1 each | K2PtCl4 | KCl | 1.24E−03 |
| 945 | UNDECYLAMINE+cyclohexylamine | 1 each | K2PtCl4 | KCl | 4.65E−04 |
| 946 | allylamine + cyclohexylamine | 1 each | K2PtCl4 | KCl | 1.34E−03 |
| 947 | diethylamine + cyclohexylamine | 1 each | K2PtCl4 | KCl | 1.85E−03 |
| 948 | dipropylamine + cyclohexylamine | 1 each | K2PtCl4 | KCl | 1.70E−03 |
| 949 | diisopropylamine + cyclohexylamine | 1 each | K2PtCl4 | KCl | 1.68E−03 |
| 950 | dibutylamine + cyclohexylamine | 1 each | K2PtCl4 | KCl | 2.14E−03 |
| 951 | dipentylamine + cyclohexylamine | 1 each | K2PtCl4 | KCl | 1.53E−03 |
| 952 | DIHEXYLAMINE+cyclohexylamine | 1 each | K2PtCl4 | KCl | 1.72E−03 |
| 953 | DIOCTYLAMINE+cyclohexylamine | 1 each | K2PtCl4 | KCl | 2.02E−03 |
| 954 | N-METHYLPROPYLAMINE+cyclohexylamine | 1 each | K2PtCl4 | KCl | 1.74E−03 |
| 955 | N-METHYLISOPROPYLAMINE+cyclohexylamine | 1 each | K2PtCl4 | KCl | 2.29E−03 |
| 956 | N-METHYLBUTYLAMINE+cyclohexylamine | 1 each | K2PtCl4 | KCl | 1.94E−03 |
| 957 | N-METHYL-TERT-BUTYLAMINE+cyclohexylamine | 1 each | K2PtCl4 | KCl | 1.93E−03 |
| 958 | N-METHYLHEXYLAMINE+cyclohexylamine | 1 each | K2PtCl4 | KCl | 2.12E−03 |
| 959 | N-ETHYLMETHYLAMINE+cyclohexylamine | 1 each | K2PtCl4 | KCl | 2.99E−03 |
| 960 | N-ETHYLISOPROPYLAMINE+cyclohexylamine | 1 each | K2PtCl4 | KCl | 1.93E−03 |
| 961 | N-ETHYLBUTYLAMINE+cyclohexylamine | 1 each | K2PtCl4 | KCl | 2.23E−03 |
| 962 | N-TERT-BUTYLISOPROPYLAMINE+cyclohexylamine | 1 each | K2PtCl4 | KCl | 1.30E−03 |
| 963 | TRIETHYLAMINE+cyclohexylamine | 1 each | K2PtCl4 | KCl | 3.46E−03 |
| 964 | TRIPROPYLAMINE+cyclohexylamine | 1 each | K2PtCl4 | KCl | 2.23E−03 |
| 965 | TRIISOPROPYLAMINE+cyclohexylamine | 1 each | K2PtCl4 | KCl | 2.25E−03 |
| 966 | TRIISOBUTYLAMINE+cyclohexylamine | 1 each | K2PtCl4 | KCl | 1.32E−03 |
| 967 | TRIHEXYLAMINE+cyclohexylamine | 1 each | K2PtCl4 | KCl | 2.02E−03 |
| 968 | TRIOCTYLAMINE+cyclohexylamine | 1 each | K2PtCl4 | KCl | 1.39E−03 |
| 969 | TRIISOOCTYLAMINE+cyclohexylamine | 1 each | K2PtCl4 | KCl | 1.18E−03 |
| 970 | TRIDECYLAMINE+cyclohexylamine | 1 each | K2PtCl4 | KCl | 2.04E−03 |
| 971 | N,N diisopropyl ethylamine + cyclohexylamine | 1 each | K2PtCl4 | KCl | 2.54E−03 |
| 972 | cyclopropylamine + cyclohexylamine | 1 each | K2PtCl4 | KCl | 2.59E−03 |
| 973 | cyclobutylamine + cyclohexylamine | 1 each | K2PtCl4 | KCl | 2.43E−03 |
| 974 | CYCLOPENTYLAMINE+cyclohexylamine | 1 each | K2PtCl4 | KCl | 2.71E−03 |
| 975 | CYCLOHEXYLAMINE+cyclohexylamine | 1 each | K2PtCl4 | KCl | 2.10E−03 |
| 976 | CYCLOHEPTYLAMINE+cyclohexylamine | 1 each | K2PtCl4 | KCl | 1.05E−03 |
| 977 | CYCLOOCTYLAMINE+cyclohexylamine | 1 each | K2PtCl4 | KCl | 2.15E−03 |
| 978 | CYCLODODECYLAMINE+cyclohexylamine | 1 each | K2PtCl4 | KCl | 2.13E−03 |
| 979 | 2-METHYLCYCLOHEXYLAMINE+cyclohexylamine | 1 each | K2PtCl4 | KCl | 2.50E−03 |
| 980 | 2,3-DIMETHYLCYCLOHEXYLAMINE+cyclohexylamine | 1 each | K2PtCl4 | KCl | 1.91E−03 |
| 981 | ALLYLCYCLOHEXYLAMINE+cyclohexylamine | 1 each | K2PtCl4 | KCl | 1.28E−03 |
| 982 | N-ALLYLCYCLOPENTYLAMINE+cyclohexylamine | 1 each | K2PtCl4 | KCl | 1.83E−03 |
| 983 | N-METHYLCYCLOHEXYLAMINE+cyclohexylamine | 1 each | K2PtCl4 | KCl | 1.20E−03 |
| 984 | N-ETHYLCYCLOHEXYLAMINE+cyclohexylamine | 1 each | K2PtCl4 | KCl | 2.75E−03 |
| 985 | N-ISOPROPYLCYCLOHEXYLAMINE+cyclohexylamine | 1 each | K2PtCl4 | KCl | 1.52E−03 |

TABLE 1-continued

| No. | Ligand(s) | Equiv. | Precursor | Leaving Group | Yld, g atm Pt |
|---|---|---|---|---|---|
| 986 | N-TERT-BUTYLCYCLOHEXYLAMINE+ cyclohexylamine | 1 each | K2PtCl4 | KCl | 1.36E−03 |
| 987 | (R)-(−)-1-CYCLOHEXYLETHYLAMINE+ cyclohexylamine | 1 each | K2PtCl4 | KCl | 1.80E−03 |
| 988 | (S)-(+)-1-CYCLOHEXYLETHYLAMINE+ cyclohexylamine | 1 each | K2PtCl4 | KCl | 1.59E−03 |
| 989 | DICYCLOHEXYLAMINE+cyclohexylamine | 1 each | K2PtCl4 | KCl | 2.08E−03 |
| 990 | 1-AMINO-2-PROPANOL + cyclohexylamine | 1 each | K2PtCl4 | KCl | 8.83E−04 |
| 991 | DL-2-AMINO-1-PROPANOL + cyclohexylamine | 1 each | K2PtCl4 | KCl | 2.44E−03 |
| 992 | (R)-(−)-1-AMINO-2-PROPANOL + cyclohexylamine | 1 each | K2PtCl4 | KCl | 1.89E−03 |
| 993 | (S)-(+)-1-AMINO-2-PROPANOL + cyclohexylamine | 1 each | K2PtCl4 | KCl | 1.68E−03 |
| 994 | (R)-(−)-2-AMINO-1-PROPANOL + cyclohexylamine | 1 each | K2PtCl4 | KCl | 1.66E−03 |
| 995 | (S)-(+)-2-AMINO-1-PROPANOL + cyclohexylamine | 1 each | K2PtCl4 | KCl | 3.51E−03 |
| 996 | 3-AMINO-1-PROPANOL + cyclohexylamine | 1 each | K2PtCl4 | KCl | 2.66E−03 |
| 997 | 2-AMINO-1-BUTANOL + cyclohexylamine | 1 each | K2PtCl4 | KCl | 1.89E−03 |
| 998 | (R)-(−)-2-AMINO-1-BUTANOL + cyclohexylamine | 1 each | K2PtCl4 | KCl | 2.95E−03 |
| 999 | (S)-(+)-2-AMINO-1-BUTANOL + cyclohexylamine | 1 each | K2PtCl4 | KCl | 1.51E−03 |
| 1000 | 4-AMINO-1-BUTANOL + cyclohexylamine | 1 each | K2PtCl4 | KCl | 2.44E−03 |
| 1001 | 5-AMINO-1-PENTANOL + cyclohexylamine | 1 each | K2PtCl4 | KCl | 2.67E−03 |
| 1002 | DL-2-AMINO-1-PENTANOL + cyclohexylamine | 1 each | K2PtCl4 | KCl | 2.06E−03 |
| 1003 | 6-AMINO-1-HEXANOL + cyclohexylamine | 1 each | K2PtCl4 | KCl | 3.02E−03 |
| 1004 | DL-2-AMINO-1-HEXANOL + cyclohexylamine | 1 each | K2PtCl4 | KCl | 2.60E−03 |
| 1005 | 2-AMINO-2-METHYL-1-PROPANOL + cyclohexylamine | 1 each | K2PtCl4 | KCl | 2.02E−03 |
| 1006 | 2-AMINO-3-METHYL-1-BUTANOL + cyclohexylamine | 1 each | K2PtCl4 | KCl | 1.78E−03 |
| 1007 | (R)-(−)-2-AMINO-3-METHYL-1-BUTANOL + cyclohexylamine | 1 each | K2PtCl4 | KCl | 1.93E−03 |
| 1008 | (S)-(+)-2-AMINO-3-METHYL-1-BUTANOL + cyclohexylamine | 1 each | K2PtCl4 | KCl | 1.38E−03 |
| 1009 | 6-AMINO-2-METHYL-2-HEPTANOL + cyclohexylamine | 1 each | K2PtCl4 | KCl | 3.59E−03 |
| 1010 | 2-(2-AMINOETHOXY)ETHANOL + cyclohexylamine | 1 each | K2PtCl4 | KCl | 2.61E−03 |
| 1011 | 2-(METHYLAMINO)ETHANOL + cyclohexylamine | 1 each | K2PtCl4 | KCl | 3.05E−03 |
| 1012 | 2-(PROPYLAMINO)ETHANOL + cyclohexylamine | 1 each | K2PtCl4 | KCl | 1.43E−03 |
| 1013 | 2-(TERT-BUTYLAMINO)ETHANOL + cyclohexylamine | 1 each | K2PtCl4 | KCl | 1.30E−03 |
| 1014 | 1-AMINOMETHYL-1-CYCLOHEXANOL + cyclohexylamine | 1 each | K2PtCl4 | KCl | 2.72E−03 |
| 1015 | TRANS-4-AMINOCYCLOHEXANOL + cyclohexylamine | 1 each | K2PtCl4 | KCl | 3.08E−03 |
| 1016 | diethanolamine + cyclohexylamine | 1 each | K2PtCl4 | KCl | 2.31E−03 |
| 1017 | 3-AMINO-1,2-PROPANEDIOL + cyclohexylamine | 1 each | K2PtCl4 | KCl | 3.48E−03 |
| 1018 | 2-AMINO-2-METHYL-1,3-PROPANEDIOL + cyclohexylamine | 1 each | K2PtCl4 | KCl | 3.28E−03 |
| 1019 | 2-AMINO-2-ETHYL-1,3-PROPANEDIOL + cyclohexylamine | 1 each | K2PtCl4 | KCl | 4.33E−03 |
| 1020 | 3-AMINO-1-PROPANOL VINYL ETHER + cyclohexylamine | 1 each | K2PtCl4 | KCl | 2.84E−03 |
| 1021 | ammonia + guanosine | 1 each | K2PtCl4 | KCl | 2.90E−03 |
| 1022 | methylamine + guanosine | 1 each | K2PtCl4 | KCl | 2.01E−03 |
| 1023 | ethylamine + guanosine | 1 each | K2PtCl4 | KCl | 1.35E−03 |
| 1024 | propylamine + guanosine | 1 each | K2PtCl4 | KCl | 2.83E−03 |
| 1025 | isopropylamine + guanosine | 1 each | K2PtCl4 | KCl | 5.55E−03 |
| 1026 | ISOBUTYLAMINE+guanosine | 1 each | K2PtCl4 | KCl | 2.17E−03 |
| 1027 | t-butylamine + guanosine | 1 each | K2PtCl4 | KCl | 2.15E−03 |
| 1028 | sec-butylamine + guanosine | 1 each | K2PtCl4 | KCl | 3.45E−03 |
| 1029 | 1,2-DIMETHYLPROPYLAMINE+guanosine | 1 each | K2PtCl4 | KCl | 2.12E−03 |
| 1030 | 1-ETHYLPROPYLAMINE+guanosine | 1 each | K2PtCl4 | KCl | 3.10E−03 |
| 1031 | 1-methylbutylamine + guanosine | 1 each | K2PtCl4 | KCl | 2.92E−03 |
| 1032 | 2-methylbutylamine + guanosine | 1 each | K2PtCl4 | KCl | 3.21E−03 |
| 1033 | hexylamine + guanosine | 1 each | K2PtCl4 | KCl | 2.17E−03 |
| 1034 | heptylamine + guanosine | 1 each | K2PtCl4 | KCl | 2.54E−03 |
| 1035 | octylamine + guanosine | 1 each | K2PtCl4 | KCl | 2.30E−03 |
| 1036 | 1-METHYLHEPTYLAMINE+guanosine | 1 each | K2PtCl4 | KCl | 2.48E−03 |
| 1037 | 1,5-DIMETHYLHEXYLAMINE+guanosine | 1 each | K2PtCl4 | KCl | 1.79E−03 |
| 1038 | 2-ETHYLHEXYLAMINE+guanosine | 1 each | K2PtCl4 | KCl | 3.01E−03 |
| 1039 | decylamine + guanosine | 1 each | K2PtCl4 | KCl | 3.94E−03 |
| 1040 | TERT-OCTYLAMINE+guanosine | 1 each | K2PtCl4 | KCl | 2.65E−03 |
| 1041 | UNDECYLAMINE+guanosine | 1 each | K2PtCl4 | KCl | 3.69E−03 |
| 1042 | allylamine + guanosine | 1 each | K2PtCl4 | KCl | 2.81E−03 |
| 1043 | diethylamine + guanosine | 1 each | K2PtCl4 | KCl | 9.29E−04 |
| 1044 | dipropylamine + guanosine | 1 each | K2PtCl4 | KCl | 1.81E−03 |
| 1045 | diisopropylamine + guanosine | 1 each | K2PtCl4 | KCl | 1.04E−03 |
| 1046 | dibutylamine + guanosine | 1 each | K2PtCl4 | KCl | 1.68E−03 |
| 1047 | dipentylamine + guanosine | 1 each | K2PtCl4 | KCl | 3.91E−03 |
| 1048 | DIHEXYLAMINE+guanosine | 1 each | K2PtCl4 | KCl | 1.61E−03 |
| 1049 | DIOCTYLAMINE+guanosine | 1 each | K2PtCl4 | KCl | 1.81E−03 |
| 1050 | N-METHYLPROPYLAMINE+guanosine | 1 each | K2PtCl4 | KCl | 2.57E−03 |
| 1051 | N-METHYLISOPROPYLAMINE+guanosine | 1 each | K2PtCl4 | KCl | 9.51E−04 |
| 1052 | N-METHYLBUTYLAMINE+guanosine | 1 each | K2PtCl4 | KCl | 2.12E−03 |

TABLE 1-continued

| No. | Ligand(s) | Equiv. | Precursor | Leaving Group | Yld, g atm Pt |
|---|---|---|---|---|---|
| 1053 | N-METHYL-TERT-BUTYLAMINE+guanosine | 1 each | K2PtCl4 | KCl | 1.04E−03 |
| 1054 | N-METHYLHEXYLAMINE+guanosine | 1 each | K2PtCl4 | KCl | 3.18E−03 |
| 1055 | N-ETHYLMETHYLAMINE+guanosine | 1 each | K2PtCl4 | KCl | 2.15E−03 |
| 1056 | N-ETHYLISOPROPYLAMINE+guanosine | 1 each | K2PtCl4 | KCl | 8.63E−04 |
| 1057 | N-ETHYLBUTYLAMINE+guanosine | 1 each | K2PtCl4 | KCl | 3.36E−03 |
| 1058 | N-TERT-BUTYLISOPROPYLAMINE+guanosine | 1 each | K2PtCl4 | KCl | 2.72E−03 |
| 1059 | TRIETHYLAMINE+guanosiue | 1 each | K2PtCl4 | KCl | 4.64E−03 |
| 1060 | TRIPROPYLAMINE+guanosine | 1 each | K2PtCl4 | KCl | 9.29E−04 |
| 1061 | TRIISOPROPYLAMINE+guanosine | 1 each | K2PtCl4 | KCl | 1.08E−03 |
| 1062 | TRIISOBUTYLAMINE+guanosine | 1 each | K2PtCl4 | KCl | 2.48E−03 |
| 1063 | TRIHEXYLAMINE+guanosine | 1 each | K2PtCl4 | KCl | 1.28E−03 |
| 1064 | TRIOCTYLAMINE+guanosine | 1 each | K2PtCl4 | KCl | 1.35E−03 |
| 1065 | TRIISOOCTYLAMINE+guanosine | 1 each | K2PtCl4 | KCl | 1.50E−03 |
| 1066 | TRIDECYLAMINE+guanosine | 1 each | K2PtCl4 | KCl | 8.35E−04 |
| 1067 | N,N diisopropyl ethylamine + guanosine | 1 each | K2PtCl4 | KCl | 3.93E−04 |
| 1068 | cyclopropylamine + guanosine | 1 each | K2PtCl4 | KCl | 9.34E−04 |
| 1069 | cyclobutylamine + guanosine | 1 each | K2PtCl4 | KCl | 2.58E−03 |
| 1070 | CYCLOPENTYLAMINE+guanosine | 1 each | K2PtCl4 | KCl | 1.97E−03 |
| 1071 | CYCLOHEXYLAMINE+guanosine | 1 each | K2PtCl4 | KCl | 5.01E−03 |
| 1072 | CYCLOHEPTYLAMINE+guanosine | 1 each | K2PtCl4 | KCl | 3.34E−03 |
| 1073 | CYCLOOCTYLAMINE+guanosine | 1 each | K2PtCl4 | KCl | 1.70E−03 |
| 1074 | CYCLODODECYLAMINE+guanosine | 1 each | K2PtCl4 | KCl | 1.40E−03 |
| 1075 | 2-METHYLCYCLOHEXYLAMINE+guanosine | 1 each | K2PtCl4 | KCl | 1.70E−03 |
| 1076 | 2,3-DIMETHYLCYCLOHEXYLAMINE+guanosine | 1 each | K2PtCl4 | KCl | 1.45E−03 |
| 1077 | ALLYLCYCLOHEXYLAMINE+guanosine | 1 each | K2PtCl4 | KCl | 2.06E−03 |
| 1078 | N-ALLYLCYCLOPENTYLAMINE+guanosine | 1 each | K2PtCl4 | KCl | 3.10E−03 |
| 1079 | N-METHYLCYCLOHEXYLAMINE+guanosine | 1 each | K2PtCl4 | KCl | 1.55E−03 |
| 1080 | N-ETHYLCYCLOHEXYLAMINE+guanosine | 1 each | K2PtCl4 | KCl | 4.57E−03 |
| 1081 | N-ISOPROPYLCYCLOHEXYLAMINE+guanosine | 1 each | K2PtCl4 | KCl | 5.33E−04 |
| 1082 | N-TERT-BUTYLCYCLOHEXYLAMINE+guanosine | 1 each | K2PtCl4 | KCl | 6.04E−04 |
| 1083 | (R)-(−)-1-CYCLOHEXYLETHYLAMINE+guanosine | 1 each | K2PtCl4 | KCl | 2.19E−03 |
| 1084 | (S)-(+)-1-CYCLOHEXYLETHYLAMINE+guanosine | 1 each | K2PtCl4 | KCl | 1.33E−03 |
| 1085 | DICYCLOHEXYLAMINE+guanosine | 1 each | K2PtCl4 | KCl | 9.59E−04 |
| 1086 | 1-AMINO-2-PROPANOL + guanosine | 1 each | K2PtCl4 | KCl | 2.75E−03 |
| 1087 | DL-2-AMINO-1-PROPANOL + guanosine | 1 each | K2PtCl4 | KCl | 2.86E−03 |
| 1088 | (R)-(−)- 1-AMINO-2-PROPANOL + guanosine | 1 each | K2PtCl4 | KCl | 3.54E−03 |
| 1089 | (S)-(+)-1-AMINO-2-PROPANOL + guanosine | 1 each | K2PtCl4 | KCl | 4.81E−03 |
| 1090 | (R)-(−)-2-AMINO-1-PROPANOL + guanosine | 1 each | K2PtCl4 | KCl | 3.29E−03 |
| 1091 | (S)-(+)-2-AMINO-1-PROPANOL + guanosine | 1 each | K2PtCl4 | KCl | 2.58E−03 |
| 1092 | 3-AMINO-1-PROPANOL + guanosine | 1 each | K2PtCl4 | KCl | 3.61E−03 |
| 1093 | 2-AMINO-1-BUTANOL + guanosine | 1 each | K2PtCl4 | KCl | 2.82E−03 |
| 1094 | (R)-(−)-2-AMINO-1-BUTANOL + guanosine | 1 each | K2PtCl4 | KCl | 3.39E−03 |
| 1095 | (S)-(+)-2-AMINO-1-BUTANOL + guanosine | 1 each | K2PtCl4 | KCl | 2.75E−03 |
| 1096 | 4-AMINO-1-BUTANOL + guanosine | 1 each | K2PtCl4 | KCl | 2.79E−03 |
| 1097 | 5-AMINO-1-PENTANOL + guanosine | 1 each | K2PtCl4 | KCl | 2.22E−03 |
| 1098 | DL-2-AMINO-1-PENTANOL + guanosine | 1 each | K2PtCl4 | KCl | 2.33E−03 |
| 1099 | 6-AMINO-1-HEXANOL + guanosine | 1 each | K2PtCl4 | KCl | 3.22E−03 |
| 1100 | DL-2-AMINO-1-HEXANOL + guanosine | 1 each | K2PtCl4 | KCl | 1.42E−03 |
| 1101 | 2-AMINO-2-METHYL-1-PROPANOL + guanosine | 1 each | K2PtCl4 | KCl | 1.62E−03 |
| 1102 | 2-AMINO-3-METHYL-1-BUTANOL + guanosine | 1 each | K2PtCl4 | KCl | 2.75E−03 |
| 1103 | (R)-(−)-2-AMINO-3-METHYL-1-BUTANOL + guanosine | 1 each | K2PtCl4 | KCl | 1.49E−03 |
| 1104 | (S)-(+)-2-AMINO-3-METHYL-1-BUTANOL + guanosine | 1 each | K2PtCl4 | KCl | 2.40E−03 |
| 1105 | 6-AMINO-2-METHYL-2-HEPTANOL + guanosine | 1 each | K2PtCl4 | KCl | 3.70E−03 |
| 1106 | 2-(2-AMINOETHOXY)ETHANOL + guanosine | 1 each | K2PtCl4 | KCl | 4.71E−03 |
| 1107 | 2-(METHYLAMINO)ETHANOL + guanosine | 1 each | K2PtCl4 | KCl | 3.62E−03 |
| 1108 | 2-(PROPYLAMINO)ETHANOL + guanosine | 1 each | K2PtCl4 | KCl | 1.39E−03 |
| 1109 | 2-(TERT-BUTYLAMINO)ETHANOL + guanosine | 1 each | K2PtCl4 | KCl | 7.11E−04 |
| 1110 | 1-AMINOMETHYL-1-CYCLOHEXANOL + guanosine | 1 each | K2PtCl4 | KCl | 1.60E−03 |
| 1111 | TRANS-4-AMINOCYCLOHEXANOL + guanosine | 1 each | K2PtCl4 | KCl | 2.10E−03 |
| 1112 | diethanolamine + guanosine | 1 each | K2PtCl4 | KCl | 4.46E−03 |
| 1113 | 3-AMINO-1,2-PROPANEDIOL + guanosine | 1 each | K2PtCl4 | KCl | 3.57E−03 |
| 1114 | 2-AMINO-2-METHYL-1,3-PROPANEDIOL + guanosine | 1 each | K2PtCl4 | KCl | 3.70E−03 |
| 1115 | 2-AMINO-2-ETHYL-1,3-PROPANEDIOL + guanosine | 1 each | K2PtCl4 | KCl | 1.72E−03 |
| 1116 | 3-AMINO-1-PROPANOL VINYL ETHER + guanosine | 1 each | K2PtCl4 | KCl | 2.59E−03 |
| 1117 | ammonia + 1,8-diaminooctane | 1 each | K2PtCl4 | KCl | 2.41E−04 |
| 1118 | methtylamine + 1,8-diaminooctane | 1 each | K2PtCl4 | KCl | 5.92E−04 |
| 1119 | ethylamine + 1,8-diaminooctane | 1 each | K2PtCl4 | KCl | 1.75E−03 |
| 1120 | propylamine + 1,8-diaminooctane | 1 each | K2PtCl4 | KCl | 3.51E−04 |
| 1121 | isopropylamine + 1,8-diaminooctane | 1 each | K2PtCl4 | KCl | 2.41E−04 |
| 1122 | ISOBUTYLAMINE+1,8-diaminooctane | 1 each | K2PtCl4 | KCl | 3.73E−04 |
| 1123 | t-butylamine + 1,8-diaminooctane | 1 each | K2PtCl4 | KCl | 2.41E−04 |
| 1124 | sec-butylamine + 1,8-diaminooctane | 1 each | K2PtCl4 | KCl | 2.63E−04 |

TABLE 1-continued

| No. | Ligand(s) | Equiv. | Precursor | Leaving Group | Yld, g atm Pt |
|---|---|---|---|---|---|
| 1125 | 1,2-DIMETHYLPROPYLAMINE+1,8-diaminooctane | 1 each | K2PtCl4 | KCl | 4.38E−04 |
| 1126 | 1-ETHYLPROPYLAMINE+1,8-diaminooctane | 1 each | K2PtCl4 | KCl | 2.63E−04 |
| 1127 | 1-methylbutylamine + 1,8-diaminooctane | 1 each | K2PtCl4 | KCl | 3.07E−04 |
| 1128 | 2-methylbutylamine + 1,8-diaminooctane | 1 each | K2PtCl4 | KCl | 3.95E−04 |
| 1129 | hexylamine + 1,8-diaminooctane | 1 each | K2PtCl4 | KCl | 6.14E−04 |
| 1130 | heptylamine + 1,8-diaminooctane | 1 each | K2PtCl4 | KCl | 6.58E−04 |
| 1131 | octylamine + 1,8-diaminooctane | 1 each | K2PtCl4 | KCl | 7.45E−04 |
| 1132 | 1-METHYLHEPTYLAMINE+1,8-diaminooctane | 1 each | K2PtCl4 | KCl | 7.67E−04 |
| 1133 | 1,5-DIMETHYLHEXYLAMINE+1,8-diaminooctane | 1 each | K2PtCl4 | KCl | 7.89E−04 |
| 1134 | 2-ETHYLHEXYLAMINE+1,8-diaminooctane | 1 each | K2PtCl4 | KCl | 6.36E−04 |
| 1135 | decylamine + 1,8-diaminooctane | 1 each | K2PtCl4 | KCl | 6.58E−04 |
| 1136 | TERT-OCTYLAMINE+1,8-diaminooctane | 1 each | K2PtCl4 | KCl | 3.29E−04 |
| 1137 | UNDECYLAMINE+1,8-diaminooctane | 1 each | K2PtCl4 | KCl | 1.07E−03 |
| 1138 | allylamine + 1,8-diaminooctane | 1 each | K2PtCl4 | KCl | 5.70E−04 |
| 1139 | diethylamine + 1,8-diaminooctane | 1 each | K2PtCl4 | KCl | 4.38E−04 |
| 1140 | dipropylamine + 1,8-diaminooctane | 1 each | K2PtCl4 | KCl | 3.95E−04 |
| 1141 | diisopropylamine + 1,8-diaminooctane | 1 each | K2PtCl4 | KCl | 3.51E−04 |
| 1142 | dibutylamine + 1,8-diaminooctane | 1 each | K2PtCl4 | KCl | 7.45E−04 |
| 1143 | dipentylamine + 1,8-diaminooctane | 1 each | K2PtCl4 | KCl | 5.04E−04 |
| 1144 | DIHEXYLAMINE+1,8-diaminooctane | 1 each | K2PtCl4 | KCl | 7.01E−04 |
| 1145 | DIOCTYLAMINE+1,8-diaminooctane | 1 each | K2PtCl4 | KCl | 5.26E−04 |
| 1146 | N-METHYLPROPYLAMINE+1,8-diaminooctane | 1 each | K2PtCl4 | KCl | 3.95E−04 |
| 1147 | N-METHYLISOPROPYLAMINE+1,8-diaminooctane | 1 each | K2PtCl4 | KCl | 5.48E−04 |
| 1148 | N-METHYLBUTYLAMINE+1,8-diaminooctane | 1 each | K2PtCl4 | KCl | 5.26E−04 |
| 1149 | N-METHTYL-TERT-BUTYLAMINE+1,8-diaminooctane | 1 each | K2PtCl4 | KCl | 6.79E−04 |
| 1150 | N-METHYLHEXYLAMINE+1,8-diaminooctane | 1 each | K2PtCl4 | KCl | 9.64E−04 |
| 1151 | N-ETHYLMETHYLAMINE+1,8-diaminooctane | 1 each | K2PtCl4 | KCl | 5.04E−04 |
| 1152 | N-ETHYLISOPROPYLAMINE+1,8-diaminooctane | 1 each | K2PtCl4 | KCl | 8.11E−04 |
| 1153 | N-ETHYLBUTYLAMINE+1,8-diaminooctane | 1 each | K2PtCl4 | KCl | 6.36E−04 |
| 1154 | N-TERT-BUTYLISOPROPYLAMINE+1,8-diaminooctane | 1 each | K2PtCl4 | KCl | 6.58E−04 |
| 1155 | TRIETHYLAMINE+1,8-diaminooctane | 1 each | K2PtCl4 | KCl | 7.23E−04 |
| 1156 | TRIPROPYLAMINE+1,8-diaminooctane | 1 each | K2PtCl4 | KCl | 4.82E−04 |
| 1157 | TRIISOPROPYLAMINE+1,8-diaminooctane | 1 each | K2PtCl4 | KCl | 7.23E−04 |
| 1158 | TRIISOBUTYLAMINE+1,8-diaminooctane | 1 each | K2PtCl4 | KCl | 7.45E−04 |
| 1159 | TRIHEXYLAMINE+1,8-diaminooctane | 1 each | K2PtCl4 | KCl | 5.70E−04 |
| 1160 | TRIOCTYLAMINE+1,8-diaminooctane | 1 each | K2PtCl4 | KCl | 6.36E−04 |
| 1161 | TRIISOOCTYLAMINE+1,8-diaminooctane | 1 each | K2PtCl4 | KCl | 5.92E−04 |
| 1162 | TRIDECYLAMINE+1,8-diaminocctane | 1 each | K2PtCl4 | KCl | 5.32E−04 |
| 1163 | N,N diisopropyl ethylamine + 1,8-diaminooctane | 1 each | K2PtCl4 | KCl | 2.36E−04 |
| 1164 | cyclopropylamine + 1,8-diaminooctane | 1 each | K2PtCl4 | KCl | 6.11E−04 |
| 1165 | cyclobutylamine + 1,8-diaminooctane | 1 each | K2PtCl4 | KCl | 9.85E−04 |
| 1166 | CYCLOPENTYLAMINE+1,8-diaminooctane | 1 each | K2PtCl4 | KCl | 5.32E−04 |
| 1167 | CYCLOHEXYLAMINE+1,8-diaminooctane | 1 each | K2PtCl4 | KCl | 5.91E−04 |
| 1168 | CYCLOHEPTYLAMINE+1,8-diaminooctane | 1 each | K2PtCl4 | KCl | 5.91E−04 |
| 1169 | CYCLOOCTYLAMINE+1,8-diaminooctane | 1 each | K2PtCl4 | KCl | 5.71E−04 |
| 1170 | CYCLODODECYLAMINE+1,8-diaminooctane | 1 each | K2PtCl4 | KCl | 5.71E−04 |
| 1171 | 2-METHYLCYCLOHEXYLAMINE + 1,8-diaminooctane | 1 each | K2PtCl4 | KCl | 7.88E−04 |
| 1172 | 2,3-DIMETHYLCYCLOHEXYLAMINE+1,8-diaminooctane | 1 each | K2PtCl4 | KCl | 7.88E−04 |
| 1173 | ALLYLCYCLOHEXYLAMINE+1,8-diaminooctane | 1 each | K2PtCl4 | KCl | 6.50E−04 |
| 1174 | N-ALLYLCYCLOPENTYLAMINE+1,8-diaminooctane | 1 each | K2PtCl4 | KCl | 6.50E−04 |
| 1175 | N-METHYLCYCLOHEXYLAMINE+1,8-diaminooctane | 1 each | K2PtCl4 | KCl | 4.34E−04 |
| 1176 | N-ETHYLCYCLOHEXYLAMINE+1,8-diaminooctane | 1 each | K2PtCl4 | KCl | 4.73E−04 |
| 1177 | N-ISOPROPYLCYCLOHEXYLAMINE+1,8-diaminooctane | 1 each | K2PtCl4 | KCl | 6.11E−04 |
| 1178 | N-TERT-BUTYLCYCLOHEXYLAMINE + 1,8-diaminooctane | 1 each | K2PtCl4 | KCl | 4.93E−04 |

TABLE 1-continued

| No. | Ligand(s) | Equiv. | Precursor | Leaving Group | Yld, g atm Pt |
|---|---|---|---|---|---|
| 1179* | (R)-(−)-1-CYCLOHEXYLETHYLAMINE + 1,8-diaminooctane | 1 each | K2PtCl4 | KCl | 1.10E−03 |
| 1180 | (S)-(+)-1-CYCLOHEXYLETHYLAMINE + 1,8-diaminooctane | 1 each | K2PtCl4 | KCl | 1.04E−03 |
| 1181 | DICYCLOHEXYLAMINE+1,8-diaminooctane | 1 each | K2PtCl4 | KCl | 5.12E−04 |
| 1182 | 1-AMINO-2-PROPANOL + 1,8-diaminooctane | 1 each | K2PtCl4 | KCl | 8.47E−04 |
| 1183 | DL-2-AMINO-1-PROPANOL + 1,8-diaminooctane | 1 each | K2PtCl4 | KCl | 7.88E−04 |
| 1184 | (R)-(−)-1-AMINO-2-PROPANOL + 1,8-diaminooctane | 1 each | K2PtCl4 | KCl | 8.08E−04 |
| 1185 | (S)-(+)-1-AMINO-2-PROPANOL + 1,8-diaminooctane | 1 each | K2PtCl4 | KCl | 7.88E−04 |
| 1186 | (R)-(−)-2-AMINO-1-PROPANOL + 1,8-diaminooctane | 1 each | K2PtCl4 | KCl | 6.70E−04 |
| 1187 | (S)-(+)-2-AMINO-1-PROPANOL + 1,8-diaminooctane | 1 each | K2PtCl4 | KCl | 9.26E−04 |
| 1188 | 3-AMINO-1-PROPANOL + 1,8-diaminooctane | 1 each | K2PtCl4 | KCl | 7.49E−04 |
| 1189 | 2-AMINO-1-BUTANOL + 1,8-diaminooctane | 1 each | K2PtCl4 | KCl | 7.49E−04 |
| 1190 | (R)-(−)-2-AMINO-1-BUTANOL + 1,8-diaminooctane | 1 each | K2PtCl4 | KCl | 6.50E−04 |
| 1191 | (S)-(+)-2-AMINO-1-BUTANOL + 1,8-diaminooctane | 1 each | K2PtCl4 | KCl | 7.29E−04 |
| 1192 | 4-AMINO-1-BUTANOL + 1,8-diaminooctane | 1 each | K2PtCl4 | KCl | 4.93E−04 |
| 1193 | 5-AMINO-1-PENTANOL + 1,8-diaminooctane | 1 each | K2PtCl4 | KCl | 5.91E−04 |
| 1194 | DL-2-AMINO-1-PENTANOL + 1,8-diaminooctane | 1 each | K2PtCl4 | KCl | 7.68E−04 |
| 1195 | 6-AMINO-1-HEXANOL + 1,8-diaminooctane | 1 each | K2PtCl4 | KCl | 6.31E−04 |
| 1196 | DL-2-AMINO-1-HEXANOL + 1,8-diaminooctane | 1 each | K2PtCl4 | KCl | 6.11E−04 |
| 1197 | 2-AMINO-2-METHYL-1-PROPANOL + 1,8-diaminooctane | 1 each | K2PtCl4 | KCl | 7.09E−04 |
| 1198 | 2-AMINO-3-METHYL-1-BUTANOL + 1,8-diaminooctane | 1 each | K2PtCl4 | KCl | 6.50E−04 |
| 1199 | (R)-(−)-2-AMINO-3-METHYL-1-BUTANOL + 1,8-diaminooctane | 1 each | K2PtCl4 | KCl | 1.20E−03 |
| 1200 | (S)-(+)-2-AMINO-3-METHYL-1-BUTANOL + 1,8-diaminooctane | 1 each | K2PtCl4 | KCl | 8.28E−04 |
| 1201 | 6-AMINO-2-METHYL-2-HEPTANOL + 1,8-diaminooctane | 1 each | K2PtCl4 | KCl | 8.28E−04 |
| 1202 | 2-(2-AMINOETHOXY)ETHANOL + 1,8-diaminooctane | 1 each | K2PtCl4 | KCl | 7.29E−04 |
| 1203 | 2-(METHYLAMINO)ETHANOL + 1,8-diaminooctane | 1 each | K2PtCl4 | KCl | 7.68E−04 |
| 1204 | 2-(PROPYLAMINO)ETHANOL + 1,8-diaminooctane | 1 each | K2PtCl4 | KCl | 5.32E−04 |
| 1205 | 2-(TERT-BUTYLAMINO)ETHANOL + 1,8-diaminooctane | 1 each | K2PtCl4 | KCl | 5.12E−04 |
| 1206 | 1-AMINOMETHYL-1-CYCLOHEXANOL + 1,8-diaminooctane | 1 each | K2PtCl4 | KCl | 1.32E−03 |
| 1207 | TRANS-4-AMINOCYCLOHEXANOL + 1,8-diaminooctane | 1 each | K2PtCl4 | KCl | 1.12E−03 |
| 1208 | diethanolamine + 1,8-diaminooctane | 1 each | K2PtCl4 | KCl | 1.06E−04 |
| 1209 | 3-AMINO-1,2-PROPANEDIOL + 1,8-diaminooctane | 1 each | K2PtCl4 | KCl | 3.17E−04 |
| 1210 | 2-AMINO-2-METHYL-1,3-PROPANEDIOL + 1,8-diaminooctane | 1 each | K2PtCl4 | KCl | 5.07E−04 |
| 1211 | 2-AMINO-2-ETHYL-1,3-PROPANEDIOL + 1,8-diaminooctane | 1 each | K2PtCl4 | KCl | 2.11E−04 |
| 1212 | 3-AMINO-1-PROPANOL VINYL ETHER + 1,8-diaminooctane | 1 each | K2PtCl4 | KCl | 1.48E−04 |
| 1213 | ammonia + 3-amino-1-propanol | 1 each | K2PtCl4 | KCl | 1.06E−03 |
| 1214 | methylamine + 3-amino-1-propanol | 1 each | K2PtCl4 | KCl | 1.25E−03 |
| 1215 | ethylamine + 3-amino-1-propanol | 1 each | K2PtCl4 | KCl | 1.12E−03 |
| 1216 | propylamine + 3-amino-1-propanol | 1 each | K2PtCl4 | KCl | 1.09E−03 |
| 1217 | isopropylamine + 3-amino-1-propanol | 1 each | K2PtCl4 | KCl | 1.82E−03 |
| 1218 | ISOBUTYLAMINE+3-amino-1-propanol | 1 each | K2PtCl4 | KCl | 1.45E−03 |
| 1219 | t-butylamine + 3-amino-1-propanol | 1 each | K2PtCl4 | KCl | 9.33E−04 |
| 1220 | sec-butylamine + 3-amino-1-propanol | 1 each | K2PtCl4 | KCl | 1.22E−03 |
| 1221 | 1,2-DIMETHYLPROPYLAMINE+3-amino-1-propanol | 1 each | K2PtCl4 | KCl | 2.81E−03 |
| 1222 | 1-ETHYLPROPYLAMINE+3-amino-1-propanol | 1 each | K2PtCl4 | KCl | 1.19E−03 |
| 1223 | 1-methylbutylamine + 3-amino-1-propanol | 1 each | K2PtCl4 | KCl | 2.39E−03 |
| 1224 | 2-methylbutylamine + 3-amino-1-propanol | 1 each | K2PtCl4 | KCl | 2.37E−03 |
| 1225 | hexylamine + 3-amino-1-propanol | 1 each | K2PtCl4 | KCl | 1.15E−03 |
| 1226 | heptylamine + 3-amino-1-propanol | 1 each | K2PtCl4 | KCl | 1.22E−03 |

TABLE 1-continued

| No. | Ligand(s) | Equiv. | Precursor | Leaving Group | Yld, g atm Pt |
|---|---|---|---|---|---|
| 1227 | octylamine + 3-amino-1-propanol | 1 each | K2PtCl4 | KCl | 1.50E-03 |
| 1228 | 1-METHYLHEPTYLAMINE+3-amino-1-propanol | 1 each | K2PtCl4 | KCl | 7.59E-04 |
| 1229 | 1,5-DIMETHYLHEXYLAMINE+3-amino-1-propanol | 1 each | K2PtCl4 | KCl | 9.64E-04 |
| 1230 | 2-ETHYLHEXYLAMINE+3-amino-1-propanol | 1 each | K2PtCl4 | KCl | 1.04E-03 |
| 1231 | decylamine + 3-amino-1-propanol | 1 each | K2PtCl4 | KCl | 1.68E-03 |
| 1232 | TERT-OCTYLAMINE+3-amino-1-propanol | 1 each | K2PtCl4 | KCl | 5.85E-04 |
| 1233 | UNDECYLAMINE+3-amino-1-propanol | 1 each | K2PtCl4 | KCl | 1.44E-03 |
| 1234 | allylamine + 3-amino-1-propanol | 1 each | K2PtCl4 | KCl | 1.79E-03 |
| 1235 | diethylamine + 3-amino-1-propanol | 1 each | K2PtCl4 | KCl | 1.96E-03 |
| 1236 | dipropylmine + 3-amino-1-propanol | 1 each | K2PtCl4 | KCl | 1.45E-03 |
| 1237 | diisopropylamine + 3-amino-1-propanol | 1 each | K2PtCl4 | KCl | 1.80E-03 |
| 1238 | dibutylamine + 3-amino-1-propanol | 1 each | K2PtCl4 | KCl | 1.20E-03 |
| 1239 | dipentylamine + 3-amino-1-propanol | 1 each | K2PtCl4 | KCl | 3.78E-03 |
| 1240 | DIHEXYLAMINE+3-amino-1-propanol | 1 each | K2PtCl4 | KCl | 2.99E-03 |
| 1241 | DIOCTYLAMINE+3-amino-1-propanol | 1 each | K2PtCl4 | KCl | 3.29E-03 |
| 1242 | N-METHYLPROPYLAMINE+3-amino-1-propanol | 1 each | K2PtCl4 | KCl | 3.83E-03 |
| 1243 | N-METHYLISOPROPYLAMINE+3-amino-1-propanol | 1 each | K2PtCl4 | KCl | 3.08E-03 |
| 1244 | N-METHYLBUTYLAMINE+3-amino-1-propanol | 1 each | K2PtCl4 | KCl | 3.12E-03 |
| 1245 | N-METHYL-TERT-BUTYLAMINE+3-amino-1-propanol | 1 each | K2PtCl4 | KCl | 4.59E-03 |
| 1246 | N-METHYLHEXYLAMINE+3-amino-1-propanol | 1 each | K2PtCl4 | KCl | 2.95E-03 |
| 1247 | N-ETHYLMETHYLAMINE+3-amino-1-propanol | 1 each | K2PtCl4 | KCl | 2.18E-03 |
| 1248 | N-ETHYLISOPROPYLAMINE+3-amino-1-propanol | 1 each | K2PtCl4 | KCl | 4.70E-03 |
| 1249 | N-ETHYLBUTYLAMINE+3-amino-1-propanol | 1 each | K2PtCl4 | KCl | 1.47E-03 |
| 1250 | N-TERT-BUTYLISOPROPYLAMINE+3-amino-1-propanol | 1 each | K2PtCl4 | KCl | 4.15E-03 |
| 1251 | TRIETHYLAMINE+3-amino-1-propanol | 1 each | K2PtCl4 | KCl | 1.90E-03 |
| 1252 | TRIPROPYLAMINE+3-amino-1-propanol | 1 each | K2PtCl4 | KCl | 1.90E-03 |
| 1253 | TRIISOPROPYLAMINE+3-amino-1-propanol | 1 each | K2PtCl4 | KCl | 3.27E-03 |
| 1254 | TRIISOBUTYLAMINE+3-amino-1-propanol | 1 each | K2PtCl4 | KCl | 1.54E-03 |
| 1255 | TRIHEXYLAMINE+3-amino-1-propanol | 1 each | K2PtCl4 | KCl | 3.50E-03 |
| 1256 | TRIOCTYLAMINE+3-amino-1-propanol | 1 each | K2PtCl4 | KCl | 1.62E-03 |
| 1257 | TRIISOOCTYLAMINE+3-amino-1-propanol | 1 each | K2PtCl4 | KCl | 3.74E-03 |
| 1258 | TRIDECYLAMINE+3-amino-1-propanol | 1 each | K2PtCl4 | KCl | 2.86E-03 |
| 1259 | N,N diisopropyl ethylamine + 3-amino-1-propanol | 1 each | K2PtCl4 | KCl | 1.48E-03 |
| 1260 | cyclopropylamine + 3-amino-1-propanol | 1 each | K2PtCl4 | KCl | 2.93E-03 |
| 1261 | cyclobutylamine + 3-amino-1-propanol | 1 each | K2PtCl4 | KCl | 3.23E-03 |
| 1262 | CYCLOPENTYLAMINE+3-amino-1-propanol | 1 each | K2PtCl4 | KCl | 1.52E-03 |
| 1263 | CYCLOHEXYLAMINE+3-amino-1-propanol | 1 each | K2PtCl4 | KCl | 2.14E-03 |
| 1264 | CYCLOHEPTYLAMINE+3-amino-1-propanol | 1 each | K2PtCl4 | KCl | 1.13E-03 |
| 1265 | CYCLOOCTYLAMINE+3-amino-1-propanol | 1 each | K2PtCl4 | KCl | 3.95E-03 |
| 1266 | CYCLODODECYLAMINE+3-amino-1-propanol | 1 each | K2PtCl4 | KCl | 4.55E-03 |
| 1267 | 2-METHYLCYCLOHEXYLAMINE+3-amino-1-propanol | 1 each | K2PtCl4 | KCl | 1.69E-03 |
| 1268 | 2,3-DIMETHYLCYCLOHEXYLAMINE+3-amino-1-propanol | 1 each | K2PtCl4 | KCl | 2.12E-03 |
| 1269 | ALLYLCYCLOHEXYLAMINE+3-amino-1-propanol | 1 each | K2PtCl4 | KCl | 1.84E-03 |
| 1270 | N-ALLYLCYCLOPENTYLAMINE+3-amino-1-propanol | 1 each | K2PtCl4 | KCl | 2.05E-03 |
| 1271 | N-METHYLCYCLOHEXYLAMINE+3-amino-1-propanol | 1 each | K2PtCl4 | KCl | 2.16E-03 |
| 1272 | N-ETHYLCYCLOHEXYLAMINE+3-amino-1-propanol | 1 each | K2PtCl4 | KCl | 2.31E-03 |
| 1273 | N-ISOPROPYLCYCLOHEXYLAMINE+3-amino-1-propanol | 1 each | K2PtCl4 | KCl | 2.18E-03 |
| 1274 | N-TERT-BUTYLCYCLOHEXYLAMINE+3-amino-1-propanol | 1 each | K2PtCl4 | KCl | 2.10E-03 |
| 1275 | (R)-(−)-1-CYCLOHEXYLETHYLAMINE+3-amino-1-propanol | 1 each | K2PtCl4 | KCl | 3.68E-03 |
| 1276 | (S)-(+)-1-CYCLOHEXYLETHYLAMINE+3-amino-1-propanol | 1 each | K2PtCl4 | KCl | 2.03E-03 |

TABLE 1-continued

| No. | Ligand(s) | Equiv. | Precursor | Leaving Group | Yld, g atm Pt |
|---|---|---|---|---|---|
| 1277 | DICYCLOHEXYLAMINE+3-amino-1-propanol | 1 each | K2PtCl4 | KCl | 3.44E−03 |
| 1278 | 1-AMINO-2-PROPANOL + 3-amino-1-propanol | 1 each | K2PtCl4 | KCl | 2.69E−03 |
| 1279 | DL-2-AMINO-1-PROPANOL + 3-amino-1-propanol | 1 each | K2PtCl4 | KCl | 2.89E−03 |
| 1280 | (R)-(−)-1-AMINO-2-PROPANOL + 3-amino-1-propanol | 1 each | K2PtCl4 | KCl | 3.72E−03 |
| 1281 | (S)-(+)-1-AMINO-2-PROPANOL + 3-amino-1-propanol | 1 each | K2PtCl4 | KCl | 2.52E−03 |
| 1282 | (R)-(−)-2-AMINO-1-PROPANOL + 3-amino-1-propanol | 1 each | K2PtCl4 | KCl | 1.84E−03 |
| 1283 | (S)-(+)-2-AMINO-1-PROPANOL + 3-amino-1-propanol | 1 each | K2PtCl4 | KCl | 1.71E−03 |
| 1284 | 3-AMINO-1-PROPANOL + 3-amino-1-propanol | 1 each | K2PtCl4 | KCl | 1.68E−03 |
| 1285 | 2-AMINO-1-BUTANOL + 3-amino-1-propanol | 1 each | K2PtCl4 | KCl | 1.22E−03 |
| 1286 | (R)-(−)-2-AMINO-1-BUTANOL + 3-amino-1-propanol | 1 each | K2PtCl4 | KCl | 2.38E−03 |
| 1287 | (S)-(+)-2-AMINO-1-BUTANOL + 3-amino-1-propanol | 1 each | K2PtCl4 | KCl | 1.94E−03 |
| 1288 | 4-AMINO-1-BUTANOL + 3-amino-1-propanol | 1 each | K2PtCl4 | KCl | 1.68E−03 |
| 1289 | 5-AMINO-1-PENTANOL + 3-amino-1-propanol | 1 each | K2PtCl4 | KCl | 1.82E−03 |
| 1290 | DL-2-AMINO-1-PENTANOL + 3-amino-1-propanol | 1 each | K2PtCl4 | KCl | 7.49E−04 |
| 1291 | 6-AMINO-1-HEXANOL + 3-amino-1-propanol | 1 each | K2PtCl4 | KCl | 9.93E−04 |
| 1292 | DL-2-AMINO-1-HEXANOL + 3-amino-1-propanol | 1 each | K2PtCl4 | KCl | 9.12E−04 |
| 1293 | 2-AMINO-2-METHYL-1-PROPANOL + 3-amino-1-propanol | 1 each | K2PtCl4 | KCl | 1.60E−03 |
| 1294 | 2-AMINO-3-METHYL-1-BUTANOL + 3-amino-1-propanol | 1 each | K2PtCl4 | KCl | 1.16E−03 |
| 1295 | (R)-(−)-2-AMINO-3-METHYL-1-BUTANOL + 3-amino-1-propanol | 1 each | K2PtCl4 | KCl | 3.50E−03 |
| 1296 | (S)-(+)-2-AMINO-3-METHYL-1-BUTANOL + 3-amino-1-propanol | 1 each | K2PtCl4 | KCl | 1.24E−03 |
| 1297 | 6-AMINO-2-METHYL-2-HEPTANOL + 3-amino-1-propanol | 1 each | K2PtCl4 | KCl | 1.47E−03 |
| 1298 | 2-(2-AMINOETHOXY)ETHANOL + 3-amino-1-propanol | 1 each | K2PtCl4 | KCl | 1.99E−03 |
| 1299 | 2-(METHYLAMINO)ETHANOL + 3-amino-1-propanol | 1 each | K2PtCl4 | KCl | 1.95E−03 |
| 1300 | 2-(PROPYLAMINO)ETHANOL + 3-amino-1-propanol | 1 each | K2PtCl4 | KCl | 9.12E−04 |
| 1301 | 2-(TERT-BUTYLAMINO)ETHANOL + 3-amino-1-propanol | 1 each | K2PtCl4 | KCl | 1.11E−03 |
| 1302 | 1-AMINOMETHYL-1-CYCLOHEXANOL + 3-amino-1-propanol | 1 each | K2PtCl4 | KCl | 8.96E−04 |
| 1303 | TRANS-4-AMINOCYCLOHEXANOL + 3-amino-1-propanol | 1 each | K2PtCl4 | KCl | 7.82E−04 |
| 1304 | diethanolamine + 3-amino-1-propanol | 1 each | K2PtCl4 | KCl | 1.45E−03 |
| 1305 | 3-AMINO-1,2-PROPANEDIOL + 3-amino-1-propanol | 1 each | K2PtCl4 | KCl | 1.03E−03 |
| 1306 | 2-AMINO-2-METHYL-1,3-PROPANEDIOL + 3-amino-1-propanol | 1 each | K2PtCl4 | KCl | 1.61E−03 |
| 1307 | 2-AMINO-2-ETHYL-1,3-PROPANEDIOL + 3-amino-1-propanol | 1 each | K2PtCl4 | KCl | 1.45E−03 |
| 1308 | 3-AMINO-1-PROPANOL VINYL ETHER + 3-amino-1-propanol | 1 each | K2PtCl4 | KCl | 3.26E−04 |
| 1309 | cyclopentyl amine | 2 | K2PtCl4 | oxalate | 2.88E−03 |
| 1310 | pyrrolidine | 2 | K2PtCl4 | oxalate | 1.42E−03 |
| 1311 | indole | 2 | K2PtCl4 | oxalate | 1.91E−03 |
| 1312 | pyrrole | 2 | K2PtCl4 | oxalate | 6.99E−04 |
| 1313 | exo-2-amino norbornane | 2 | K2PtCl4 | oxalate | 1.66E−03 |
| 1314 | 2-methyl-1-pyrroline | 2 | K2PtCl4 | oxalate | 4.51E−03 |
| 1315 | indoline | 2 | K2PtCl4 | oxalate | 5.06E−03 |
| 1316 | 2,4-dimethyl pyrrole | 2 | K2PtCl4 | oxalate | 2.37E−03 |
| 1317 | cyclopentyl amine + ammonia | 1 each | K2PtCl4 | oxalate | 4.34E−03 |
| 1318 | pyrrolidine + ammonia | 1 each | K2PtCl4 | oxalate | 6.81E−04 |
| 1319 | indole + ammonia | 1 each | K2PtCl4 | oxalate | 1.47E−04 |
| 1320 | pyrrole + ammonia | 1 each | K2PtCl4 | oxalate | 2.39E−04 |
| 1321 | exo-2-amino norbornane + ammonia | 1 each | K2PtCl4 | oxalate | 2.19E−03 |
| 1322 | 2-methyl-1-pyrroline + ammonia | 1 each | K2PtCl4 | oxalate | 5.04E−03 |

TABLE 1-continued

| No. | Ligand(s) | Equiv. | Precursor | Leaving Group | Yld, g atm Pt |
|---|---|---|---|---|---|
| 1323 | indoline + ammonia | 1 each | K2PtCl4 | oxalate | 1.44E−03 |
| 1324 | 2,4-dimethyl pyrrole + ammonia | 1 each | K2PtCl4 | oxalate | 2.87E−03 |
| 1325 | cyclopentyl amine | 2 | K2PtCl4 | malonate | 2.78E−03 |
| 1326 | pyrrolidine | 2 | K2PtCl4 | malonate | 5.10E−03 |
| 1327 | indole | 2 | K2PtCl4 | malonate | 1.29E−04 |
| 1328 | pyrrole | 2 | K2PtCl4 | malonate | 9.53E−05 |
| 1329 | exo-2-amino norbornane | 2 | K2PtCl4 | malonate | 4.44E−03 |
| 1330 | 2-methyl-1-pyrroline | 2 | K2PtCl4 | malonate | 2.87E−03 |
| 1331 | indoline | 2 | K2PtCl4 | malonate | 1.97E−03 |
| 1332 | 2,4-dimethyl pyrrole | 2 | K2PtCl4 | malonate | 1.21E−03 |
| 1333 | cyclopentyl amine + ammonia | 1 each | K2PtCl4 | malonate | 6.99E−04 |
| 1334 | pyrrolidine + ammonia | 1 each | K2PtCl4 | malonate | 2.23E−03 |
| 1335 | indole + ammonia | 1 each | K2PtCl4 | malonate | 1.47E−04 |
| 1336 | pyrrole + ammonia | 1 each | K2PtCl4 | malonate | 1.47E−04 |
| 1337 | exo-2-amino norbornane + ammonia | 1 each | K2PtCl4 | malonate | 2.23E−03 |
| 1338 | 2-methyl-1-pyrroline + ammonia | 1 each | K2PtCl4 | malonate | 9.57E−04 |
| 1339 | indoline + ammonia | 1 each | K2PtCl4 | malonate | 2.02E−04 |
| 1340 | 2,4-dimethyl pyrrole + ammonia | 1 each | K2PtCl4 | malonate | 2.02E−04 |
| 1341 | cyclopentyl amine | 2 | K2PtCl4 | 2-ketobutyrate | 1.44E−03 |
| 1342 | pyrrolidine | 2 | K2PtCl4 | 2-ketobutyrate | 1.40E−03 |
| 1343 | indole | 2 | K2PtCl4 | 2-ketobutyrate | 3.13E−04 |
| 1344 | pyrrole | 2 | K2PtCl4 | 2-ketobutyrate | 1.66E−04 |
| 1345 | exo-2-amino norbornane | 2 | K2PtCl4 | 2-ketobutyrate | 2.37E−03 |
| 1346 | 2-methyl-1-pyrroline | 2 | K2PtCl4 | 2-ketobutyrate | 2.63E−03 |
| 1347 | indoline | 2 | K2PtCl4 | 2-ketobutyrate | 3.31E−04 |
| 1348 | 2,4-dimethyl pyrrole | 2 | K2PtCl4 | 2-ketobutyrate | 8.65E−04 |
| 1349 | cyclopentyl amine + ammonia | 1 each | K2PtCl4 | 2-ketobutyrate | 8.25E−04 |
| 1350 | pyrrolidine + ammonia | 1 each | K2PtCl4 | 2-ketobutyrate | 1.47E−03 |
| 1351 | indole + ammonia | 1 each | K2PtCl4 | 2-ketobutyrate | 2.76E−04 |
| 1352 | pyrrole + ammonia | 1 each | K2PtCl4 | 2-ketobutyrate | 2.02E−04 |
| 1353 | exo-2-amino norbornane + ammonia | 1 each | K2PtCl4 | 2-ketobutyrate | 2.65E−03 |
| 1354 | 2-methyl-1-pyrroline + ammonia | 1 each | K2PtCl4 | 2-ketobutyrate | 1.42E−03 |
| 1355 | indoline + ammonia | 1 each | K2PtCl4 | 2-ketobutyrate | 5.69E−04 |
| 1356 | 2,4-dimethyl pyrrole + ammonia | 1 each | K2PtCl4 | 2-ketobutyrate | 9.01E−04 |
| 1357 | cyclopentyl amine | 2 | K2PtCl4 | butyrate | 5.37E−04 |
| 1358 | pyrrolidine | 2 | K2PtCl4 | butyrate | 1.91E−03 |
| 1359 | indole | 2 | K2PtCl4 | butyrate | 6.32E−05 |
| 1360 | pyrrole | 2 | KtPtCl4 | butyrate | 4.74E−05 |
| 1361 | exo-2-amino norbornane | 2 | K2PtCl4 | butyrate | 3.16E−05 |
| 1362 | 2-methyl-1-pyrroline | 2 | K2PtCl4 | butyrate | 8.69E−04 |
| 1363 | indoline | 2 | K2PtCl4 | butyrate | 1.90E−04 |
| 1364 | 2,4-dimethyl pyrrole | 2 | K2PtCl4 | butyrate | 1.58E−04 |
| 1365 | cyclopentyl amine + ammonia | 1 each | K2PtCl4 | butyrate | 1.12E−03 |
| 1366 | pyrrolidine + ammonia | 1 each | K2PtCl4 | butyrate | 1.04E−03 |
| 1367 | indole + ammonia | 1 each | K2PtCl4 | butyrate | 2.69E−04 |
| 1368 | pyrrole + ammonia | 1 each | K2PtCl4 | butyrate | 4.27E−04 |
| 1369 | exo-2-amino norbornane + ammonia | 1 each | K2PtCl4 | butyrate | 3.95E−04 |
| 1370 | 2-methyl-1-pyrroline + ammonia | 1 each | K2PtCl4 | butyrate | 4.42E−04 |
| 1371 | indoline + ammonia | 1 each | K2PtCl4 | butyrate | 2.37E−04 |
| 1372 | 2,4-dimethyl pyrrole + ammonia | 1 each | K2PtCl4 | butyrate | 4.42E−04 |
| 1373 | cyclopentyl amine | 2 | K2PtCl4 | propionate | 7.11E−04 |
| 1374 | pyrrolidine | 2 | K2PtCl4 | propionate | 9.48E−04 |
| 1375 | indole | 2 | K2PtCl4 | propionate | 4.42E−04 |
| 1376 | pyrrole | 2 | K2PtCl4 | propionate | 1.42E−04 |
| 1377 | exo-2-amino norbornane | 2 | K2PtCl4 | propionate | 1.42E−04 |
| 1378 | 2-methyl-1-pyrroline | 2 | K2PtCl4 | propionate | 5.53E−04 |
| 1379 | indoline | 2 | K2PtCl4 | propionate | 1.11E−04 |
| 1380 | 2,4-dimethyl pyrrole | 2 | K2PtCl4 | propionate | 5.06E−04 |
| 1381 | cyclopentyl amine + ammonia | 1 each | K2PtCl4 | propionate | 5.69E−04 |
| 1382 | pyrrolidine + ammonia | 1 each | K2PtCl4 | propionate | 8.37E−04 |
| 1383 | indole + ammonia | 1 each | K2PtCl4 | propionate | 4.74E−04 |
| 1384 | pyrrole + ammonia | 1 each | K2PtCl4 | propionate | 1.90E−04 |
| 1385 | exo-2-amino norbornane + ammonia | 1 each | K2PtCl4 | propionate | 3.32E−04 |
| 1386 | 2-methyl-1-pyrroline + ammonia | 1 each | K2PtCl4 | propionate | 4.58E−04 |
| 1387 | indoline + ammonia | 1 each | K2PtCl4 | propionate | 2.84E−04 |
| 1388 | 2,4-dimethyl pyrrole + ammonia | 1 each | K2PtCl4 | propionate | 4.27E−04 |
| 1389 | cyclopentyl amine | 2 | K2PtCl4 | acetate | 8.36E−04 |
| 1390 | pyrrolidine | 2 | K2PtCl4 | acetate | 7.66E−04 |
| 1391 | indole | 2 | K2PtCl4 | acetate | 5.05E−04 |
| 1392 | pyrrole | 2 | K2PtCl4 | acetate | 3.66E−04 |
| 1393 | exo-2-amino norbornane | 2 | K2PtCl4 | acetate | 3.66E−04 |
| 1394 | 2-methyl-1-pyrroline | 2 | K2PtCl4 | acetate | 9.58E−05 |
| 1395 | indoline | 2 | K2PtCl4 | acetate | 3.14E−04 |
| 1396 | 2,4-dimethyl pyrrole | 2 | K2PtCl4 | acetate | 7.66E−04 |
| 1397 | cyclopentyl amine + ammonia | 1 each | K2PtCl4 | acetate | 6.97E−04 |
| 1398 | pyrrolidine + ammonia | 1 each | K2PtCl4 | acetate | 8.19E−04 |
| 1399 | indole + ammonia | 1 each | K2PtCl4 | acetate | 6.44E−04 |

TABLE 1-continued

| No. | Ligand(s) | Equiv. | Precursor | Leaving Group | Yld, g atm Pt |
|---|---|---|---|---|---|
| 1400 | pyrrole + ammonia | 1 each | K2PtCl4 | acetate | 3.48E−04 |
| 1401 | exo-2-amino norbornane + ammonia | 1 each | K2PtCl4 | acetate | 5.75E−04 |
| 1402 | 2-methyl-1-pyrroline + ammonia | 1 each | K2PtCl4 | acetate | 6.27E−04 |
| 1403 | indoline + ammonia | 1 each | K2PtCl4 | acetate | 3.48E−04 |
| 1404 | 2,4-dimethyl pyrrole + ammonia | 1 each | K2PtCl4 | acetate | 8.13E−04 |
| 1405 | cyclopentyl amine + pyrrole | 1 each | K2PtCl4 | oxalate | 1.04E−03 |
| 1406 | cyclopentyl amine + pyrrole | 1 each | K2PtCl4 | malonate | 1.29E−03 |
| 1407 | cyclopentyl amine + pyrrole | 1 each | K2PtCl4 | succinate | 1.55E−03 |
| 1408 | cyclopentyl amine + pyrrole | 1 each | K2PtCl4 | acetate | 1.32E−03 |
| 1409 | cyclopentyl amine + pyrrole | 1 each | K2PtCl4 | propionate | 1.10E−03 |
| 1410 | cyclopentyl amine + pyrrole | 1 each | K2PtCl4 | butyrate | 1.23E−03 |
| 1411 | cyclopentyl amine + pyrrole | 1 each | K2PtCl4 | isobutyrate | 8.51E−04 |
| 1412 | cyclopentyl amine + pyrrole | 1 each | K2PtCl4 | 2-ketobutyrate | 1.32E−03 |
| 1413 | pyrrolidine + pyrrole | 1 each | K2PtCl4 | oxalate | 1.40E−03 |
| 1414 | pyrrolidine + pyrrole | 1 each | K2PtCl4 | malonate | 1.21E−03 |
| 1415 | pyrrolidine + pyrrole | 1 each | K2PtCl4 | succinate | 6.24E−04 |
| 1416 | pyrrolidine + pyrrole | 1 each | K2PtCl4 | acetate | 8.13E−04 |
| 1417 | pyrrolidine + pyrrole | 1 each | K2PtCl4 | propionate | 7.94E−04 |
| 1418 | pyrrolidine + pyrrole | 1 each | K2PtCl4 | butyrate | 7.94E−04 |
| 1419 | pyrrolidine + pyrrole | 1 each | K2PtCl4 | isobutyrate | 7.18E−04 |
| 1420 | pyrrolidine + pyrrole | 1 each | K2PtCl4 | 2-ketobutyrate | 1.97E−03 |
| 1421 | 2,5-dimethylpyrroline + pyrrole | 1 each | K2PtCl4 | oxalate | 3.59E−04 |
| 1422 | 2,5-dimethylpyrroline + pyrrole | 1 each | K2PtCl4 | malonate | 2.46E−04 |
| 1423 | 2,5-dimethylpyrroline + pyrrole | 1 each | K2PtCl4 | succinate | 9.45E−05 |
| 1424 | 2,5-dimethylpyrroline + pyrrole | 1 each | K2PtCl4 | acetate | 4.35E−04 |
| 1425 | 2,5-dimethylpyrroline + pyrrole | 1 each | K2PtCl4 | propionate | 3.02E−04 |
| 1426 | 2,5-dimethylpyrroline + pyrrole | 1 each | K2PtCl4 | butyrate | 2.65E−04 |
| 1427 | 2,5-dimethylpyrroline + pyrrole | 1 each | K2PtCl4 | isobutyrate | 3.02E−04 |
| 1428 | 2,5-dimethylpyrroline + pyrrole | 1 each | K2PtCl4 | 2-ketobutyrate | 4.35E−04 |
| 1429 | indole + pyrrole | 1 each | K2PtCl4 | oxalate | 2.65E−04 |
| 1430 | indole + pyrrole | 1 each | K2PtCl4 | malonate | 1.51E−04 |
| 1431 | indole + pyrrole | 1 each | K2PtCl4 | succinate | 9.45E−05 |
| 1432 | indole + pyrrole | 1 each | K2PtCl4 | acetate | 2.46E−04 |
| 1433 | indole + pyrrole | 1 each | K2PtCl4 | propionate | 1.51E−04 |
| 1434 | indole + pyrrole | 1 each | K2PtCl4 | butyrate | 1.89E−04 |
| 1435 | indole + pyrrole | 1 each | K2PtCl4 | isobutyrate | 4.43E−04 |
| 1436 | indole + pyrrole | 1 each | K2PtCl4 | 2-ketobutyrate | 4.63E−04 |
| 1437 | indoline + pyrrole | 1 each | K2PtCl4 | oxalate | 7.71E−04 |
| 1438 | indoline + pyrrole | 1 each | K2PtCl4 | malonate | 3.86E−04 |
| 1439 | indoline + pyrrole | 1 each | K2PtCl4 | succinate | 4.82E−04 |
| 1440 | indoline + pyrrole | 1 each | K2PtCl4 | acetate | 4.24E−04 |
| 1441 | indoline + pyrrole | 1 each | K2PtCl4 | propionate | 4.43E−04 |
| 1442 | indoline + pyrrole | 1 each | K2PtCl4 | butyrate | 4.43E−04 |
| 1443 | indoline + pyrrole | 1 each | K2PtCl4 | isobutyrate | 8.29E−04 |
| 1444 | indoline + pyrrole | 1 each | K2PtCl4 | 2-ketobutyrate | 7.13E−04 |
| 1445 | exo-2-norbornane + pyrrole | 1 each | K2PtCl4 | oxalate | 5.78E−04 |
| 1446 | exo-2-norbornane + pyrrole | 1 each | K2PtCl4 | malonate | 7.90E−04 |
| 1447 | exo-2-norbornane + pyrrole | 1 each | K2PtCl4 | succinate | 5.78E−04 |
| 1448 | exo-2-norbornane + pyrrole | 1 each | K2PtCl4 | acetate | 7.33E−04 |
| 1449 | exo-2-norbornane + pyrrole | 1 each | K2PtCl4 | propionate | 1.10E−03 |
| 1450 | exo-2-norbornane + pyrrole | 1 each | K2PtCl4 | butyrate | 5.78E−04 |
| 1451 | exo-2-norbornane + pyrrole | 1 each | K2PtCl4 | isobutyrate | 5.20E−04 |
| 1452 | exo-2-norbornane + pyrrole | 1 each | K2PtCl4 | 2-ketobutyrate | 5.59E−04 |
| 1453 | 2,4-dimethylpyrrole + pyrrole | 1 each | K2PtCl4 | oxalate | 6.36E−04 |
| 1454 | 2,4-dimethylpyrrole + pyrrole | 1 each | K2PtCl4 | malonate | 5.98E−04 |
| 1455 | 2,4-dimethylpyrrole + pyrrole | 1 each | K2PtCl4 | succinate | 5.78E−04 |
| 1456 | 2,4-dimethylpyrrole + pyrrole | 1 each | K2PtCl4 | acetate | 5.78E−04 |
| 1457 | 2,4-dimethylpyrrole + pyrrole | 1 each | K2PtCl4 | propionate | 5.98E−04 |
| 1458 | 2,4-dimethylpyrrole + pyrrole | 1 each | K2PtCl4 | butyrate | 5.98E−04 |
| 1459 | 2,4-dimethylpyrrole + pyrrole | 1 each | K2PtCl4 | isobutyrate | 5.98E−04 |
| 1460 | 2,4-dimethylpyrrole + pyrrole | 1 each | K2PtCl4 | 2-ketobutyrate | 9.45E−04 |
| 1461 | 2-methyl-1-pyrroline | 1 each | K2PtCl4 | oxalate | 1.43E−03 |
| 1462 | 2-methyl-1-pyrroline | 1 each | K2PtCl4 | malonate | 1.52E−03 |
| 1463 | 2-methyl-1-pyrroline | 1 each | K2PtCl4 | succinate | 1.21E−03 |
| 1464 | 2-methyl-1-pyrroline | 1 each | K2PtCl4 | acetate | 1.50E−03 |
| 1465 | 2-methyl-1-pyrroline | 1 each | K2PtCl4 | propionate | 1.45E−03 |
| 1466 | 2-methyl-1-pyrroline | 1 each | K2PtCl4 | butyrate | 1.23E−03 |
| 1467 | 2-methyl-1-pyrroline | 1 each | K2PtCl4 | isobutyrate | 1.10E−03 |
| 1468 | 2-methyl-1-pyrroline | 1 each | K2PtCl4 | 2-ketobutyrate | 1.48E−03 |
| 1469 | pyrazine + pyrrole | 1 each | K2PtCl4 | oxalate | 9.25E−04 |
| 1470 | pyrazine + pyrrole | 1 each | K2PtCl4 | malonate | 7.33E−04 |
| 1471 | pyrazine + pyrrole | 1 each | K2PtCl4 | succinate | 1.75E−03 |
| 1472 | pyrazine + pyrrole | 1 each | K2PtCl4 | acetate | 1.43E−03 |
| 1473 | pyrazine + pyrrole | 1 each | K2PtCl4 | propionate | 1.75E−03 |
| 1474 | pyrazine + pyrrole | 1 each | K2PtCl4 | butylate | 1.47E−03 |
| 1475 | pyrazine + pyrrole | 1 each | K2PtCl4 | isobutyrate | 1.29E−03 |
| 1476 | pyrazine + pyrrole | 1 each | K2PtCl4 | 2-ketobutyrate | 1.29E−03 |

TABLE 1-continued

| No. | Ligand(s) | Equiv. | Precursor | Leaving Group | Yld, g atm Pt |
|---|---|---|---|---|---|
| 1477 | 2,5-dimethylpyrrole + pyrrole | 1 each | K2PtCl4 | oxalate | 6.55E−04 |
| 1478 | 2,5-dimethylpyrrole + pyrrole | 1 each | K2PtCl4 | malonate | 6.55E−04 |
| 1479 | 2,5-dimethylpyrrole + pyrrole | 1 each | K2PtCl4 | succinate | 6.50E−04 |
| 1480 | 2,5-dimethylpyrrole + pyrrole | 1 each | K2PtCl4 | acetate | 1.98E−04 |
| 1481 | 2,5-dimethylpyrrole + pyrrole | 1 each | K2PtCl4 | propionate | 2.52E−04 |
| 1482 | 2,5-dimethylpyrrole + pyrrole | 1 each | K2PtCl4 | butyrate | 3.06E−04 |
| 1483 | 2,5-dimethylpyrrole + pyrrole | 1 each | K2PtCl4 | isobutyrate | 2.88E−04 |
| 1484 | 2,5-dimethylpyrrole + pyrrole | 1 each | K2PtCl4 | 2-ketobutyrate | 1.91E−03 |
| 1485 | imidazole + pyrrole | 1 each | K2PtCl4 | oxalate | 1.08E−03 |
| 1486 | imidazole + pyrrole | 1 each | K2PtCl4 | malonate | 1.48E−03 |
| 1487 | imidazole + pyrrole | 1 each | K2PtCl4 | succinate | 8.10E−04 |
| 1488 | imidazole + pyrrole | 1 each | K2PtCl4 | acetate | 4.86E−04 |
| 1489 | imidazole + pyrrole | 1 each | K2PtCl4 | propionate | 1.46E−03 |
| 1490 | imidazole + pyrrole | 1 each | K2PtCl4 | butyrate | 1.35E−03 |
| 1491 | imidazole + pyrrole | 1 each | K2PtCl4 | isobutyrate | 9.90E−04 |
| 1492 | imidazole + pyrrole | 1 each | K2PtCl4 | 2-ketobutyrate | 1.62E−03 |
| 1493 | 2-methyl-1-imidazole + pyrrole | 1 each | K2PtCl4 | oxalate | 8.82E−04 |
| 1494 | 2-methyl-1-imidazole + pyrrole | 1 each | K2PtCl4 | malonate | 9.72E−04 |
| 1495 | 2-methyl-1-imidazole + pyrrole | 1 each | K2PtCl4 | succinate | 6.12E−04 |
| 1496 | 2-methyl-1-imidazole + pyrrole | 1 each | K2PtCl4 | acetate | 7.92E−04 |
| 1497 | 2-methyl-1-imidazole + pyrrole | 1 each | K2PtCl4 | propionate | 4.68E−04 |
| 1498 | 2-methyl-1-imidazole + pyrrole | 1 each | K2PtCl4 | butyrate | 6.12E−04 |
| 1499 | 2-methyl-1-imidazole + pyrrole | 1 each | K2PtCl4 | isobutyrate | 7.02E−04 |
| 1500 | 2-methyl-1-imidazole + pyrrole | 1 each | K2PtCl4 | 2-ketobutyrate | 7.02E−04 |
| 1501 | butylamine + 3-aminopyridine | 1 each | K2PtCl4 | oxalate | 1.53E−03 |
| 1502 | butylamine + 3-aminopyridine | 1 each | K2PtCl4 | malonate | 2.12E−04 |
| 1503 | butylamine + 3-aminopyridine | 1 each | K2PtCl4 | succinate | 3.76E−04 |
| 1504 | butylamine + 3-aminopyridine | 1 each | K2PtCl4 | acetate | 3.29E−04 |
| 1505 | butylamine + 3-aminopyridine | 1 each | K2PtCl4 | propionate | 1.88E−04 |
| 1506 | butylamine + 3-aminopyridine | 1 each | K2PtCl4 | butyrate | 1.41E−04 |
| 1507 | butylamine + 3-aminopyridine | 1 each | K2PtCl4 | isobutyrate | 4.23E−04 |
| 1508 | butylamine + 3-aminopyridine | 1 each | K2PtCl4 | 2-ketobutyrate | 3.29E−04 |
| 1509 | butylamine + 2-hydroxypyridine | 1 each | K2PtCl4 | oxalate | 9.64E−04 |
| 1510 | butylamine + 2-hydroxypyridine | 1 each | K2PtCl4 | malonate | 5.88E−04 |
| 1511 | butylamine + 2-hydroxypyridine | 1 each | K2PtCl4 | succinate | 9.17E−04 |
| 1512 | butylamine + 2-hydroxypyridine | 1 each | K2PtCl4 | acetate | 5.64E−04 |
| 1513 | butylamine + 2-hydroxypyridine | 1 each | K2PtCl4 | propionate | 4.94E−04 |
| 1514 | butylamine + 2-hydroxypyridine | 1 each | K2PtCl4 | butyrate | 9.17E−04 |
| 1515 | butylamine + 2-hydroxypyridine | 1 each | K2PtCl4 | isobutyrate | 1.55E−03 |
| 1516 | butylamine + 2-hydroxypyridine | 1 each | K2PtCl4 | 2-ketobutyrate | 5.64E−04 |
| 1517 | butylamine + 2,6-diaminopyridine | 1 each | K2PtCl4 | oxalate | 5.64E−04 |
| 1518 | butylamine + 2,6-diaminopyridine | 1 each | K2PtCl4 | malonate | 6.11E−04 |
| 1519 | butylamine + 2,6-diaminopyridine | 1 each | K2PtCl4 | succinate | 6.11E−04 |
| 1520 | butylamine + 2,6-diaminopyridine | 1 each | K2PtCl4 | acetate | 3.29E−04 |
| 1521 | butylamine + 2,6-diaminopyridine | 1 each | K2PtCl4 | propionate | 7.52E−04 |
| 1522 | butylamine + 2,6-diaminopyridine | 1 each | K2PtCl4 | butyrate | 4.00E−04 |
| 1523 | butylamine + 2,6-diaminopyridine | 1 each | K2PtCl4 | isobutyrate | 9.40E−04 |
| 1524 | butylamine + 2,6-diaminopyridine | 1 each | K2PtCl4 | 2-ketobutyrate | 9.17E−04 |
| 1525 | butylamine + 3-hydroxy-2-nitropyridine | 1 each | K2PtCl4 | oxalate | 4.70E−04 |
| 1526 | butylamine + 3-hydroxy-2-nitropyridine | 1 each | K2PtCl4 | malonate | 5.17E−04 |
| 1527 | butylamine + 3-hydroxy-2-nitropyridine | 1 each | K2PtCl4 | succinate | 3.76E−04 |
| 1528 | butylamine + 3-hydroxy-2-nitropyridine | 1 each | K2PtCl4 | acetate | 4.00E−04 |
| 1529 | butylamine + 3-hydroxy-2-nitnopyridine | 1 each | K2PtCl4 | propionate | 8.93E−04 |
| 1530 | butylamine + 3-hydroxy-2-nitropyridine | 1 each | K2PtCl4 | butyrate | 4.94E−04 |
| 1531 | butylamine + 3-hydroxy-2-nitropyridine | 1 each | K2PtCl4 | isobutyrate | 6.82E−04 |
| 1532 | butylamine + 3-hydroxy-2-nitropyridine | 1 each | K2PtCl4 | 2-ketobutyrate | 5.88E−04 |
| 1533 | butylamine + 2-mercaptopyridine | 1 each | K2PtCl4 | oxalate | 1.95E−03 |
| 1534 | butylamine + 2-mercaptopyridine | 1 each | K2PtCl4 | malonate | 6.82E−04 |
| 1535 | butylamine + 2-mercaptopyridine | 1 each | K2PtCl4 | succinate | 4.70E−04 |
| 1536 | butylamine + 2-mercaptopyridine | 1 each | K2PtCl4 | acetate | 1.06E−03 |
| 1537 | butylamine + 2-mercaptopyridine | 1 each | K2PtCl4 | propionate | 4.94E−04 |
| 1538 | butylamine + 2-mercaptopyridine | 1 each | K2PtCl4 | butyrate | 5.64E−04 |
| 1539 | butylamine + 2-mercaptopyridine | 1 each | K2PtCl4 | isobutyrate | 1.03E−03 |
| 1540 | butylamine + 2-mercaptopyridine | 1 each | K2PtCl4 | 2-ketobutyrate | 1.03E−03 |
| 1541 | butylamine + 2-cyanopyridine | 1 each | K2PtCl4 | oxalate | 2.46E−03 |
| 1542 | butylamine + 2-cyanopyridine | 1 each | K2PtCl4 | malonate | 2.60E−03 |
| 1543 | butylamine + 2-cyanopyridine | 1 each | K2PtCl4 | succinate | 2.43E−03 |
| 1544 | butylamine + 2-cyanopyridine | 1 each | K2PtCl4 | acetate | 3.47E−03 |
| 1545 | butylamine + 2-cyanopyridine | 1 each | K2PtCl4 | propionate | 4.20E−03 |
| 1546 | butylamine + 2-cyanopyridine | 1 each | K2PtCl4 | butyrate | 3.31E−03 |
| 1547 | butylamine + 2-cyanopyridine | 1 each | K2PtCl4 | isobutyrate | 2.05E−03 |
| 1548 | butylamine + 2-cyanopyridine | 1 each | K2PtCl4 | 2-ketobutyrate | 1.42E−03 |
| 1549 | butylamine + 2-amino-3-hydroxypyridine | 1 each | K2PtCl4 | oxalate | 8.50E−04 |
| 1550 | butylamine + 2-amino-3-hydroxypyridine | 1 each | K2PtCl4 | malonate | 1.18E−04 |
| 1551 | butylamine + 2-amino-3-hydroxypyridine | 1 each | K2PtCl4 | succinate | 3.35E−03 |
| 1552 | butylamine + 2-amino-3-hydroxypyridine | 1 each | K2PtCl4 | acetate | 6.34E−04 |
| 1553 | butylamine + 2-amino-3-hydroxypyridine | 1 each | K2PtCl4 | propionate | 2.52E−03 |

TABLE 1-continued

| No. | Ligand(s) | Equiv. | Precursor | Leaving Group | Yld, g atm Pt |
|---|---|---|---|---|---|
| 1554 | butylamine + 2-amino-3-hydroxypyridine | 1 each | K2PtCl4 | butyrate | 3.21E−03 |
| 1555 | butylamine + 2-amino-3-hydroxypyridine | 1 each | K2PtCl4 | isobutyrate | 5.15E−04 |
| 1556 | butylamine + 2-amino-3-hydroxypyridine | 1 each | K2PtCl4 | 2-ketobutyrate | 3.53E−03 |
| 1557 | butylamine + imidazole | 1 each | K2PtCl4 | oxalate | 1.19E−03 |
| 1558 | butylamine + imidazole | 1 each | K2PtCl4 | malonate | 8.92E−04 |
| 1559 | butylamine + imidazole | 1 each | K2PtCl4 | succinate | 2.58E−03 |
| 1560 | butylamine + imidazole | 1 each | K2PtCl4 | acetate | 3.17E−03 |
| 1561 | butylamine + imidazole | 1 each | K2PtCl4 | propionate | 1.29E−03 |
| 1562 | butylamine + imidazole | 1 each | K2PtCl4 | butyrate | 3.93E−03 |
| 1563 | butylamine + imidazole | 1 each | K2PtCl4 | isobutyrate | 3.43E−03 |
| 1564 | butylamine + imidazole | 1 each | K2PtCl4 | 2-ketobutyrate | 3.67E−03 |
| 1565 | butylamine + 1-methylimidazole | 1 each | K2PtCl4 | oxalate | 4.18E−03 |
| 1566 | butylamine + 1-methylimidazole | 1 each | K2PtCl4 | malonate | 3.97E−03 |
| 1567 | butylamine + 1-methylimidazole | 1 each | K2PtCl4 | succinate | 5.17E+00 |
| 1568 | butylamine + 1-methylimidazole | 1 each | K2PtCl4 | acetate | 4.10E−03 |
| 1569 | butylamine + 1-methylimidazole | 1 each | K2PtCl4 | propionate | 2.06E−03 |
| 1570 | butylamine + 1-methylimidazole | 1 each | K2PtCl4 | butyrate | 3.15E−03 |
| 1571 | butylamine + 1-methylimidazole | 1 each | K2PtCl4 | isobutyrate | 4.57E−03 |
| 1572 | butylamine + 1-methylimidazole | 1 each | K2PtCl4 | 2-ketobutyrate | 3.60E−03 |
| 1573 | butylamine + 2-methylimidazole | 1 each | K2PtCl4 | oxalate | 5.02E−03 |
| 1574 | butylamine + 2-methylimidazole | 1 each | K2PtCl4 | malonate | 9.14E−04 |
| 1575 | butylamine + 2-methylimidazole | 1 each | K2PtCl4 | succinate | 2.17E−03 |
| 1576 | butylamine + 2-methylimidazole | 1 each | K2PtCl4 | acetate | 2.60E−03 |
| 1577 | butylamine + 2-methylimidazole | 1 each | K2PtCl4 | propionate | 2.13E−03 |
| 1578 | butylamine + 2-methylimidazole | 1 each | K2PtCl4 | butyrate | 3.76E−03 |
| 1579 | butylamine + 2-methylimidazole | 1 each | K2PtCl4 | isobutyrate | 1.59E−03 |
| 1580 | butylamine + 2-methylimidazole | 1 each | K2PtCl4 | 2-ketobutyrate | 1.28E−03 |
| 1581 | butylamine + 1,2-trimethylimidazole | 1 each | K2PtCl4 | oxalate | 1.42E−03 |
| 1582 | butylamine + 1,2-trimethylimidazole | 1 each | K2PtCl4 | malonate | 1.22E−03 |
| 1583 | butylamine + 1,2-trimethylimidazole | 1 each | K2PtCl4 | succinate | 8.53E−04 |
| 1584 | butylamine + 1,2-trimethylimidazole | 1 each | K2PtCl4 | acetate | 2.17E−03 |
| 1585 | butylamine + 1,2-trimethylimidazole | 1 each | K2PtCl4 | propionate | 3.37E−03 |
| 1586 | butylamine + 1,2-trimethylimidazole | 1 each | K2PtCl4 | butyrate | 3.11E−03 |
| 1587 | butylamine + 1,2-trimethylimidazole | 1 each | K2PtCl4 | isobutyrate | 4.00E−03 |
| 1581 | butylamine + 1,2-trimethylimidazole | 1 each | K2PtCl4 | 2-ketobutyrate | 2.42E−03 |
| 1589 | butylamine + ammonia | 1 each | K2PtCl4 | oxalate | 5.28E−04 |
| 1590 | butylamine + ammonia | 1 each | K2PtCl4 | malonate | 4.27E−03 |
| 1591 | butylamine + ammonia | 1 each | K2PtCl4 | succinate | 1.24E−03 |
| 1592 | butylamine + ammonia | 1 each | K2PtCl4 | acetate | 1.26E−03 |
| 1593 | butylamine + ammonia | 1 each | K2PtCl4 | propionate | 9.96E−04 |
| 1594 | butylamine + ammonia | 1 each | K2PtCl4 | butyrate | 1.16E−03 |
| 1595 | butylamine + ammonia | 1 each | K2PtCl4 | isobutyrate | 1.34E−03 |
| 1596 | butylamine + ammonia | 1 each | K2PtCl4 | 2-ketobutyrate | 2.66E−03 |
| 1597 | cyclopentylamine + 2-mercaptopyridine | 1 each | K2PtCl4 | acetate | 5.04E−03 |
| 1598 | cyclopentylamine + 2-cyanopyridine | 1 each | K2PtCl4 | acetate | 9.18E−04 |
| 1599 | cyclopentylamine + pyrazole | 1 each | K2PtCl4 | acetate | 7.20E−04 |
| 1600 | cyclopentylamine + imidazole | 1 each | K2PtCl4 | acetate | 7.20E−04 |
| 1601 | cyclopentylamine + 1-methylimidazole | 1 each | K2PtCl4 | acetate | 1.24E−03 |
| 1602 | cyclopentylamine + 2-methylimidazole | 1 each | K2PtCl4 | acetate | 7.94E−04 |
| 1603 | cyclopentylamine + 3,5-dimethylpyrazole | 1 each | K2PtCl4 | acetate | 8.44E−04 |
| 1604 | cyclopentylamine + butylamine | 1 each | K2PtCl4 | acetate | 7.69E−04 |
| 1605 | 4-amino-1-butanol + 2-mercaptopyridine | 1 each | K2PtCl4 | acetate | 1.69E−03 |
| 1606 | 4-amino-1-butanol + 2-cyanopyridine | 1 each | K2PtCl4 | acetate | 9.43E−04 |
| 1607 | 4-amino-1-butanol + pyrazole | 1 each | K2PtCl4 | acetate | 1.14E−03 |
| 1608 | 4-amino-1-butanol + imidazole | 1 each | K2PtCl4 | acetate | 7.94E−04 |
| 1609 | 4-amino-1-butanol + 1-methylimidazole | 1 each | K2PtCl4 | acetate | 1.41E−03 |
| 1610 | 4-amino-1-butanol + 2-methylimidazole | 1 each | K2PtCl4 | acetate | 1.04E−03 |
| 1611 | 4-amino-1-butanol + 3,5-dimethylpyrazole | 1 each | K2PtCl4 | acetate | 1.27E−03 |
| 1612 | 4-amino-1-butanol + butylamine | 1 each | K2PtCl4 | acetate | 1.09E−03 |
| 1613 | indoline + 2-mercaptopyridine | 1 each | K2PtCl4 | acetate | 1.44E−03 |
| 1614 | indoline + 2-cyanopyridine | 1 each | K2PtCl4 | acetate | 8.69E−04 |
| 1615 | indoline + pyrazole | 1 each | K2PtCl4 | acetate | 1.59E−03 |
| 1616 | indoline + imidazole | 1 each | K2PtCl4 | acetate | 1.24E−03 |
| 1617 | indoline + 1-methylimidazole | 1 each | K2PtCl4 | acetate | 1.69E−03 |
| 1618 | indoline + 2-methylimidazole | 1 each | K2PtCl4 | acetate | 1.37E−03 |
| 1619 | indoline + 3,5-dimethylpyrazole | 1 each | K2PtCl4 | acetate | 2.61E−03 |
| 1620 | indoline + butylamine | 1 each | K2PtCl4 | acetate | 1.07E−03 |
| 1621 | (R)-(−)-2-amino-1-butanol + 2-mercaptopyridine | 1 each | K2PtCl4 | acetate | 1.44E−03 |
| 1622 | (R)-(−)-2-amino-1-butanol + 2-cyanopyridine | 1 each | K2PtCl4 | acetate | 1.14E−03 |
| 1623 | (R)-(−)-2-amino-1-butanol + pyrazole | 1 each | K2PtCl4 | acetate | 1.41E−03 |
| 1624 | (R)-(−)-2-amino-1-butanol + imidazole | 1 each | K2PtCl4 | acetate | 1.12E−03 |
| 1625 | (R)-(−)-2-amino-1-butanol + 1-methylimidazole | 1 each | K2PtCl4 | acetate | 1.24E−03 |
| 1626 | (R)-(−)-2-amino-1-butanol + 2-methylimidazole | 1 each | K2PtCl4 | acetate | 1.22E−03 |
| 1627 | (R)-(−)-2-amino-1-butanol + 3,5-dimethylpyrazole | 1 each | K2PtCl4 | acetate | 2.96E−04 |
| 1628 | (R)-(−)-2-amino-1-butanol + butylamine | 1 each | K2PtCl4 | acetate | 3.35E−04 |

TABLE 1-continued

| No. | Ligand(s) | Equiv. | Precursor | Leaving Group | Yld, g atm Pt |
|---|---|---|---|---|---|
| 1629 | DL-1-amino-2-propanol + 2-mercaptopyridine | 1 each | K2PtCl4 | acetate | 3.35E−04 |
| 1630 | DL-1-amino-2-propanol + 2-cyanopyridine | 1 each | K2PtCl4 | acetate | 4.14E−04 |
| 1631 | DL-1-amino-2-propanol + pyrazole | 1 each | K2PtCl4 | acetate | 4.14E−04 |
| 1632 | DL-1-amino-2-propanol + imidazole | 1 each | K2PtCl4 | acetate | 4.53E−04 |
| 1633 | DL-1-amino-2-propanol + 1-methylimidazole | 1 each | K2PtCl4 | acetate | 4.73E−04 |
| 1634 | DL-1-amino-2-propanol + 2-methylimidazole | 1 each | K2PtCl4 | acetate | 4.34E−04 |
| 1635 | DL-1-amino-2-propanol + 3,5-dimethylpyrazole | 1 each | K2PtCl4 | acetate | 4.73E−04 |
| 1636 | DL-1-amino-2-propanol + butylamine | 1 each | K2PtCl4 | acetate | 5.52E−04 |
| 1637 | 2-methyl-1-pyrroline + 2-mercaptopyridine | 1 each | K2PtCl4 | acetate | 5.52E−04 |
| 1638 | 2-methyl-1-pyrroline + 2-cyanopyridine | 1 each | K2PtCl4 | acetate | 5.32E−04 |
| 1639 | 2-methyl-1-pyrroline + pyrazole | 1 each | K2PtCl4 | acetate | 5.32E−04 |
| 1640 | 2-methyl-1-pyrroline + imidazole | 1 each | K2PtCl4 | acetate | 5.52E−04 |
| 1641 | 2-methyl-1-pyrroline + 1-methylimidazole | 1 each | K2PtCl4 | acetate | 5.52E−04 |
| 1642 | 2-methyl-1-pyrroline + 2-methylimidazole | 1 each | K2PtCl4 | acetate | 5.91E−04 |
| 1643 | 2-methyl-1-pyrroline + 3,5-dimethylpyrazole | 1 each | K2PtCl4 | acetate | 7.88E−04 |
| 1644 | 2-methyl-1-pyrroline + butylamine | 1 each | K2PtCl4 | acetate | 6.11E−04 |
| 1645 | 2,5-dimethyl-3-pyrroline + 2-mercaptopyridine | 1 each | K2PtCl4 | acetate | 9.85E−04 |
| 1646 | 2,5-dimethyl-3-pyrroline + 2-cyanopyridine | 1 each | K2PtCl4 | acetate | 6.90E−04 |
| 1647 | 2,5-dimethyl-3-pyrroline + pyrazole | 1 each | K2PtCl4 | aeetate | 1.00E−03 |
| 1648 | 2,5-dimethyl-3-pyrroline + imidazole | 1 each | K2PtCl4 | acetate | 6.90E−04 |
| 1649 | 2,5-dimethyl-3-pyrroline + 1-methylimidazole | 1 each | K2PtCl4 | acetate | 6.90E−04 |
| 1650 | 2,5-dimethyl-3-pyrroline + 2-methylimidazole | 1 each | K2PtCl4 | acetate | 7.29E−04 |
| 1651 | 2,5-dimethyl-3-pyrroline + 3,5-dimethylpyrazole | 1 each | K2PtCl4 | acetate | 7.49E−04 |
| 1652 | 2,5-dimethyl-3-pyrroline + butylamine | 1 each | K2PtCl4 | acetate | 7.29E−04 |
| 1653 | indole + 2-mercaptopyridine | 1 each | K2PtCl4 | acetate | 9.06E−04 |
| 1654 | indole + 2-cyanopyridine | 1 each | K2PtCl4 | acetate | 1.02E−03 |
| 1655 | indole + pyrazole | 1 each | K2PtCl4 | acetate | 7.68E−04 |
| 1656 | indole + imidazole | 1 each | K2PtCl4 | acetate | 8.87E−04 |
| 1657 | indole + 1-methylimidazole | 1 each | K2PtCl4 | acetate | 1.18E−03 |
| 1658 | indole + 2-methylimidazole | 1 each | K2PtCl4 | acetate | 1.12E−03 |
| 1659 | indole + 3,5-dimethylpylazole | 1 each | K2PtCl4 | acetate | 8.87E−04 |
| 1660 | indole + butylamine | 1 each | K2PtCl4 | acetate | 8.28E−04 |
| 1661 | 3-aminopyridine + 2-mercaptopyridine | 1 each | K2PtCl4 | acetate | 8.08E−04 |
| 1662 | 3-aminopyridine + 2-cyanopyridine | 1 each | K2PtCl4 | acetate | 8.67E−04 |
| 1663 | 3-aminopyridine + pyrazole | 1 each | K2PtCl4 | acetate | 8.28E−04 |
| 1664 | 3-aminopyridine + imidazole | 1 each | K2PtCl4 | acetate | 8.08E−04 |
| 1665 | 3-aminopyridine + 1-methylimidazole | 1 each | K2PtCl4 | acetate | 8.08E−04 |
| 1666 | 3-aminopyridine + 2-methylimidazole | 1 each | K2PtCl4 | acetate | 8.28E−04 |
| 1667 | 3-aminopyridine + 3,5-dimethylpyrazole | 1 each | K2PtCl4 | acetate | 7.33E−05 |
| 1668 | 3-aminopyridine + butylamine | 1 each | K2PtCl4 | acetate | 7.33E−05 |
| 1669 | 2-hydroxypyridine + 2-mercaptopyridine | 1 each | K2PtCl4 | acetate | 3.67E−04 |
| 1670 | 2-hydroxypyridine + 2-cyanopyridine | 1 each | K2PtCl4 | acetate | 1.83E−04 |
| 1671 | 2-hydroxypyridine + pyrazole | 1 each | K2PtCl4 | acetate | 2.02E−04 |
| 1672 | 2-hydroxypyridine + imidazole | 1 each | K2PtCl4 | acetate | 2.93E−04 |
| 1673 | 2-hydroxypyridine + 1-methylimidazole | 1 each | K2PtCl4 | acetate | 5.68E−04 |
| 1674 | 2-hydroxypyridine + 2-methylimidazole | 1 each | K2PtCl4 | acetate | 3.67E−04 |
| 1675 | 2-hydroxypyridine + 3,5-dimethylpyrazole | 1 each | K2PtCl4 | acetate | 1.01E−03 |
| 1676 | 2-hydroxypyridine + butylamine | 1 each | K2PtCl4 | acetate | 1.47E−04 |
| 1677 | 2,6-diaminopyridine + 2-mercaptopyridine | 1 each | K2PtCl4 | acetate | 1.47E−04 |
| 1678 | 2,6-diaminopyridine + 2-cyanopyridine | 1 each | K2PtCl4 | acetate | 1.47E−04 |
| 1679 | 2,6-diaminopyridine + pyrazole | 1 each | K2PtCl4 | acetate | 1.10E−04 |
| 1680 | 2,6-diaminopyridine + imidazole | 1 each | K2PtCl4 | acetate | 1.47E−04 |
| 1681 | 2,6-diaminopyridine + 1-methylimidazole | 1 each | K2PtCl4 | acetate | 1.10E−04 |
| 1682 | 2,6-diaminopyridine + 2-methylimidazole | 1 each | K2PtCl4 | acetate | 1.65E−04 |
| 1683 | 2,6-diaminopyridine + 3,5-dimethylpyrazole | 1 each | K2PtCl4 | acetate | 2.20E−04 |
| 1684 | 2,6-diaminopyridine + butylamine | 1 each | K2PtCl4 | acetate | 1.65E−04 |
| 1685 | 3-hydroxy-2-nitropyridine + 2-mercaptopyridine | 1 each | K2PtCl4 | acetate | 3.67E−01 |
| 1686 | 3-hydroxy-2-nitropyridine + 2-cyanopyridine | 1 each | K2PtCl4 | acetate | 2.20E−04 |
| 1687 | 3-hydroxy-2-nitropyridine + pyrazole | 1 each | K2PtCl4 | acetate | 9.53E−05 |
| 1688 | 3-hydroxy-2-nitropyridine + imidazole | 1 each | K2PtCl4 | acetate | 3.12E−04 |
| 1689 | 3-hydroxy-2-nitropyridine + 1-methylimidazole | 1 each | K2PtCl4 | acetate | 6.97E−04 |
| 1690 | 3-hydroxy-2-nitropyridine + 2-methylimidazole | 1 each | K2PtCl4 | acetate | 3.85E−04 |
| 1691 | 3-hydroxy-2-nitropyridine + 3,5-dimethylpyrazole | 1 each | K2PtCl4 | acetate | 1.10E−03 |
| 1692 | 3-hydroxy-2-nitropyridine + butylamine | 1 each | K2PtCl4 | acetate | 2.57E−04 |
| 1693 | 3-aminopyridine + 3-hydroxy-2-nitropyridine | 1 each | K2PtCl4 | KCl | 1.76E−03 |
| 1694 | 3-aminopyridine + 2-cyanopyridine | 1 each | K2PtCl4 | KCl | 1.96E−03 |
| 1695 | 3-aminopyridine + (R)-(−)-2-amino-1-propanol | 1 each | K2PtCl4 | KCl | 9.95E−05 |
| 1696 | 3-aminopyridine + imidazole | 1 each | K2PtCl4 | KCl | 1.33E−04 |
| 1697 | 3-aminopyridine +2-methyl-1-pyrroline | 1 each | K2PtCl4 | KCl | 1.33E−04 |
| 1698 | 3-aminopyridine + 2-methylimidazole | 1 each | K2PtCl4 | KCl | 1.16E−04 |
| 1699 | 3-aminopyridine + indole | 1 each | K2PtCl4 | KCl | 2.32E−04 |
| 1700 | 3-aminopyridine + butylamine | 1 each | K2PtCl4 | KCl | 1.66E−04 |
| 1701 | 2,6-diaminopyridine + 3-hydroxy-2-nitropyridine | 1 each | K2PtCl4 | KCl | 9.95E−05 |
| 1702 | 2,6-diaminopyridine + 2-cyanopyridine | 1 each | K2PtCl4 | KCl | 2.32E−04 |
| 1703 | 2,6-diaminopyridine + (R)-(−)-2-amino-1- | 1 each | K2PtCl4 | KCl | 1.49E−04 |

TABLE 1-continued

| No. | Ligand(s) | Equiv. | Precursor | Leaving Group | Yld, g atm Pt |
|---|---|---|---|---|---|
| | propanol | | | | |
| 1704 | 2,6-diaminopyridine + imidazole | 1 each | K2PtCl4 | KCl | 1.82E−04 |
| 1705 | 2,6-diaminopyridine + 2-methyl-1-pyrroline | 1 each | K2PtCl4 | KCl | 1.82E−04 |
| 1706 | 2,6-diaminopyridine + 2-methylimidazole | 1 each | K2PtCl4 | KCl | 1.82E−04 |
| 1707 | 2,6-diaminopyridine + indole | 1 each | K2PtCl4 | KCl | 2.99E−04 |
| 1708 | 2,6-diaminopyridine + butylamine | 1 each | K2PtCl4 | KCl | 2.49E−04 |
| 1709 | 2-mercaptopyridine + 3-hydroxy-2-nitropyridine | 1 each | K2PtCl4 | KCl | 2.49E−04 |
| 1710 | 2-mercaptopyridine + 2-cyanopyridine | 1 each | K2PtCl4 | KCl | 3.48E−04 |
| 1711 | 2-mercaptopyridine + (R)-(−)-2-amino-1-propanol | 1 each | K2PtCl4 | KCl | 5.81E−04 |
| 1712 | 2-mercaptopyridine + imidazole | 1 each | K2PtCl4 | KCl | 9.12E−04 |
| 1713 | 2-mercaptopyridine + 2-methyl-1-pyrroline | 1 each | K2PtCl4 | KCl | 7.46E−04 |
| 1714 | 2-mercaptopyridine + 2-methylimidazole | 1 each | K2PtCl4 | KCl | 3.98E−04 |
| 1715 | 2-mercaptopyridine + indole | 1 each | K2PtCl4 | KCl | 3.32E−04 |
| 1716 | 2-mercaptopyridine + butylamine | 1 each | K2PtCl4 | KCl | 4.64E−04 |
| 1717 | pyrazole + 3-hydroxy-2-nitropyridine | 1 each | K2PtCl4 | KCl | 4.81E−04 |
| 1718 | pyrazole + 2-cyanopyridine | 1 each | K2PtCl4 | KCl | 4.23E−04 |
| 1719 | pyrazole + (R)-(−)-2-amino-1-propanol | 1 each | K2PtCl4 | KCl | 1.19E−03 |
| 1720 | pyrazole + imidazole | 1 each | K2PtCl4 | KCl | 1.64E−03 |
| 1721 | pyrazole + 2-methyl-1-pyrroline | 1 each | K2PtCl4 | KCl | 6.64E−04 |
| 1722 | pyrazole + 2-methylimidazole | 1 each | K2PtCl4 | KCl | 6.64E−04 |
| 1723 | pyrazole + indole | 1 each | K2PtCl4 | KCl | 1.23E−03 |
| 1724 | pyrazole + butylamine | 1 each | K2PtCl4 | KCl | 4.54E−04 |
| 1725 | 1-methylimidazole + 3-hydroxy-2-nitropyridine | 1 each | K2PtCl4 | KCl | 4.64E−04 |
| 1726 | 1-methylimidazole + 2-cyanopyridine | 1 each | K2PtCl4 | KCl | 6.97E−04 |
| 1727 | 1-methylimidazole + (R)-(−)-2-amino-1-propanol | 1 each | K2PtCl4 | KCl | 4.48E−04 |
| 1728 | 1-methylimidazole + imidazole | 1 each | K2PtCl4 | KCl | 1.05E−03 |
| 1729 | 1-methylimidazole +2-methyl-1-pyroline | 1 each | K2PtCl4 | KCl | 1.38E−03 |
| 1730 | 1-methylimidazole + 2-methylimidazole | 1 each | K2PtCl4 | KCl | 6.64E−04 |
| 1731 | 1-methylimidazole + indole | 1 each | K2PtCl4 | KCl | 4.15E−04 |
| 1732 | 1-methylimidazole + butylamine | 1 each | K2PtCl4 | KCl | 2.99E−04 |
| 1733 | 3,5-dimethylpyrazole + 3-hydroxy-2-nitropyridine | 1 each | K2PtCl4 | KCl | 8.96E−04 |
| 1734 | 3,5-dimethylpyrazole + 2-cyanopyridine | 1 each | K2PtCl4 | KCl | 1.33E−03 |
| 1735 | 3,5-dimethylpyrazole + (R)-(−)-2-amino-1-propanol | 1 each | K2PtCl4 | KCl | 5.81E−04 |
| 1736 | 3,5-dimethylpyrazole + imidazole | 1 each | K2PtCl4 | KCl | 1.03E−03 |
| 1737 | 3,5-dimethylpyrazole + 2-methyl-1-pyrroline | 1 each | K2PtCl4 | KCl | 1.56E−04 |
| 1738 | 3,5-dimethylpyrazole + 2-methylimidazole | 1 each | K2PtCl4 | KCl | 1.34E−04 |
| 1739 | 3,5-dimethylpyrazole + indole | 1 each | K2PtCl4 | KCl | 2.01E−04 |
| 1740 | 3,5-dimethylpyrazole + butylamine | 1 each | K2PtCl4 | KCl | 1.56E−04 |
| 1741 | cyclopentylamine + 3-hydroxy-2-nitropyridine | 1 each | K2PtCl4 | KCl | 2.01E−04 |
| 1742 | cyclopentylamine + 2-cyanopyridine | 1 each | K2PtCl4 | KCl | 1.56E−04 |
| 1743 | cyclopentylamine + (R)-(−)-2-amino-1-propanol | 1 each | K2PtCl4 | KCl | 1.56E−04 |
| 1744 | cyclopentylamine + imidazole | 1 each | K2PtCl4 | KCl | 2.01E−04 |
| 1745 | cyclopentylamine + 2-methyl-1-pyrroline | 1 each | K2PtCl4 | KCl | 2.01E−04 |
| 1746 | cyclopentylamine + 2-methylimidazole | 1 each | K2PtCl4 | KCl | 2.01E−04 |
| 1747 | cyclopentylamine + indole | 1 each | K2PtCl4 | KCl | 2.01E−04 |
| 1748 | cyclopentylamine + butylamine | 1 each | K2PtCl4 | KCl | 2.68E−04 |
| 1749 | indoline + 3-hydroxy-2-nitropyridine | 1 each | K2PtCl4 | KCl | 2.68E−04 |
| 1750 | indoline + 2-cyanopyridine | 1 each | K2PtCl4 | KCl | 2.23E−04 |
| 1751 | indoline + (R)-(−)-2-amino-1-propanol | 1 each | K2PtCl4 | KCl | 2.90E−04 |
| 1752 | indoline + imidazole | 1 each | K2PtCl4 | KCl | 2.23E−04 |
| 1753 | indoline + 2-methyl-1-pyrroline | 1 each | K2PtCl4 | KCl | 2.90E−04 |
| 1754 | indoline + 2-methylimidazole | 1 each | K2PtCl4 | KCl | 3.12E−04 |
| 1755 | indoline + indole | 1 each | K2PtCl4 | KCl | 5.13E−04 |
| 1756 | indoline + butylamine | 1 each | K2PtCl4 | KCl | 3.79E−04 |
| 1757 | DL-1-amino-2-propanol + 3-hydroxy-2-nitropyridine | 1 each | K2PtCl4 | KCl | 4.46E−04 |
| 1758 | DL-1-amino-2-propanol + 2-cyanopyridine | 1 each | K2PtCl4 | KCl | 3.57E−04 |
| 1759 | DL-1-amino-2-propanol + (R)-(−)-2-amino-1-propanol | 1 each | K2PtCl4 | KCl | 4.69E−04 |
| 1760 | DL-1-amino-2-propanol + imidazole | 1 each | K2PtCl4 | KCl | 8.26E−04 |
| 1761 | DL-1-amino-2-propanol + 2-methyl-1-pyrroline | 1 each | K2PtCl4 | KCl | 6.25E−04 |
| 1762 | DL-1-amino-2-propanol + 2-methylimidazole | 1 each | K2PtCl4 | KCl | 6.25E−04 |
| 1763 | DL-1-amino-2-propanol + indole | 1 each | K2PtCl4 | KCl | 8.04E−04 |
| 1764 | DL-1-amino-2-propanol + butylamine | 1 each | K2PtCl4 | KCl | 8.04E−04 |
| 1765 | 2,5-dimethyl-3-pyrroline + 3-hydroxy-2-nitropyridine | 1 each | K2PtCl4 | KCl | 6.03E−04 |
| 1766 | 2,5-dimethyl-3-pyrroline + 2-cyanopyridine | 1 each | K2PtCl4 | KCl | 6.25E−04 |
| 1767 | 2,5-dimethyl-3-pyrroline + (R)-(−)-2-amino-1-propanol | 1 each | K2PtCl4 | KCl | 5.58E−04 |
| 1768 | 2,5-dimethyl-3-pyrroline + imidazole | 1 each | K2PtCl4 | KCl | 6.92E−04 |
| 1769 | 2,5-dimethyl-3-pyrroline + 2-methyl-1-pyrroline | 1 each | K2PtCl4 | KCl | 7.59E−04 |

TABLE 1-continued

| No. | Ligand(s) | Equiv. | Precursor | Leaving Group | Yld, g atm Pt |
|---|---|---|---|---|---|
| 1770 | 2,5-dimethyl-3-pyrroline + 2-methylimidazole | 1 each | K2PtCl4 | KCl | 6.25E−04 |
| 1771 | 2,5-dimethyl-3-pyrroline + indole | 1 each | K2PtCl4 | KCl | 1.36E−03 |
| 1772 | 2,5-dimethyl-3-pyrroline + butylamine | 1 each | K2PtCl4 | KCl | 1.00E−03 |
| 1773 | 2-hydroxypyridine + 3-hydroxy-2-nitropyridine | 1 each | K2PtCl4 | KCl | 6.70E−04 |
| 1774 | 2-hydroxypyridine + 2-cyanopyridine | 1 each | K2PtCl4 | KCl | 6.70E−04 |
| 1775 | 2-hydroxypyridine + (R)-(−)-2-amino-1-propanol | 1 each | K2PtCl4 | KCl | 6.03E−04 |
| 1776 | 2-hydroxypyridine + imidazole | 1 each | K2PtCl4 | KCl | 1.18E−03 |
| 1777 | 2-hydroxypyridine + 2-methyl-1-pyrroline | 1 each | K2PtCl4 | KCl | 1.27E−03 |
| 1778 | 2-hydroxypyridine + 2-methylimidazole | 1 each | K2PtCl4 | KCl | 6.47E−04 |
| 1779 | 2-hydroxypyridine + indole | 1 each | K2PtCl4 | KCl | 8.48E−04 |
| 1780 | 2-hydroxypyridine + butylamine | 1 each | K2PtCl4 | KCl | 6.03E−04 |
| 1781 | 4-amino-1-butanol + 3-hydroxy-2-nitropyridine | 1 each | K2PtCl4 | KCl | 6.03E−04 |
| 1782 | 4-amino-1-butanol + 2-cyanopyridine | 1 each | K2PtCl4 | KCl | 1.12E−03 |
| 1783 | 4-amino-1-butanol + (R)-(−)-2-amino-1-propanol | 1 each | K2PtCl4 | KCl | 4.72E−04 |
| 1784 | 4-amino-1-butanol + imidazole | 1 each | K2PtCl4 | KCl | 4.47E−04 |
| 1785 | 4-amino-1-butanol + 2-methyl-1-pyrroline | 1 each | K2PtCl4 | KCl | 5.46E−04 |
| 1786 | 4-amino-1-butanol + 2-methylimidazole | 1 each | K2PtCl4 | KCl | 4.96E−04 |
| 1787 | 4-amino-1-butanol + indole | 1 each | K2PtCl4 | KCl | 6.20E−04 |
| 1788 | 4-amino-1-butanol + butylamine | 1 each | K2PtCl4 | KCl | 6.00E−03 |
| 1789 | imidazole + 2-mercaptopyridine | 1 each | K2PtCl4 | propionate | 2.27E−03 |
| 1790 | imidazole + 3-aminopyridine | 1 each | K2PtCl4 | propionate | 3.95E−04 |
| 1791 | imidazole + 3,5-dimethylpyrazole | 1 each | K2PtCl4 | propionate | 1.19E−03 |
| 1792 | imidazole + 2,5-dimethyl-3-pyrroline | 1 each | K2PtCl4 | propionate | 3.62E−04 |
| 1793 | imidazole + 2-hydroxypyridine | 1 each | K2PtCl4 | propionate | 1.12E−03 |
| 1794 | imidazole + 2-methylimidazole | 1 each | K2PtCl4 | propionate | 6.92E−04 |
| 1795 | imidazole + 4-amino-1-butanol | 1 each | K2PtCl4 | propionate | 3.62E−04 |
| 1796 | imidazole + butylamine | 1 each | K2PtCl4 | propionate | 5.27E−04 |
| 1797 | indole + 2-mercaptopyridine | 1 each | K2PtCl4 | propionate | 1.15E−03 |
| 1798 | indole + 3-aminopyridine | 1 each | K2PtCl4 | propionate | 2.63E−04 |
| 1799 | indole + 3,5-dimethylpyrazole | 1 each | K2PtCl4 | propionate | 3.49E−03 |
| 1800 | indole + 2,5-dimethyl-3-pyrroline | 1 each | K2PtCl4 | propionate | 5.27E−04 |
| 1801 | indole + 2-hydroxypyridine | 1 each | K2PtCl4 | propionate | 2.60E−03 |
| 1802 | indole + 2-methylimidazole | 1 each | K2PtCl4 | propionate | 1.35E−03 |
| 1803 | indole + 4-amino-1-butanol | 1 each | K2PtCl4 | propionate | 9.55E−04 |
| 1804 | indole + butylamine | 1 each | K2PtCl4 | propionate | 1.32E−03 |
| 1805 | 2-cyanopyridine + 2-mercaptopyridine | 1 each | K2PtCl4 | propionate | 1.22E−03 |
| 1806 | 2-cyanopyridine + 3-aminopyridine | 1 each | K2PtCl4 | propionate | 4.28E−04 |
| 1807 | 2-cyanopyridine + 3,5-dimethylpyazole | 1 each | K2PtCl4 | propionate | 3.82E−03 |
| 1808 | 2-cyanopyridine + 2,5-dimethyl-3-pyrroline | 1 each | K2PtCl4 | propionate | 6.26E−04 |
| 1809 | 2-cyanopyridine + 2-hydroxypyridine | 1 each | K2PtCl4 | propionate | 6.26E−04 |
| 1810 | 2-cyanopyridine + 2-methylimidazole | 1 each | K2PtCl4 | propionate | 1.32E−03 |
| 1811 | 2-cyanopyridine + 4-amino-1-butanol | 1 each | K2PtCl4 | propionate | 7.24E−04 |
| 1812 | 2-cyanopyridine + butylamine | 1 each | K2PtCl4 | propionate | 5.93E−04 |
| 1813 | (R)-(−)-2-amino-1-propanol + 2-mercaptopyridine | 1 each | K2PtCl4 | propionate | 9.55E−04 |
| 1814 | (R)-(−)-2-amino-1-propanol + 3-aminopyridine | 1 each | K2PtCl4 | propionate | 7.24E−04 |
| 1815 | (R)-(−)-2-amino-1-propanol + 3,5-dimethylpyrazole | 1 each | K2PtCl4 | propionate | 1.51E−03 |
| 1816 | (R)-(−)-2-amino-1-propanol + 2,5-dimethyl-3-pyrroline | 1 each | K2PtCl4 | propionate | 6.59E−04 |
| 1817 | (R)-(−)-2-amino-1-propanol + 2-hydroxypyridine | 1 each | K2PtCl4 | propionate | 6.59E−04 |
| 1818 | (R)-(−)-2-amino-1-propanol + 2-methylimidazole | 1 each | K2PtCl4 | propionate | 7.24E−04 |
| 1819 | (R)-(−)-2-amino-1-propanol + 4-amino-1-butanol | 1 each | K2PtCl4 | propionate | 1.65E−04 |
| 1820 | (R)-(−)-2-amino-1-propanol + butylamine | 1 each | K2PtCl4 | propionate | 2.63E−04 |
| 1821 | DL-1-amino-2-butanol + 2-mercaptopyridine | 1 each | K2PtCl4 | propionate | 3.29E−04 |
| 1822 | DL-1-amino-2-butanol + 3-aminopyridine | 1 each | K2PtCl4 | propionate | 1.65E−04 |
| 1823 | DL-1-amino-2-butanol + 3,5-dimethylpyazole | 1 each | K2PtCl4 | propionate | 3.29E−04 |
| 1824 | DL-1-amino-2-butanol + 2,5-dimethyl-3-pyrroline | 1 each | K2PtCl4 | propionate | 1.12E−03 |
| 1825 | DL-1-amino-2-butanol + 2-hydroxypyridine | 1 each | K2PtCl4 | propionate | 9.55E−04 |
| 1826 | DL-1-amino-2-butanol + 2-methylimidazole | 1 each | K2PtCl4 | propionate | 9.22E−04 |
| 1827 | DL-1-amino-2-butanol + 4-amino-1-butanol | 1 each | K2PtCl4 | propionate | 4.28E−04 |
| 1828 | DL-1-amino-2-butanol + butylamine | 1 each | K2PtCl4 | propionate | 5.60E−04 |
| 1829 | 1-methylimidazole + 2-mercaptopyridine | 1 each | K2PtCl4 | propionate | 7.57E−04 |
| 1830 | 1-methylimidazole + 3-aminopyridine | 1 each | K2PtCl4 | propionate | 3.95E−04 |
| 1831 | 1-methylimidazole + 3,5-dimethylpyrazole | 1 each | K2PtCl4 | propionate | 1.81E−03 |
| 1832 | 1-methylimidazole + 2,5-dimethyl-3-pyrroline | 1 each | K2PtCl4 | propionate | 1.78E−03 |
| 1833 | 1-methylimidazole + 2-hydroxypyridine | 1 each | K2PtCl4 | propionate | 1.22E−03 |
| 1834 | 1-methylimidazole + 2-methylimidazole | 1 each | K2PtCl4 | propionate | 1.28E−03 |
| 1835 | 1-methylimidazole + 4-amino-1-butanol | 1 each | K2PtCl4 | propionate | 9.55E−04 |
| 1836 | 1-methylimidazole + butylamine | 1 each | K2PtCl4 | propionate | 6.92E−04 |
| 1837 | pyrazole + 2-mercaptopyridine | 1 each | K2PtCl4 | propionate | 8.56E−04 |

TABLE 1-continued

| No. | Ligand(s) | Equiv. | Precursor | Leaving Group | Yld, g atm Pt |
|---|---|---|---|---|---|
| 1838 | pyrazole + 3-aminopyridine | 1 each | K2PtCl4 | propionate | 3.95E−04 |
| 1839 | pyrazole + 3,5-dimethylpyrazole | 1 each | K2PtCl4 | propionate | 4.94E−04 |
| 1840 | pyrazole + 2-hydroxypyridine | 1 each | K2PtCl4 | propionate | 3.95E−04 |
| 1841 | pyrazole + 2-methylimidazole | 1 each | K2PtCl4 | propionate | 5.60E−04 |
| 1842 | pyrazole + 4-amino-1-butanol | 1 each | K2PtCl4 | propionate | 3.95E−04 |
| 1843 | pyrazole + butylamine | 1 each | K2PtCl4 | propionate | 3.95E−04 |
| 1844 | 2-methyl-1-pyrroline + 2-metcaptopyridine | 1 each | K2PtCl4 | propionate | 8.56E−04 |
| 1845 | 2-methyl-1-pyrroline + 3-aminopyridine | 1 each | K2PtCl4 | propionate | 4.94E−04 |
| 1846 | 2-methyl-1-pyrroline + 3,5-dimethylpyrazole | 1 each | K2PtCl4 | propionate | 7.90E−04 |
| 1847 | 2-methyl-1-pyrroline + 2,5-dimethyl-3-pyrroline | 1 each | K2PtCl4 | propionate | 6.26E−04 |
| 1848 | 2-methyl-1-pyrroline + 2-hydroxypyridine | 1 each | K2PtCl4 | propionate | 7.57E−04 |
| 1849 | 2-methyl-1-pyrroline + 2-methylimidazole | 1 each | K2PtCl4 | propionate | 7.57E−04 |
| 1850 | 2-methyl-1-pyrroline + 4-amino-1-butanol | 1 each | K2PtCl4 | propionate | 7.90E−04 |
| 1851 | 2-methyl-1-pyrroline + butylamine | 1 each | K2PtCl4 | propionate | 6.59E−04 |
| 1852 | 3-hydroxy-1-nitropyridine + 2-mercaptopyridine | 1 each | K2PtCl4 | propionate | 1.75E−03 |
| 1853 | 3-hydroxy-1-nitropyridine + 3-aminopyridine | 1 each | K2PtCl4 | propionate | 5.27E−04 |
| 1854 | 3-hydroxy-1-nitropyridine + 3,5-dimethylpyrazole | 1 each | K2PtCl4 | propionate | 1.22E−03 |
| 1855 | 3-hydroxy-1-nitropyridine + 2,5-dimethyl-3-pyrrolein | 1 each | K2PtCl4 | propionate | 5.60E−04 |
| 1856 | 3-hydroxy-1-nitropyridine + 2-hydroxypyridine | 1 each | K2PtCl4 | propionate | 5.27E−04 |
| 1857 | 3-hydroxy-1-nitropyridine + 2-methylimidazole | 1 each | K2PtCl4 | propionate | 7.57E−04 |
| 1858 | 3-hydroxy-1-nitropyridine + 4-amino-1-butanol | 1 each | K2PtCl4 | propionate | 5.60E−04 |
| 1859 | 3-hydroxy-1-nitropyridine + butylamine | 1 each | K2PtCl4 | propionate | 5.93E−04 |
| 1860 | indoline + 2-mercaptopyridine | 1 each | K2PtCl4 | propionate | 1.25E−03 |
| 1861 | indoline + 3-aminopyridine | 1 each | K2PtCl4 | propionate | 5.60E−04 |
| 1862 | indoline + 3,5-dimethylpyrazole | 1 each | K2PtCl4 | propionate | 7.24E−04 |
| 1863 | indoline + 2,5-dimethyl-3-pyrroline | 1 each | K2PtCl4 | propionate | 5.93E−04 |
| 1864 | indoline + 2-hydroxypyridine | 1 each | K2PtCl4 | propionate | 7.28E−05 |
| 1865 | indoline + 2-methylimidazole | 1 each | K2PtCl4 | propionate | 1.82E−04 |
| 1866 | indoline + 4-amino-1-butanol | 1 each | K2PtCl4 | propionate | 6.55E−04 |
| 1867 | indoline + butylamine | 1 each | K2PtCl4 | propionate | 1.60E−03 |
| 1868 | 2,6-diaminopyridine + 2-mercaptopyridine | 1 each | K2PtCl4 | propionate | 1.96E−03 |
| 1869 | 2,6-diaminopyridine + 3-aminopyridine | 1 each | K2PtCl4 | propionate | 1.42E−03 |
| 1870 | 2,6-diaminopyridine + 3,5-dimethylpyrazole | 1 each | K2PtCl4 | propionate | 1.38E−03 |
| 1871 | 2,6-diaminopyridine + 2,5-dimethyl-3-pyrroline | 1 each | K2PtCl4 | propionate | 1.27E−03 |
| 1872 | 2,6-diaminopyridine + 2-hydroxypyridine | 1 each | K2PtCl4 | propionate | 1.31E−03 |
| 1873 | 2,6-diaminopyridine + 2-methylimidazole | 1 each | K2PtCl4 | propionate | 1.27E−03 |
| 1874 | 2,6-diaminopyridine + 4-amino-1-butanol | 1 each | K2PtCl4 | propionate | 1.42E−03 |
| 1875 | 2,6-diaminopyridine + butylamine | 1 each | K2PtCl4 | propionate | 1.31E−03 |
| 1876 | cyclopentylamine + 2-mercaptopyridine | 1 each | K2PtCl4 | propionate | 3.78E−03 |
| 1877 | cyclopentylamine + 3-aminopyridine | 1 each | K2PtCl4 | propionate | 1.56E−03 |
| 1878 | cyclopentylamine + 3,5-dimethylpyrazole | 1 each | K2PtCl4 | propionate | 1.38E−03 |
| 1879 | cyclopentylamine + 2,5-dimethyl-3-pyrroline | 1 each | K2PtCl4 | propionate | 1.46E−03 |
| 1880 | cyclopentylamine + 2-hydroxypyridine | 1 each | K2PtCl4 | propionate | 1.49E−03 |
| 1881 | cyclopentylamine + 2-methylimidazole | 1 each | K2PtCl4 | propionate | 1.46E−03 |
| 1882 | cyclopentylamine + 4-amino-1-butatol | 1 each | K2PtCl4 | propionate | 1.35E−03 |
| 1883 | cyclopentylamine + butylamine | 1 each | K2PtCl4 | propionate | 1.35E−03 |
| 1884 | 3-aminopyridine + 2-aminonorbornane | 1 each | K2PtCl4 | acetate | 5.53E−03 |
| 1885 | 3-aminopyridine + 4-aminobenzoic acid | 1 each | K2PtCl4 | acetate | 3.51E−04 |
| 1886 | 3-aminopyridine + aminoacetalaldehyde dimethyl acetal | 1 each | K2PtCl4 | acetate | 3.51E−04 |
| 1887 | 3-aminopyridine + trimethylamine-N-oxidedihydrate | 1 each | K2PtCl4 | acetate | 3.51E−04 |
| 1888 | 3-aminopyridine + pyrrolidine | 1 each | K2PtCl4 | acetate | 4.39E−04 |
| 1889 | 3-aminopyridine + pyrazine | 1 each | K2PtCl4 | acetate | 3.51E−04 |
| 1890 | 3-aminopyridine + ethylenediamine | 1 each | K2PtCl4 | acetate | 5.26E−04 |
| 1891 | 3-aminopyridine + 1,4-diaminobutane | 1 each | K2PtCl4 | acetate | 4.68E−04 |
| 1892 | 2-hydroxypyridine + 2-aminonorbornane | 1 each | K2PtCl4 | acetate | 4.39E−04 |
| 1893 | 2-hydroxypyridine + 4-aminobenzoic acid | 1 each | K2PtCl4 | acetate | 4.39E−04 |
| 1894 | 2-hydroxypyridine + aminoacetaldehyde dimethyl acetal | 1 each | K2PtCl4 | acetate | 6.14E−04 |
| 1895 | 2-hydroxypyridine + trimethylamine-N-oxidedihydrate | 1 each | K2PtCl4 | acetate | 4.97E−04 |
| 1896 | 2-hydroxypyridine + pyrrolidine | 1 each | K2PtCl4 | acetate | 5.56E−04 |
| 1897 | 2-hydroxypyridine + pyrazine | 1 each | K2PtCl4 | acetate | 5.26E−04 |
| 1898 | 2-hydroxypyridine + ethylenediamine | 1 each | K2PtCl4 | acetate | 1.20E−03 |
| 1899 | 2-hydroxypyridine + 1,4-diaminobutane | 1 each | K2PtCl4 | acetate | 6.14E−04 |
| 1900 | 2,6-diaminopyridine + 2-aminonorbornane | 1 each | K2PtCl4 | acetate | 5.85E−04 |
| 1901 | 2,6-diaminopyridine + 4-aminobenzoic acid | 1 each | K2PtCl4 | acetate | 7.31E−04 |
| 1902 | 2,6-diaminopyridine + aminoacetalaldehyde dimethyl acetal | 1 each | K2PtCl4 | acetate | 6.43E−04 |
| 1903 | 2,6-diaminopyridine + trimethylamine-N-oxidedihydrate | 1 each | K2PtCl4 | acetate | 7.02E−04 |

TABLE 1-continued

| No. | Ligand(s) | Equiv. | Precursor | Leaving Group | Yld, g atm Pt |
|---|---|---|---|---|---|
| 1904 | 2,6-diaminopyridine + pyrrolidine | 1 each | K2PtCl4 | acetate | 6.43E−04 |
| 1905 | 2,6-diaminopyridine + pyrazine | 1 each | K2PtCl4 | acetate | 6.73E−04 |
| 1906 | 2,6-diaminepyridine + ethylenediamine | 1 each | K2PtCl4 | acetate | 1.11E−03 |
| 1907 | 2,6-diaminopyridine + 1,4-diaminobutane | 1 each | K2PtCl4 | acetate | 7.90E−04 |
| 1908 | 3-hydroxy-2-nitropyridine + 2-aminonorbornane | 1 each | K2PtCl4 | acetate | 7.60E−04 |
| 1909 | 3-hydroxy-2-nitropyridine + 4-aminobenzoic acid | 1 each | K2PtCl4 | acetate | 7.60E−04 |
| 1910 | 3-hydroxy-2-nitropyridine + aminoacetaldehyde dimethyl acetal | 1 each | K2PtCl4 | acetate | 1.17E−03 |
| 1911 | 3-hydroxy-2-nitropyridine + trimethylamine-N-oxidedihydrate | 1 each | K2PtCl4 | acetate | 7.90E−04 |
| 1912 | 3-hydroxy-2-nitropyridine + pyrrolidine | 1 each | K2PtCl4 | acetate | 7.60E−04 |
| 1913 | 3-hydroxy-2-nitropyridine + pyrazine | 1 each | K2PtCl4 | acetate | 7.60E−04 |
| 1914 | 3-hydroxy-2-nitropyridine + ethylenediamine | 1 each | K2PtCl4 | acetate | 1.46E−03 |
| 1915 | 3-hydroxy-2-nitropyridine + 1,4-diaminobutane | 1 each | K2PtCl4 | acetate | 8.77E−04 |
| 1916 | 2-mercaptopyridine + 2-aminonorbornane | 1 each | K2PtCl4 | acetate | 9.94E−04 |
| 1917 | 2-mercaptopyridine + 2-aminobenzoic acid | 1 each | K2PtCl4 | acetate | 1.46E−03 |
| 1918 | 2-mercaptopyridine + aminoacetaladehyde dimethyl acetal | 1 each | K2PtCl4 | acetate | 1.40E−03 |
| 1919 | 2-mercaptopyridine + trimethylamine-N-oxidedihydrate | 1 each | K2PtCl4 | acetate | 1.52E−03 |
| 1920 | 2-mercaptopyridine + pyrrolidine | 1 each | K2PtCl4 | acetate | 1.78E−03 |
| 1921 | 2-mercaptopyridine + pyrazine | 1 each | K2PtCl4 | acetate | 1.55E−03 |
| 1922 | 2-mercaptopyridine + ethylenediamine | 1 each | K2PtCl4 | acetate | 2.25E−03 |
| 1923 | 2-mercaptopyridine + 1,4-diaminobutane | 1 each | K2PtCl4 | acetate | 1.20E−03 |
| 1924 | cyclopentylamine + 2-aminonorbornane | 1 each | K2PtCl4 | acetate | 1.11E−03 |
| 1925 | cyclopentylamine + 4-aminobenzoic acid | 1 each | K2PtCl4 | acetate | 1.02E−03 |
| 1926 | cyclopentylamine + aminoacetalaldehyde dimethyl acetal | 1 each | K2PtCl4 | acetate | 1.20E−03 |
| 1927 | cyclopentylamine + trimethylamine-N-oxidedihydrate | 1 each | K2PtCl4 | acetate | 9.94E−04 |
| 1928 | cyclopentylamine + pyrrolidine | 1 each | K2PtCl4 | acetate | 1.02E−03 |
| 1929 | cyclopentylamine + pyrazine | 1 each | K2PtCl4 | acetate | 2.41E−03 |
| 1930 | cyclopentylamine + ethylenediamine | 1 each | K2PtCl4 | acetate | 6.90E−04 |
| 1931 | cyclcpentylamine + 1,4-diaminobutane | 1 each | K2PtCl4 | acetate | 2.30E−04 |
| 1932 | 2-amino-3-hydroxypyridine + 2-aminonorbornane | 1 each | K2PtCl4 | acetate | 2.59E−04 |
| 1933 | 2-amino-3-hydroxypyridine + 4-aminobenzoic acid | 1 each | K2PtCl4 | acetate | 3.45E−04 |
| 1934 | 2-amino-3-hydroxypyridine + aminoacetalaldehyde dimethyl acetal | 1 each | K2PtCl4 | acetate | 3.45E−04 |
| 1935 | 2-amino-3-hydroxypyridine + trimethylamine-N-oxidedihydrate | 1 each | K2PtCl4 | acetate | 1.44E−04 |
| 1936 | 2-amino-3-hydroxypyridine + pyrrolidine | 1 each | K2PtCl4 | acetate | 8.62E−05 |
| 1937 | 2-amino-3-hydroxypyridine + pyrazine | 1 each | K2PtCl4 | acetate | 1.15E−04 |
| 1938 | 2-amino-3-hydroxypyridine + ethylenediamine | 1 each | K2PtCl4 | acetate | 5.46E−04 |
| 1939 | 2-amino-3-hydroxypyridine + 1,4-diaminobutane | 1 each | K2PtCl4 | acetate | 2.59E−04 |
| 1940 | imidazole + 2-aminonorbornane | 1 each | K2PtCl4 | acetate | 1.78E−04 |
| 1941 | imidazole + 4-aminobenzoic acid | 1 each | K2PtCl4 | acetate | 2.50E−04 |
| 1942 | imidazole + aminoacetalaldehyde dimethyl acetal | 1 each | K2PtCl4 | acetate | 1.78E−04 |
| 1943 | imidazole + trimethylamine-N-oxidedihydrate | 1 each | K2PtCl4 | acetate | 2.50E−04 |
| 1944 | imidazole + pyrrolidine | 1 each | K2PtCl4 | acetate | 2.50E−04 |
| 1945 | imidazole + pyrazine | 1 each | K2PtCl4 | acetate | 2.50E−04 |
| 1946 | imidazole + ethylenediamine | 1 each | K2PtCl4 | acetate | 2.14E−04 |
| 1947 | imidazole + 1,4-diaminobutane | 1 each | K2PtCl4 | acetate | 2.14E−04 |
| 1948 | 1-methylimidazole + 2-aminonorbornane | 1 each | K2PtCl4 | acetate | 3.57E−04 |
| 1949 | 1-methylimidazole + 4-aminobenzoic acid | 1 each | K2PtCl4 | acetate | 3.21E−04 |
| 1950 | 1-methylimidazole + aminoacetalaldehyde dimethyl acetal | 1 each | K2PtCl4 | acetate | 2.85E−04 |
| 1951 | 1-methylimidazole + trimethylamine-N-oxidedihydrate | 1 each | K2PtCl4 | acetate | 6.78E−04 |
| 1952 | 1-methylimidazole + pyrrolidine | 1 each | K2PtCl4 | acetate | 8.20E−04 |
| 1953 | 1-methylimidazole + pyrazine | 1 each | K2PtCl4 | acetate | 9.99E−04 |
| 1954 | 1-methylimidazole + ethylenediamine | 1 each | K2PtCl4 | acetate | 1.11E−03 |
| 1955 | 1-methylimidazole + 1,4-dimainobutane | 1 each | K2PtCl4 | acetate | 5.35E−04 |
| 1956 | 2-methylimidazole + 2-aminonorbornane | 1 each | K2PtCl4 | acetate | 5.35E−04 |
| 1957 | 2-methylimidazole + 4-aminobenzoic acid | 1 each | K2PtCl4 | acetate | 4.99E−04 |
| 1958 | 2-methylimidazole + aminoacetalaldehyde dimethyl acetal | 1 each | K2PtCl4 | acetate | 5.35E−04 |
| 1959 | 2-methylimidazole + trimethylamine-N-oxidedihydrate | 1 each | K2PtCl4 | acetate | 4.64E−04 |
| 1960 | 2-methylimidazole + pyrrolidine | 1 each | K2PtCl4 | acetate | 5.71E−04 |
| 1961 | 2-methylimidazole + pyrazine | 1 each | K2PtCl4 | acetate | 5.71E−04 |
| 1962 | 2-methylimidazole + ethylenediamine | 1 each | K2PtCl4 | acetate | 1.07E−03 |

TABLE 1-continued

| No. | Ligand(s) | Equiv. | Precursor | Leaving Group | Yld, g atm Pt |
|---|---|---|---|---|---|
| 1963 | 2-methylimidazole + 1,4-diaminobutane | 1 each | K2PtCl4 | acetate | 6.78E−04 |
| 1964 | pyrazole + 2-aminonorbornane | 1 each | K2PtCl4 | acetate | 5.35E−04 |
| 1965 | pyrazole + 4-aminobenzoic acid | 1 each | K2PtCl4 | acetate | 9.99E−04 |
| 1966 | pyrazole + aminoacetalaldehyde dimethyl acetal | 1 each | K2PtCl4 | acetate | 7.13E−04 |
| 1967 | pyrazole + trimethylamine-N-oxidedihydrate | 1 each | K2PtCl4 | acetate | 2.89E−03 |
| 1968 | pyrazole + pyrrolidine | 1 each | K2PtCl4 | acetate | 6.42E−04 |
| 1969 | pyrazole + pyrazine | 1 each | K2PtCl4 | acetate | 7.13E−04 |
| 1970 | pyrazole + ethylenediamine | 1 each | K2PtCl4 | acetate | 7.49E−04 |
| 1971 | pyrazole + 1,4-diaminobutane | 1 each | K2PtCl4 | acetate | 2.64E−03 |
| 1972 | 2-aminonorbornane | 2 | K2PtCl4 | acetate | 2.60E−03 |
| 1973 | 4-aminobenzoic acid | 2 | K2PtCl4 | acetate | 9.27E−04 |
| 1974 | aminoacetalaldehyde dimethyl acetal | 2 | K2PtCl4 | acetate | 7.49E−04 |
| 1975 | trimethylamine-N-oxidedihydrate | 2 | K2PtCl4 | acetate | 7.49E−04 |
| 1976 | pyrrolidine | 2 | K2PtCl4 | acetate | 7.85E−04 |
| 1977 | pyrazine | 2 | K2PtCl4 | acetate | 7.85E−04 |
| 1978 | ethylenediamine | 2 | K2PtCl4 | acetate | 1.07E−03 |
| 1979 | 1,4-diaminobutane | 2 | K2PtCl4 | acetate | 8.20E−04 |
| 1980 | 2-aminonorbornane + 2-hydroxypyridine | 1 each | K2PtCl4 | oxalate | 1.84E−04 |
| 1981 | 2-aminonorbornane + 4-aminobenzoic acid | 1 each | K2PtCl4 | oxalate | 2.21E−04 |
| 1982 | 2-aminonorbornane + 3-aminopyridine | 1 each | K2PtCl4 | oxalate | 2.57E−04 |
| 1983 | 2-aminonorbornane + 2,6-diaminopyridine | 1 each | K2PtCl4 | oxalate | 2.94E−04 |
| 1984 | 2-aminonorbornane + pyrrolidine | 1 each | K2PtCl4 | oxalate | 2.57E−04 |
| 1985 | 2-aminonorbornane + 3-hydroxy-2-nitropyridine | 1 each | K2PtCl4 | oxalate | 4.04E−04 |
| 1986 | 2-aminonorbornane + ethylenediamine | 1 each | K2PtCl4 | oxalate | 3.68E−04 |
| 1987 | 2-aminonorbornane + 1,4-diaminobutane | 1 each | K2PtCl4 | oxalate | 4.04E−04 |
| 1988 | aminoacetalaldehyde dimethyl acetal + 2-hydroxypyridine | 1 each | K2PtCl4 | oxalate | 3.68E−04 |
| 1989 | aminoacetalaldehyde dimethyl acetal + 4-aminobenzoic acid | 1 each | K2PtCl4 | oxalate | 4.78E−04 |
| 1990 | aminoacetalaldehyde dimethyl acetal + 3-aminopyridine | 1 each | K2PtCl4 | oxalate | 4.78E−04 |
| 1991 | aminoacetalaldehyde dimethyl acetal + 2,6-diaminopyridine | 1 each | K2PtCl4 | oxalate | 5.15E−04 |
| 1992 | aminoacetalaldehyde dimethyl acetal + pyrrolidine | 1 each | K2PtCl4 | oxalate | 4.78E−04 |
| 1993 | aminoacetalaldehyde dimethyl acetal + 3-hydroxy-2-nitropyridine | 1 each | K2PtCl4 | oxalate | 5.15E−04 |
| 1994 | aminoacetalaldehyde dimethyl acetal + ethylenediamine | 1 each | K2PtCl4 | oxalate | 9.19E−04 |
| 1995 | aminoacetalaldehyde dimethyl acetal + 1,4-diaminobutane | 1 each | K2PtCl4 | oxalate | 6.62E−04 |
| 1996 | pyrazine + 2-hydroxypyridine | 1 each | K2PtCl4 | oxalate | 5.51E−04 |
| 1997 | pyrazine + 4-aminobenzoic acid | 1 each | K2PtCl4 | oxalate | 5.15E−04 |
| 1998 | pyrazine + 3-aminopyridine | 1 each | K2PtCl4 | oxalate | 6.25E−04 |
| 1999 | pyrazine + 2,6-diaminopyridine | 1 each | K2PtCl4 | oxalate | 6.62E−04 |
| 2000 | pyrazine + pyrrolidine | 1 each | K2PtCl4 | oxalate | 6.62E−04 |
| 2001 | pyrazine + 3-hydroxy-2-nitropyridine | 1 each | K2PtCl4 | oxalate | 6.62E−04 |
| 2002 | pyrazine + ethylenediaimine | 1 each | K2PtCl4 | oxalate | 9.56E−04 |
| 2003 | pyrazine + 1,4-diaminobutane | 1 each | K2PtCl4 | oxalate | 6.98E−04 |
| 2004 | trimethylamine-N-oxidedihydrate + 2-hydroxypyridine | 1 each | K2PtCl4 | oxalate | 7.35E−04 |
| 2005 | trimethylamine-N-oxidedihydrate + 4-aminobenzoic acid | 1 each | K2PtCl4 | oxalate | 7.35E−04 |
| 2006 | trimethylamine-N-oxidedihydrate + 3-aminopyridine | 1 each | K2PtCl4 | oxalate | 7.72E−04 |
| 2007 | trimethylamine-N-oxidedihydrate + 2,6-diaminopyridine | 1 each | K2PtCl4 | oxalate | 8.45E−04 |
| 2008 | trimethylamine-N-oxidedihydrate + pyrrolidine | 1 each | K2PtCl4 | oxalate | 7.72E−04 |
| 2009 | trimethylamine-N-oxidedihydrate + 3-hydroxy-2-nitropyridine | 1 each | K2PtCl4 | oxalate | 8.09E−04 |
| 2010 | trimethylamine-N-oxidedihydrate + ethylenediamine | 1 each | K2PtCl4 | oxalate | 1.03E−03 |
| 2011 | trimethylamine-N-oxidedihydrate + 1,4-diaminobutane | 1 each | K2PtCl4 | oxalate | 8.82E−04 |
| 2012 | 2-mercaptopyridine + 2-hydroxypyridine | 1 each | K2PtCl4 | oxalate | 1.07E−03 |
| 2013 | 2-mercaptopyridine + 4-aminobenzoic acid | 1 each | K2PtCl4 | oxalate | 1.10E−03 |
| 2014 | 2-mercaptopyridine + 3-aminopyridine | 1 each | K2PtCl4 | oxalate | 1.14E−03 |
| 2015 | 2-mercaptopyridine + 2,6-diaminopyridine | 1 each | K2PtCl4 | oxalate | 1.29E−03 |
| 2016 | 2-mercaptopyridine + pyrrolidine | 1 each | K2PtCl4 | oxalate | 1.18E−03 |
| 2017 | 2-mercaptopyridine + 3-hydroxy-2-nitropyridine | 1 each | K2PtCl4 | oxalate | 1.47E−03 |
| 2018 | 2-mercaptopyridine + ethylenediamine | 1 each | K2PtCl4 | oxalate | 1.69E−03 |
| 2019 | 2-mercaptopyridine + 1,4-diaminobutane | 1 each | K2PtCl4 | oxalate | 1.18E−03 |
| 2020 | cyclopentylamine + 2-hydroxypyridine | 1 each | K2PtCl4 | oxalate | 1.03E−03 |
| 2021 | cyclopentylamine + 4-aminobenzoic acid | 1 each | K2PtCl4 | oxalate | 1.10E−03 |

TABLE 1-continued

| No. | Ligand(s) | Equiv. | Precursor | Leaving Group | Yld, g atm Pt |
|---|---|---|---|---|---|
| 2022 | cyclopentylamine + 3-aminopyridine | 1 each | K2PtCl4 | oxalate | 1.14E−03 |
| 2023 | cyclopentylamine + 2,6-dimainopyridine | 1 each | K2PtCl4 | oxalate | 1.10E−03 |
| 2024 | cyclopentylamine + pyrrolidine | 1 each | K2PtCl4 | oxalate | 1.29E−03 |
| 2025 | cyclopentylamine + 3-hydroxy-2-nitropyridine | 1 each | K2PtCl4 | oxalate | 2.57E−04 |
| 2026 | cyclopentylamine + ethylenediamine | 1 each | K2PtCl4 | oxalate | 3.14E−04 |
| 2027 | cyclopentylamine + 1,4-diaminobutane | 1 each | K2PtCl4 | oxalate | 3.14E−04 |
| 2028 | 2-amino-3-hydroxypyridine + 2-hydroxypyridine | 1 each | K2PtCl4 | oxalate | 3.14E−04 |
| 2029 | 2-amino-3-hydroxypyridine + 4-aminobenzoic acid | 1 each | K2PtCl4 | oxalate | 3.42E−04 |
| 2030 | 2-amino-3-hydroxypyridine + 3-aminopyridine | 1 each | K2PtCl4 | oxalate | 3.42E−04 |
| 2031 | 2-amino-3-hydroxypyridine + 2,6-diaminopyridine | 1 each | K2PtCl4 | oxalate | 3.71E−04 |
| 2032 | 2-amino-3-hydroxypyridine + pyrrolidine | 1 each | K2PtCl4 | oxalate | 4.56E−04 |
| 2033 | 2-amino-3-hydroxypyridine + 3-hydroxy-2-nitropyridine | 1 each | K2PtCl4 | oxalate | 3.99E−04 |
| 2034 | 2-amino-3-hydroxypyridine + ethylenediamine | 1 each | K2PtCl4 | oxalate | 4.56E−04 |
| 2035 | 2-amino-3-hydroxypyridine + 1,4-diaminobutane | 1 each | K2PtCl4 | oxalate | 4.85E−04 |
| 2036 | imidazole + 2-hydroxypyridine | 1 each | K2PtCl4 | oxalate | 4.85E−04 |
| 2037 | imidazole + 4-aminobenzoic acid | 1 each | K2PtCl4 | oxalate | 5.42E−04 |
| 2038 | imidazole + 3-aminopyridine | 1 each | K2PtCl4 | oxalate | 5.42E−04 |
| 2039 | imidazole + 2,6-diaminopyridine | 1 each | K2PtCl4 | oxalate | 5.70E−04 |
| 2040 | imidazole + pyrrolidine | 1 each | K2PtCl4 | oxalate | 5.42E−04 |
| 2041 | imidazole + 3-hydroxy-2-nitropyridine | 1 each | K2PtCl4 | oxalate | 5.42E−04 |
| 2042 | imidazole + ethylenediamine | 1 each | K2PtCl4 | oxalate | 6.27E−04 |
| 2043 | imidazole + 1,4-diaminobutane | 1 each | K2PtCl4 | oxalate | 5.70E−04 |
| 2044 | 1-methylimidazole + 2-hydroxypyridine | 1 each | K2PtCl4 | oxalate | 5.99E−04 |
| 2045 | 1-methylimidazole + 4-aminobenzoic acid | 1 each | K2PtCl4 | oxalate | 6.27E−04 |
| 2046 | 1-methylimidazole + 3-aminopyridine | 1 each | K2PtCl4 | oxalate | 5.99E−04 |
| 2047 | 1-methylimidazole + 2,6-diaminopyridine | 1 each | K2PtCl4 | oxalate | 5.70E−04 |
| 2048 | 1-methylimidazole + pyrrolidine | 1 each | K2PtCl4 | oxalate | 5.99E−04 |
| 2049 | 1-methylimidazole + 3-hydroxy-2-nitropyridine | 1 each | K2PtCl4 | oxalate | 6.56E−04 |
| 2050 | 1-methylimidazole + ethylenediamine | 1 each | K2PtCl4 | oxalate | 6.84E−04 |
| 2051 | 1-methylimidazole + 1,4-diaminobutane | 1 each | K2PtCl4 | oxalate | 6.84E−04 |
| 2052 | 2-methylimidazole + 2-hydroxypyridine | 1 each | K2PtCl4 | oxalate | 7.41E−04 |
| 2053 | 2-methylimidazole + 4-aminobenzoic acid | 1 each | K2PtCl4 | oxalate | 7.13E−04 |
| 2054 | 2-methylimidazole + 3-aminopyridine | 1 each | K2PtCl4 | oxalate | 7.41E−04 |
| 2055 | 2-methylimidazole + 2,6-diaminopyridine | 1 each | K2PtCl4 | oxalate | 7.13E−04 |
| 2056 | 2-methylimidazole + pyrrolidine | 1 each | K2PtCl4 | oxalate | 7.41E−04 |
| 2057 | 2-methylimidazole + 3-hydroxy-2-nitropyridine | 1 each | K2PtCl4 | oxalate | 7.41E−04 |
| 2058 | 2-methylimidazole + ethylenediamine | 1 each | K2PtCl4 | oxalate | 7.70E−04 |
| 2059 | 2-methylimidazole + 1,4-diaminobutane | 1 each | KtPtCl4 | oxalate | 8.27E−04 |
| 2060 | pyrazole + 2-hydroxypyridine | 1 each | K2PtCl4 | oxalate | 7.98E−04 |
| 2061 | pyrazole + 4-aminobenzoic acid | 1 each | K2PtCl4 | oxalate | 8.55E−04 |
| 2062 | pyrazole + 3-aminopyridine | 1 each | K2PtCl4 | oxalate | 7.98E−04 |
| 2063 | pyrazole + 2,6-diaminopyridine | 1 each | K2PtCl4 | oxalate | 8.27E−04 |
| 2064 | pyrazole + pyrrolidine | 1 each | K2PtCl4 | oxalate | 9.12E−04 |
| 2065 | pyrazole + 3-hydroxy-2-nitropyridine | 1 each | K2PtCl4 | oxalate | 8.84E−04 |
| 2066 | pyrazole + ethylenediamine | 1 each | K2PtCl4 | oxalate | 8.84E−04 |
| 2067 | pyrazole + 1,4-diaminobutane | 1 each | K2PtCl4 | oxalate | 8.55E−04 |
| 2068 | 2-hydroxypyridine | 2 | K2PtCl4 | oxalate | 9.12E−04 |
| 2069 | 4-aminobenzoic acid | 2 | K2PtCl4 | oxalate | 9.12E−04 |
| 2070 | 3-aminopyridine | 2 | K2PtCl4 | oxalate | 2.56E−04 |
| 2071 | 2,6-diaminopyridine | 2 | K2PtCl4 | oxalate | 2.24E−04 |
| 2072 | pyrrolidine | 2 | K2PtCl4 | oxalate | 2.56E−04 |
| 2073 | 3-hydroxy-2-nitropyridine | 2 | K2PtCl4 | oxalate | 2.88E−04 |
| 2074 | ethylenediamine | 2 | K2PtCl4 | oxalate | 6.09E−04 |
| 2075 | 1,4-diaminobutane | 2 | K2PtCl4 | oxalate | 2.88E−04 |
| 2076 | triethylamine-N-oxidedihydrate + ethylendiamine | 1 each | K2PtCl4 | KCl | 1.12E−03 |
| 2077 | aminoacetalaldehyde dimethyl acetal + ethylendiamine | 1 each | K2PtCl4 | KCl | 6.54E−04 |
| 2078 | 3-hydroxy-2-nitropyridine + ethylendiamine | 1 each | K2PtCl4 | KCl | 7.01E−04 |
| 2079 | 2,6-diaminopyridine + ethylendiamine | 1 each | K2PtCl4 | KCl | 6.54E−04 |
| 2080 | 2-amino-3-hydroxypyridine + ethylendiamine | 1 each | K2PtCl4 | KCl | 8.88E−04 |
| 2081 | 2-methylimidazole + ethylendiamine | 1 each | K2PtCl4 | KCl | 9.82E−04 |
| 2082 | 2-aminonorbornane + ethylendiamine | 1 each | K2PtCl4 | KCl | 1.08E−03 |
| 2083 | 4-picoline + ethylendiamine | 1 each | K2PtCl4 | KCl | 3.18E−03 |
| 2084 | triethylamine-N-oxidedihydrate + 1,4-diaminobutane | 1 each | K2PtCl4 | KCl | 7.01E−04 |
| 2085 | aminoacetalaldehyde dimethyl acetal + 1,4-diaminobutane | 1 each | K2PtCl4 | KCl | 8.88E−04 |
| 2086 | 3-hydroxy-2-nitropyridine + 1,4-diaminobutane | 1 each | K2PtCl4 | KCl | 8.41E−04 |
| 2087 | 2,6-diaminopyridine + 1,4-diaminobutane | 1 each | K2PtCl4 | KCl | 8.88E−04 |
| 2088 | 2-amino-3-hydroxypyridine + 1,4-diaminobutane | 1 each | K2PtCl4 | KCl | 9.82E−04 |

TABLE 1-continued

| No. | Ligand(s) | Equiv. | Precursor | Leaving Group | Yld, g atm Pt |
|---|---|---|---|---|---|
| 2089 | 2-methylimidazole + 1,4-diaminobutane | 1 each | K2PtCl4 | KCl | 9.82E−04 |
| 2090 | 2-aminonorbornane + 1,4-diaminobutane | 1 each | K2PtCl4 | KCl | 9.82E−04 |
| 2091 | 4-picoline + 1,4-diaminobutane | 1 each | K2PtCl4 | KCl | 2.85E−03 |
| 2092 | triethylamine-N-oxidedihydrate + 2-methylimidazole | 1 each | K2PtCl4 | KCl | 1.08E−03 |
| 2093 | aminoacetalaldehyde dimethyl acetal + 2-methylimidazole | 1 each | K2PtCl4 | KCl | 1.31E−03 |
| 2094 | 3-hydroxy-2-nitropyridine + 2-methylimidazole | 1 each | K2PtCl4 | KCl | 1.36E−03 |
| 2095 | 2,6-diaminopyridine + 2-methylimidazole | 1 each | K2PtCl4 | KCl | 1.22E−03 |
| 2096 | 2-amino-3-hydroxypyridine + 2-methylimidazole | 1 each | K2PtCl4 | KCl | 1.36E−03 |
| 2097 | 2-methylimidazole + 2-methylimidazole | 1 each | K2PtCl4 | KCl | 1.36E−03 |
| 2098 | 2-aminonorbornane + 2-methylimidazole | 1 each | K2PtCl4 | KCl | 1.96E−03 |
| 2099 | 4-picoline + 2-methylimidazole | 1 each | K2PtCl4 | KCl | 3.79E−03 |
| 2100 | triethylamine-N-oxidedihydrate + pyrrolidine | 1 each | K2PtCl4 | KCl | 1.36E−03 |
| 2101 | aminoacetalaldehyde dimethyl acetal + pyrrolidine | 1 each | K2PtCl4 | KCl | 1.40E−03 |
| 2102 | 3-hydroxy-2-nitropyridine + pyrrolidine | 1 each | K2PtCl4 | KCl | 1.40E−03 |
| 2103 | 2,6-diaminopyridine + pyrrolidine | 1 each | K2PtCl4 | KCl | 1.50E−03 |
| 2104 | 2-amino-3-hydroxypyridine + pyrrolidine | 1 each | K2PtCl4 | KCl | 1.59E−03 |
| 2105 | 2-methylimidazole + pyrrolidine | 1 each | K2PtCl4 | KCl | 1.59E−03 |
| 2106 | 2-aminonorbornane + pyrrolidine | 1 each | K2PtCl4 | KCl | 1.54E−03 |
| 2107 | 4-picoline + pyrrolidine | 1 each | K2PtCl4 | KCl | 3.41E−03 |
| 2108 | triethylamine-N-oxidedihydrate + pyrazine | 1 each | K2PtCl4 | KCl | 1.54E−03 |
| 2109 | aminoacetalaldehyde dimethyl acetal + pyrazine | 1 each | K2PtCl4 | KCl | 1.82E−03 |
| 2110 | 3-hydroxy-2-nitropyridine + pyrazine | 1 each | K2PtCl4 | KCl | 1.68E−03 |
| 2111 | 2,6-diaminopyridine + pyrazine | 1 each | K2PtCl4 | KCl | 1.78E−03 |
| 2112 | 2-amino-3-hydroxypyridine + pyrazine | 1 each | K2PtCl4 | KCl | 1.87E−03 |
| 2113 | 2-methylimidazole + pyrazine | 1 each | K2PtCl4 | KCl | 1.78E−03 |
| 2114 | 2-aminonorbornane + pyrazine | 1 each | K2PtCl4 | KCl | 1.78E−03 |
| 2115 | 4-picoline + pyrazine | 1 each | K2PtCl4 | KCl | 3.13E−03 |
| 2116 | triethylamine-N-oxidedihydrate + 3-aminopyridine | 1 each | K2PtCl4 | KCl | 1.82E−03 |
| 2117 | aminoacetalaldehyde dimethyl acetal + 3-aminopyridine | 1 each | K2PtCl4 | KCl | 1.92E−03 |
| 2118 | 3-hydroxy-2-nitropyridine + 3-aminopyridine | 1 each | K2PtCl4 | KCl | 1.87E−03 |
| 2119 | 2,6-diaminopyridine + 3-aminopyridine | 1 each | K2PtCl4 | KCl | 1.96E−03 |
| 2120 | 2-amino-3-hydroxypyridine + 3-aminopyridine | 1 each | K2PtCl4 | KCl | 2.06E−03 |
| 2121 | 2-methylimidazole + 3-aminopyridine | 1 each | K2PtCl4 | KCl | 4.93E−04 |
| 2122 | 2-aminonorbornane + 3-aminopyridine | 1 each | K2PtCl4 | KCl | 4.55E−04 |
| 2123 | 4-picoline + 3-aminopyridine | 1 each | K2PtCl4 | KCl | 5.31E−04 |
| 2124 | triethylamine-N-oxidedihydrate + 2-hydroxypyridine | 1 each | K2PtCl4 | KCl | 5.69E−04 |
| 2125 | aminoacetalaldehyde dimethyl acetal + 2-hydroxypyridine | 1 each | K2PtCl4 | KCl | 6.82E−04 |
| 2126 | 3-bydroxy-2-nitropyridine + 2-hydroxypyridine | 1 each | K2PtCl4 | KCl | 7.58E−04 |
| 2127 | 2,6-diaminopyridine + 2-hydroxypyridine | 1 each | K2PtCl4 | KCl | 7.58E−04 |
| 2128 | 2-amino-3-hydroxypyridine + 2-hydroxypyridine | 1 each | K2PtCl4 | KCl | 8.34E−04 |
| 2129 | 2-methylimidazole + 2-hydroxypyridine | 1 each | K2PtCl4 | KCl | 7.96E−04 |
| 2130 | 2-aminonorbornane + 2-hydroxypyridine | 1 each | K2PtCl4 | KCl | 8.34E−04 |
| 2131 | 4-picoline + 2-hydroxypyridine | 1 each | K2PtCl4 | KCl | 9.48E−04 |
| 2132 | triethylamine-N-oxidedihydrate + 2-mercaptopyridine | 1 each | K2PtCl4 | KCl | 9.48E−04 |
| 2133 | aminoacetalaldehyde dimethyl acetal + 2-mercaptopyridine | 1 each | K2PtCl4 | KCl | 9.48E−04 |
| 2134 | 3-hydroxy-2-nitropyridine + 2-mercaptopyridine | 1 each | K2PtCl4 | KCl | 1.10E−03 |
| 2135 | 2,6-diaminopyridine + 2-mercaptopyridine | 1 each | K2PtCl4 | KCl | 1.02E−03 |
| 2136 | 2-amino-3-hydroxypyridine + 2-mercaptopyridine | 1 each | K2PtCl4 | KCl | 1.10E−03 |
| 2137 | 2-methylimidazole + 2-mercaptopyridine | 1 each | K2PtCl4 | KCl | 1.18E−03 |
| 2138 | 2-aminonorbornane + 2-mercaptopyridine | 1 each | K2PtCl4 | KCl | 1.10E−03 |
| 2139 | 4-picoline + 2-mercaptopyridine | 1 each | K2PtCl4 | KCl | 1.10E−03 |
| 2140 | triethylamine-N-oxidedihydrate + cyclopentylamine | 1 each | K2PtCl4 | KCl | 1.21E−03 |
| 2141 | aminoacetalaldehyde dimethyl acetal + cyclopentylamine | 1 each | K2PtCl4 | KCl | 1.29E−03 |
| 2142 | 3-hydroxy-2-nitropyridine + cyclopentylamine | 1 each | K2PtCl4 | KCl | 1.29E−03 |
| 2143 | 2,6-diaminopyridine + cyclopentylamine | 1 each | K2PtCl4 | KCl | 1.21E−03 |
| 2144 | 2-amino-3-hydroxypyridine + cyclopentylamine | 1 each | K2PtCl4 | KCl | 1.33E−03 |
| 2145 | 2-methylimidazole + cyclopentylamine | 1 each | K2PtCl4 | KCl | 1.33E−03 |
| 2146 | 2-aminonorbornane + cyclopentylamine | 1 each | K2PtCl4 | KCl | 1.59E−03 |
| 2147 | 4-picoline + cyclopentylamine | 1 each | K2PtCl4 | KCl | 1.14E−03 |

TABLE 1-continued

| No. | Ligand(s) | Equiv. | Precursor | Leaving Group | Yld, g atm Pt |
|---|---|---|---|---|---|
| 2148 | triethylamine-N-oxidedihydrate + imidazole | 1 each | K2PtCl4 | KCl | 1.44E−03 |
| 2149 | aminoacetalaldehyde dimethyl acetal + imidazole | 1 each | K2PtCl4 | KCl | 1.55E−03 |
| 2150 | 3-hydnoxy-2-nitropyridine + imidazole | 1 each | K2PtCl4 | KCl | 2.16E−03 |
| 2151 | 2,6-diaminopyridine + imidazole | 1 each | K2PtCl4 | KCl | 2.05E−03 |
| 2152 | 2-amino-3-hydroxypyridine + imidazole | 1 each | K2PtCl4 | KCl | 1.93E−03 |
| 2153 | 2-methylimidazole + imidazole | 1 each | K2PtCl4 | KCl | 1.97E−03 |
| 2154 | 2-aminonorbornane + imidazole | 1 each | K2PtCl4 | KCl | 2.77E−03 |
| 2155 | 4-picoline + imidazole | 1 ecch | K2PtCl4 | KCl | 4.74E−03 |
| 2156 | triethylamine-N-oxidedihydrate + pyrazole | 1 each | K2PtCl4 | KCl | 2.96E−03 |
| 2157 | aminoacetalaldehyde dimethyl acetal + pyrazole | 1 each | K2PtCl4 | KCl | 2.58E−03 |
| 2158 | 3-hydroxy-2-nitropyridine + pyrazole | 1 each | K2PtCl4 | KCl | 2.84E−03 |
| 2159 | 2,6-diaminopyridine + pyrazole | 1 each | K2PtCl4 | KCl | 2.31E−03 |
| 2160 | 2-amino-3-hydroxypyridine + pyrazole | 1 each | K2PtCl4 | KCl | 2.54E−03 |
| 2161 | 2-methylimidazole + pyrazole | 1 each | K2PtCl4 | KCl | 2.84E−03 |
| 2162 | 2-aminonorbornane + pyrazole | 1 each | K2PtCl4 | KCl | 2.84E−03 |
| 2163 | 4-picoline + pyrazole | 1 each | K2PtCl4 | KCl | 4.70E−03 |
| 2164 | triethylamine-N-oxidedihydrate + 1-methylimidazole | 1 each | K2PtCl4 | KCl | 2.31E−03 |
| 2165 | aminoacetalaldehyde dimethyl acetal + 1-methylimidazole | 1 each | K2PtCl4 | KCl | 2.46E−03 |
| 2166 | 3-hydroxy-2-nitropyridine + 1-methylimidazole | 1 each | K2PtCl4 | KCl | 9.48E−01 |
| 2167 | 2,6-diaminopyridine + 1-methylimidazole | 1 each | K2PtCl4 | KCl | 5.69E−04 |
| 2168 | 2-amino-3-hydroxypyridine + 1-methylimidazole | 1 each | K2PtCl4 | KCl | 9.10E−04 |
| 2169 | 2-methylimidazole + 1-methylimidazole | 1 each | K2PtCl4 | KCl | 5.69E−04 |
| 2170 | 2-aminonorbornane + 1-methylimidazole | 1 each | K2PtCl4 | KCl | 5.69E−04 |
| 2171 | 4-picoline + 1-methylimidazole | 1 each | K2PtCl4 | KCl | 2.58E−03 |
| 2172 | propylamine + bis-mercaptomethylsulfide | 1 each | K2PtCl4 | KCl | 3.80E−03 |
| 2173 | 1,2-diaminocyclohexane + bis-mercaptomethylsulfide | 1 each | K2PtCl4 | KCl | 9.12E−04 |
| 2174 | 2,5-dimethylpyrrole + bis-mercaptomethylsulfide | 1 each | K2PtCl4 | KCl | 4.06E−04 |
| 2175 | 3-bromopropylamine-HBr + bis-mercaptomethylsulfide | 1 each | K2PtCl4 | KCl | 5.07E−04 |
| 2176 | 2-chloroethylamine-HCl + bis-mercaptomethylsulfide | 1 each | K2PtCl4 | KCl | 3.55E−04 |
| 2177 | 2-mercaptoethanol + bis-mercaptomethylsulfide | 1 each | K2PtCl4 | KCl | 4.56E−04 |
| 2178 | 2-aminoethyldihydrogenphosphate + bis-mercaptomethylsulfide | 1 each | K2PtCl4 | KCl | 4.56E−04 |
| 2179 | tris(2-aminoethyl)amine + bis-mercaptomethylsulfide | 1 each | K2PtCl4 | KCl | 8.62E−04 |
| 2180 | propylamine + indoline | 1 each | K2PtCl4 | KCl | 6.59E−04 |
| 2181 | 1,2-diaminocyclohexane + indoline | 1 each | K2PtCl4 | KCl | 2.03E−03 |
| 2182 | 2,5-dimethylpyrrole + indoline | 1 each | K2PtCl4 | KCl | 1.57E−03 |
| 2183 | 3-bromopropylamine-HBr + indoline | 1 each | K2PtCl4 | KCl | 1.17E−03 |
| 2184 | 2-chloroethylamine-HCl + indoline | 1 each | K2PtCl4 | KCl | 1.98E−03 |
| 2185 | 2-mercaptoethanol + indoline | 1 each | K2PtCl4 | KCl | 1.12E−03 |
| 2186 | 2-aminoethyldihydrogenphosphate + indoline | 1 each | K2PtCl4 | KCl | 8.11E−04 |
| 2187 | tris(2-aminoethyl)amine + indoline | 1 each | K2PtCl4 | KCl | 1.27E−03 |
| 2188 | propylamine + acrylamide | 1 each | K2PtCl4 | KCl | 8.11E−04 |
| 2189 | 1,2-diaminocyclohexane +acrylamide | 1 each | K2PtCl4 | KCl | 9.12E−04 |
| 2190 | 2,5-dimethylpyrrole + acrylamide | 1 each | K2PtCl4 | KCl | 9.63E−04 |
| 2191 | 3-bromopropylamine-HBr + acrylamide | 1 each | K2PtCl4 | KCl | 8.11E−04 |
| 2192 | 2-chloroethylamine-HCl + acrylamide | 1 each | K2PtCl4 | KCl | 9.63E−04 |
| 2193 | 2-mercaptoethanol + acrylamide | 1 each | K2PtCl4 | KCl | 9.63E−04 |
| 2194 | 2-aminoethyldihydrogenphosphate + acrylamide | 1 each | K2PtCl4 | KCl | 1.01E−03 |
| 2195 | tris(2-aminoethyl)amine + acrylamide | 1 each | K2PtCl4 | KCl | 1.01E−03 |
| 2196 | propylamine + 3-amino-1-propanol | 1 each | K2PtCl4 | KCl | 1.06E−03 |
| 2197 | 1,2-diaminocyclohexane + 3-amino-1-propanol | 1 each | K2PtCl4 | KCl | 1.12E−03 |
| 2198 | 2,5-dimethylpyrrole + 3-amino-1-propanol | 1 each | K2PtCl4 | KCl | 1.06E−03 |
| 2199 | 3-bromopropylamine-HBr + 3-amino-1-propanol | 1 each | K2PtCl4 | KCl | 1.06E−03 |
| 2200 | 2-chloroethylamine-HCl + 3-amino-1-propanol | 1 each | K2PtCl4 | KCl | 1.12E−03 |
| 2201 | 2-mercaptoethanol + 3-amino-1-propanol | 1 each | K2PtCl4 | KCl | 1.47E−03 |
| 2202 | 2-aminoethyldihydrogenphosphate + 3-amino-1 propanol | 1 each | K2PtCl4 | KCl | 1.37E−03 |
| 2203 | tris(2-aminoethyl)amine + 3-amino-1-propanol | 1 each | K2PtCl4 | KCl | 2.21E−04 |
| 2204 | propylamine + L-serine | 1 each | K2PtCl4 | KCl | 1.48E−04 |
| 2205 | 1,2-diaminocyclohexane + L-serine | 1 each | K2PtCl4 | KCl | 2.21E−04 |
| 2206 | 2,5-dimethylpyrrole + L-serine | 1 each | K2PtCl4 | KCl | 1.85E−04 |
| 2207 | 3-bromopropylamine-HBr + L-serine | 1 each | K2PtCl4 | KCl | 2.58E−04 |
| 2208 | 2-chloroethylamine-HCl + L-serine | 1 each | K2PtCl4 | KCl | 3.32E−04 |

TABLE 1-continued

| No. | Ligand(s) | Equiv. | Precursor | Leaving Group | Yld, g atm Pt |
|---|---|---|---|---|---|
| 2209 | 2-mercaptoethanol + L-serine | 1 each | K2PtCl4 | KCl | 2.95E−04 |
| 2210 | 2-aminoethyldihydrogenphosphate + L-serine | 1 each | K2PtCl4 | KCl | 2.58E−04 |
| 2211 | tris(2-aminoethyl)amine + L-serine | 1 each | K2PtCl4 | KCl | 9.96E−04 |
| 2212 | propylamine + pyridazine | 1 each | K2PtCl4 | KCl | 1.03E−03 |
| 2213 | 1,2-diaminocyclohexane + pyridazine | 1 each | K2PtCl4 | KCl | 3.06E−03 |
| 2214 | 2,5-dimethylpyrrole + pyridazine | 1 each | K2PtCl4 | KCl | 1.03E−03 |
| 2215 | 3-bromopropylamine-HBr + pyridazine | 1 each | K2PtCl4 | KCl | 8.49E−04 |
| 2216 | 2-chloroethylamine-HCl + pyridazine | 1 each | K2PtCl4 | KCl | 1.29E−03 |
| 2217 | 2-mercaptoethanol + pyridazine | 1 each | K2PtCl4 | KCl | 1.59E−03 |
| 2218 | 2-aminoethyldihydrogenphosphate + pyridazine | 1 each | K2PtCl4 | KCl | 1.59E−03 |
| 2219 | tris(2-aminoethyl)amine + pyridazine | 1 each | K2PtCl4 | KCl | 1.59E−03 |
| 2220 | propylamine + 2-trimethylaminoethylamine | 1 each | K2PtCl4 | KCl | 8.86E−04 |
| 2221 | 1,2-diaminocyclohexane + 2-dimethylaminoethylamine | 1 each | K2PtCl4 | KCl | 1.29E−03 |
| 2222 | 2,5-dimethylpyrrole + 2-dimethylaminoethylamine | 1 each | K2PtCl4 | KCl | 1.18E−03 |
| 2223 | 3-bromopropylamine-HBr + 2-dimethylaminoethylamine | 1 each | K2PtCl4 | KCl | 2.63E−03 |
| 2224 | 2-chloroethylamine-HCl + 2-dimethylaminoethylamine | 1 each | K2PtCl4 | KCl | 2.56E−03 |
| 2225 | 2-mercaptoethanol + 2-dimethylaminoethylamine | 1 each | K2PtCl4 | KCl | 6.31E−04 |
| 2226 | 2-aminoethyldihydrogenphosphate + 2-dimethylaminoethylamine | 1 each | K2PtCl4 | KCl | 2.00E−03 |
| 2227 | tris(2-aminoethyl)amine + 2-dimethylaminoethylamine | 1 each | K2PtCl4 | KCl | 8.06E−04 |
| 2228 | propylamine + pyrazine | 1 each | K2PtCl4 | KCl | 2.10E−04 |
| 2229 | 1,2-diaminocyclohexane + pyrazine | 1 each | K2PtCl4 | KCl | 4.56E−04 |
| 2230 | 2,5-dimethylpyrrole + pyrazine | 1 each | K2PtCl4 | KCl | 1.40E−04 |
| 2231 | 3-bromopropylamino-HBr + pyrazine | 1 each | K2PtCl4 | KCl | 3.15E−04 |
| 2232 | 2-chloroethylamine-HCl + pyrazine | 1 each | K2PtCl4 | KCl | 3.15E−04 |
| 2233 | 2-mercaptoethanol + pyrazine | 1 each | K2PtCl4 | KCl | 3.15E−04 |
| 2234 | 2-aminoethyldihydrogenphosphate + pyrazine | 1 each | K2PtCl4 | KCl | 3.85E−04 |
| 2235 | tris(2-aminoethyl)amine + pyrazine | 1 each | K2PtCl4 | KCl | 8.41E−04 |
| 2236 | propylamine + 2-hydroxy-5-nitropyridine | 1 each | K2PtCl4 | KCl | 3.85E−04 |
| 2237 | 1,2-diaminocyclohexane + 2-hydroxy-5-nitropyridine | 1 each | K2PtCl4 | KCl | 1.26E−03 |
| 2238 | 2,5-dimethylpyrrole + 2-hydroxy-5-nitropyridine | 1 each | K2PtCl4 | KCl | 6.66E−04 |
| 2239 | 3-bromopropylamine-HBr + 2-hydroxy-5-nitropyridine | 1 each | K2PtCl4 | KCl | 4.93E−04 |
| 2240 | 2-chloroethylamine-HCl + 2-hydroxy-5-nitropyridine | 1 each | K2PtCl4 | KCl | 5.26E−04 |
| 2241 | 2-mercaptoethanol + 2-hydroxy-5-nitropyridine | 1 each | K2PtCl4 | KCl | 4.56E−04 |
| 2242 | 2-aminoethyldihydrogenphosphate + 2-hydroxy-5-nitropyridine | 1 each | K2PtCl4 | KCl | 4.56E−04 |
| 2243 | tris(2-aminoethyl)amine + 2-hydroxy-5-nitropyridine | 1 each | K2PtCl4 | KCl | 7.71E−04 |
| 2244 | propylamine + 1,3-diaminopropane | 1 each | K2PtCl4 | KCl | 7.01E−04 |
| 2245 | 1,2-diaminocyclohexane + 1,3-diaminopropane | 1 each | K2PtCl4 | KCl | 1.44E−03 |
| 2246 | 2,5-dimethylpyrrole + 1,3-diaminopropane | 1 each | K2PtCl4 | KCl | 7.71E−04 |
| 2247 | 3-bromopropylamine-HBr + 1,3-diaminopropane | 1 each | K2PtCl4 | KCl | 1.79E−03 |
| 2248 | 2-chloroethylamine-HCl + 1,3-diaminopropane | 1 each | KtPtCl4 | KCl | 1.89E−03 |
| 2249 | 2-mercaptoethanol + 1,3-diaminopropane | 1 each | K2PtCl4 | KCl | 6.66E−04 |
| 2250 | 2-aminoethyldihydrogenphosphate + 1,3-diaminopropane | 1 each | K2PtCl4 | KCl | 8.76E−04 |
| 2251 | tris(2-aminoethyl)amine + 1,3-diaminopropane | 1 each | K2PtCl4 | KCl | 1.19E−03 |
| 2252 | propylamine + 4-picoline | 1 each | K2PtCl4 | KCl | 1.40E−03 |
| 2253 | 1,2-diaminocyclohexane + 4-picoline | 1 each | K2PtCl4 | KCl | 2.98E−03 |
| 2254 | 2,5-dimethylpyrrole + 4-picoline | 1 each | K2PtCl4 | KCl | 2.00E−03 |
| 2255 | 3-bromopropylamino-HBr + 4-picoline | 1 each | K2PtCl4 | KCl | 1.54E−03 |
| 2256 | 2-chloroethylamine-HCl + 4-picoline | 1 each | K2PtCl4 | KCl | 1.93E−03 |
| 2257 | 2-mercaptoethanol + 4-picoline | 1 each | K2PtCl4 | KCl | 7.71E−04 |
| 2258 | 2-aminoethyldihydrogenphosphate + 4-picoline | 1 each | K2PtCl4 | KCl | 2.03E−03 |
| 2259 | tris(2-aminoethyl)amine + 4-picoline | 1 each | K2PtCl4 | KCl | 1.33E−03 |
| 2260 | propylamine + 2,4-dimethylpyrrole | 1 each | K2PtCl4 | KCl | 8.76E−04 |
| 2261 | 1,2-diaminocyclohexane + 2,4-dimethylpyrrole | 1 each | K2PtCl4 | KCl | 2.00E−03 |
| 2262 | 2,5-dimethylpyrrole + 2,4-dimethylpyrrole | 1 each | K2PtCl4 | KCl | 1.02E−03 |
| 2263 | 3-bromopropylamine-HBr + 2,4-dimethylpyrrole | 1 each | K2PtCl4 | KCl | 9.46E−04 |
| 2264 | 2-chloroethylamine-HCl + 2,4-dimethylpyrrole | 1 each | K2PtCl4 | KCl | 9.81E−04 |
| 2265 | 2-mercaptoethanol + 2,4-dimethylpyrrole | 1 each | K2PtCl4 | KCl | 9.81E−04 |
| 2266 | 2-aminoethyldihydrogenphosphate + 2,4-dimethylpyrrole | 1 each | K2PtCl4 | KCl | 9.46E−04 |
| 2267 | tris(2-aminoethyl)amine + 2,4-dimethylpyrrole | 1 each | K2PtCl4 | KCl | 1.30E−03 |
| 2268 | propylamine + bis-mercaptomethylsulfide | 1 each | K2PtCl4 | oxalate | 1.99E−03 |

TABLE 1-continued

| No. | Ligand(s) | Equiv. | Precursor | Leaving Group | Yld, g atm Pt |
|---|---|---|---|---|---|
| 2269 | 3-amino-1-propanol + bis-mercaptomethylsulfide | 1 each | K2PtCl4 | oxalate | 5.04E−04 |
| 2270 | cyclopentylamine + bis-mercaptomethylsulfide | 1 each | K2PtCl4 | oxalate | 6.15E−04 |
| 2271 | 2-dimethylaminoethylamine + bis-mercaptomethylsulfide | 1 each | K2PtCl4 | oxalate | 8.39E−04 |
| 2272 | 3-chloroethylamine-HCl + bis-mercaptomethylsulfide | 1 each | K2PtCl4 | oxalate | 5.04E−04 |
| 2273 | pyrazine + bis-mercaptomethylsulfide | 1 each | K2PtCl4 | oxalate | 5.60E−04 |
| 2274 | 2-aminoethyldihydrogenphosphate + bis-mercaptomethylsulfide | 1 each | K2PtCl4 | oxalate | 5.32E−04 |
| 2275 | pyrrolidine + bis-mercaptomethylsulfide | 1 each | K2PtCl4 | oxalate | 5.32E−04 |
| 2276 | propylamine + indoline | 1 each | K2PtCl4 | oxalate | 6.15E−04 |
| 2277 | 3-amino-1-propanol + indoline | 1 each | K2PtCl4 | oxalate | 6.99E−04 |
| 2278 | cyclopentylamine + indoline | 1 each | K2PtCl4 | oxalate | 6.71E−04 |
| 2279 | 2-dimethylaminoethylamine + indoline | 1 each | K2PtCl4 | oxalate | 1.26E−03 |
| 2280 | 3-chloroethylamine-HCl + indoline | 1 each | K2PtCl4 | oxalate | 9.79E−04 |
| 2281 | pyrazine + indoline | 1 each | K2PtCl4 | oxalate | 6.71E−04 |
| 2282 | 2-aminoethyldihydrogenphosphate + indoline | 1 each | K2PtCl4 | oxalate | 6.99E−04 |
| 2283 | pyrrolidine + indoline | 1 each | K2PtCl4 | oxalate | 7.83E−04 |
| 2284 | propylamine + acrylamide | 1 each | K2PtCl4 | oxalate | 7.83E−04 |
| 2285 | 3-amino-1-propanol + acrylamide | 1 each | K2PtCl4 | oxalate | 1.62E−03 |
| 2286 | cyclopentylamine + acrylamide | 1 each | K2PtCl4 | oxalate | 9.23E−04 |
| 2287 | 2-dimethylaminoethylamine + acrylamide | 1 each | K2PtCl4 | oxalate | 3.08E−03 |
| 2288 | 3-chloroethylamine-HCl + acrylamide | 1 each | K2PtCl4 | oxalate | 1.18E−03 |
| 2289 | pyrazine + acrylamide | 1 each | K2PtCl4 | oxalate | 7.83E−04 |
| 2290 | 2-aminoethyldihydrogenphosphate + acrylamide | 1 each | K2PtCl4 | oxalate | 1.62E−03 |
| 2291 | pyrrolidine + acrylamide | 1 each | K2PtCl4 | oxalate | 1.23E−03 |
| 2292 | propylamine + 1,2-diaminocyclohexane | 1 each | K2PtCl4 | oxalate | 1.29E−03 |
| 2293 | 3-amino-1-propanol + 1,2-diaminocyclohexane | 1 each | K2PtCl4 | oxalate | 1.90E−03 |
| 2294 | cyclopentylamine + 1,2-diaminocyclohexane | 1 each | K2PtCl4 | oxalate | 1.29E−03 |
| 2295 | 2-dimethylaminoethylamine + 1,2-diaminocyclohexane | 1 each | K2PtCl4 | oxalate | 2.32E−03 |
| 2296 | 3-chloroethylamine-HCl + 1,2-diaminocyclohexane | 1 each | K2PtCl4 | oxalate | 1.40E−03 |
| 2297 | pyrazine + 1,2-diaminocyclohexane | 1 each | K2PtCl4 | oxalate | 1.26E−03 |
| 2298 | 2-aminoethyldihydrogenphosphate + 1,2-diaminocyclohexane | 1 each | K2PtCl4 | oxalate | 2.91E−03 |
| 2299 | pyrrolidine + 1,2-diaminocyclohexane | 1 each | K2PtCl4 | oxalate | 1.65E−03 |
| 2300 | propylamine + L-serine | 1 each | K2PtCl4 | oxalate | 1.06E−03 |
| 2301 | 3-amino-1-propanol + L-serine | 1 each | K2PtCl4 | oxalate | 1.15E−03 |
| 2302 | cyclopentylamine + L-serine | 1 each | K2PtCl4 | oxalate | 2.52E−03 |
| 2303 | 2-dimethylaminoethylamine + L-serine | 1 each | K2PtCl4 | oxalate | 2.91E−03 |
| 2304 | 3-chloroethylamine-HCl + L-serine | 1 each | K2PtCl4 | oxalate | 1.29E−03 |
| 2305 | pyrazine + L-serine | 1 each | K2PtCl4 | oxalate | 1.20E−03 |
| 2306 | 2-aminoethyldihydrogenphosphate + L-serine | 1 each | K2PtCl4 | oxalate | 1.15E−03 |
| 2307 | pyrrolidine + L-serine | 1 each | K2PtCl4 | oxalate | 1.12E−03 |
| 2308 | propylamine + pyridazine | 1 each | K2PtCl4 | oxalate | 1.31E−03 |
| 2309 | 3-amino-1-propanol + pyridazine | 1 each | K2PtCl4 | oxalate | 2.10E−03 |
| 2310 | cyclopentylamine + pyridazine | 1 each | K2PtCl4 | oxalate | 1.39E−03 |
| 2311 | 2-dimethylaminoethylamine + pyridazine | 1 each | K2PtCl4 | oxalate | 3.22E−03 |
| 2312 | 3-chloroethylamine-HCl + pyridazine | 1 each | K2PtCl4 | oxalate | 3.08E−03 |
| 2313 | pyrazine + pyridazine | 1 each | K2PtCl4 | oxalate | 1.29E−03 |
| 2314 | 2-aminoethyldihydrogenphosphate + pyridazine | 1 each | K2PtCl4 | oxalate | 2.34E−02 |
| 2315 | pyrrolidine + pyridazine | 1 each | K2PtCl4 | oxalate | 1.46E−03 |
| 2316 | propylamine + 3-bromopropylamine-HBr | 1 each | K2PtCl4 | oxalate | 4.76E−04 |
| 2317 | 3-amino-1-propanol + 3-bromopropylamine-HBr | 1 each | K2PtCl4 | oxalate | 8.50E−04 |
| 2318 | cyclopentylamine + 3-bromopropylamine-HBr | 1 each | K2PtCl4 | oxalate | 1.02E−03 |
| 2319 | 2-dimethylaminoethylamine + 3-bromopropylamine-HBr | 1 each | K2PtCl4 | oxalate | 2.11E−03 |
| 2320 | 3-chloroethylamine-HCl + 3-bromopropylamine-HBr | 1 each | K2PtCl4 | oxalate | 1.29E−03 |
| 2321 | pyrazine + 3-bromopropylamine-HBr | 1 each | K2PtCl4 | oxalate | 5.78E−04 |
| 2322 | 2-aminoethyldihydrogenphosphate + 3-bromopropylamine-HBr | 1 each | K2PtCl4 | oxalate | 6.12E−04 |
| 2323 | pyrrolidine + 3-bromopropylamine-HBr | 1 each | K2PtCl4 | oxalate | 9.52E−04 |
| 2324 | propylamine + 2-mercaptoethanol | 1 each | K2PtCl4 | oxalate | 6.80E−04 |
| 2325 | 3-amino-1-propanol + 2-mercaptoethanol | 1 each | K2PtCl4 | oxalate | 7.82E−04 |
| 2326 | cyclopentylamine + 2-mercaptoethanol | 1 each | K2PtCl4 | oxalate | 7.48E−04 |
| 2327 | 2-dimethylaminoethylamine + 2-mercaptoethanol | 1 each | K2PtCl4 | oxalate | 1.02E−03 |
| 2328 | 3-chloroethylamine-HCl + 2-mercaptoethanol | 1 each | K2PtCl4 | oxalate | 1.53E−03 |
| 2329 | pyrazine + 2-mercaptoethanol | 1 each | K2PtCl4 | oxalate | 9.52E−04 |
| 2330 | 2-aminoethyldihydrogenphosphate + 2-mercaptoethanol | 1 each | K2PtCl4 | oxalate | 8.50E−04 |
| 2331 | pyrrolidine + 2-mercaptoethanol | 1 each | K2PtCl4 | oxalate | 8.16E−04 |

TABLE 1-continued

| No. | Ligand(s) | Equiv. | Precursor | Leaving Group | Yld, g atm Pt |
|---|---|---|---|---|---|
| 2332 | propylamine + 2-hydroxy-5-nitropyridine | 1 each | K2PtCl4 | oxalate | 1.05E−03 |
| 2333 | 3-amino-1-propanol + 2-hydroxy-5-nitropyridine | 1 each | K2PtCl4 | oxalate | 9.86E−04 |
| 2334 | cyclopentylamine + 2-hydroxy-5-nitropyridine | 1 each | K2PtCl4 | oxalate | 9.86E−04 |
| 2335 | 2-dimethylaminoethylamine + 2-hydroxy-5-nitropyridine | 1 each | K2PtCl4 | oxalate | 2.07E−03 |
| 2336 | 3-chloroethylamine-HCl + 2-hydroxy-5-nitropyridine | 1 each | K2PtCl4 | oxalate | 1.09E−03 |
| 2337 | pyrazine + 2-hydroxy-5-nitropyridine | 1 each | K2PtCl4 | oxalate | 1.05E−03 |
| 2338 | 2-aminoethyldihydrogenphosphate + 2-hydroxy 5-nitropyridine | 1 each | K2PtCl4 | oxalate | 1.19E−03 |
| 2339 | pyrrolidine + 2-hydroxy-5-nitropyridine | 1 each | K2PtCl4 | oxalate | 1.12E−03 |
| 2340 | propylamine + 1,3-diaminopropane | 1 each | K2PtCl4 | oxalate | 1.16E−03 |
| 2341 | 3-amino-1-propanol + 1,3-diaminopropane | 1 each | K2PtCl4 | oxalate | 1.19E−03 |
| 2342 | cyclopentylamine + 1,3-diaminopropane | 1 each | K2PtCl4 | oxalate | 1.29E−03 |
| 2343 | 2-dimethylaminoethylamine + 1,3-diaminopropane | 1 each | K2PtCl4 | oxalate | 1.46E−03 |
| 2344 | 3-chloroethylamine-HCl + 1,3-diaminopropane | 1 each | K2PtCl4 | oxalate | 2.34E−03 |
| 2345 | pyrazine + 1,3-diaminopropane | 1 each | K2PtCl4 | oxalate | 1.29E−03 |
| 2346 | 2-aminoethyldihydrogenphosphate + 1,3-diaminopropane | 1 each | K2PtCl4 | oxalate | 1.33E−03 |
| 2347 | pyrrolidine + 1,3-diaminopropane | 1 each | K2PtCl4 | oxalate | 1.33E−03 |
| 2348 | propylamine + 4-picoline | 1 each | K2PtCl4 | oxalate | 1.56E−03 |
| 2349 | 3-amino-1-propanol + 4-picoline | 1 each | K2PtCl4 | oxalate | 2.00E−03 |
| 2350 | cyclopentylamine + 4-picoline | 1 each | K2PtCl4 | oxalate | 2.14E−03 |
| 2351 | 2-dimethylaminoethylamine + 4-picoline | 1 each | K2PtCl4 | oxalate | 2.21E−03 |
| 2352 | 3-chloroethylamine-HCl + 4-picoline | 1 each | K2PtCl4 | oxalate | 2.85E−03 |
| 2353 | pyrazine + 4-picoline | 1 each | K2PtCl4 | oxalate | 1.77E−03 |
| 2354 | 2-aminoethyldihydrogenphosphate + 4-picoline | 1 each | K2PtCl4 | oxalate | 2.28E−03 |
| 2355 | pyrrolidine + 4-picoline | 1 each | K2PtCl4 | oxalate | 2.07E−03 |
| 2356 | propylamine + tris(2-aminoethyl)amine | 1 each | K2PtCl4 | oxalate | 2.55E−03 |
| 2357 | 3-amino-1-propanol + tris(2-aminoethyl)amine | 1 each | K2PtCl4 | oxalate | 1.98E−03 |
| 2358 | cyclopentylamine + tris(2-aminoethyl)amine | 1 each | K2PtCl4 | oxalate | 6.86E−04 |
| 2359 | 2-dimethylaminoethylamine + tris(2-aminoethyl)amine | 1 each | K2PtCl4 | oxalate | 9.74E−04 |
| 2360 | 3-chloroethylamine-HCl + tris(2-aminoethyl)amine | 1 each | K2PtCl4 | oxalate | 6.86E−04 |
| 2361 | pyrazine + tris(2-aminoethyl)amine | 1 each | K2PtCl4 | oxalate | 2.89E−04 |
| 2362 | 2-aminoethyldihydrogenphosphate + tris(2-aminoethyl)amine | 1 each | K2PtCl4 | oxalate | 3.25E−04 |
| 2363 | pyrrolidine + tris(2-aminoethyl)amine | 1 each | K2PtCl4 | oxalate | 4.69E−04 |
| 2364 | isopropylaimine + 4-picoline | 1 each | K2PtCl4 | KCl | 8.22E−01 |
| 2365 | L-serine + 4-picoline | 1 each | K2PtCl4 | KCl | 9.72E−01 |
| 2366 | pyridazine + 4-picoline | 1 each | K2PtCl4 | KCl | 1.37E+00 |
| 2367 | 2-chloroethylamine-HCl + 4-picoline | 1 each | K2PtCl4 | KCl | 1.29E+00 |
| 2368 | pyrrolidine + 4-picoline | 1 each | K2PtCl4 | KCl | 7.22E−01 |
| 2369 | pyrazine + 4-picoline | 1 each | K2PtCl4 | KCl | 5.72E−01 |
| 2370 | acrylamide + 4-picoline | 1 each | K2PtCl4 | KCl | 9.32E−01 |
| 2371 | propylamine + 4-picoline | 1 each | K2PtCl4 | KCl | 9.20E−01 |
| 2372 | isopropylamine + 3-bromopropylamine-HBr | 1 each | K2PtCl4 | KCl | 7.31E−02 |
| 2373 | L-serine + 3-bromopropylamine-HBr | 1 each | K2PtCl4 | KCl | 9.47E−02 |
| 2374 | pyridazine + 3-bromopropylamine-HBr | 1 each | K2PtCl4 | KCl | 8.31E−01 |
| 2375 | 2-chloroethylamine-HCl + 3-bromopropylamine-HBr | 1 each | K2PtCl4 | KCl | 5.45E−01 |
| 2376 | pyrrolidine + 3-bromopropylamine-HBr | 1 each | K2PtCl4 | KCl | 4.59E−01 |
| 2377 | pyrazine + 3-bromopropylamine-HBr | 1 each | K2PtCl4 | KCl | 3.36E−01 |
| 2378 | acrylamide + 3-bromopropylamine-HBr | 1 each | K2PtCl4 | KCl | 3.73E−01 |
| 2379 | propylamine + 3-bromopropylamino-HBr | 1 each | K2PtCl4 | KCl | 1.16E−01 |
| 2380 | isopropylamine + 2-hydroxy-5-nitropyridine | 1 each | K2PtCl4 | KCl | 0.00E+00 |
| 2381 | L-serine + 2-hydroxy-5-nitropyridine | 1 each | K2PtCl4 | KCl | 7.82E−02 |
| 2382 | pyridazine + 2-hydroxy-5-nitropyridine | 1 each | K2PtCl4 | KCl | 1.15E+00 |
| 2383 | 2-chloroethylamino-HCl + 2-hydroxy-5-nitropyridine | 1 each | K2PtCl4 | KCl | 1.99E−01 |
| 2384 | pyrrolidine + 2-hydroxy-5-nitropyridine | 1 each | K2PtCl4 | KCl | 0.00E+00 |
| 2385 | pyrazine + 2-hydroxy-5-nitropyridine | 1 each | K2PtCl4 | KCl | 0.00E+00 |
| 2386 | acrylamide + 2-hydroxy-5-nitropyridine | 1 each | K2PtCl4 | KCl | 2.23E−01 |
| 2387 | propylamine + 2-hydroxy-5-nitropyridine | 1 each | K2PtCl4 | KCl | 0.00E+00 |
| 2388 | isopropylamine + 2-aminoethyldihydrogenphophate | 1 each | K2PtCl4 | KCl | 0.00E+00 |
| 2389 | L-serine + 2-aminoethyldihydrogenphophate | 1 each | K2PtCl4 | KCl | 0.00E+00 |
| 2390 | pyridazine + 2-aminoethyldihydrogenphophate | 1 each | K2PtCl4 | KCl | 1.47E+00 |
| 2391 | 2-chloroethylamine-HCl + 2-aminoethyldihydrogenphophate | 1 each | K2PtCl4 | KCl | 5.12E−01 |
| 2392 | pyrrolidine + 2-aminoethyldihydrogenphophate | 1 each | K2PtCl4 | KCl | 0.00E+00 |
| 2393 | pyrazine + 2-aminoethyldihydrogenphophate | 1 each | K2PtCl4 | KCl | 0.00E+00 |
| 2394 | acrylamide + 2-aminoethyldihydrogenphophate | 1 each | K2PtCl4 | KCl | 1.69E−01 |
| 2395 | propylamine + 2-aminoethyldihydrogenphophate | 1 each | K2PtCl4 | KCl | 0.00E+00 |

TABLE 1-continued

| No. | Ligand(s) | Equiv. | Precursor | Leaving Group | Yld, g atm Pt |
|---|---|---|---|---|---|
| 2396 | isopropylamine + 2-dimethylaminoethylamine | 1 each | K2PtCl4 | KCl | 1.36E−01 |
| 2397 | L-serine + 2-dimethylaminoethylamine | 1 each | K2PtCl4 | KCl | 1.23E+00 |
| 2398 | pyridazine + 2-dimethylaminoethylamine | 1 each | K2PtCl4 | KCl | 1.39E+00 |
| 2399 | 2-chloroethylamine-HCl + 2-dimethylaminoethylamine | 1 each | K2PtCl4 | KCl | 1.91E+00 |
| 2400 | pyrrolidine + 2-dimethylaminoethylamine | 1 each | K2PtCl4 | KCl | 1.41E+00 |
| 2401 | pyrazine +2-dimethylaminoethylamine | 1 each | K2PtCl4 | KCl | 2.01E−01 |
| 2402 | acrylamide + 2-dimethylaminoethylamine | 1 each | K2PtCl4 | KCl | 1.58E+00 |
| 2403 | propylamine + 2-dimethylaminoethylamine | 1 each | K2PtCl4 | KCl | 1.23E+00 |
| 2404 | isopropylamine + 2-mercaptoethanol | 1 each | K2PtCl4 | KCl | 0.00E+00 |
| 2405 | L-serine + 2-mercaptoethanol | 1 each | K2PtCl4 | KCl | 3.86E−01 |
| 2406 | pyridazine + 2-mercaptoethanol | 1 each | K2PtCl4 | KCl | 6.97E−01 |
| 2407 | 2-chloroethylamine-HCl + 2-mercaptoethanol | 1 each | K2PtCl4 | KCl | 0.00E+00 |
| 2408 | pyrrolidine + 2-mercaptoethanol | 1 each | K2PtCl4 | KCl | 0.00E+00 |
| 2409 | pyrazine + 2-mercaptoethanol | 1 each | K2PtCl4 | KCl | 0.00E+00 |
| 2410 | acrylamide + 2-mercaptoethanol | 1 each | K2PtCl4 | KCl | 2.75E−01 |
| 2411 | propylamine + 2-mercaptoethanol | 1 each | K2PtCl4 | KCl | 4.28E−01 |
| 2412 | isopropylamine + indoline | 1 each | K2PtCl4 | KCl | 0.00E+00 |
| 2413 | L-serine + indoline | 1 each | K2PtCl4 | KCl | 4.15E−01 |
| 2414 | pyridazine + indoline | 1 each | K2PtCl4 | KCl | 1.73E+00 |
| 2415 | 2-chloroethylamine-HCl + indoline | 1 each | K2PtCl4 | KCl | 3.06E−01 |
| 2416 | pyrrolidine + indoline | 1 each | K2PtCl4 | KCl | 0.00E+00 |
| 2417 | pyrazine + indoline | 1 each | K2PtCl4 | KCl | 0.00E+00 |
| 2418 | acrylamide + indoline | 1 each | K2PtCl4 | KCl | 2.25E−01 |
| 2419 | propylamine + indoline | 1 each | K2PtCl4 | KCl | 0.00E+00 |
| 2420 | isopropylamine + cyclopentylamine | 1 each | K2PtCl4 | KCl | 2.51E−02 |
| 2421 | L-serine + cyclopentylamine | 1 each | K2PtCl4 | KCl | 1.55E−02 |
| 2422 | pyridazine + cyclopentylamine | 1 each | K2PtCl4 | KCl | 7.86E−01 |
| 2423 | 2-chloroethylamine-HCl + cyclopentylamine | 1 each | K2PtCl4 | KCl | 3.84E−01 |
| 2424 | pyrrolidine + cyclopentylamine | 1 each | K2PtCl4 | KCl | 0.00E+00 |
| 2425 | pyrazine + cyclopentylamine | 1 each | K2PtCl4 | KCl | 0.00E+00 |
| 2426 | acrylamide + cyclopentylamine | 1 each | K2PtCl4 | KCl | 2.94E−01 |
| 2427 | propylamine + cyclopentylamine | 1 each | K2PtCl4 | KCl | 0.00E+00 |
| 2428 | isopropylamine + tris(2-aminoethyl)amine | 1 each | K2PtCl4 | KCl | 2.17E−01 |
| 2429 | L-serine + tris(2-aminoethyl)amine | 1 each | K2PtCl4 | KCl | 0.00E+00 |
| 2430 | pyridazine + tris(2-aminoethyl)amine | 1 each | K2PtCl4 | KCl | 5.03E−01 |
| 2431 | 2-chloroethylamine-HCl + tris(2-aminoethyl)amine | 1 each | K2PtCl4 | KCl | 6.63E−01 |
| 2432 | pyrrolidine + tris(2-aminoethyl)amine | 1 each | K2PtCl4 | KCl | 0.00E+00 |
| 2433 | pyrazine + tris(2-aminoethyl)amine | 1 each | K2PtCl4 | KCl | 0.00E+00 |
| 2434 | acrylamide + tris(2-aminoethyl)amine | 1 each | K2PtCl4 | KCl | 6.66E−02 |
| 2435 | propylamine + tris(2-aminoethyl)amine | 1 each | K2PtCl4 | KCl | 0.00E+00 |
| 2436 | isopropylamine + 1,3-diaminopropane | 1 each | K2PtCl4 | KCl | 0.00E+00 |
| 2437 | L-serine + 1,3-diaminopropane | 1 each | K2PtCl4 | KCl | 1.05E−01 |
| 2438 | pyridazine + 1,3-diaminopropane | 1 each | K2PtCl4 | KCl | 6.88E−01 |
| 2439 | 2-chloroethylamine-HCl + 1,3-diaminopropane | 1 each | K2PtCl4 | KCl | 1.36E+00 |
| 2440 | pyrrolidine + 1,3-diaminopropane | 1 each | K2PtCl4 | KCl | 1.53E−01 |
| 2441 | pyrazine + 1,3-diaminopropane | 1 each | K2PtCl4 | KCl | 1.04E−02 |
| 2442 | acrylamide + 1,3-diaminopropane | 1 each | K2PtCl4 | KCl | 1.97E−02 |
| 2443 | propylamine + 1,3-diaminopropane | 1 each | K2PtCl4 | KCl | 1.04E−01 |
| 2444 | isopropylamine + 3-amino-1-propanol | 1 each | K2PtCl4 | KCl | 3.15E−02 |
| 2445 | L-serine + 3-amino-1-propanol | 1 each | K2PtCl4 | KCl | 5.69E−02 |
| 2446 | pyridazine + 3-amino-1-propanol | 1 each | K2PtCl4 | KCl | 6.24E−01 |
| 2447 | 2-chloroethylamine-HCl + 3-amino-1-propanol | 1 each | K2PtCl4 | KCl | 4.00E−01 |
| 2448 | pyrrolidine + 3-amino-1-propanol | 1 each | K2PtCl4 | KCl | 2.58E−02 |
| 2449 | pyrazine + 3-amino-1-propanol | 1 each | K2PtCl4 | KCl | 0.00E+00 |
| 2450 | acrylamide + 3-amino-1-propanol | 1 each | K2PtCl4 | KCl | 5.67E−02 |
| 2451 | propylamine + 3-amino-1-propanol | 1 each | K2PtCl4 | KCl | 0.00E+00 |
| 2452 | isopropylamine + 1,2-diaminocyclohexane | 1 each | K2PtCl4 | KCl | 2.44E+00 |
| 2453 | L-serine + 1,2-diaminocyclohexane | 1 each | K2PtCl4 | KCl | 2.03E+00 |
| 2454 | pyridazine + 1,2-diaminocyclohexane | 1 each | K2PtCl4 | KCl | 1.58E+00 |
| 2455 | 2-chloroethylamine-HCl + 1,2-diaminocyclohexane | 1 each | K2PtCl4 | KCl | 1.22E+00 |
| 2456 | pyrrolidine + 1,2-diaminocyclohexane | 1 each | K2PtCl4 | KCl | 3.23E−01 |
| 2457 | pyrazine + 1,2-diaminocyclohexane | 1 each | K2PtCl4 | KCl | 7.81E−02 |
| 2458 | acrylamide + 1,2-diaminocyclohexane | 1 each | K2PtCl4 | KCl | 2.01E−01 |
| 2459 | propylamine + 1,2-diaminocyclohexane | 1 each | K2PtCl4 | KCl | 0.00E+00 |
| 2460 | isopropylamine | 2 | K2PtCl4 | KCl | 1.31E+00 |
| 2461 | isopropylamine | 2 | K2PtCl4 | acetate | 0.00E+00 |
| 2462 | isopropylamine | 2 | K2PtCl4 | propionate | 6.42E−02 |
| 2463 | isopropylamine | 2 | K2PtCl4 | butyrate | 3.72E−03 |
| 2464 | isopropylamine | 2 | KtPtCl4 | isobutyrate | 0.00E+00 |
| 2465 | isopropylamine | 2 | K2PtCl4 | oxalate | 6.42E−02 |
| 2466 | isopropylamine | 2 | K2PtCl4 | malonate | 0.00E+00 |
| 2467 | isopropylamine | 2 | K2PtCl4 | succinate | 0.00E+00 |
| 2468 | isopropylamine + 2-methyl-1-pyrroline | 1 each | K2PtCl4 | KCl | 2.89E−01 |
| 2469 | isopropylamine + 2-methyl-1-pyrroline | 1 each | K2PtCl4 | acetate | 1.24E−01 |

TABLE 1-continued

| No. | Ligand(s) | Equiv. | Precursor | Leaving Group | Yld, g atm Pt |
|---|---|---|---|---|---|
| 2470 | isopropylamine + 2-methyl-1-pyrroline | 1 each | K2PtCl4 | propionate | 9.73E−02 |
| 2471 | isopropylamine + 2-methyl-1-pyrroline | 1 each | K2PtCl4 | butyrate | 1.29E−01 |
| 2472 | isopropylamine + 2-methyl-1-pyrroline | 1 each | K2PtCl4 | isobutyrate | 1.89E−01 |
| 2473 | isopropylamine + 2-methyl-1-pyrroline | 1 each | K2PtCl4 | oxalate | 2.49E−01 |
| 2474 | isopropylamine + 2-methyl-1-pyrroline | 1 each | K2PtCl4 | malonate | 5.67E−01 |
| 2475 | isopropylamine + 2-methyl-1-pyrroline | 1 each | K2PtCl4 | succinate | 6.91E−03 |
| 2476 | isopropylamine + 2-methylimidazole | 1 each | K2PtCl4 | KCl | 9.24E−02 |
| 2477 | isopropylamine + 2-methylimidazole | 1 each | K2PtCl4 | acetate | 0.00E+00 |
| 2478 | isopropylamine + 2-methylimidazole | 1 each | K2PtCl4 | propionate | 1.87E−02 |
| 2479 | isopropylamine + 2-methylimidazole | 1 each | KtPtCl4 | butyrate | 2.70E−02 |
| 2480 | isopropylamine + 2-methylimidazole | 1 each | K2PtCl4 | isobutyrate | 7.53E−02 |
| 2481 | isopropylamine + 2-methylimidazole | 1 each | K2PtCl4 | oxalate | 1.02E−01 |
| 2482 | isopropylamine + 2-methylimidazole | 1 each | K2PtCl4 | malonate | 7.17E−02 |
| 2483 | isopropylamine + 2-methylimidazole | 1 each | K2PtCl4 | succinate | 6.06E−02 |
| 2484 | isopropylamine + 2,5-dimethyl-3-pyrroline | 1 each | K2PtCl4 | KCl | 1.51E−01 |
| 2485 | isopropylamine + 2,5-dimethyl-3-pyrroline | 1 each | K2PtCl4 | acetate | 3.95E−02 |
| 2486 | isopropylamine + 2,5-dimethyl-3-pyrroline | 1 each | K2PtCl4 | propionate | 2.88E−01 |
| 2487 | isopropylamine + 2,5-dimethyl-3-pyrroline | 1 each | K2PtCl4 | butyrate | 3.33E−01 |
| 2488 | isopropylamine + 2,5-dimethyl-3-pyrroline | 1 each | K2PtCl4 | isobutyrate | 8.39E−02 |
| 2489 | isopropylamine + 2,5-dimethyl-3-pyrroline | 1 each | K2PtCl4 | oxalate | 0.00E+00 |
| 2490 | isopropylamine + 2,5-dimethyl-3-pyrroline | 1 each | K2PtCl4 | malonate | 0.00E+00 |
| 2491 | isopropylamine + 2,5-dimethyl-3-pyrroline | 1 each | K2PtCl4 | suocinate | 0.00E+00 |
| 2492 | isopropylamine + propylamine | 1 each | K2PtCl4 | KCl | 0.00E+00 |
| 2493 | isopropylamine + propylamine | 1 each | K2PtCl4 | acetate | 0.00E+00 |
| 2494 | isopropylamine + propylamine | 1 each | K2PtCl4 | propionate | 5.44E−03 |
| 2495 | isopropylamine + propylamine | 1 each | K2PtCl4 | butyrate | 0.00E+00 |
| 2496 | isopropylamine + propylamine | 1 each | K2PtCl4 | isobutyrate | 0.00E+00 |
| 2497 | isopropylamine + propylamine | 1 each | K2PtCl4 | oxalate | 0.00E+00 |
| 2498 | isopropylamine + propylamine | 1 each | K2PtCl4 | malonate | 0.00E+00 |
| 2499 | isopropylamine + propylamine | 1 each | K2PtCl4 | succinate | 1.85E−03 |
| 2500 | isopropylamine + 4-picoline | 1 each | K2PtCl4 | KCl | 8.62E−03 |
| 2501 | isopropylamine + 4-picoline | 1 each | K2PtCl4 | acetate | 1.56E−01 |
| 2502 | isopropylamine + 4-picoline | 1 each | K2PtCl4 | propionate | 2.78E−01 |
| 2303 | isopropylamine + 4-picoline | 1 each | KtPtCl4 | butyrate | 3.59E−01 |
| 2504 | isopropylamine + 4-picoline | 1 each | K2PtCl4 | isobutyate | 3.98E−01 |
| 2505 | isopropylamine + 4-picoline | 1 each | K2PtCl4 | oxalate | 4.29E−01 |
| 2506 | isopropylamine + 4-picoline | 1 each | K2PtCl4 | malonate | 7.32E−01 |
| 2507 | isopropylamine + 4-picoline | 1 each | K2PtCl4 | succinate | 1.37E−01 |
| 2508 | isopropylamine + 3-amino-1-propanol | 1 each | K2PtCl4 | KCl | 1.40E−01 |
| 2509 | isopropylamine + 3-amino-1-propanol | 1 each | K2PtCl4 | acetate | 6.13E−02 |
| 2510 | isopropylamine + 3-amino-1-propanol | 1 each | K2PtCl4 | propionate | 8.74E−02 |
| 2511 | isopropylamine + 3-amino-1-propanol | 1 each | K2PtCl4 | butyrate | 8.89E−02 |
| 2512 | isopropylamine + 3-amino-1-propanol | 1 each | K2PtCl4 | isobutyrate | 1.33E−01 |
| 2513 | isopropylamine + 3-amino-1-propanol | 1 each | K2PtCl4 | oxalate | 7.90E−02 |
| 2514 | isopropylamine + 3-amino-1-propanol | 1 each | K2PtCl4 | malonate | 0.00E+00 |
| 2515 | isopropylamine + 3-amino-1-propanol | 1 each | K2PtCl4 | succinate | 0.00E+00 |
| 2516 | isopropylamine + pyridazine | 1 each | K2PtCl4 | KCl | 6.66E−01 |
| 2517 | isopropylamine + pyridazine | 1 each | K2PtCl4 | acetate | 7.00E−01 |
| 2518 | isopropylamine + pyridazine | 1 each | K2PtCl4 | propionate | 5.27E−01 |
| 2519 | isopropylamine + pyridazine | 1 each | K2PtCl4 | butyrate | 2.91E−01 |
| 2520 | isopropylamine + pyridazine | 1 each | K2PtCl4 | isobutyrate | 0.00E+00 |
| 2521 | isopropylamine + pyridazine | 1 each | K2PtCl4 | oxalate | 0.00E+00 |
| 2522 | isopropylamine + pyridazine | 1 each | K2PtCl4 | malonate | 0.00E+00 |
| 2523 | isopropylamine + pyridazine | 1 each | K2PtCl4 | succinate | 0.00E+00 |
| 2524 | isopropylamine + pyrrolidine | 1 each | K2PtCl4 | KCl | 0.00E+00 |
| 2525 | isopropylamine + pyrrolidine | 1 each | K2PtCl4 | acetate | 9.89E−02 |
| 2526 | isopropylamine + pyrrolidine | 1 each | K2PtCl4 | propionate | 0.00E+00 |
| 2527 | isopropylamine + pyrrolidine | 1 each | K2PtCl4 | butyrate | 3.46E−02 |
| 2528 | isopropylamine + pyrrolidine | 1 each | K2PtCl4 | isobutyrate | 9.12E−02 |
| 2529 | isopropylamine + pyrrolidine | 1 each | K2PtCl4 | oxalate | 6.75E−03 |
| 2530 | isopropylamine + pyrrolidine | 1 each | K2PtCl4 | malonate | 5.21E−02 |
| 2531 | isopropylamine + pyrrolidine | 1 each | K2PtCl4 | succinate | 0.00E+00 |
| 2532 | isopropylamine + pyrazine | 1 each | K2PtCl4 | KCl | 0.00E+00 |
| 2533 | isopropylamine + pyrazine | 1 each | K2PtCl4 | acetate | 0.00E+00 |
| 2534 | isopropylamine + pyrazine | 1 each | K2PtCl4 | propionate | 0.00E+00 |
| 2535 | isopropylamine + pyrazine | 1 each | K2PtCl4 | butyrate | 0.00E+00 |
| 2536 | isopropylamine + pyrazine | 1 each | K2PtCl4 | isobutyrate | 2.21E−02 |
| 2537 | isopropylamine + pyrazine | 1 each | K2PtCl4 | oxalate | 0.00E+00 |
| 2538 | isopropylamine + pyrazine | 1 each | K2PtCl4 | malonate | 0.00E+00 |
| 2539 | isopropylamine + pyrazine | 1 each | K2PtCl4 | succinate | 0.00E+00 |
| 2540 | isopropylamine + cyclopentylamine | 1 each | K2PtCl4 | KCl | 1.29E−01 |
| 2541 | isopropylamine + cyclopentylamine | 1 each | K2PtCl4 | acetate | 3.07E−02 |
| 2542 | isopropylamine + cyclopentylamine | 1 each | K2PtCl4 | propionate | 1.07E−01 |
| 2543 | isopropylamine + cyclopentylamine | 1 each | K2PtCl4 | butyrate | 0.00E+00 |
| 2544 | isopropylamine + cyclopentylamine | 1 each | K2PtCl4 | isobutyrate | 2.09E−01 |
| 2545 | isopropylamine + cyclopentylamine | 1 each | K2PtCl4 | oxalate | 1.65E+00 |
| 2546 | isopropylamine + cyclopentylamine | 1 each | K2PtCl4 | malonate | 6.81E−01 |

TABLE 1-continued

| No. | Ligand(s) | Equiv. | Precursor | Leaving Group | Yld, g atm Pt |
|---|---|---|---|---|---|
| 2547 | isopropylamine + cyclopentylamine | 1 each | K2PtCl4 | succinate | 2.73E−01 |
| 2548 | isopropylamine + L-serine | 1 each | K2PtCl4 | KCl | 0.00E+00 |
| 2549 | isopropylamine + L-serine | 1 each | K2PtCl4 | acetate | 0.00E+00 |
| 2550 | isopropylamine + L-serine | 1 each | K2PtCl4 | propionate | 0.00E+00 |
| 2551 | isopropylamine + L-serine | 1 each | K2PtCl4 | butyrate | 0.00E+00 |
| 2552 | isopropylamine + L-serine | 1 each | K2PtCl4 | isobutyrate | 0.00E+00 |
| 2553 | isopropylamine + L-serine | 1 each | K2PtCl4 | oxalate | 0.00E+00 |
| 2554 | isopropylamine + L-serine | 1 each | K2PtCl4 | malonate | 0.00E+00 |
| 2555 | isopropylamine + L-serine | 1 each | K2PtCl4 | succinate | 0.00E+00 |
| 2556 | thioacetamide + isopropylamine | 1 each | K2PtCl4 | KCl | 2.44E−03 |
| 2557 | thioacetamide + isopropylamine | 1 each | K2PtCl4 | acetate | 3.64E−03 |
| 2558 | thioacetamide + isopropylamine | 1 each | K2PtCl4 | propionate | 0.00E+00 |
| 2559 | thioacetamide + isopropylamine | 1 each | K2PtCl4 | butyrate | 2.90E−04 |
| 2560 | thioacetamide + isopropylamine | 1 each | K2PtCl4 | isobutyrte | 2.66E−04 |
| 2561 | thioacetamide + isopropylamine | 1 each | K2PtCl4 | oxalate | 2.34E−04 |
| 2562 | thioacetamide + isopropylamine | 1 each | K2PtCl4 | malonate | 0.00E+00 |
| 2563 | thioacetamide + isopropylamine | 1 each | K2PtCl4 | succinate | 5.07E−04 |
| 2564 | thioacetamide + 2-methyl-1-pyrroline | 1 each | K2PtCl4 | KCl | 4.40E−04 |
| 2565 | thioacetamide + 2-methyl-1-pyrroline | 1 each | K2PtCl4 | acetate | 4.67E−04 |
| 2566 | thioacetamide + 2-methyl-1-pyrroline | 1 each | K2PtCl4 | propionate | 5.42E−04 |
| 2567 | thioacetamide + 2-methyl-1-pyrroline | 1 each | K2PtCl4 | butyrate | 7.33E−04 |
| 2568 | thioacetamidc + 2-methyl-1-pyrroline | 1 each | K2PtCl4 | isobutyrate | 5.77E−04 |
| 2569 | thioacetamide + 2-methyl-1-pyrroline | 1 each | K2PtCl4 | oxalate | 9.48E−04 |
| 2570 | thioacetamide + 2-methyl-1-pyrroline | 1 each | K2PtCl4 | malonate | 1.19E−03 |
| 2571 | thioacetamide + 2-methyl-1-pyrroline | 1 each | K2PtCl4 | succinate | 4.83E−04 |
| 2572 | thioacetamide + 2-methylimidazole | 1 each | K2PtCl4 | KCl | 1.34E−04 |
| 2573 | thioacetamide + 2-methylimidazole | 1 each | K2PtCl4 | acetate | 6.08E−04 |
| 2574 | thioacetamide + 2-methylimidazole | 1 each | K2PtCl4 | propionate | 5.42E−04 |
| 2575 | thioacetamide + 2-methylimidazole | 1 each | K2PtCl4 | butyrate | 3.47E−04 |
| 2576 | thioacetamide + 2-methylimidazole | 1 each | K2PtCl4 | isobutyrate | 3.56E−04 |
| 2577 | thioacetamide + 2-methylimidazole | 1 each | K2PtCl4 | oxalate | 8.54E−04 |
| 2578 | thioacetamide + 2-methylimidazole | 1 each | K2PtCl4 | malonate | 5.82E−04 |
| 2579 | thioacetamide + 2-methylimidazole | 1 each | K2PtCl4 | succinate | 5.80E−04 |
| 2580 | thioacetamide + 2,5-dimethyl-3-pyrroline | 1 each | K2PtCl4 | KCl | 6.65E−04 |
| 2581 | thioacetamide + 2,5-dimethyl-3-pyrroline | 1 each | K2PtCl4 | acetate | 6.40E−04 |
| 2582 | thioacetamide + 2,5-dimethyl-3-pyrroline | 1 each | K2PtCl4 | propionate | 7.51E−04 |
| 2583 | thioacetamide + 2,5-dimethyl-3-pyrroline | 1 each | K2PtCl4 | butyrate | 5.90E−04 |
| 2584 | thioacetamide + 2,5-dimethyl-3-pyrroline | 1 each | K2PtCl4 | isobutyrate | 1.18E−03 |
| 2585 | thioacetamide + 2,5-dimethyl-3-pyrroline | 1 each | K2PtCl4 | oxalate | 6.82E−04 |
| 2586 | thioacetamide + 2,5-dimethyl-3-pyrroline | 1 each | K2PtCl4 | malonate | 5.69E−04 |
| 2587 | thioacetamide + 2,5-dimethyl-3-pyrroline | 1 each | K2PtCl4 | succinate | 7.05E−04 |
| 2588 | thioacetamide + propylamine | 1 each | K2PtCl4 | KCl | 7.75E−04 |
| 2589 | thioacetamide + propylamine | 1 each | K2PtCl4 | acetate | 6.59E−04 |
| 2590 | thioacetamide + propylamine | 1 each | K2PtCl4 | propionate | 9.45E−04 |
| 2591 | thioacetamide + propylamine | 1 each | K2PtCl4 | butyrate | 9.23E−04 |
| 2592 | thioacetamide + propylamine | 1 each | K2PtCl4 | isobutyrate | 1.08E−03 |
| 2593 | thioacetamide + propylamine | 1 each | K2PtCl4 | oxalate | 9.14E−04 |
| 2594 | thioacetamide + propylamine | 1 each | K2PtCl4 | malonate | 1.58E−03 |
| 2595 | thioacetamide + propylamine | 1 each | K2PtCl4 | succinate | 1.10E−03 |
| 2596 | thioacetamide + 4-picoline | 1 each | K2PtCl4 | KCl | 1.09E−03 |
| 2597 | thioacetamide + 4-picoline | 1 each | K2PtCl4 | acetate | 1.43E−03 |
| 2598 | thioacetamide + 4-picoline | 1 each | K2PtCl4 | propionate | 1.53E−03 |
| 2599 | thioacetamide + 4-picoline | 1 each | K2PtCl4 | butyrate | 1.29E−03 |
| 2600 | thioacetamide + 4-picoline | 1 each | K2PtCl4 | isobutyrate | 1.00E−03 |
| 2601 | thioacetamide + 4-picoline | 1 each | K2PtCl4 | oxalate | 8.81E−04 |
| 2602 | thioacetamide + 4-picoline | 1 each | K2PtCl4 | malonate | 1.33E−03 |
| 2603 | thioacetamide + 4-picoline | 1 each | K2PtCl4 | succinate | 9.40E−04 |
| 2604 | thioacetamide + 3-amino-1-propanol | 1 each | K2PtCl4 | KCl | 5.42E−04 |
| 2605 | thioacetamide + 3-amino-1-propanol | 1 each | K2PtCl4 | acetate | 5.14E−04 |
| 2606 | thioacetamide + 3-amino-1-propanol | 1 each | K2PtCl4 | propionate | 4.87E−04 |
| 2607 | thioacetamide + 3-amino-1-propanol | 1 each | K2PtCl4 | butyrate | 6.09E−04 |
| 2608 | thioacetamide + 3-amino-1-propanol | 1 each | K2PtCl4 | isobutyrate | 8.95E−04 |
| 2609 | thioacetamide + 3-amino-1-propanol | 1 each | K2PtCl4 | oxalate | 7.24E−04 |
| 2610 | thioacetamide + 3-amino-1-propanol | 1 each | K2PtCl4 | malonate | 6.65E−04 |
| 2611 | thioacetamide + 3-amino-1-propanol | 1 each | K2PtCl4 | succinate | 4.53E−04 |
| 2612 | thioacetamide + pyridazine | 1 each | K2PtCl4 | KCl | 8.83E−05 |
| 2613 | thioacetamide + pyridazine | 1 each | K2PtCl4 | acetate | 1.71E−04 |
| 2614 | thioacetamide + pyridazine | 1 each | K2PtCl4 | propionate | 2.58E−04 |
| 2615 | thioacetamide + pyridazine | 1 each | K2PtCl4 | butyrate | 3.73E−04 |
| 2616 | thioacetamide + pyridazine | 1 each | K2PtCl4 | isobutyrate | 3.12E−04 |
| 2617 | thioacetamide + pyridazine | 1 each | K2PtCl4 | oxalate | 4.52E−04 |
| 2618 | thioacetamide + pyridazine | 1 each | K2PtCl4 | malonate | 4.63E−04 |
| 2619 | thioacetamide + pyridazine | 1 each | K2PtCl4 | succinate | 2.49E−04 |
| 2620 | thioacetamide + pyrrolidine | 1 each | K2PtCl4 | KCl | 6.92E−04 |
| 2621 | thioacetamide + pyrrolidine | 1 each | K2PtCl4 | acetate | 4.00E−04 |
| 2622 | thioacetamide + pyrrolidine | 1 each | K2PtCl4 | propionate | 1.32E−04 |
| 2623 | thioacetamide + pyrrolidine | 1 each | K2PtCl4 | butyrate | 3.85E−04 |

TABLE 1-continued

| No. | Ligand(s) | Equiv. | Precursor | Leaving Group | Yld, g atm Pt |
|---|---|---|---|---|---|
| 2624 | thioacetamide + pyrrolidine | 1 each | K2PtCl4 | isobutyrate | 3.78E−04 |
| 2625 | thioacetamide + pyrrolidine | 1 each | K2PtCl4 | oxalate | 3.73E−04 |
| 2626 | thioacetamide + pyrrolidine | 1 each | K2PtCl4 | malonate | 5.88E−04 |
| 2627 | thioacetamide + pyrrolidine | 1 each | K2PtCl4 | succinate | 5.30E−04 |
| 2628 | thioacetamide + pyrazine | 1 each | K2PtCl4 | KCl | 2.27E−05 |
| 2629 | thioacetamide + pyrazine | 1 each | K2PtCl4 | acetate | 2.69E−04 |
| 2630 | thioacetamide + pyrazine | 1 each | K2PtCl4 | propionate | 2.17E−04 |
| 2631 | thioacetamide + pyrazine | 1 each | K2PtCl4 | butyrate | 2.47E−04 |
| 2632 | thioacetamide + pyrazine | 1 each | K2PtCl4 | isobutyrate | 2.58E−04 |
| 2633 | thioacetamide + pyrazine | 1 each | K2PtCl4 | oxalate | 0.00E+00 |
| 2634 | thioacetamide + pyrazine | 1 each | K2PtCl4 | malonate | 0.00E+00 |
| 2635 | thioacetamide + pyrazine | 1 each | K2PtCl4 | succinate | 2.70E−04 |
| 2636 | thioacetamide + cyclopentylamine | 1 each | K2PtCl4 | KCl | 5.21E−04 |
| 2637 | thioacetamide + cyclopentylamine | 1 each | K2PtCl4 | acetate | 6.34E−04 |
| 2638 | thioacetamide + cyclopentylamine | 1 each | K2PtCl4 | propionate | 4.02E−04 |
| 2639 | thioacetamide + cyclopentylamine | 1 each | K2PtCl4 | butyrate | 3.92E−04 |
| 2640 | thioacetamide + cyclopentylamine | 1 each | K2PtCl4 | isobutyrate | 1.33E−04 |
| 2641 | thioacetamide + cyclopentylamine | 1 each | K2PtCl4 | oxalate | 3.03E−04 |
| 2642 | thioacetamide + cyclopentylamine | 1 each | K2PtCl4 | malonate | 1.99E−04 |
| 2643 | thioacetamide + cyclopentylamine | 1 each | K2PtCl4 | succinate | 2.71E−05 |
| 2644 | thioacetamide + L-serine | 1 each | K2PtCl4 | KCl | 3.68E−04 |
| 2645 | thioacetamide + L-serine | 1 each | K2PtCl4 | acetate | 0.00E+00 |
| 2646 | thioacetamide + L-serine | 1 each | K2PtCl4 | propionate | 2.63E−04 |
| 2647 | thioacetamide + L-serine | 1 each | K2PtCl4 | butyrate | 7.64E−05 |
| 2648 | thioacetamide + L-serine | 1 each | K2PtCl4 | isobutyrate | 4.70E−04 |
| 2649 | thioacetamide + L-serine | 1 each | K2PtCl4 | oxalate | 2.23E−04 |
| 2650 | thioacetamide + L-serine | 1 each | K2PtCl4 | malonate | 5.27E−04 |
| 2651 | thioacetamide + L-serine | 1 each | K2PtCl4 | succinate | 3.08E−04 |
| 2652 | propylamine + thioacetamide | 1 each | K2PtCl4 | KCl | 1.09E−03 |
| 2653 | propylamine + thioacetamide | 1 each | K2PtCl4 | acetate | 1.71E−04 |
| 2654 | propylamine + thioacetamide | 1 each | K2PtCl4 | propioinate | 2.34E−04 |
| 2655 | propylamine + thioacetamide | 1 each | K2PtCl4 | butyrate | 2.49E−04 |
| 2656 | propylamine + thioacetamide | 1 each | K2PtCl4 | isobutyrate | 2.94E−04 |
| 2657 | propylamine + thioacetamide | 1 each | K2PtCl4 | oxalate | 3.76E−04 |
| 2658 | propylamine + thioacetamide | 1 each | K2PtCl4 | malonate | 4.29E−04 |
| 2659 | propylamine + thioacetamide | 1 each | K2PtCl4 | succinate | 3.50E−04 |
| 2660 | propylamine + 2-methyl-1-pyrroline | 1 each | K2PtCl4 | KCl | 5.38E−04 |
| 2661 | propylamine + 2-methyl-1-pyrroline | 1 each | K2PtCl4 | acetate | 3.42E−04 |
| 2662 | propylamine + 2-methyl-1-pyrroline | 1 each | K2PtCl4 | propionate | 3.23E−04 |
| 2663 | propylamine + 2-methyl-1-pyrroline | 1 each | K2PtCl4 | butyrate | 3.17E−04 |
| 2664 | propylamine + 2-methyl-1-pyrroline | 1 each | K2PtCl4 | isobutyrate | 3.38E−04 |
| 2665 | propylamine + 2-methyl-1-pyrroline | 1 each | K2PtCl4 | oxalate | 5.27E−04 |
| 2666 | propylamine + 2-methyl-1-pyrroline | 1 each | K2PtCl4 | malonate | 1.69E−04 |
| 2667 | propylamine + 2-methyl-1-pyrroline | 1 each | K2PtCl4 | succinate | 5.28E−04 |
| 2668 | propylamine + 2-methylimidazole | 1 each | K2PtCl4 | KCl | 7.05E−04 |
| 2669 | propylamine + 2-methylimidazole | 1 each | K2PtCl4 | acetate | 5.68E−04 |
| 2670 | propylamine + 2-methylimidazole | 1 each | K2PtCl4 | propionate | 4.88E−04 |
| 2671 | propylamine + 2-methylimidazole | 1 each | K2PtCl4 | butyrate | 7.03E−04 |
| 2672 | propylamine + 2-methylimidazole | 1 each | K2PtCl4 | isobutyrate | 1.04E−03 |
| 2673 | propylamine + 2-methylimidazole | 1 each | K2PtCl4 | oxalate | 9.14E−04 |
| 2674 | propylamine + 2-methylimidazole | 1 each | K2PtCl4 | malonate | 1.07E−03 |
| 2675 | propylamine + 2-methylimidazole | 1 each | K2PtCl4 | succinate | 1.05E−03 |
| 2676 | propylamine + 2,5-dimethyl-3-pyrroline | 1 each | K2PtCl4 | KCl | 7.46E−04 |
| 2677 | propylamine + 2,5-dimethyl-3-pyrroline | 1 each | K2PtCl4 | acetate | 7.26E−04 |
| 2678 | propylamine + 2,5-dimethyl-3-pyrroline | 1 each | K2PtCl4 | propionate | 7.51E−04 |
| 2679 | propylamine + 2,5-dimethyl-3-pyrroline | 1 each | K2PtCl4 | butyrate | 9.44E−04 |
| 2680 | propylamine + 2,5-dimethyl-3-pyrroline | 1 each | K2PtCl4 | isobutyrate | 1.09E−03 |
| 2681 | propylamine + 2,5-dimethyl-3-pyrroline | 1 each | K2PtCl4 | oxalate | 5.67E−04 |
| 2682 | propylamine + 2,5-dimethyl-3-pyrroline | 1 each | K2PtCl4 | malonate | 7.98E−04 |
| 2683 | propylamine + 2,5-dimethyl-3-pyrroline | 1 each | K2PtCl4 | succinate | 1.06E−03 |
| 2684 | propylamine + isopropylamine | 1 each | K2PtCl4 | KCl | 1.55E−03 |
| 2685 | propylamine + isopropylamine | 1 each | K2PtCl4 | acetate | 1.29E−03 |
| 2686 | propylamine + isopropylamine | 1 each | K2PtCl4 | propionate | 8.76E−04 |
| 2687 | propylamine + isopropylamine | 1 each | K2PtCl4 | butyrate | 1.22E−03 |
| 2688 | propylamine + isopropylamine | 1 each | K2PtCl4 | isobutyrate | 1.70E−03 |
| 2689 | propylamine + isopropylamine | 1 each | K2PtCl4 | oxalate | 1.58E−03 |
| 2690 | propylamine + isopropylamine | 1 each | K2PtCl4 | malonate | 1.67E−03 |
| 2691 | propylamine + isopropylamine | 1 each | K2PtCl4 | succinate | 1.59E−03 |
| 2692 | propylamine + 4-picoline | 1 each | K2PtCl4 | KCl | 2.65E−03 |
| 2693 | propylamine + 4-picoline | 1 each | K2PtCl4 | acetate | 3.43E−03 |
| 2694 | propylamine + 4-picoline | 1 each | K2PtCl4 | propionate | 3.73E−03 |
| 2695 | propylamine + 4-picoline | 1 each | K2PtCl4 | butyrate | 2.46E−03 |
| 2696 | propylamine + 4-picoline | 1 each | K2PtCl4 | isobutyrate | 3.89E−03 |
| 2697 | propylamine + 4-picoline | 1 each | K2PtCl4 | oxalate | 1.23E−03 |
| 2698 | propylamine + 4-picoline | 1 each | K2PtCl4 | malonate | 1.09E−03 |
| 2699 | propylamine + 4-picoline | 1 each | K2PtCl4 | succinate | 6.88E−04 |
| 2700 | propylamine + 3-amino-1-propanol | 1 each | K2PtCl4 | KCl | 6.05E−04 |

TABLE 1-continued

| No. | Ligand(s) | Equiv. | Precursor | Leaving Group | Yld, g atm Pt |
|---|---|---|---|---|---|
| 2701 | propylamine + 3-amino-1-propanol | 1 each | K2PtCl4 | acetate | 6.73E−04 |
| 2702 | propylamine + 3-amino-1-propanol | 1 each | K2PtCl4 | propionate | 6.25E−04 |
| 2703 | propylamine + 3-amino-1-propanol | 1 each | K2PtCl4 | butyrate | 5.59E−04 |
| 2704 | propylamine + 3-amino-1-propanol | 1 each | K2PtCl4 | isobutyrate | 4.38E−04 |
| 2705 | propylamine + 3-amino-1-propanol | 1 each | KlPtCl4 | oxalate | 6.47E−04 |
| 2706 | propylamine + 3-amino-1-propanol | 1 each | K2PtCl4 | malonate | 4.16E−04 |
| 2707 | propylamine + 3-amino-1-propanol | 1 each | K2PtCl4 | succinate | 4.08E−04 |
| 2708 | propylamine + pyridazine | 1 each | K2PtCl4 | KCl | 6.36E−04 |
| 2709 | propylamine + pyridazine | 1 each | K2PtCl4 | acetate | 1.25E−03 |
| 2710 | propylamine + pyridazine | 1 each | K2PtCl4 | propionate | 1.34E−03 |
| 2711 | propylamine + pyridazine | 1 each | K2PtCl4 | butyrate | 1.67E−03 |
| 2712 | propylamine + pyridazine | 1 each | K2PtCl4 | isobutyrate | 1.89E−03 |
| 2713 | propylamine + pyridazine | 1 each | K2PtCl4 | oxalate | 2.15E−03 |
| 2714 | propylamine + pyridazine | 1 each | K2PtCl4 | malonate | 1.12E−03 |
| 2715 | propylamine + pyridazine | 1 each | K2PtCl4 | succinate | 5.80E−04 |
| 2716 | propylamine + pyrrolidine | 1 each | K2PtCl4 | KCl | 5.63E−04 |
| 2717 | propylamine + pyrrolidine | 1 each | K2PtCl4 | acetate | 4.13E−04 |
| 2718 | propylamine + pyrrolidine | 1 each | K2PtCl4 | propionate | 4.49E−04 |
| 2719 | propylamine + pyrrolidine | 1 each | K2PtCl4 | butyrate | 3.82E−04 |
| 2720 | propylamine + pyrrolidine | 1 each | K2PtCl4 | isobutyrate | 3.44E−04 |
| 2721 | propylamine + pyrrolidine | 1 each | KlPtCl4 | oxalate | 6.07E−04 |
| 2722 | propylamine + pyrrolidine | 1 each | K2PtCl4 | malonate | 3.51E−04 |
| 2723 | propylamine + pyrrolidine | 1 each | K2PtCl4 | succinate | 3.24E−04 |
| 2724 | propylamine + pyrazine | 1 each | K2PtCl4 | KCl | 4.27E−04 |
| 2725 | propylamine + pyrazine | 1 each | K2PtCl4 | acetate | 3.49E−04 |
| 2726 | propylamine + pyrazine | 1 each | K2PtCl4 | propionate | 5.44E−04 |
| 2727 | propylamine + pyrazine | 1 each | K2PtCl4 | butyrate | 3.43E−04 |
| 2728 | propylamine + pyrazine | 1 each | K2PtCl4 | isobutyrate | 3.82E−04 |
| 2729 | propylamine + pyrazine | 1 each | K2PtCl4 | oxalate | 5.48E−04 |
| 2730 | propylamine + pyrazine | 1 each | K2PtCl4 | malonate | 2.92E−04 |
| 2731 | propylamine + pyrazine | 1 each | K2PtCl4 | succinate | 3.45E−04 |
| 2732 | propylamine + cyclopentylamine | 1 each | K2PtCl4 | KCl | 4.37E−04 |
| 2733 | propylamine + cyclopentylamine | 1 each | K2PtCl4 | acetate | 6.71E−04 |
| 2734 | propylamine + cyclopentylamine | 1 each | K2PtCl4 | propionate | 3.86E−04 |
| 2735 | propylamine + cyclopentylamine | 1 each | K2PtCl4 | butyrate | 3.19E−04 |
| 2736 | propylamine + cyclopentylamine | 1 each | K2PtCl4 | isobutyrate | 4.68E−04 |
| 2737 | propylamine + cyclopentylamine | 1 each | K2PtCl4 | oxalate | 6.19E−04 |
| 2738 | propylamine + cyclopentylamine | 1 each | K2PtCl4 | malonate | 5.22E−04 |
| 2739 | propylamine + cyclopentylamine | 1 each | K2PtCl4 | succinate | 2.44E−04 |
| 2740 | propylamine + L-serine | 1 each | K2PtCl4 | KCl | 4.53E−04 |
| 2741 | propylamine + L-serine | 1 each | K2PtCl4 | acetate | 1.99E−04 |
| 2742 | propylamine + L-serine | 1 each | K2PtCl4 | propionate | 4.30E−04 |
| 2743 | propylamine + L-serine | 1 each | K2PtCl4 | butyrate | 2.94E−04 |
| 2744 | propylamine + L-serine | 1 each | K2PtCl4 | isobutyrate | 2.82E−04 |
| 2745 | propylamine + L-serine | 1 each | K2PtCl4 | oxalate | 1.51E−04 |
| 2746 | propylamine + L-serine | 1 each | K2PtCl4 | malonate | 2.28E−04 |
| 2747 | propylamine + L-serine | 1 each | K2PtCl4 | succinate | 0.00E+00 |
| 2748 | 4-hydroxy-2-mercapto-6-methylpyrimidine + isopropylamine | 1 each | K2PtCl4 | KCl | 3.07E−03 |
| 2749 | 4-hydroxy-2-mercapto-6-methylpyrimidine + isopropylamine | 1 each | K2PtCl4 | acetate | 3.12E−04 |
| 2750 | 4-hydroxy-2-mercapto-6-methylpyrimidine + isopropylamine | 1 each | K2PtCl4 | propionate | 2.52E−04 |
| 2751 | 4-hydroxy-2-mercapto-6-methylpyrimidine + isopropylamine | 1 each | K2PtCl4 | butyrate | 1.62E−04 |
| 2752 | 4-hydroxy-2-mercapto-6-methylpyrimidine + isopropylamine | 1 each | K2PtCl4 | isobutyrate | 3.34E−04 |
| 2753 | 4-hydroxy-2-mercapto-6-methylpyrimidine + isopropylamine | 1 each | K2PtCl4 | 2-ketobutyrate | 2.74E−04 |
| 2754 | 4-hydroxy-2-mercapto-6-methylpyrimidine + isopropylamine | 1 each | K2PtCl4 | malonate | 2.44E−04 |
| 2755 | 4-hydroxy-2-mercapto-6-methylpyrimidine + isopropylamine | 1 each | K2PtCl4 | succinate | 2.12E−04 |
| 2756 | DL-beta-aminobutyrate + isopropylamine | 1 each | K2PtCl4 | KCl | 4.29E−04 |
| 2757 | DL-beta-aminobutyrate + isopropylamine | 1 each | K2PtCl4 | acetate | 1.96E−04 |
| 2758 | DL-beta-aminobutyrate + isopropylamire | 1 each | K2PtCl4 | propionate | 4.26E−04 |
| 2759 | DL-beta-aminobutyrate + isopropylamine | 1 each | K2PtCl4 | butyrate | 2.82E−04 |
| 2760 | DL-beta-aminobutyrate + isopropylamine | 1 each | K2PtCl4 | isobutyrate | 3.52E−04 |
| 2761 | DL-beta-aminobutyrate + isopropylamine | 1 each | K2PtCl4 | 2-ketobutyrate | 2.74E−04 |
| 2762 | DL-beta-aminobutyrate + isopropylamine | 1 each | K2PtCl4 | malonate | 2.95E−04 |
| 2763 | DL-beta-aminobutyrate + isopropylamine | 1 each | K2PtCl4 | succinate | 2.98E−04 |
| 2764 | 2-picoline + isopropylamine | 1 each | K2PtCl4 | KCl | 1.29E−03 |
| 2765 | 2-picoiine + isopropylamine | 1 each | K2PtCl4 | acetate | 1.27E−03 |
| 2766 | 2-picoline + isopropylamine | 1 each | KtPtCl4 | propionate | 1.29E−03 |
| 2767 | 2-picoline + isopropylamine | 1 each | K2PtCl4 | butyrate | 1.06E−03 |
| 2768 | 2-picotine + isopropylamine | 1 each | K2PtCl4 | isobutyrate | 6.23E−04 |
| 2769 | 2-picoline + isopropylamine | 1 each | K2PtCl4 | 2-ketobutyrate | 1.59E−03 |

TABLE 1-continued

| No. | Ligand(s) | Equiv. | Precursor | Leaving Group | Yld, g atm Pt |
|---|---|---|---|---|---|
| 2770 | 2-picoline + isopropylamine | 1 each | K2PtCl4 | malonate | 7.44E−04 |
| 2771 | 2-picoline + isopropylamine | 1 each | K2PtCl4 | succinate | 2.44E−04 |
| 2772 | 2-amino-2-methyl-1-propanol + isopropylamine | 1 each | K2PtCl4 | KCl | 3.47E−04 |
| 2773 | 2-amino-2-methyl-1-propanol + isopropylamine | 1 each | K2PtCl4 | acetate | 2.39E−04 |
| 2774 | 2-amino-2-methyl-1-propanol + isopropylamine | 1 each | K2PtCl4 | propionate | 2.24E−04 |
| 2775 | 2-amino-2-methyl-1-propanol + isopropylamine | 1 each | K2PtCl4 | butyrate | 2.94E−04 |
| 2776 | 2-amino-2-methyl-1-propanol + isopropylamine | 1 each | K2PtCl4 | isobutyrate | 4.99E−04 |
| 2777 | 2-amino-2-methyl-1-propanol + isopropylamine | 1 each | K2PtCl4 | 2-ketobutyrate | 4.89E−04 |
| 2778 | 2-amino-2-methyl-1-propanol + isopropylamine | 1 each | K2PtCl4 | malonate | 1.29E−04 |
| 2779 | 2-amino-2-methyl-1-propanol + isopropylamine | 1 each | K2PtCl4 | succinate | 2.79E−04 |
| 2780 | N-(2-aminoethyl)-1,3-propanediamine + isopropylamine | 1 each | K2PtCl4 | KCl | 9.42E−04 |
| 2781 | N-(2-aminoethyl)-1,3-propanediamine + isopropylamine | 1 each | K2PtCl4 | acetate | 9.71E−04 |
| 2782 | N-(2-aminoethyl)-1,3-propanediamine + isopropylamine | 1 each | K2PtCl4 | propionate | 9.92E−04 |
| 2783 | N-(2-aminoethyl)-1,3-propanediamine + isopropylamine | 1 each | K2PtCl4 | butyrate | 6.88E−04 |
| 2784 | N-(2-aminoethyl)-1,3-propanediamine + isopropylamine | 1 each | K2PtCl4 | isobutyrate | 9.32E−04 |
| 2785 | N-(2-aminoethyl)-1,3-propanediamine + isopropylamine | 1 each | K2PtCl4 | 2-ketobutyrate | 1.14E−03 |
| 2786 | N-(2-aminoethyl)-1,3-propanediamine + isopropylamine | 1 each | K2PtCl4 | malonate | 8.10E−04 |
| 2787 | N-(2-aminoethyl)-1,3-propanediamine + isopropylamine | 1 each | K2PtCl4 | succinate | 5.56E−04 |
| 2788 | 2-aminoethanol + isopropylamine | 1 each | K2PtCl4 | KCl | 3.09E−04 |
| 2789 | 2-aminoethanol + isopropylamine | 1 each | K2PtCl4 | acetate | 2.76E−04 |
| 2790 | 2-aminoethanol + isopropylamine | 1 each | K2PtCl4 | propionate | 2.61E−04 |
| 2791 | 2-aminoethanol + isopropylamine | 1 each | K2PtCl4 | butyrate | 3.20E−04 |
| 2792 | 2-aminoethanol + isopropylamine | 1 each | K2PtCl4 | isobutyrate | 3.24E−04 |
| 2793 | 2-aminoethanol + isopropylamine | 1 each | K2PtCl4 | 2-ketobutyrate | 2.14E−04 |
| 2794 | 2-aminoethonol + isopropylamine | 1 each | K2PtCl4 | malonate | 6.61E−05 |
| 2795 | 2-aminoetnanol + isopropylamine | 1 each | K2PtCl4 | succinate | 2.60E−04 |
| 2796 | 4,5-imidazoledicarboxylic acid + isopropylamine | 1 each | K2PtCl4 | KCl | 6.54E−04 |
| 2797 | 4,5-imidazoledicarboxylic acid + isopropylamine | 1 each | K2PtCl4 | acetate | 7.02E−04 |
| 2798 | 4,5-imidazoledicarboxylic acid + isopropylamine | 1 each | K2PtCl4 | propionate | 5.56E−04 |
| 2799 | 4,5-imidazoledicarboxylic acid + isopropylamine | 1 each | K2PtCl4 | butyrate | 6.62E−04 |
| 2800 | 4,5-imidazoledicarboxylic acid + isopropylamine | 1 each | K2PtCl4 | isobutyrate | 6.46E−04 |
| 2801 | 4,5-imidazoledicarboxylic acid + isopropylamine | 1 each | K2PtCl4 | 2-ketobutyrate | 7.23E−04 |
| 2802 | 4,5-imidazoledicarboxylic acid + isopropylamine | 1 each | K2PtCl4 | malonate | 6.60E−04 |
| 2803 | 4,5-imidazoledicarboxylic acid + isopropylamine | 1 each | K2PtCl4 | succinate | 6.57E−04 |
| 2804 | 1,3-diamino-2-hydroxypropane + isopropylamine | 1 each | K2PtCl4 | KCl | 1.11E−03 |
| 2805 | 1,3-diamino-2-hydroxypropane + isopropylamine | 1 each | K2PtCl4 | acetate | 8.10E−04 |
| 2806 | 1,3-diamino-2-hydroxypropane + isopropylamine | 1 each | K2PtCl4 | propionate | 8.75E−04 |
| 2807 | 1,3-diamino-2-hydroxypropane + isopropylamine | 1 each | K2PtCl4 | butyrate | 8.05E−04 |
| 2808 | 1,3-diamino-2-hydroxypropane + isopropylamine | 1 each | K2PtCl4 | isobutyrate | 9.80E−04 |
| 2809 | 1,3-diamino-2-hydroxypropane + isopropylamine | 1 each | K2PtCl4 | 2-ketobutyrate | 1.18E−03 |
| 2810 | 1,3-diamino-2-hydroxypropane + isopropylamine | 1 each | K2PtCl4 | malonate | 6.93E−04 |
| 2811 | 1,3-diamino-2-hydroxypropane + isopropylamine | 1 each | K2PtCl4 | succinate | 8.14E−04 |
| 2812 | 2-aminoethanethiol-HCl + isopropylamine | 1 each | K2PtCl4 | KCl | 8.79E−04 |
| 2813 | 2-aminoethanethiol-HCl + isopropylamine | 1 each | K2PtCl4 | acetate | 1.55E−03 |
| 2814 | 2-aminoethanethiol-HCl + isopropylamine | 1 each | K2PtCl4 | propionate | 1.52E−03 |

TABLE 1-continued

| No. | Ligand(s) | Equiv. | Precursor | Leaving Group | Yld, g atm Pt |
|---|---|---|---|---|---|
| 2815 | 2-aminoethanethiol-HCl + isopropylamine | 1 each | K2PtCl4 | butyrate | 1.39E−03 |
| 2816 | 2-aminoethanethiol-HCl + isopropylamine | 1 each | K2PtCl4 | isobutyrate | 1.51E−03 |
| 2817 | 2-aminoethanethiol-HCl + isopropylamine | 1 each | K2PtCl4 | 2-ketobutyrate | 9.85E−04 |
| 2818 | 2-aminoethanethiol-HCl + isopropylamine | 1 each | K2PtCl4 | malonate | 7.48E−04 |
| 2819 | 2-aminoethanethiol-HCl + isopropylamine | 1 each | K2PtCl4 | succinate | 7.58E−04 |
| 2820 | 2,4,6-trichloropyrimidine + isopropylamine | 1 each | K2PtCl4 | KCl | 6.70E−04 |
| 2821 | 2,4,6-trichloropyrimidine + isopropylamine | 1 each | K2PtCl4 | acetate | 5.28E−04 |
| 2822 | 2,4,6-trichloropyrimidine + isopropylamine | 1 each | K2PtCl4 | propionate | 6.67E−04 |
| 2823 | 2,4,6-trichloropyrimidine + isopropylamine | 1 each | K2PtCl4 | butyrate | 5.14E−04 |
| 2824 | 2,4,6-trichloropyrimidine + isopropylamine | 1 each | K2PtCl4 | isobutyrate | 6.90E−04 |
| 2825 | 2,4,6-trichloropyrimidine + isopropylamine | 1 each | K2PtCl4 | 2-ketobutyrate | 7.93E−04 |
| 2826 | 2,4,6-trichloropyrimidine + isopropylamine | 1 each | K2PtCl4 | malonate | 4.41E−04 |
| 2827 | 2,4,6-trichloropyrimidine + isopropylamine | 1 each | K2PtCl4 | succinate | 5.86E−04 |
| 2828 | 3-picoline + isopropylamine | 1 each | K2PtCl4 | KCl | 1.21E−03 |
| 2829 | 3-picoline + isopropylamine | 1 each | K2PtCl4 | acetate | 1.29E−03 |
| 2830 | 3-picoline + isopropylamine | 1 each | K2PtCl4 | propionate | 1.20E−03 |
| 2831 | 3-picoline + isopropylamine | 1 each | KtPtCl4 | butyrate | 1.41E−03 |
| 2832 | 3-picoline + isopropylamine | 1 each | K2PtCl4 | isobutyrate | 1.24E−03 |
| 2833 | 3-picoline + isopropylamine | 1 each | K2PtCl4 | 2-ketobutyrate | 1.31E−03 |
| 2834 | 3-picoline + isopropylamine | 1 each | K2PtCl4 | malonate | 8.78E−04 |
| 2835 | 3-picoline + isopropylamine | 1 each | K2PtCl4 | succinate | 6.44E−04 |
| 2836 | 3-aminobenzotrifluoride + isopropylamine | 1 each | K2PtCl4 | KCl | 5.98E−04 |
| 2837 | 3-aminobenzotrifluoride + isopropylamine | 1 each | K2PtCl4 | acetate | 4.91E−03 |
| 2838 | 3-aminobenzotrifluoride + isopropylamine | 1 each | K2PtCl4 | propionate | 2.17E−03 |
| 2839 | 3-aminobenzotrifluoride + isopropylamine | 1 each | K2PtCl4 | butyrate | 3.48E−04 |
| 2840 | 3-aminobenzotrifluoride + isopropylamine | 1 each | K2PtCl4 | isobutyrate | 5.00E−04 |
| 2841 | 3-aminobenzotrifluoride + isopropylamine | 1 each | K2PtCl4 | 2-ketobutyrate | 3.68E−04 |
| 2842 | 3-aminobenzotrifluoride + isopropylamine | 1 each | K2PtCl4 | malonate | 1.42E−03 |
| 2843 | 3-aminobenzotrifluoride + isopropylamine | 1 each | K2PtCl4 | succinate | 1.43E−03 |
| 2844 | 4-hydroxy-2-mercapto-6-methylpyrimidine + acetamidine-HCl | 1 each | K2PtCl4 | KCl | 1.19E−04 |
| 2845 | 4-hydroxy-2-mercapto-6-methylpyrimidine + isopropylamine | 1 each | K2PtCl4 | KCl | 1.14E−04 |
| 2846 | 4-hydroxy-2-mercapto-6-methylpyrimidine + piperdine | 1 each | K2PtCl4 | KCl | 3.73E−05 |
| 2847 | 4-hydroxy-2-mercapto-6-methylpyrimidine + mechlorethamine-HCl | 1 each | K2PtCl4 | KCl | 1.57E−04 |
| 2848 | 4-hydroxy-2-mercapto-6-methylpyrimidine + thioacetamide | 1 each | K2PtCl4 | KCl | 3.07E−05 |
| 2849 | 4-hydroxy-2-mercapto-6-methylpyrimidine + 3-bromopyridine | 1 each | K2PtCl4 | KCl | 2.55E−04 |
| 2850 | 4-hydroxy-2-mercapto-6-methylpyrimidine + 2-picoline | 1 each | K2PtCl4 | KCl | 3.55E−04 |
| 2851 | 4-hydroxy-2-mercapto-6-methylpyrimidine + 4-picoline | 1 each | K2PtCl4 | KCl | 5.80E−04 |
| 2852 | DL-beta-aminobutyrate + acetamidine-HCl | 1 each | K2PtCl4 | KCl | 2.10E−04 |
| 2853 | DL-beta-aminobutyrate + isopropylamine | 1 each | K2PtCl4 | KCl | 1.83E−04 |
| 2854 | DL-beta-aminobutyrate + piperdine | 1 each | K2PtCl4 | KCl | 3.42E−04 |
| 2855 | DL-beta-aminobutyrate + mechlorethamine-HCl | 1 each | K2PtCl4 | KCl | 0.00E+00 |
| 2856 | DL-beta-aminobutyrate + thioacetamide | 1 each | K2PtCl4 | KCl | 2.02E−04 |
| 2857 | DL-beta-aminoburyrate + 3-bromopyridine | 1 each | K2PtCl4 | KCl | 4.23E−04 |
| 2858 | DL-beta-aminobutyrate + 2-picoline | 1 each | K2PtCl4 | KCl | 8.44E−04 |
| 2859 | DL-beta-aminobutyrate + 4-picoline | 1 each | K2PtCl4 | KCl | 8.39E−04 |
| 2860 | 2,4-diamino-6-hydroxypropane + acetamidine-HCl | 1 each | K2PtCl4 | KCl | 2.37E−04 |
| 2861 | 2,4-diamino-6-hydroxypropane + isopropylamine | 1 each | K2PtCl4 | KCl | 2.79E−04 |
| 2862 | 2,4-diamino-6-hydroxypropane + piperdine | 1 each | K2PtCl4 | KCl | 2.80E−04 |
| 2863 | 2,4-diamino-6-hydroxypropane + mechlorethamine-HCl | 1 each | K2PtCl4 | KCl | 2.60E−04 |
| 2864 | 2,4-diamino-6-hydroxypropane + thioacetamide | 1 each | K2PtCl4 | KCl | 3.80E−06 |
| 2865 | 2,4-diamino-6-hydroxypropane + 3-bromopyridine | 1 each | K2PtCl4 | KCl | 3.55E−04 |
| 2866 | 2,4-diamino-6-hydroxypropane + 2-picoline | 1 each | K2PtCl4 | KCl | 9.98E−04 |
| 2867 | 2,4-diamino-6-hydroxypropane + 4-picoline | 1 each | K2PtCl4 | KCl | 1.48E−03 |
| 2868 | 2-amino-2-methyl-1-propanol + acetamidine-HCl | 1 each | K2PtCl4 | KCl | 3.85E−04 |
| 2869 | 2-amino-2-methyl-1-propanol + isopropylamine | 1 each | K2PtCl4 | KCl | 2.75E−04 |
| 2870 | 2-amino-2-methyl-1-propanol + piperdine | 1 each | K2PtCl4 | KCl | 3.96E−04 |
| 2871 | 2-amino-2-methyl-1-propanol + mechlorethamine-HCl | 1 each | K2PtCl4 | KCl | 7.56E−04 |
| 2872 | 2-amino-2-methyl-1-propanol + thioacetamide | 1 each | K2PtCl4 | KCl | 1.61E−04 |
| 2873 | 2-amino-2-methyl-1-propanol + 3-bromopyridine | 1 each | K2PtCl4 | KCl | 9.22E−04 |

TABLE 1-continued

| No. | Ligand(s) | Equiv. | Precursor | Leaving Group | Yld, g atm Pt |
|---|---|---|---|---|---|
| 2874 | 2-amino-2-methyl-1-propanol + 2-picoline | 1 each | K2PtCl4 | KCl | 6.30E−04 |
| 2875 | 2-amino-2-methyl-1-propanol + 4-picoline | 1 each | K2PtCl4 | KCl | 1.24E−03 |
| 2876 | N-(2-aminoethyl)-1,3-propanediamine + acetamidine-HCl | 1 each | K2PtCl4 | KCl | 5.74E−04 |
| 2877 | N-(2-aminoethyl)-1,3-propanediamine + isopropylamine | 1 each | K2PtCl4 | KCl | 5.01E−04 |
| 2878 | N-(2-aminoethyl)-1,3-propanediamine + piperdine | 1 each | K2PtCl4 | KCl | 6.22E−04 |
| 2879 | N-(2-aminoethyl)-1,3-propanediamine + mechlorethamine-HCl | 1 each | K2PtCl4 | KCl | 1.33E−03 |
| 2880 | N-(2-aminoethyl)-1,3-propanediamine + thioacetamide | 1 each | K2PtCl4 | KCl | 6.46E−04 |
| 2881 | N-(2-aminoethyl)-1,3-propanediamine + 3-bromopyridine | 1 each | K2PtCl4 | KCl | 9.42E−04 |
| 2882 | N-(2-aminoethyl)-1,3-propanediamine + 2-picoline | 1 each | K2PtCl4 | KCl | 7.63E−04 |
| 2883 | N-(2-aminoethyl)-1,3-propanediamine + 4-picoline | 1 each | K2PtCl4 | KCl | 1.30E−03 |
| 2884 | 2-aminoethanol + acetamidine-HCl | 1 each | K2PtCl4 | KCl | 5.87E−04 |
| 2885 | 2-aminoethanol + isopropylamine | 1 each | K2PtCl4 | KCl | 3.53E−04 |
| 2886 | 2-aminoethanol + piperdine | 1 each | K2PtCl4 | KCl | 1.53E−04 |
| 2887 | 2-aminoethanol + mechlorethamine-HCl | 1 each | K2PtCl4 | KCl | 0.00E+00 |
| 2888 | 2-aminoethanol + thioacetamide | 1 each | K2PtCl4 | KCl | 3.59E−05 |
| 2889 | 2-aminoethanol + 3-bromopyridine | 1 each | K2PtCl4 | KCl | 5.83E−04 |
| 2890 | 2-aminoethanol + 2-picoline | 1 each | K2PtCl4 | KCl | 1.00E−04 |
| 2891 | 2-aminoethanol + 4-picoline | 1 each | K2PtCl4 | KCl | 5.65E−04 |
| 2892 | 4,5-imidazoledicarboxylic acid + acetamidine-HCl | 1 each | K2PtCl4 | KCl | 0.00E+00 |
| 2893 | 4,5-imidazoledicarboxylic acid + isopropylamine | 1 each | K2PtCl4 | KCl | 3.04E−04 |
| 2894 | 4,5-imidazoledicarboxylic acid + piperdine | 1 each | K2PtCl4 | KCl | 1.43E−04 |
| 2895 | 4,5-imidazoledicarboxylic acid + mechlorethamine-HCl | 1 each | K2PtCl4 | KCl | 2.89E−04 |
| 2896 | 4,5-imidazoledicarboxylic acid + thioacetamide | 1 each | K2PtCl4 | KCl | 1.93E−04 |
| 2897 | 4,5-imidazoledicarboxylic acid + 3-bromopyridine | 1 each | K2PtCl4 | KCl | 6.11E−04 |
| 2898 | 4,5-imidazoledicarboxylic acid + 2-picoline | 1 each | K2PtCl4 | KCl | 5.42E−05 |
| 2899 | 4,5-imidazoledicarboxylic acid + 4-picoline | 1 each | K2PtCl4 | KCl | 1.01E−03 |
| 2900 | 1,3-diamino-2-hydroxypropane + acetamidine-HCl | 1 each | K2PtCl4 | KCl | 3.39E−05 |
| 2901 | 1,3-diamino-2-hydroxypropane + isopropylamine | 1 each | K2PtCl4 | KCl | 0.00E+00 |
| 2902 | 1,3-diamino-2-hydroxypropane + piperdine | 1 each | K2PtCl4 | KCl | 1.12E−04 |
| 2903 | 1,3-diamino-2-hydroxypropane + mechlorethamine-HCl | 1 each | K2PtCl4 | KCl | 2.02E−04 |
| 2904 | 1,3-diamino-2-hydroxypropane + thioacetamide | 1 each | K2PtCl4 | KCl | 1.58E−04 |
| 2905 | 1,3-diamino-2-hydroxypropane + 3-bromopyridine | 1 each | K2PtCl4 | KCl | 3.52E−03 |
| 2906 | 1,3-diamino-2-hydroxypropane + 2-picoline | 1 each | K2PtCl4 | KCl | 1.07E−03 |
| 2907 | 1,3-diamino-2-hydroxypropane + 4-picoline | 1 each | K2PtCl4 | KCl | 2.05E−03 |
| 2908 | 2-aminoethanethiol-HCl + acetamidine-HCl | 1 each | K2PtCl4 | KCl | 5.79E−04 |
| 2909 | 2-aminoethanethiol-HCl + isopropylamine | 1 each | K2PtCl4 | KCl | 4.79E−04 |
| 2910 | 2-aminoethanethiol-HCl + piperdine | 1 each | K2PtCl4 | KCl | 5.32E−05 |
| 2911 | 2-aminoethanethiol-HCl + mechlorethamine-HCl | 1 each | K2PtCl4 | KCl | 1.75E−03 |
| 2912 | 2-aminoethanethiol-HCl + thioacetamide | 1 each | K2PtCl4 | KCl | 5.87E−05 |
| 2913 | 2-aminoethanethiol-HCl + 3-bromopyridine | 1 each | K2PtCl4 | KCl | 1.97E−03 |
| 2914 | 2-aminoethanethiol-HCl + 2-picoline | 1 each | K2PtCl4 | KCl | 7.81E−04 |
| 2915 | 2-aminoethanethiol-HCl + 4-picoline | 1 each | K2PtCl4 | KCl | 1.69E−03 |
| 2916 | 2,4,6-trichloropyrimidine + acetamidine-HCl | 1 each | K2PtCl4 | KCl | 3.90E−04 |
| 2917 | 2,4,6-trichloropyrimidine + isopropylamine | 1 each | K2PtCl4 | KCl | 1.15E−04 |
| 2918 | 2,4,6-trichloropyrimidine + piperdine | 1 each | K2PtCl4 | KCl | 2.20E−04 |
| 2919 | 2,4,6-trichloropyrimidine + mechlorethamine-HCl | 1 each | K2PtCl4 | KCl | 2.29E−05 |
| 2920 | 2,4,6-trichloropyrimidine + thioacetamide | 1 each | K2PtCl4 | KCl | 7.86E−05 |
| 2921 | 2,4,6-trichloropyrimidine + 3-bromopyridine | 1 each | K2PtCl4 | KCl | 6.11E−04 |
| 2922 | 2,4,6-trichloropyrimidine + 2-picoline | 1 each | K2PtCl4 | KCl | 1.09E−03 |
| 2923 | 2,4,6-trichloropyrimidine + 4-picoline | 1 each | KZPtCl4 | KCl | 2.66E−03 |
| 2924 | 3-picoline + acetamidine-HCl | 1 each | K2PtCl4 | KCl | 4.66E−04 |
| 2925 | 3-picoline + isopropylamine | 1 each | K2PtCl4 | KCl | 1.75E−03 |
| 2926 | 3-picoline + piperdine | 1 each | K2PtCl4 | KCl | 1.57E−03 |
| 2927 | 3-picoline + mechlorethamine-HCl | 1 each | K2PtCl4 | KCl | 1.65E−03 |
| 2928 | 3-picoline + thioacetamide | 1 each | K2PtCl4 | KCl | 8.17E−04 |
| 2929 | 3-picoline + 3-bromopyridine | 1 each | K2PtCl4 | KCl | 2.56E−03 |
| 2930 | 3-picoline + 2-picoline | 1 each | K2PtCl4 | KCl | 5.61E−04 |
| 2931 | 3-picoline + 4-picoline | 1 each | K2PtCl4 | KCl | 0.00E+00 |

TABLE 1-continued

| No. | Ligand(s) | Equiv. | Precursor | Leaving Group | Yld, g atm Pt |
|---|---|---|---|---|---|
| 2932 | 3-aminobenzotrifluoride + acetamidine-HCl | 1 each | K2PtCl4 | KCl | 5.29E−05 |
| 2933 | 3-aminobenzotrifluoride + isopropylamine | 1 each | K2PtCl4 | KCl | 3.38E−03 |
| 2934 | 3-aminobenzotrifluoride + piperdine | 1 each | K2PtCl4 | KCl | 5.38E−04 |
| 2935 | 3-aminobenzotrifluoride + mechlorethamine-HCl | 1 each | K2PtCl4 | KCl | 1.77E−03 |
| 2936 | 3-aminobenzotrifluoride + thioacetamide | 1 each | K2PtCl4 | KCl | 2.69E−04 |
| 2937 | 3-aminobenzotrifluoride + 3-bromopyridine | 1 each | K2PtCl4 | KCl | 5.57E−04 |
| 2938 | 3-aminobenzotrifluoride + 2-picoline | 1 each | K2PtCl4 | KCl | 9.47E−04 |
| 2939 | 3-aminobenzotrifluoride + 4-picoline | 1 each | K2PtCl4 | KCl | 1.44E−03 |
| 2940 | acetamidine-HCl + piperdine | 1 each | K2PtCl4 | KCl | 3.58E−03 |
| 2941 | acetamidine-HCl + piperdine | 1 each | K2PtCl4 | acetate | 1.57E−03 |
| 2942 | acetamidine-HCl + piperdine | 1 each | K2PtCl4 | propionate | 2.32E−03 |
| 2943 | acetamidine-HCl + piperdine | 1 each | K2PtCl4 | butyrate | 2.21E−03 |
| 2944 | acetamidine-HCl + piperdine | 1 each | K2PtCl4 | isobutyrate | 1.84E−03 |
| 2945 | acetamidine-HCl + piperdine | 1 each | K2PtCl4 | 2-ketobutyrate | 2.48E−03 |
| 2946 | acetamidine-HCl + piperdine | 1 each | K2PtCl4 | malonate | 2.16E−03 |
| 2947 | acetamidine-HCl + piperdine | 1 each | K2PtCl4 | succinate | 2.34E−03 |
| 2948 | DL-beta-aminobutyrate + piperdine | 1 each | K2PtCl4 | KCl | 3.90E−03 |
| 2949 | DL-beta-aminobutyrate + piperdine | 1 each | K2PtCl4 | acetate | 1.35E−03 |
| 2950 | DL-beta-aminobutyrate + piperdine | 1 each | K2PtCl4 | propionate | 1.34E−03 |
| 2951 | DL-beta-aminobutyrate + piperdine | 1 each | K2PtCl4 | butyrate | 1.65E−03 |
| 2952 | DL-beta-aminobutyrate + piperdine | 1 each | K2PtCl4 | isobutyrate | 1.74E−03 |
| 2953 | DL-beta-aminobutyrate + piperdine | 1 each | K2PtCl4 | 2-ketobutyrate | 2.23E−03 |
| 2954 | DL-beta-aminobutyrate + pipeidine | 1 each | K2PtCl4 | malonate | 2.13E−03 |
| 2955 | DL-beta-aminobutyrate + piperdine | 1 each | K2PtCl4 | succinate | 2.50E−03 |
| 2956 | 2-picoline + piperdine | 1 each | K2PtCl4 | KCl | 2.56E−03 |
| 2957 | 2-picoline + piperdine | 1 each | K2PtCl4 | acetate | 1.66E−03 |
| 2958 | 2-picoline + piperdine | 1 each | K2PtCl4 | propionate | 2.78E−03 |
| 2959 | 2-picoline + piperdine | 1 each | K2PtCl4 | butyrate | 1.89E−03 |
| 2960 | 2-picoline + piperdine | 1 each | K2PtCl4 | isobutyrate | 3.69E−03 |
| 2961 | 2-picoline + piperdine | 1 each | K2PtCl4 | 2-ketobutyrate | 3.57E−03 |
| 2962 | 2-picoline + piperdine | 1 each | K2Ptcl4 | malonate | 1.55E−03 |
| 2963 | 2-picoline + piperdine | 1 each | K2PtCl4 | succinate | 1.50E−03 |
| 2964 | 2-amino-2-methyl-1-propanol + piperdine | 1 each | K2PtCl4 | KCl | 3.46E−03 |
| 2965 | 2-amino-2-methyl-1-propanol + piperdine | 1 each | K2PtCl4 | acetate | 2.04E−03 |
| 2966 | 2-amino-2-methyl-1-propanol + piperdine | 1 each | K2PtCl4 | propionate | 9.90E−04 |
| 2967 | 2-amino-2-methyl-1-propanol + piperdine | 1 each | K2PtCl4 | butyrate | 2.33E−03 |
| 2968 | 2-amino-2-methyl-1-propanol + piperdine | 1 each | K2PtCl4 | isobutyrate | 7.46E−04 |
| 2969 | 2-amino-2-methyl-1-propanol + piperdine | 1 each | K2PtCl4 | 2-ketobutyrate | 7.46E−04 |
| 2970 | 2-amino-2-methyl-1-propanol + piperdine | 1 each | K2PtCl4 | malonate | 9.67E−04 |
| 2971 | 2-amino-2-methyl-1-propanol + piperdine | 1 each | K2PtCl4 | succinate | 1.29E−03 |
| 2972 | mechlorethamine-HCl + piperdine | 1 each | K2PtCl4 | KCl | 2.75E−04 |
| 2973 | mechlorethamine-HC1 + piperdine | 1 each | K2PtCl4 | acetate | 2.66E−04 |
| 2974 | mechlorethamine-HCl + piperdine | 1 each | K2PtCl4 | propionate | 2.45E−04 |
| 2975 | mechlorethamine-HCl + piperdine | 1 each | K2PtCl4 | butyrate | 6.98E−05 |
| 2976 | mechlorethamine-HCl + piperdine | 1 each | K2PtCl4 | isobutyrate | 7.71E−04 |
| 2977 | mechlorethamine-HCl + piperdine | 1 each | K2PtCl4 | 2-ketobutyrate | 2.79E−04 |
| 2978 | mechlorethamine-HCl + piperdine | 1 each | K2PtCl4 | malonate | 8.71E−05 |
| 2979 | mechlorethamine-HCl + piperdine | 1 each | K2PtCl4 | succinate | 3.34E−04 |
| 2980 | 2-aminoethanol + piperdine | 1 each | K2PtCl4 | KCl | 3.28E−03 |
| 2981 | 2-aminoethanol + piperdine | 1 each | K2PtCl4 | acetate | 5.93E−04 |
| 2982 | 2-aminoethanol + piperdine | 1 each | K2PtCl4 | propionate | 1.84E−03 |
| 2983 | 2-aminoethanol + piperdine | 1 each | K2PtCl4 | butyrate | 1.54E−03 |
| 2984 | 2-aminoethanol + piperdine | 1 each | K2PtCl4 | isobutyrate | 1.56E−03 |
| 2985 | 2-aminoethanol + piperdine | 1 each | K2PtCl4 | 2-ketobutyrate | 2.65E−03 |
| 2986 | 2-aminoethanol + piperdine | 1 each | K2PtCl4 | malonate | 2.38E−03 |
| 2987 | 2-aminoethanol + piperdine | 1 each | K2PtCl4 | succinate | 1.36E−03 |
| 2988 | thioacetamide + piperdine | 1 each | K2PtCl4 | KCl | 1.00E−03 |
| 2989 | thioacetamide + piperdine | 1 each | K2PtCl4 | acetate | 1.46E−04 |
| 2990 | thioacetamide + piperdine | 1 each | K2PtCl4 | propionate | 3.49E−04 |
| 2991 | thioacetamide + piperdine | 1 each | K2PtCl4 | butyrate | 4.17E−04 |
| 2992 | thioacetamide + piperdine | 1 each | K2PtCl4 | isobutyrate | 1.29E−04 |
| 2993 | thioacetamide + piperdine | 1 each | K2PtCl4 | 2-ketobutyrate | 2.90E−04 |
| 2994 | thioacetamide + piperdine | 1 each | K2PtCl4 | malonate | 6.65E−05 |
| 2995 | thioacetamide + piperdine | 1 each | K2PtCl4 | succinate | 1.72E−04 |
| 2996 | 1,3-diamino-2-hydroxypropane + piperdine | 1 each | K2PtCl4 | KCl | 1.02E−03 |
| 2997 | 1,3-diamino-2-hydroxypropane + piperdine | 1 each | K2PtCl4 | acetate | 8.71E−04 |
| 2998 | 1,3-diamino-2-hydroxypropane + piperdine | 1 each | K2PtCl4 | propionate | 1.04E−03 |
| 2999 | 1,3-diamino-2-hydroxypropane + piperdine | 1 each | K2PtCl4 | butyrate | 1.53E−03 |
| 3000 | 1,3-diamino-2-hydroxypropane + piperdine | 1 each | K2PtCl4 | isobutyrate | 8.69E−04 |
| 3001 | 1,3-diamino-2-hydroxypropane + piperdine | 1 each | K2PtCl4 | 2-ketobutyrate | 9.78E−04 |
| 3002 | 1,3-diamino-2-hydroxypropane + piperdine | 1 each | K2PtCl4 | malonate | 8.68E−04 |
| 3003 | 1,3-diamino-2-hydroxypropane + piperdine | 1 each | K2PtCl4 | succinate | 8.46E−04 |
| 3004 | 2-aminoethanethiol-HCl + piperdine | 1 each | K2PtCl4 | KCl | 5.45E−04 |
| 3005 | 2-aminoethanethiol-HCl + piperdine | 1 each | K2PtCl4 | acetate | 1.07E−03 |
| 3006 | 2-aminoethanethiol-HCl + piperdine | 1 each | K2PtCl4 | propionate | 4.26E−04 |
| 3007 | 2-aminoethanethiol-HCl + piperdine | 1 each | K2PtCl4 | butyrate | 6.04E−04 |

TABLE 1-continued

| No. | Ligand(s) | Equiv. | Precursor | Leaving Group | Yld, g atm Pt |
|---|---|---|---|---|---|
| 3008 | 2-aminoethanethiol-HCl + piperdine | 1 each | K2PtCl4 | isobutyrate | 1.88E−03 |
| 3009 | 2-aminoethanethiol-HCl + piperdine | 1 each | K2PtCl4 | 2-ketobutyrate | 2.22E−03 |
| 3010 | 2-aminoethanethiol-HCl + piperdine | 1 each | K2PtCl4 | malonate | 6.64E−04 |
| 3011 | 2-aminoethanethiol-HCl + piperdine | 1 each | K2PtCl4 | succinate | 6.17E−04 |
| 3012 | 2,4,6-trichloropyrimidine + piperdine | 1 each | KtPtCl4 | KCl | 2.34E−03 |
| 3013 | 2,4,6-trichloropyrimidine + piperdine | 1 each | KtPtCl4 | acetate | 1.23E−03 |
| 3014 | 2,4,6-trichloropyrimidine + piperdine | 1 each | K2PtCl4 | propionate | 1.11E−03 |
| 3015 | 2,4,6-trichloropyrimidine + piperdine | 1 each | K2PtCl4 | butyrate | 1.30E−03 |
| 3016 | 2,4,6-trichloropyrimidine + piperdine | 1 each | K2PtCl4 | isobutyrate | 1.46E−03 |
| 3017 | 2,4,6-trichloropyrimidine + piperdine | 1 each | K2PtCl4 | 2-ketobutyrate | 2.57E−03 |
| 3018 | 2,4,6-trichloropyrimidine + piperdine | 1 each | K2PtCl4 | malonate | 1.87E−03 |
| 3019 | 2,4,6-trichloropyrimidine + piperdine | 1 each | K2PtCl4 | succinate | 1.96E−03 |
| 3020 | 3-picoline + piperdine | 1 each | K2PtCl4 | KCl | 3.10E−03 |
| 3021 | 3-picoline + piperdine | 1 each | K2PtCl4 | acetate | 2.15E−03 |
| 3022 | 3-picoline + piperdine | 1 each | K2PtCl4 | propionate | 2.01E−03 |
| 3023 | 3-picoline + piperdine | 1 each | K2PtCl4 | butyrate | 2.24E−03 |
| 3024 | 3-picoline + piperdine | 1 each | K2PtCl4 | isobutyrate | 1.82E−03 |
| 3025 | 3-picoline + piperdine | 1 each | K2PtCl4 | 2-ketobutyrate | 2.16E−03 |
| 3026 | 3-picoline + piperdine | 1 each | K2PtCl4 | malonate | 2.64E−03 |
| 3027 | 3-picoline + piperdine | 1 each | K2PtCl4 | succinate | 2.26E−03 |
| 3028 | 3-aminobenzotrifluoride + piperdine | 1 each | K2PtCl4 | KCl | 2.91E−03 |
| 3029 | 3-aminobenzotrifluoride + piperdine | 1 each | K2PtCl4 | acetate | 1.84E−03 |
| 3030 | 3-aminobenzotrifluoride + piperdine | 1 each | K2PtCl4 | propionate | 1.90E−03 |
| 3031 | 3-aminobenzotrifluoride + piperdine | 1 each | K2PtCl4 | butyrate | 7.40E−04 |
| 3032 | 3-aminobenzotrifluoride + piperdine | 1 each | K2PtCl4 | isobutyrate | 1.50E−03 |
| 3033 | 3-aminobenzotrifluoride + piperdine | 1 each | K2PtCl4 | 2-ketobutyrate | 1.32E−03 |
| 3034 | 3-aminobenzotrifluoride + piperdine | 1 each | KtPtCl4 | malonate | 5.33E−04 |
| 3035 | 3-aminobenzotrifluoride + piperdine | 1 each | K2PtCl4 | succinate | 3.61E−04 |
| 3036 | 3-bromopyridine + 3,4-lutidine | 1 each | K2PtCl4 | KCl | 2.94E−03 |
| 3037 | 3-picoline + 3,4-lutidine | 1 each | K2PtCl4 | KCl | 2.31E−03 |
| 3038 | 4-picoline + 3,4-lutidine | 1 each | K2PtCl4 | KCl | 3.00E−03 |
| 3039 | 2-picoline + 3,4-lutidine | 1 each | K2PtCl4 | KCl | 2.03E−03 |
| 3040 | 2,4,6-trichloropyrimidine + 3,4-lutidine | 1 each | K2PtCl4 | KCl | 1.35E−03 |
| 3041 | piperidine + 3,4-lutidine | 1 each | K2PtCl4 | KCl | 2.05E−03 |
| 3042 | 3-aminobenzotrifluoride + 3,4-lutidine | 1 each | K2PtCl4 | KCl | 8.50E−03 |
| 3043 | 2-aminoethanol + 3,4-lutidine | 1 each | K2PtCl4 | KCl | 2.21E−03 |
| 3044 | 3-bromopyridine + 3,5-lutidine | 1 each | K2PtCl4 | KCl | 3.07E−03 |
| 3045 | 3-picoline + 3,5-lutidine | 1 each | K2PtCl4 | KCl | 2.79E−03 |
| 3046 | 4-picoline + 3,5-lutidine | 1 each | K2PtCl4 | KCl | 2.13E−03 |
| 3047 | 2-picoline + 3,5-lutidine | 1 each | K2PtCl4 | KCl | 3.03E−03 |
| 3048 | 2,4,6-trichloropyrimidine + 3,5-lutidine | 1 each | K2PtCl4 | KCl | 9.60E−04 |
| 3049 | piperidine + 3,5-lutidine | 1 each | K2PtCl4 | KCl | 3.48E−03 |
| 3050 | 3-aminobenzotrifluoride + 3,5-lutidine | 1 each | K2PtCl4 | KCl | 1.10E−03 |
| 3051 | 2-aminoethanol + 3,5-lutidine | 1 each | K2PtCl4 | KCl | 1.60E−03 |
| 3052 | 3-bromopyridine + 2-(2-hydroxyethyl)-pyridine | 1 each | K2PtCl4 | KCl | 1.39E−03 |
| 3053 | 3-picoline + 2-(2-hydroxyethyl)-pyridine | 1 each | K2PtCl4 | KCl | 2.57E−03 |
| 3054 | 3-picoline + 2-(2-hydroxyethyl)-pyridine | 1 each | K2PtCl4 | KCl | 4.09E−03 |
| 3055 | 2-picoline + 2-(2-hydroxyethyl)-pyridine | 1 each | K2PtCl4 | KCl | 2.41E−03 |
| 3056 | 2,4,6-trichloropyrimidine + 2-(2-hydroxyethyl)-pyridine | 1 each | K2PtCl4 | KCl | 1.76E−03 |
| 3057 | piperidine + 2-(2-hydroxyethyl)-pyridine | 1 each | K2PtCl4 | KCl | 3.05E−03 |
| 3058 | 3-aminobenzotrifluoride + 2-(2-hydroxyethyl)-pyridine | 1 each | K2PtCl4 | KCl | 1.45E−03 |
| 3059 | 2-aminoethanol + 2-(2-hydroxyethyl)-pyridine | 1 each | K2PtCl4 | KCl | 3.27E−03 |
| 3060 | 3-bromopyridine + D-(−)-penicillamine | 1 each | K2PtCl4 | KCl | 3.20E−03 |
| 3061 | 3-picoline + D-(−)-penicillamine | 1 each | K2PtCl4 | KCl | 1.23E−03 |
| 3062 | 4-picoline + D-(−)-penicillamine | 1 each | K2PtCl4 | KCl | 1.03E−03 |
| 3063 | 2-picoline + D-(−)-penicillamine | 1 each | K2PtCl4 | KCl | 5.28E−04 |
| 3064 | 2,4,6-trichloropyrimidine + D-(−)-penicillamine | 1 each | K2PtCl4 | KCl | 3.70E−04 |
| 3065 | piperidine + D-(−)-penicillamine | 1 each | K2PtCl4 | KCl | 7.35E−04 |
| 3066 | 3-aminobenzotrifluoride + D-(−)-penicillamine | 1 each | K2PtCl4 | KCl | 7.10E−04 |
| 3067 | 2-aminoethanol + D-(−)-penicillamine | 1 each | K2PtCl4 | KCl | 5.24E−04 |
| 3068 | 3-bromopyridine + cyclopentylamine | 1 each | K2PtCl4 | KCl | 2.33E−03 |
| 3069 | 3-picoline + cyclopentylamine | 1 each | K2PtCl4 | KCl | 3.55E−03 |
| 3070 | 4-picoline + cyclopentylamine | 1 each | K2PtCl4 | KCl | 3.80E−03 |
| 3071 | 2-picoline + cyclopentylamine | 1 each | K2PtCl4 | KCl | 4.38E−03 |
| 3072 | 2,4,6-trichloropyrimidine + cyclopentylamine | 1 each | K2PtCl4 | KCl | 2.36E−03 |
| 3073 | piperidine + cyclopentylamine | 1 each | K2PtCl4 | KCl | 3.67E−03 |
| 3074 | 3-aminobenzotrifluoride + cyclopentylamine | 1 each | K2PtCl4 | KCl | 2.37E−03 |
| 3075 | 2-aminoethanol + cyclopentylamine | 1 each | K2PtCl4 | KCl | 2.99E−03 |
| 3076 | 3-bromopyridine + tris(dimethylamino)-phosphine | 1 each | K2PtCl4 | KCl | 2.53E−03 |
| 3077 | 3-picoline + tris(dimethylamino)-phosphine | 1 each | K2PtCl4 | KCl | 2.46E−03 |
| 3078 | 4-picoline + tris(dimethylamino)-phosphine | 1 each | K2PtCl4 | KCl | 3.18E−03 |
| 3079 | 2-picoline + tris(dimethylamino)-phosphine | 1 each | K2PtCl4 | KCl | 2.24E−03 |
| 3080 | 2,4,6-trichloropyrimidine + tris(dimethylamino) phosphine | 1 each | K2PtCl4 | KCl | 1.10E−04 |

TABLE 1-continued

| No. | Ligand(s) | Equiv. | Precursor | Leaving Group | Yld, g atm Pt |
|---|---|---|---|---|---|
| 3081 | piperidine + tris(dimethylamino)-phosphine | 1 each | K2PtCl4 | KCl | 3.01E−03 |
| 3082 | 3-aminobenzotrifluoride + tris(dimethylamino)-phosphine | 1 each | K2PtCl4 | KCl | 1.99E−03 |
| 3083 | 2-aminoethanol + tris(dimethylamino)-phosphine | 1 each | K2PtCl4 | KCl | 1.17E−03 |
| 3084 | 3-bromopyridine + tris(2-aminoethyl)amine | 1 each | K2PtCl4 | KCl | 1.68E−03 |
| 3085 | 3-picoline + tris(2-aminoethyl)amine | 1 each | K2PtCl4 | KCl | 4.77E−04 |
| 3086 | 4-picoline + tris(2-aminoethyl)amine | 1 each | K2PtCl4 | KCl | 0.00E+00 |
| 3087 | 2-picoline + tris(2-aminoethyl)amine | 1 each | K2PtCl4 | KCl | 0.00E+00 |
| 3088 | 2,4,6-trichloropyrimidine + tris(2-aminoethyl)amine | 1 each | K2PtCl4 | KCl | 8.26E−05 |
| 3089 | piperidine + tris(2-aminoethyl)amine | 1 each | K2PtCl4 | KCl | 5.14E−04 |
| 3090 | 3-aminobenzotrifluoride + tris(2-aminoethyl)amine | 1 each | K2PtCl4 | KCl | 0.00E+00 |
| 3091 | 2-aminoethanol + tris(2-aminoethyl)amine | 1 each | K2PtCl4 | KCl | 0.00E+00 |
| 3092 | 3-bromopyridine + N-nitrosodiethylamine | 1 each | K2PtCl4 | KCl | 7.21E−04 |
| 3093 | 3-picoline + N-nitrosodiethylamine | 1 each | K2PtCl4 | KCl | 1.10E−03 |
| 3094 | 4-picoline + N-nitrosodiethylamine | 1 each | K2PtCl4 | KCl | 3.22E−03 |
| 3095 | 2-picoline + N-nitrosodiethylamine | 1 each | K2PtCl4 | KCl | 3.79E−03 |
| 3096 | 2,4,6-trichloropyrimidine + N-nitrosodiethylamine | 1 each | K2PtCl4 | KCl | 3.40E−04 |
| 3097 | piperidine + N-nitrosodiethylamine | 1 each | K2PtCl4 | KCl | 2.78E−03 |
| 3098 | 3-aminobenzotrifluoride + N-nitrosodiethylamine | 1 each | K2PtCl4 | KCl | 2.06E−04 |
| 3099 | 2-aminoethanol + N-nitrosodiethylamine | 1 each | K2PtCl4 | KCl | 1.87E−03 |
| 3100 | 3-bromopyridine + 3,5-pyrazoledicarboxylic acid | 1 each | K2PtCl4 | KCl | 5.69E−04 |
| 3101 | 3-picoline + 3,5-pyrazoledicarboxylic acid | 1 each | K2PtCl4 | KCl | 2.77E−03 |
| 3102 | 4-picoline + 3,5-pyrazoledicarboxylic acid | 1 each | K2PtCl4 | KCl | 4.18E−03 |
| 3103 | 2-picoline + 3,5-pyrazoledicarboxylic acid | 1 each | K2PtCl4 | KCl | 1.84E−03 |
| 3104 | 2,4,6-trichloropyrimidine + 3,5-pyrazoledicarboxylic acid | 1 each | K2PtCl4 | KCl | 2.77E−03 |
| 3105 | piperidine + 3,5-pyrazoledicarboxylic acid | 1 each | K2PtCl4 | KCl | 2.26E−03 |
| 3106 | 3-aminobenzotrifluoride + 3,5-pyrazoledicarboxylic acid | 1 each | K2PtCl4 | KCl | 3.07E−04 |
| 3107 | 2-aminoethanol + 3,5-pyrazoledicarboxylic acid | 1 each | K2PtCl4 | KCl | 2.71E−03 |
| 3108 | 3-bromopyridine + 2-amino-3-picoline | 1 each | K2PtCl4 | KCl | 2.19E−03 |
| 3109 | 3-picoline + 2-amino-3-picoline | 1 each | K2PtCl4 | KCl | 2.71E−03 |
| 3110 | 4-picoline + 2-amino-3-picoline | 1 each | K2PtCl4 | KCl | 3.36E−03 |
| 3111 | 2-picoline + 2-amino-3-picoline | 1 each | K2PtCl4 | KCl | 2.68E−03 |
| 3112 | 2,4,6-trichloropyrimidine + 2-amino-3-picoline | 1 each | K2PtCl4 | KCl | 2.05E−03 |
| 3113 | piperidine + 2-amino-3-picoline | 1 each | K2PtCl4 | KCl | 3.54E−03 |
| 3114 | 3-aminobenzotrifluoride + 2-amino-3-picoline | 1 each | K2PtCl4 | KCl | 2.05E−03 |
| 3115 | 2-aminoethanol + 2-amino-3-picoline | 1 each | K2PtCl4 | KCl | 2.70E−03 |
| 3116 | 3-bromopyridine + 1,4-dimethylpiperazine | 1 each | K2PtCl4 | KCl | 1.15E−03 |
| 3117 | 3-picoline + 1,4-dimethylpiperazine | 1 each | K2PtCl4 | KCl | 1.88E−03 |
| 3118 | 4-picoline + 1,4-dimethylpiperazine | 1 each | K2PtCl4 | KCl | 3.08E−03 |
| 3119 | 2-picoline + 1,4-dimethylpiperazine | 1 each | K2PtCl4 | KCl | 1.86E−03 |
| 3120 | 2,4,6-trichloropyrimidine + 1,4-dimethylpiperazine | 1 each | K2PtCl4 | KCl | 9.61E−05 |
| 3121 | piperidine + 1,4-dimethylpiperazine | 1 each | K2PtCl4 | KCl | 1.65E−03 |
| 3122 | 3-aminobenzotrifluoride + 1,4-dimethylpiperazine | 1 each | K2PtCl4 | KCl | 3.21E−04 |
| 3123 | 2-aminoethanol + 1,4-dimethylpiperazine | 1 each | K2PtCl4 | KCl | 1.70E−03 |
| 3124 | 3-bromopyridine + 2-amino-2-methyl-1-propanol | 1 each | K2PtCl4 | KCl | 2.06E−03 |
| 3125 | 3-picoline + 2-amino-2-methyl-1-propanol | 1 each | K2PtCl4 | KCl | 2.87E−03 |
| 3126 | 4-picoline + 2-amino-2-methyl-1-propanol | 1 each | K2PtCl4 | KCl | 3.48E−03 |
| 3127 | 2-picoline + 2-amino-2-methyl-1-propanol | 1 each | K2PtCl4 | KCl | 2.80E−03 |
| 3128 | 2,4,6-trichloropyrimidine + 2-amino-2-methyl-1-propanol | 1 each | K2PtCl4 | KCl | 5.78E−04 |
| 3129 | piperidine + 2-amino-2-methyl-1-propanol | 1 each | K2PtCl4 | KCl | 1.81E−03 |
| 3130 | 3-aminobenzotrifluoride + 2-amino-2-methyl-1-propanol | 1 each | K2PtCl4 | KCl | 6.45E−04 |
| 3131 | 2-aminoethanol + 2-amino-2-methyl-1-propanol | 1 each | K2PtCl4 | KCl | 1.48E−03 |
| 3132 | ammonia + 3,4-lutidine | 1 each | K2PtCl4 | KCl | 2.10E−03 |
| 3133 | ammonia + 3,4-lutidine | 1 each | K2PtCl4 | acetate | 1.90E−03 |
| 3134 | ammonia + 3,4-lutidine | 1 each | K2PtCl4 | propionate | 1.75E−03 |
| 3135 | ammonia + 3,4-lutidine | 1 each | K2PtCl4 | butyrate | 2.01E−03 |
| 3136 | ammonia + 3,4-lutidine | 1 each | K2PtCl4 | isobutyrate | 2.10E−03 |
| 3137 | ammonia + 3,4-lutidine | 1 each | K2PtCl4 | 2-ketobutyrate | 2.09E−03 |
| 3138 | ammonia + 3,4-lutidine | 1 each | K2PtCl4 | malonate | 1.57E−03 |
| 3139 | ammonia + 3,4-lutidine | 1 each | K2PtCl4 | succinate | 1.97E−03 |
| 3140 | ammonia + 3,5-lutidine | 1 each | K2PtCl4 | KCl | 1.99E−03 |
| 3141 | ammonia + 3,5-lutidine | 1 each | K2PtCl4 | acetate | 1.73E−03 |

TABLE 1-continued

| No. | Ligand(s) | Equiv. | Precursor | Leaving Group | Yld, g atm Pt |
|---|---|---|---|---|---|
| 3142 | ammonia + 3,5-lutidine | 1 each | K2PtCl4 | propionate | 2.31E−03 |
| 3143 | ammonia + 3,5-lutidine | 1 each | K2PtCl4 | butyrate | 2.12E−03 |
| 3144 | ammonia + 3,5-lutidine | 1 each | K2PtCl4 | isobutyrate | 1.23E−03 |
| 3145 | ammonia + 3,5-lutidine | 1 each | K2PtCl4 | 2-ketobutyrate | 2.08E−03 |
| 3146 | ammonia + 3,5-lutidine | 1 each | K2PtCl4 | malonate | 1.53E−03 |
| 3147 | ammonia + 3,5-lutidine | 1 each | K2PtCl4 | succinate | 8.60E−04 |
| 3148 | ammonia + 2-(2-hydroxyethyl)-pyridine | 1 each | K2PtCl4 | KCl | 1.31E−03 |
| 3149 | ammonia + 2-(2-hydroxyethyl)-pyridine | 1 each | K2PtCl4 | acetate | 1.42E−03 |
| 3150 | ammonia + 2-(2-hydroxyethyl)-pyridine | 1 each | K2PtCl4 | propionate | 2.49E−03 |
| 3151 | ammonia + 2-(2-hydroxyethyl)-pyridine | 1 each | K2PtCl4 | butyrate | 1.68E−03 |
| 3152 | ammonia + 2-(2-hydroxyethyl)-pyridine | 1 each | K2PtCl4 | isobutyrate | 1.90E−03 |
| 3153 | ammonia + 2-(2-hydroxyethyl)-pyridine | 1 each | K2PtCl4 | 2-ketobutyrate | 1.86E−03 |
| 3154 | ammonia + 2-(2-hydroxyethyl)-pyridine | 1 each | K2PtCl4 | malonate | 1.76E−03 |
| 3155 | ammonia + 2-(2-hydroxyethyl)-pyridine | 1 each | K2PtCl4 | succinate | 1.20E−03 |
| 3156 | ammonia + D-(−)-penicillamine | 1 each | K2PtCl4 | KCl | 1.43E−03 |
| 3157 | ammonia + D-(−)-penicillamine | 1 each | K2PtCl4 | acetate | 3.73E−04 |
| 3158 | ammonia + D-(−)-penicillamine | 1 each | K2PtCl4 | propionate | 7.35E−04 |
| 3159 | ammonia + D-(−)-penicillamine | 1 each | K2PtCl4 | butyrate | 6.63E−04 |
| 3160 | ammonia + D-(−)-penicillamine | 1 each | K2PtCl4 | isobutyrate | 7.33E−04 |
| 3161 | ammonia + D-(−)-penicillamine | 1 each | K2PtCl4 | 2-ketobutyrate | 6.33E−04 |
| 3162 | ammonia + D-(−)-penicillamine | 1 each | K2PtCl4 | malonate | 7.02E−04 |
| 3163 | ammonia + D-(−)-penicillamine | 1 each | K2PtCl4 | succinate | 9.19E−04 |
| 3164 | ammonia + cyclopentylamine | 1 each | K2PtCl4 | KCl | 1.74E−03 |
| 3165 | ammonia + cyclopentylamine | 1 each | K2PtCl4 | acetate | 1.70E−03 |
| 3166 | ammonia + cyclopentylamine | 1 each | K2PtCl4 | propionate | 2.56E−03 |
| 3167 | ammonia + cyclopentylamine | 1 each | K2PtCl4 | butyrate | 1.85E−03 |
| 3168 | ammonia + cyclopentylamine | 1 each | K2PtCl4 | isobutyrate | 1.72E−03 |
| 3169 | ammonia + cyclopentylamine | 1 each | K2PtCl4 | 2-ketobutyrate | 2.46E−03 |
| 3170 | ammonia + cyclopentylamine | 1 each | K2PtCl4 | malonate | 9.76E−04 |
| 3171 | ammonia + cyclopentylamine | 1 each | K2PtCl4 | succinate | 1.01E−03 |
| 3172 | ammonia + tris(dimethylamino)-phosphine | 1 each | K2PtCl4 | KCl | 2.17E−03 |
| 3173 | ammonia + tris(dimethylamino)-phosphine | 1 each | K2PtCl4 | acetate | 2.26E−03 |
| 3174 | ammonia + tris(dimethylamino)-phosphine | 1 each | K2PtCl4 | propionate | 2.69E−03 |
| 3175 | ammonia + tris(dimethylamino)-phosphine | 1 each | K2PtCl4 | butyrate | 2.55E−03 |
| 3176 | ammonia + tris(dimethylamino)-phosphine | 1 each | K2PtCl4 | isobutyrate | 1.95E−03 |
| 3177 | ammonia + tris(dimethylamino)-phosphine | 1 each | K2PtCl4 | 2-ketobutyrate | 2.83E−03 |
| 3178 | ammonia + tris(dimethylamino)-phosphine | 1 each | K2PtCl4 | malonate | 4.17E−03 |
| 3179 | ammonia + tris(dimethylamino)-phosphine | 1 each | K2PtCl4 | succinate | 1.56E−03 |
| 3180 | ammonia + tris(2-aminoethyl)amine | 1 each | K2PtCl4 | KCl | 2.23E−03 |
| 3181 | ammonia + tris(2-aminoethyl)amine | 1 each | K2PtCl4 | acetate | 1.02E−03 |
| 3182 | ammonia + tris(2-aminoethyl)amine | 1 each | K2PtCl4 | propionate | 5.85E−04 |
| 3183 | ammonia + tris(2-aminoethyl)amine | 1 each | K2PtCl4 | butyrate | 2.30E−04 |
| 3184 | ammonia + tris(2-aminoethyl)amine | 1 each | K2PtCl4 | isobutyrate | 5.00E−04 |
| 3185 | ammonia + tris(2-aminoethyl)amine | 1 each | K2PtCl4 | 2-ketobutyrate | 7.82E−04 |
| 3186 | ammonia + tris(2-aminoethyl)amine | 1 each | K2PtCl4 | malonate | 2.14E−04 |
| 3187 | ammonia + tris(2-aminoethyl)amine | 1 each | K2PtCl4 | succinate | 4.19E−04 |
| 3188 | ammonia + N-nitrosodiethylamine | 1 each | K2PtCl4 | KCl | 8.50E−04 |
| 3189 | ammonia + N-nitrosodiethylamine | 1 each | K2PtCl4 | acetate | 7.50E−04 |
| 3190 | ammonia + N-nitrosodiethylamine | 1 each | K2PtCl4 | propionate | 4.29E−04 |
| 3191 | ammonia + N-nitrosodiethylamine | 1 each | K2PtCl4 | butyrate | 6.46E−04 |
| 3192 | ammonia + N-nitrosodiethylamine | 1 each | K2PtCl4 | isobutyrate | 7.22E−04 |
| 3193 | ammonia + N-nitrosodiethylamine | 1 each | K2PtCl4 | 2-ketobutyrate | 7.40E−04 |
| 3194 | ammonia + N-nitrosodiethylamine | 1 each | K2PtCl4 | malonate | 2.26E−04 |
| 3195 | ammonia + N-nitrosodiethylamine | 1 each | K2PtCl4 | succinate | 4.88E−04 |
| 3196 | ammonia + 3,5-pyrazoledicarboxylic acid | 1 each | K2PtCl4 | KCl | 8.96E−04 |
| 3197 | ammonia + 3,5-pyrazoledicarboxylic acid | 1 each | K2PtCl4 | acetate | 6.05E−04 |
| 3198 | ammonia + 3,5-pyrazoledicarboxylic acid | 1 each | K2PtCl4 | propionate | 5.85E−04 |
| 3199 | ammonia + 3,5-pyrazoledicarboxylic acid | 1 each | K2PtCl4 | butyrate | 7.54E−04 |
| 3200 | ammonia + 3,5-pyrazoledicarboxylic acid | 1 each | K2PtCl4 | isobutyrate | 1.27E−03 |
| 3201 | ammonia + 3,5-pyrazoledicarboxylic acid | 1 each | K2PtCl4 | 2-ketobutyrate | 8.56E−04 |
| 3202 | ammonia + 3,5-pyrazoledicarboxylic acid | 1 each | K2PtCl4 | malonate | 5.92E−04 |
| 3203 | ammonia + 3,5-pyrazoledicarboxylic acid | 1 each | K2PtCl4 | succinate | 6.04E−04 |
| 3204 | ammonia + 2-amino-3-picoline | 1 each | K2PtCl4 | KCl | 2.96E−03 |
| 3205 | ammonia + 2-amino-3-picoline | 1 each | K2PtCl4 | acetate | 2.40E−03 |
| 3206 | ammonia + 2-amino-3-picoline | 1 each | K2PtCl4 | propionate | 1.79E−03 |
| 3207 | ammonia + 2-amino-3-picoline | 1 each | K2PtCl4 | butyrate | 1.93E−03 |
| 3208 | ammonia + 2-amino-3-picoline | 1 each | K2PtCl4 | isobutyrate | 3.76E−03 |
| 3209 | ammonia + 2-amino-3-picoline | 1 each | K2PtCl4 | 2-ketobutyrate | 3.05E−03 |
| 3210 | ammonia + 2-amino-3-picoline | 1 each | K2PtCl4 | malonate | 1.78E−03 |
| 3211 | ammonia + 2-amino-3-picoline | 1 each | K2PtCl4 | succinate | 2.26E−03 |
| 3212 | ammonia + 1,4-dimethylpiperazine | 1 each | K2PtCl4 | KCl | 1.98E−03 |
| 3213 | ammonia + 1,4-dimethylpiperazine | 1 each | K2PtCl4 | acetate | 1.72E−03 |
| 3214 | ammonia + 1,4-dimethylpiperazine | 1 each | K2PtCl4 | propionate | 2.11E−03 |
| 3215 | ammonia + 1,4-dimethylpiperazine | 1 each | K2PtCl4 | butyrate | 1.66E−03 |
| 3216 | ammonia + 1,4-dimethylpiperazine | 1 each | K2PtCl4 | isobutyrate | 1.65E−03 |
| 3217 | ammonia + 1,4-dimethylpiperazine | 1 each | K2PtCl4 | 2-ketobutyrate | 1.62E−03 |
| 3218 | ammonia + 1,4-dimethylpiperazine | 1 each | K2PtCl4 | malonate | 1.15E−03 |

TABLE 1-continued

| No. | Ligand(s) | Equiv. | Precursor | Leaving Group | Yld, g atm Pt |
|---|---|---|---|---|---|
| 3219 | ammonia + 1,4-dimethylpiperazine | 1 each | K2PtCl4 | succinate | 7.85E-04 |
| 3220 | ammonia + 2-amino-2-methyl-1-propanol | 1 each | K2PtCl4 | KCl | 1.50E-03 |
| 3221 | ammonia + 2-amino-2-methyl-1-propanol | 1 each | K2PtCl4 | acetate | 2.99E-03 |
| 3222 | ammonia + 2-amino-2-methyl-1-propanol | 1 each | K2PtCl4 | propionate | 2.92E-03 |
| 3223 | ammonia + 2-amino-2-methyl-1-propanol | 1 each | K2PtCl4 | butyrate | 1.82E-03 |
| 3224 | ammonia + 2-amino-2-methyl-1-propanol | 1 each | K2PtCl4 | isobutyrate | 2.04E-03 |
| 3225 | ammonia + 2-amino-2-methyl-1-propanol | 1 each | K2PtCl4 | 2-ketobutyrate | 1.90E-03 |
| 3226 | ammonia + 2-amino-2-methyl-1-propanol | 1 each | K2PtCl4 | malonate | 1.31E-03 |
| 3227 | ammonia + 2-amino-2-methyl-1-propanol | 1 each | K2PtCl4 | succinate | 1.75E-03 |
| 3228 | 3-bromopyridine + 3,4-lutidine | 1 each | K2PtCl4 | acetate | 6.25E-04 |
| 3229 | 3-picoline + 3,4-lutidine | 1 each | K2PtCl4 | acetate | 7.46E-04 |
| 3230 | 4-picoline + 3,4-lutidine | 1 each | K2PtCl4 | acetate | 5.83E-04 |
| 3231 | 2-picoline + 3,4-lutidine | 1 each | K2PtCl4 | acetate | 1.56E-03 |
| 3232 | 2,4,6-trichloropyrimidine + 3,4-lutidine | 1 each | K2PtCl4 | acetate | 5.63E-04 |
| 3233 | piperidine + 3,4-lutidine | 1 each | K2PtCl4 | acetate | 1.70E-03 |
| 3234 | 3-aminobenzotrifluoride + 3,4-lutidine | 1 each | K2PtCl4 | acetate | 4.74E-04 |
| 3235 | 2-aminoethanol + 3,4-lutidine | 1 each | K2PtCl4 | acetate | 9.86E-04 |
| 3236 | 3-bromopyridine + 3,5-lutidine | 1 each | K2PtCl4 | acetate | 5.22E-05 |
| 3237 | 3-picoline + 3,5-lutidine | 1 each | K2PtCl4 | acetate | 7.68E-04 |
| 3238 | 4-picoline + 3,5-lutidine | 1 each | K2PtCl4 | acetate | 1.07E-03 |
| 3239 | 2-picoline + 3,5-lutidine | 1 each | K2PtCl4 | acetate | 7.52E-04 |
| 3240 | 2,4,6-trichloropyrimidine + 3,5-lutidine | 1 each | K2PtCl4 | acetate | 4.21E-04 |
| 3241 | piperidine + 3,5-lutidine | 1 each | K2PtCl4 | acetate | 5.63E-04 |
| 3242 | 3-aminobenzotrifluoride + 3,5-lutidine | 1 each | K2PtCl4 | acetate | 4.11E-04 |
| 3243 | 2-aminoethanol + 3,5-lutidine | 1 each | K2PtCl4 | acetate | 1.65E-04 |
| 3244 | 3-bromopyridine + 2-(2-hydroxyethyl)-pyridine | 1 each | K2PtCl4 | acetate | 2.82E-04 |
| 3245 | 3-picoline + 2-(2-hydroxyethyl)-pyridine | 1 each | K2PtCl4 | acetate | 6.33E-04 |
| 3246 | 4-picoline + 2-(2-hydroxyethyl)-pyridine | 1 each | K2PtCl4 | acetate | 1.09E-03 |
| 3247 | 2-picoline + 2-(2-hydroxyethyl)-pyridine | 1 each | K2PtCl4 | acetate | 6.69E-04 |
| 3248 | 2,4,6-trichloropyrimidine + 2-(2-hydroxyethyl)pyridine | 1 each | K2PtCl4 | acetate | 2.25E-04 |
| 3249 | piperidine + 2-(2-hydroxyethyl)-pyridine | 1 each | K2PtCl4 | acetate | 6.76E-04 |
| 3250 | 3-aminobenzotrifluoride + 2-(2-hydroxyethyl)-pyridine | 1 each | K2PtCl4 | acetate | 1.81E-04 |
| 3251 | 2-aminoethanol + 2-(2-hydroxyethyl)-pyridine | 1 each | K2PtCl4 | acetate | 5.86E-04 |
| 3252 | 3-bromopyridine + D-(-)-penicillamine | 1 each | K2PtCl4 | acetate | 5.73E-05 |
| 3253 | 3-picoline + D-(-)-penicillamine | 1 each | K2PtCl4 | acetate | 0.00E+00 |
| 3254 | 4-picoline + D-(-)-penicillamine | 1 each | K2PtCl4 | acetate | 4.38E-07 |
| 3255 | 2-picoline + D-(-)-penicillamine | 1 each | K2PtCl4 | acetate | 0.00E+00 |
| 3256 | 2,4,6-trichloropyrimidine + D-(-)-penicillamine | 1 each | K2PtCl4 | acetate | 0.00E+00 |
| 3257 | piperidine + D-(-)-penicillamine | 1 each | K2PtCl4 | acetate | 0.00E+00 |
| 3258 | 3-aminobenzotrifluoride + D-(-)-penicillamine | 1 each | K2PtCl4 | acetate | 0.00E+00 |
| 3259 | 2-aminoethanol + D-(-)-penicillamine | 1 each | K2PtCl4 | acetate | 0.00E+00 |
| 3260 | 3-bromopyridine + cyclopentylamine | 1 each | K2PtCl4 | actaate | 4.19E-04 |
| 3261 | 3-picoline + cyclopentylamine | 1 each | K2PtCl4 | acetate | 8.81E-04 |
| 3262 | 4-picoline + cyclopentylamine | 1 each | K2PtCl4 | acetate | 1.89E-03 |
| 3263 | 2-picoline + cyclopentylaimine | 1 each | K2PtCl4 | acetate | 8.51E-04 |
| 3264 | 2,4,6-trichloropyrimidine + cyclopentylamine | 1 each | K2PtCl4 | acetate | 7.04E-04 |
| 3265 | piperidine + cyclopentylaimine | 1 each | K2PtCl4 | acetate | 8.24E-04 |
| 3266 | 3-aminobenzotrifluoride + cyclopentylamine | 1 each | K2PtCl4 | acetate | 6.29E-04 |
| 3267 | 2-aminoethanol + cyclopentylamine | 1 each | K2PtCl4 | acetate | 7.98E-04 |
| 3268 | 3-bromopyridine + tris(dimethylamino)-phosphine | 1 each | K2PtCl4 | acetate | 5.94E-04 |
| 3269 | 3-picoline + tris(dimethylamino)-phosphine | 1 each | K2PtCl4 | acetate | 9.45E-04 |
| 3270 | 4-picoline + tris(dimethylamino)-phosphine | 1 each | K2PtCl4 | acetate | 1.70E-03 |
| 3271 | 2-picoline + tris(dimethylamino)-phosphine | 1 each | K2PtCl4 | acetate | 1.30E-03 |
| 3272 | 2,4,6-trichloropyrimidine + tris(dimethylamino)phosphine | 1 each | K2PtCl4 | acetate | 2.46E-04 |
| 3273 | piperidine + tris(dimethylamino)-phosphine | 1 each | K2PtCl4 | acetate | 1.63E-03 |
| 3274 | 3-aminobenzotrifluoride + tris(dimethylamino)-phosphine | 1 each | K2PtCl4 | acetate | 5.63E-04 |
| 3275 | 2-aminoethanol + tris(dimethylamino)-phosphine | 1 each | K2PtCl4 | acetate | 4.38E-04 |
| 3276 | 3-bromopyridine + tris(2-aminoethyl)amine | 1 each | K2PtCl4 | acetate | 9.67E-05 |
| 3277 | 3-picoline + tris(2-aminoethyl)amine | 1 each | K2PtCl4 | acetate | 6.24E-05 |
| 3278 | 4-picoline + tris(2-aminoethyl)amine | 1 each | K2PtCl4 | acetate | 0.00E+00 |
| 3279 | 2-picoline + tris(2-aminoethyl)amine | 1 each | K2PtCl4 | acetate | 0.00E+00 |
| 3280 | 2,4,6-trichloropyrimidine + tris(2-aminoethyl)amine | 1 each | K2PtCl4 | acetate | 0.00E+00 |
| 3281 | piperidine + tris(2-aminoethyl)amine | 1 each | K2PtCl4 | acetate | 0.00E+00 |
| 3282 | 3-aminobenzotrifluoride + tris(2-aminoethyl)amine | 1 each | K2PtCl4 | acetate | 0.00E+00 |
| 3283 | 2-aminoethanol + tris(2-aminoethyl)amine | 1 each | K2PtCl4 | acetate | 0.00E+00 |
| 3284 | 3-bromopyridine + N-nitrosodiethylamine | 1 each | K2PtCl4 | acetate | 2.33E-04 |
| 3285 | 3-picoline + N-nitrosodiethylamine | 1 each | K2PtCl4 | acetate | 6.38E-06 |
| 3286 | 4-picoline + N-nitrosodiethylamine | 1 each | K2PtCl4 | acetate | 2.42E-03 |
| 3287 | 2-picoline + N-nitrosodiethylamine | 1 each | K2PtCl4 | acetate | 1.03E-03 |

TABLE 1-continued

| No. | Ligand(s) | Equiv. | Precursor | Leaving Group | Yld, g atm Pt |
|---|---|---|---|---|---|
| 3288 | 2,4,6-trichloropyrimidine + N-nitrosodiethylamine | 1 each | K2PtCl4 | acetate | 0.00E+00 |
| 3289 | piperidine + N-nitrosodiethylamine | 1 each | K2PtCl4 | acetate | 1.92E−03 |
| 3290 | 3-aminobenzotrifluoride + N-nitrosodiethylamine | 1 each | K2PtCl4 | acetate | 2.08E−04 |
| 3291 | 2-aminoethanol + N-nitrosodiethylamine | 1 each | K2PtCl4 | acetate | 1.10E−04 |
| 3292 | 3-bromopyridine + 3,5-pyrazoledicarboxylic acid | 1 each | K2PtCl4 | acetate | 1.31E−04 |
| 3293 | 3-picoline + 3,5-pyrazoledicarboxylic acid | 1 each | K2PtCl4 | acetate | 7.44E−05 |
| 3294 | 4-picoline + 3,5-pyrazoledicarboxylic acid | 1 each | K2PtCl4 | acetate | 4.47E−03 |
| 3295 | 2-picoline + 3,5-pyrazoledicarboxylic acid | 1 each | K2PtCl4 | acetate | 4.88E−04 |
| 3296 | 2,4,6-trichloropyrimidine + 3,5-pyrazoledicarboxylic acid | 1 each | K2PtCl4 | acetate | 0.00E+00 |
| 3297 | piperidine + 3,5-pyrazoledicarboxylic acid | 1 each | K2PtCl4 | acetate | 3.37E−04 |
| 3298 | 3-aminobenzotrifluoride + 3,5-pyrazoledicarboxylic acid | 1 each | K2PtCl4 | acetate | 0.00E+00 |
| 3299 | 2-aminoethanol + 3,5-pyrazoledicarboxylic acid | 1 each | K2PtCl4 | acetate | 1.06E−03 |
| 3300 | 3-bromopyridine + 2-amino-3-picoline | 1 each | K2PtCl4 | acetate | 0.00E+00 |
| 3301 | 3-picoline + 2-amino-3-picoline | 1 each | K2PtCl4 | acetate | 0.00E+00 |
| 3302 | 4-picoline + 2-amino-3-picoline | 1 each | K2PtCl4 | acetate | 2.53E−04 |
| 3303 | 2-picoline + 2-amino-3-picoline | 1 each | K2PtCl4 | acetate | 7.96E−05 |
| 3304 | 2,4,6-trichloropyrimidine + 2-amino-3-picoline | 1 each | K2PtCl4 | acetate | 4.78E−04 |
| 3305 | piperidine + 2-amino-3-picoline | 1 each | K2PtCl4 | acetate | 0.00E+00 |
| 3306 | 3-aminobenzotrifluoride + 2-amino-3-picoline | 1 each | K2PtCl4 | acetate | 2.36E−04 |
| 3307 | 2-aminoethanol + 2-amino-3-picoline | 1 each | K2PtCl4 | acetate | 9.82E−05 |
| 3308 | 3-bromopyridine + 1,4-dimethylpiperazine | 1 each | K2PtCl4 | acetate | 4.14E−04 |
| 3309 | 3-picoline + 1,4-dimethylpiperazine | 1 each | K2PtCl4 | acetate | 1.15E−03 |
| 3310 | 4-picoline + 1,4-dimethylpiperazine | 1 each | K2PtCl4 | acetate | 1.98E−03 |
| 3311 | 2-picoline + 1,4-dimethylpiperazine | 1 each | K2PtCl4 | acetate | 0.00E+00 |
| 3312 | 2,4,6-trichloropyrimidine + 1,4-dimethylpiperazine | 1 each | K2PtCl4 | acetate | 0.00E+00 |
| 3313 | piperidine + 1,4-dimethylpiperazine | 1 each | K2PtCl4 | acetate | 0.00E+00 |
| 3314 | 3-aminobenzotrifluoride + 1,4-dimethylpiperazine | 1 each | K2PtCl4 | acetate | 0.00E+00 |
| 3315 | 2-aminoethanol + 1,4-dimethylpiperazine | 1 each | K2PtCl4 | acetate | 2.39E−04 |
| 3316 | 3-bromopyridine + 2-amino-2-methyl-1-propanol | 1 each | K2PtCl4 | acetate | 2.44E−04 |
| 3317 | 3-picoline + 2-amino-2-methyl-1-propanol | 1 each | K2PtCl4 | acetate | 1.21E−04 |
| 3318 | 4-picoline + 2-amino-2-methyl-1-propanol | 1 each | K2PtCl4 | acetate | 2.03E−03 |
| 3319 | 2-picoline + 2-amino-2-methyl-1-propanol | 1 each | K2PtCl4 | acetate | 5.60E−04 |
| 3320 | 2,4,6-trichloropyrimidine + 2-amino-2-methyl-1-propanol | 1 each | K2PtCl4 | acetate | 2.87E−04 |
| 3321 | piperidine + 2-amino-2-methyl-1-propanol | 1 each | K2PtCl4 | acetate | 6.02E−04 |
| 3322 | 3-aminobenzotrifluoride + 2-amino-2-methyl-1-propanol | 1 each | K2PtCl4 | acetate | 4.06E−04 |
| 3323 | 2-aminoethanol + 2-amino-2-methyl-1-propanol | 1 each | K2PtCl4 | acetate | 1.03E−03 |
| 3324 | isopropylamine + 3,4-lutidine | 1 each | K2PtCl4 | KCl | 1.88E−03 |
| 3325 | isopropylamine + 3,4-lutidine | 1 each | K2PtCl4 | acetate | 1.45E−03 |
| 3326 | isopropylamine + 3,4-lutidine | 1 each | K2PtCl4 | propionate | 2.20E−03 |
| 3327 | isopropylamine + 3,4-lutidine | 1 each | K2PtCl4 | butyrtate | 1.76E−03 |
| 3328 | isopropylamine + 3,4-lutidine | 1 each | K2PtCl4 | isobutyrate | 1.83E−03 |
| 3329 | isopropylamine + 3,4-lutidine | 1 each | K2PtCl4 | 2-ketobutyrate | 2.04E−03 |
| 3330 | isopropylamine + 3,4-lutidine | 1 each | K2PtCl4 | malonate | 1.82E−03 |
| 3331 | isopropylamine + 3,4-lutidine | 1 each | K2PtCl4 | succinate | 1.10E−03 |
| 3332 | isopropylamine + 3,5-lutidine | 1 each | K2PtCl4 | KCl | 1.03E−03 |
| 3333 | isopropylamine + 3,5-lutidine | 1 each | K2PtCl4 | acetate | 6.19E−04 |
| 3334 | isopropylamine + 3,5-lutidine | 1 each | K2PtCl4 | propionate | 1.11E−03 |
| 3335 | isopropylamine + 3,5-lutidine | 1 each | K2PtCl4 | butyrate | 1.34E−03 |
| 3336 | isopropylamine + 3,5-lutidine | 1 each | K2PtCl4 | isobutyrate | 1.43E−03 |
| 3337 | isopropylamine + 3,5-lutidine | 1 each | K2PtCl4 | 2-ketobutyrate | 9.81E−04 |
| 3338 | isopropylamine + 3,5-lutidine | 1 each | K2PtCl4 | malonate | 1.64E−03 |
| 3339 | isopropylamine + 3,5-lutidine | 1 each | K2PtCl4 | succinate | 6.70E−04 |
| 3340 | iscpropylamine + 2-(2-hydroxyethyl)-pyridine | 1 each | K2PtCl4 | KCl | 1.03E−03 |
| 3341 | isopropylamine + 2-(2-hydroxyethyl)-pyridine | 1 each | K2PtCl4 | acetate | 1.10E−03 |
| 3342 | isopropylamine + 2-(2-hydroxyethyl)-pyridine | 1 each | K2PtCl4 | propionate | 1.57E−03 |
| 3343 | isopropylamine + 2-(2-hydroxyethyl)-pyridine | 1 each | K2PtCl4 | butyrate | 1.36E−03 |
| 3344 | isopropylamine + 2-(2-hydroxyethyl)-pyridine | 1 each | K2PtCl4 | isobutyrate | 1.41E−03 |
| 3345 | isopropylamine + 2-(2-hydroxyethyl)-pyridine | 1 each | K2PtCl4 | 2-ketobutyrate | 1.48E−03 |
| 3346 | isopropylamine + 2-(2-hydroxyethyl)-pyridine | 1 each | K2PtCl4 | malonate | 1.35E−03 |
| 3347 | isopropylamine + 2-(2-hydroxyethyl)-pyridine | 1 each | K2PtCl4 | succinate | 1.16E−03 |
| 3348 | isopropylamine + D-(−)-penicillamine | 1 each | K2PtCl4 | KCl | 3.88E−03 |
| 3349 | isopropylamine + D-(−)-penicillamine | 1 each | K2PtCl4 | acetate | 5.09E−04 |
| 3350 | isopropylamine + D-(−)-penicillamine | 1 each | K2PtCl4 | propionate | 7.53E−04 |
| 3351 | isopropylamine + D-(−)-penicillamine | 1 each | K2PtCl4 | butyrate | 7.99E−04 |
| 3352 | isopropylamine + D-(−)-penicillamine | 1 each | K2PtCl4 | isobutyrate | 6.80E−04 |

TABLE 1-continued

| No. | Ligand(s) | Equiv. | Precursor | Leaving Group | Yld, g atm Pt |
|---|---|---|---|---|---|
| 3353 | isopropylamine + D-(−)-penicillamine | 1 each | K2PtCl4 | 2-ketobutyrate | 6.00E−04 |
| 3354 | isopropylamine + D-(−)-penicillamine | 1 each | K2PtCl4 | malonate | 1.18E−03 |
| 3355 | isopropylamine + D-(−)-penicillamine | 1 each | K2PtCl4 | succinate | 0.00E+00 |
| 3356 | isopropylamine + cyclopentylamine | 1 each | K2PtCl4 | KCl | 6.21E−04 |
| 3357 | isopropylamine + cyclopentylamine | 1 each | K2PtCl4 | acetate | 1.25E−03 |
| 3358 | isopropylamine + cyclopentylamine | 1 each | K2PtCl4 | propionate | 8.09E−04 |
| 3359 | isopropylamine + cyclopentylamine | 1 each | K2PtCl4 | butyrate | 6.11E−04 |
| 3360 | isopropylamine + cyclopentylamine | 1 each | K2PtCl4 | isobutyrate | 8.12E−04 |
| 3361 | isopropylamine + cyclopentylamine | 1 each | KtPICl4 | 2-ketobutyrate | 5.48E−04 |
| 3362 | isopropylamine + cyclopentylamine | 1 each | K2PtCl4 | malonate | 7.18E−04 |
| 3363 | isopropylamine + cyclopentylamine | 1 each | K2PtCl4 | succinate | 2.03E−05 |
| 3364 | isopropylamine + tris(dimethylamino)-phosphine | 1 each | K2PtCl4 | KCl | 1.14E−04 |
| 3365 | isopropylamine + tris(dimethylamino)-phosphine | 1 each | K2PtCl4 | acetate | 1.49E−03 |
| 3366 | isopropylamine + tris(dimethylamino)-phosphine | 1 each | K2PtCl4 | propionate | 7.18E−04 |
| 3367 | isopropylamine + tris(dimethylamino)-phosphine | 1 each | K2PtCl4 | butyrate | 9.49E−04 |
| 3368 | isopropylamine + tris(dimethylamino)-phosphine | 1 each | K2PtCl4 | isobutysate | 2.94E−04 |
| 3369 | isopropylamine + tris(dimethylamino)-phosphine | 1 each | KtPICl4 | 2-ketobutyrate | 0.00E+00 |
| 3370 | isopropylamine + tris(dimethylamino)-phosphine | 1 each | K2PtCl4 | malonate | 6.76E−04 |
| 3371 | isopropylamine + tris(dimethylamino)-phosphine | 1 each | K2PtCl4 | succinate | 8.22E−05 |
| 3372 | isopropylamine + tris(2-aminoethyl)amine | 1 each | K2PtCl4 | KCl | 0.00E+00 |
| 3373 | isopropylamine + tris(2-aminoethyl)amine | 1 each | K2PtCl4 | acetate | 0.00E+00 |
| 3374 | isopropylamine + tris(2-aminoethyl)amine | 1 each | K2PtCl4 | propionate | 0.00E+00 |
| 3375 | isopropylamine + tris(2-aminoethyl)amine | 1 each | K2PtCl4 | butyrate | 0.00E+00 |
| 3376 | isopropylamine + tris(2-aminoethyl)amine | 1 each | K2PtCl4 | isobutyrate | 0.00E+00 |
| 3377 | isopropylamine + tris(2-aminoethyl)amine | 1 each | KtPICl4 | 2-ketobutyrate | 0.00E+00 |
| 3378 | isopropylamine + tris(2-aminoethyl)amine | 1 each | K2PtCl4 | malonate | 0.00E+00 |
| 3379 | isopropylamine + tris(2-aminoethyl)amine | 1 each | K2PtCl4 | succinate | 0.00E+00 |
| 3380 | isopropylamine + N-nitrosodiethylamine | 1 each | K2PtCl4 | KCl | 5.77E−05 |
| 3381 | isopropylamine + N-nitrosodiethylamine | 1 each | K2PtCl4 | acetate | 0.00E+00 |
| 3382 | isopropylamine + N-nitrosodiethylamine | 1 each | K2PtCl4 | propionate | 2.10E−04 |
| 3383 | isopropylamine + N-nitrosodiethylamine | 1 each | K2PtCl4 | butyrate | 2.75E−03 |
| 3384 | isopropylamine + N-nitrosodiethylamine | 1 each | K2PtCl4 | isobutyrate | 0.00E+00 |
| 3385 | isopropylamine + N-nitrosodiethylamine | 1 each | KtPICl4 | 2-ketobutyrate | 4.68E−04 |
| 3386 | isopropylamine + N-nitrosodiethylamine | 1 each | K2PtCl4 | malonate | 8.83E−04 |
| 3387 | isopropylamine + N-nitrosodiethylamine | 1 each | K2PtCl4 | succinate | 9.29E−04 |
| 3388 | isopropylamine + 3-aminobenzotrifluoride | 1 each | K2PtCl4 | KCl | 2.27E−04 |
| 3389 | isopropylamine + 3-aminobenzotrifluoride | 1 each | K2PtCl4 | acetate | 8.81E−05 |
| 3390 | isopropylamine + 3-aminobenzotrifluoride | 1 each | K2PtCl4 | propionate | 1.47E−04 |
| 3391 | isopropylamine + 3-aminobenzotrifluoride | 1 each | K2PtCl4 | butyrate | 1.09E−04 |
| 3392 | isopropylamine + 3-aminobenzotrifluoride | 1 each | K2PtCl4 | isobutyrate | 1.04E−03 |
| 3393 | isopropylamine + 3-aminobenzotrifluoride | 1 each | KtPICl4 | 2-ketobutyrate | 1.37E−03 |
| 3394 | isopropylamine + 3-aminobenzotrifluoride | 1 each | K2PtCl4 | malonate | 5.58E−04 |
| 3395 | isopropylamine + 3-aminobenzotrifluoride | 1 each | K2PtCl4 | succinate | 1.60E−03 |
| 3396 | isopropylamine + 2-amino-3-picoline | 1 each | K2PtCl4 | KCl | 1.14E−03 |
| 3397 | isopropylamine + 2-amino-3-picoline | 1 each | K2PtCl4 | acetate | 6.08E−04 |
| 3398 | isopropylamine + 2-amino-3-picoline | 1 each | K2PtCl4 | propionate | 3.69E−04 |
| 3399 | isopropylamine + 2-amino-3-picoline | 1 each | K2PtCl4 | butyrate | 4.24E−04 |
| 3400 | isopropylamine + 2-amino-3-picoline | 1 each | K2PtCl4 | isobutyrate | 1.77E−03 |
| 3401 | isopropylamine + 2-amino-3-picoline | 1 each | KtPICl4 | 2-ketobutyrate | 2.29E−03 |
| 3402 | isopropylamine + 2-amino-3-picoline | 1 each | K2PtCl4 | malonate | 1.61E−03 |
| 3403 | isopropylamine + 2-amino-3-picoline | 1 each | K2PtCl4 | succinate | 1.03E−03 |
| 3404 | isopropylamine + 1,4-dimethylpiperazine | 1 each | K2PtCl4 | KCl | 2.74E−03 |
| 3405 | isopropylamine + 1,4-dimethylpiperazine | 1 each | K2PtCl4 | acetate | 2.13E−03 |
| 3406 | isopropylamine + 1,4-dimethylpiperazine | 1 each | K2PtCl4 | propionate | 2.52E−03 |
| 3407 | isopropylamine + 1,4-dimethylpiperazine | 1 each | K2PtCl4 | butyrate | 3.35E−03 |
| 3408 | isopropylamine + 1,4-dimethylpiperazine | 1 each | K2PtCl4 | isobutyrate | 2.63E−03 |
| 3409 | isopropylamine + 1,4-dimethylpiperazine | 1 each | KtPICl4 | 2-ketobutyrate | 1.64E−03 |
| 3410 | isopropylamine + 1,4-dimethylpiperazine | 1 each | K2PtCl4 | malonate | 5.60E−04 |
| 3411 | isopropylamine + 1,4-dimethylpiperazine | 1 each | K2PtCl4 | succinate | 1.15E−03 |
| 3412 | isopropylamine + 2-amino-2-methyl-1-propanol | 1 each | KtPtCl4 | KCl | 4.10E−03 |
| 3413 | isopropylamine + 2-amino-2-methyl-1-propanol | 1 each | K2PtCl4 | acetate | 4.50E−03 |
| 3414 | isopropylamine + 2-amino-2-methyl-1-propanol | 1 each | K2PtCl4 | propionate | 1.17E−03 |
| 3415 | isopropylamine + 2-amino-2-methyl-1-propanol | 1 each | K2PtCl4 | butyrate | 9.69E−04 |
| 3416 | isopropylamine + 2-amino-2-methyl-1-propanol | 1 each | K2PtCl4 | isobutyrate | 2.60E−03 |

TABLE 1-continued

| No. | Ligand(s) | Equiv. | Precursor | Leaving Group | Yld, g atm Pt |
|---|---|---|---|---|---|
| 3417 | isopropylamine + 2-amino-2-methyl-1-propanol | 1 each | K2PtCl4 | 2-ketobutyrate | 6.68E−04 |
| 3418 | isopropylamine + 2-amino-2-methyl-1-propanol | 1 each | K2PtCl4 | malonate | 1.25E−03 |
| 3419 | isopropylamine + 2-amino-2-methyl-1-propanol | 1 each | K2PtCl4 | succinate | 7.43E−04 |
| 3420 | diisopropylamine + N,N'-(3-aminopropyl)ethylenediamine | 1 each | K2PtCl4 | KCl | 1.27E−03 |
| 3421 | diisopropylamine + N,N'-(3-aminopropyl)ethylenediamine | 1 each | K2PtCl4 | acetate | 6.63E−04 |
| 3422 | diisopropylamine + N,N'-(3-aminopropyl)ethylenediamine | 1 each | K2PtCl4 | propionate | 1.66E−03 |
| 3423 | diisopropylamine + N,N'-(3-aminopropyl)ethylenediamine | 1 each | K2PtCl4 | butyrate | 2.00E−03 |
| 3424 | diisopropylamine + N,N'-(3-aminopropyl)ethylenediamine | 1 each | K2PtCl4 | 2-ketobutyrate | 2.29E−03 |
| 3425 | diisopropylamine + N,N'-(3-aminopropyl)ethylenediamine | 1 each | K2PtCl4 | 2-ketoglutarate | 2.29E−03 |
| 3426 | diisopropylamine + N,N'-(3-aminopropyl)ethylenediamine | 1 each | K2PtCl4 | L-ascorbate | 1.77E−03 |
| 3427 | diisopropylamine + N,N'-(3-aminopropyl)ethylenediamine | 1 each | K2PtCl4 | 1,1-cyclobutanedicarboxylate | 1.32E−03 |
| 3428 | diisopropylamine + tetraethylenepentamine | 1 each | K2PtCl4 | KCl | 2.58E−04 |
| 3429 | diisopropylamine + tetraethylenepentamine | 1 each | K2PtCl4 | acetate | 0.00E+00 |
| 3430 | diisopropylamine + tetraethylenepentamine | 1 each | K2PtCl4 | propionate | 1.30E−04 |
| 3431 | diisopropylamine + tetraethylenepentamine | 1 each | K2PtCl4 | butyrate | 2.30E−04 |
| 3432 | diisopropylamine + tetraethylenepentamine | 1 each | K2PtCl4 | 2-ketobutyrate | 9.61E−04 |
| 3433 | diisopropylamine + tetraethylenepentamine | 1 each | K2PtCl4 | 2-ketoglutarate | 2.69E−03 |
| 3434 | diisopropylamine + tetraethylenepentamine | 1 each | K2PtCl4 | L-ascorbate | 3.18E−04 |
| 3435 | diisopropylamine + tetraethylenepentamine | 1 each | K2PtCl4 | 1,1-cyclobutanedicarboxylate | 1.33E−03 |
| 3436 | diisopropylamine + 3,3'iminobis(N,N-dimethylpropylamine) | 1 each | K2PtCl4 | KCl | 1.26E−03 |
| 3437 | diisopropylamine + 3,3'iminobis(N,N-dimethylpropylamine) | 1 each | K2PtCl4 | acetate | 6.49E−04 |
| 3438 | diisopropylamine + 3,3'iminobis(N,N-dimethylpropylamine) | 1 each | K2PtCl4 | propionate | 1.34E−03 |
| 3439 | diisopropylamine + 3,3'iminobis(N,N-dimethylpropylamine) | 1 each | K2PtCl4 | butyrate | 1.93E−03 |
| 3440 | diisopropylamine + 3,3'iminobis(N,N-dimethylpropylamine) | 1 each | K2PtCl4 | 2-ketobutyrate | 1.48E−03 |
| 3441 | diisopropylamine + 3,3'iminobis(N,N-dimethylpropylamine) | 1 each | K2PtCl4 | 2-ketoglutarate | 1.09E−03 |
| 3442 | diisopropylamine + 3,3'iminobis(N,N-dimethylpropylamine) | 1 each | K2PtCl4 | L-ascorbate | 1.80E−03 |
| 3443 | diisopropylamine + 3,3'iminobis(N,N-dimethylpropylamine) | 1 each | K2PtCl4 | 1,1-cyclobutanedicarboxylate | 1.18E−03 |
| 3444 | diisopropylamine + 3,5-dimethyl-1-phenylpyrazole | 1 each | K2PtCl4 | KCl | 4.70E−04 |
| 3445 | diisopropylamine + 3,5-dimethyl-1-phenylpyrazole | 1 each | K2PtCl4 | acetate | 1.96E−04 |
| 3446 | diisopropylamine + 3,5-dimethyl-1-phenylpyrazole | 1 each | K2PtCl4 | propionate | 1.68E−04 |
| 3447 | diisopropylamine + 3,5-dimethyl-1-phenylpyrazole | 1 each | K2PtCl4 | butyrate | 2.26E−04 |
| 3448 | diisopropylamine + 3,5-dimethyl-1-phenylpyrazole | 1 each | K2PtCl4 | 2-ketobutyrate | 3.63E−04 |
| 3449 | diisopropylamine + 3,5-dimethyl-1-phenylpyrazole | 1 each | K2PtCl4 | 2-ketoglutarate | 3.55E−04 |
| 3450 | diisopropylamine + 3,5-dimethyl-1-phenylpyrazole | 1 each | K2PtCl4 | L-ascorbate | 2.28E−04 |
| 3451 | diisopropylamine + 3,5-dimethyl-1-phenylpyrazole | 1 each | K2PtCl4 | 1,1-cyclobutanedicarboxylate | 1.39E−04 |
| 3452 | diisopropylamine + N,N-diisopropylethylamine | 1 each | K2PtCl4 | KCl | 1.50E−04 |
| 3453 | diisopropylamine + N,N-diisopropylethylamine | 1 each | K2PtCl4 | acetate | 6.10E−05 |
| 3454 | diisopropylamine + N,N-diisopropylethylamine | 1 each | K2PtCl4 | propionate | 1.35E−04 |
| 3455 | diisopropylamine + N,N-diisopropylethylamine | 1 each | K2PtCl4 | butyrate | 1.49E−04 |
| 3456 | diisopropylamine + N,N-diisopropylethylamine | 1 each | K2PtCl4 | 2-ketobutyrate | 6.63E−05 |
| 3457 | diisopropylamine + N,N-diisopropylethylamine | 1 each | K2PtCl4 | 2-ketoglutarate | 8.04E−05 |
| 3458 | diisopropylamine + N,N-diisopropylethylamine | 1 each | K2PtCl4 | L-ascorbate | 0.00E+00 |
| 3459 | diisopropylamine + N,N-diisopropylethylamine | 1 each | K2PtCl4 | 1,1-cyclobutanedicarboxylate | 0.00E+00 |
| 3460 | diisopropylamine + 2,6-dimethylaniline | 1 each | K2PtCl4 | KCl | 2.82E−05 |
| 3461 | diisopropylamine + 2,6-dimethylaniline | 1 each | K2PtCl4 | acetate | 0.00E+00 |
| 3462 | diisopropylamine + 2,6-dimethylaniline | 1 each | K2PtCl4 | propionate | 0.00E+00 |
| 3463 | diisopropylamine + 2,6-dimethylaniline | 1 each | K2PtCl4 | butyrate | 5.52E−05 |
| 3464 | diisopropylamine + 2,6-dimethylaniline | 1 each | K2PtCl4 | 2-ketobutyrate | 0.00E+00 |
| 3465 | diisopropylamine + 2,6-dimethylaniline | 1 each | K2PtCl4 | 2-ketoglutarate | 3.63E−04 |
| 3466 | diisopropylamine + 2,6-dimethylaniline | 1 each | K2PtCl4 | L-ascorbate | 0.00E+00 |

TABLE 1-continued

| No. | Ligand(s) | Equiv. | Precursor | Leaving Group | Yld, g atm Pt |
|---|---|---|---|---|---|
| 3467 | diisopropylamine + 2,6-dimethylaniline | 1 each | K2PtCl4 | 1,1-cyclobutanedicarboxylate | 0.00E+00 |
| 3468 | diisopropylamine + bis-2-aminoethylsulfide | 1 each | K2PtCl4 | KCl | 3.76E−05 |
| 3469 | diisopropylamine + bis-2-aminoethylsulfide | 1 each | K2PtCl4 | acetate | 0.00E+00 |
| 3470 | diisopropylamine + bis-2-aminoethylsulfide | 1 each | K2PtCl4 | propionate | 0.00E+00 |
| 3471 | diisopropylamine + bis-2-aminoethylsulfide | 1 each | K2PtCl4 | butyrate | 0.00E+00 |
| 3472 | diisopropylamine + bis-2-aminoethylsulfide | 1 each | K2PtCl4 | 2-ketobutyrate | 9.63E−05 |
| 3473 | diisopropylamine + bis-2-aminoethylsulfide | 1 each | K2PtCl4 | 2-ketoglutarate | 1.28E−03 |
| 3474 | diisopropylamine + bis-2-aminoethylsulfide | 1 each | K2PtCl4 | L-ascorbate | 0.00E+00 |
| 3475 | diisopropylamine + bis-2-aminoethylsulfide | 1 each | K2PtCl4 | 1,1-cyclobutanedicarboxylate | 6.83E−04 |
| 3476 | diisopropylamine + N-nitrosodiethylamine | 1 each | K2PtCl4 | KCl | 0.00E+00 |
| 3477 | diisopropylamine + N-nitrosodiethylamine | 1 each | K2PtCl4 | acetate | 0.00E+00 |
| 3478 | diisopropylamine + N-nitrosodiethylamine | 1 each | K2PtCl4 | propionate | 2.97E−05 |
| 3479 | diisopropylamine + N-nitrosodiethylamine | 1 each | K2PtCl4 | butyrate | 0.00E+00 |
| 3480 | diisopropylamine + N-nitrosodiethylamine | 1 each | K2PtCl4 | 2-ketobutyrate | 0.00E+00 |
| 3481 | diisopropylamine + N-nitrosodiethylamine | 1 each | K2PtCl4 | 2-ketoglutarate | 2.74E−04 |
| 3482 | diisopropylamine + N-nitrosodiethylamine | 1 each | K2PtCl4 | L-ascorbate | 2.98E−04 |
| 3483 | diisopropylamine + N-nitrosodiethylamine | 1 each | K2PtCl4 | 1,1-cyclobutanedicarboxylate | 5.02E−04 |
| 3484 | diisopropylamine + 3-picoline | 1 each | K2PtCl4 | KCl | 6.48E−04 |
| 3485 | diisopropylamine + 3-picoline | 1 each | K2PtCl4 | acetate | 8.21E−04 |
| 3486 | diisopropylamine + 3-picoline | 1 each | K2PtCl4 | propionate | 1.84E−03 |
| 3487 | diisopropylamine + 3-picoline | 1 each | K2PtCl4 | butyrate | 1.10E−03 |
| 3488 | diisopropylamine + 3-picoline | 1 each | K2PtCl4 | 2-ketobutyrate | 1.00E−03 |
| 3489 | diisopropylamine + 3-picoline | 1 each | K2PtCl4 | 2-ketoglutarate | 1.50E−03 |
| 3490 | diisopropylamine + 3-picoline | 1 each | K2PtCl4 | L-ascorbate | 1.02E−03 |
| 3491 | diisopropylamine + 3-picoline | 1 each | K2PtCl4 | 1,1-cyclobutanedicarboxylate | 5.58E−04 |
| 3492 | diisopropylamine + 2-amino-3-picoline | 1 each | K2PtCl4 | KCl | 1.23E−03 |
| 3493 | diisopropylamine + 2-amino-3-picoline | 1 each | K2PtCl4 | acetate | 5.15E−04 |
| 3494 | diisopropylamine + 2-amino-3-picoline | 1 each | K2PtCl4 | propionate | 7.37E−04 |
| 3495 | diisopropylamine + 2-amino-3-picoline | 1 each | K2PtCl4 | butyrate | 1.94E−04 |
| 3496 | diisopropylamine + 2-amino-3-picoline | 1 each | K2PtCl4 | 2-ketobutyrate | 1.56E−03 |
| 3497 | diisopropylamine + 2-amino-3-picoline | 1 each | K2PtCl4 | 2-ketoglutarate | 2.89E−03 |
| 3498 | diisopropylamine + 2-amino-3-picoline | 1 each | K2PtCl4 | L-ascorbate | 7.65E−04 |
| 3499 | diisopropylamine + 2-amino-3-picoline | 1 each | K2PtCl4 | 1,1-cyclobutanedicarboxylate | 5.02E−04 |
| 3500 | diisopropylamine + 1,4-dimethylpiperazine | 1 each | K2PtCl4 | KCl | 1.63E−03 |
| 3501 | diisopropylamine + 1,4-dimethylpiperazine | 1 each | K2PtCl4 | acetate | 9.83E−04 |
| 3502 | diisopropylamine + 1,4-dimethylpiperazine | 1 each | K2PtCl4 | propionate | 5.07E−04 |
| 3503 | diisopropylamine + 1,4-dimethylpiperazine | 1 each | K2PtCl4 | butyrate | 5.14E−04 |
| 3504 | diisopropylamine + 1,4-dimethylpiperazine | 1 each | K2PtCl4 | 2-ketobutyrate | 8.20E−04 |
| 3505 | diisopropylamine + 1,4-dimethylpiperazine | 1 each | K2PtCl4 | 2-ketoglutarate | 9.75E−04 |
| 3506 | diisopropylamine + 1,4-dimethylpiperazine | 1 each | K2PtCl4 | L-ascorbate | 9.72E−04 |
| 3507 | diisopropylamine + 1,4-dimethylpiperazine | 1 each | K2PtCl4 | 1,1-cyclobutanedicarboxylate | 7.79E−04 |
| 3508 | diisopropylamine + ammonia | 1 each | K2PtCl4 | KCl | 7.79E−04 |
| 3509 | diisopropylamine + ammonia | 1 each | K2PtCl4 | acetate | 3.43E−04 |
| 3510 | diisopropylamine + ammonia | 1 each | K2PtCl4 | propionate | 2.79E−04 |
| 3511 | diisopropylamine + ammonia | 1 each | K2PtCl4 | butyrate | 3.04E−04 |
| 3512 | diisopropylamine + ammonia | 1 each | K2PtCl4 | 2-ketobutyrate | 3.40E−04 |
| 3513 | diisopropylamine + ammonia | 1 each | K2PtCl4 | 2-ketoglutarate | 5.43E−04 |
| 3514 | diisopropylamine + ammonia | 1 each | K2PtCl4 | L-ascorbate | 1.67E−06 |
| 3515 | diisopropylamine + ammonia | 1 each | K2PtCl4 | 1,1-cyclobutanedicarboxylate | 6.68E−05 |
| 4669 | R-(−)-2-amino-1-propanol | 1 | trans-DDP | KCl | 2.10E−03 |
| 4670 | R-(−)-2-amino-1-propanol | 1 | trans-DDP | acetate | 2.27E−03 |
| 4671 | R-(−)-2-amino-1-propanol | 1 | trans-DDP | propionate | 3.52E−03 |
| 4672 | R-(−)-2-amino-1-propanol | 1 | trans-DDP | butyrate | 3.72E−03 |
| 4673 | R-(−)-2-amino-1-propanol | 1 | trans-DDP | isobutyrate | 3.80E−03 |
| 4674 | R-(−)-2-amino-1-propanol | 1 | trans-DDP | oxalate | 2.96E−03 |
| 4675 | R-(−)-2-amino-1-propanol | 1 | trans-DDP | malonate | 4.65E−04 |
| 4676 | R-(−)-2-amino-1-propanol | 1 | trans-DDP | succinate | 1.01E−03 |
| 4677 | ethylamine | 1 | trans-DDP | KCl | 3.09E−03 |
| 4678 | ethylamine | 1 | trans-DDP | acetate | 2.28E−03 |
| 4679 | ethylamine | 1 | trans-DDP | propionate | 3.42E−03 |
| 4680 | ethylamine | 1 | trans-DDP | butyrate | 3.67E−03 |
| 4681 | ethylamine | 1 | trans-DDP | isobutyrate | 3.91E−03 |
| 4682 | ethylamine | 1 | trans-DDP | oxalate | 2.63E−03 |
| 4683 | ethylamine | 1 | trans-DDP | malonate | 6.10E−04 |
| 4684 | ethylamine | 1 | trans-DDP | succinate | 8.00E−04 |
| 4685 | propylamine | 1 | trans-DDP | KCl | 2.77E−03 |
| 4686 | propylamine | 1 | trans-DDP | acetate | 1.62E−03 |
| 4687 | propylamine | 1 | trans-DDP | propionate | 3.01E−03 |
| 4688 | propylamine | 1 | trans-DDP | butyrate | 3.37E−03 |
| 4689 | propylamine | 1 | trans-DDP | isobutyrate | 3.44E−03 |
| 4690 | propylamine | 1 | trans-DDP | oxalate | 2.87E−03 |
| 4691 | propylamine | 1 | trans-DDP | malonate | 7.53E−04 |
| 4692 | propylamine | 1 | trans-DDP | succinate | 1.00E−03 |
| 4693 | isopropylamine | 1 | trans-DDP | KCl | 2.13E−03 |
| 4694 | isopropylamine | 1 | trans-DDP | acetate | 1.83E−03 |
| 4695 | isopropylamine | 1 | trans-DDP | propionate | 3.10E−03 |
| 4696 | isopropylamine | 1 | trans-DDP | butyrate | 2.80E−03 |

TABLE 1-continued

| No. | Ligand(s) | Equiv. | Precursor | Leaving Group | Yld, g atm Pt |
|---|---|---|---|---|---|
| 4697 | isopropylamine | 1 | trans-DDP | isobutyrate | 2.62E−03 |
| 4698 | isopropylamine | 1 | trans-DDP | oxalate | 1.74E−03 |
| 4699 | isopropylamine | 1 | trans-DDP | malonate | 5.92E−04 |
| 4700 | isopropylamine | 1 | trans-DDP | succinate | 9.24E−04 |
| 4701 | 3-amino-1-propanol | 1 | trans-DDP | KCl | 2.11E−03 |
| 4702 | 3-amino-1-propanol | 1 | trans-DDP | acetate | 2.31E−03 |
| 4703 | 3-amino-1-propanol | 1 | trans-DDP | propionate | 2.62E−03 |
| 4704 | 3-amino-1-propanol | 1 | trans-DDP | butyrate | 2.98E−03 |
| 4705 | 3-amino-1-propanol | 1 | trans-DDP | isobutyrate | 2.88E−03 |
| 4706 | 3-amino-1-propanol | 1 | trans-DDP | oxalate | 1.58E−03 |
| 4707 | 3-amino-1-propanol | 1 | trans-DDP | malonate | 5.65E−04 |
| 4708 | 3-amino-1-propanol | 1 | trans-DDP | succinate | 1.16E−03 |
| 4709 | 2-amino-1-ethanol | 1 | trans-DDP | KCl | 1.71E−03 |
| 4710 | 2-amino-1-ethanol | 1 | trans-DDP | acetate | 1.16E−03 |
| 4711 | 2-amino-1-ethanol | 1 | trans-DDP | propionate | 1.30E−03 |
| 4712 | 2-amino-1-ethanol | 1 | trans-DDP | butyrate | 1.93E−03 |
| 4713 | 2-amino-1-ethanol | 1 | trans-DDP | isobutyrate | 2.46E−03 |
| 4714 | 2-amino-1-ethanol | 1 | trans-DDP | oxalate | 1.63E−03 |
| 4715 | 2-amino-1-ethanol | 1 | trans-DDP | malonate | 9.91E−04 |
| 4716 | 2-amino-1-ethanol | 1 | trans-DDP | succinate | 1.19E−03 |
| 4717 | cyclobutylamine | 1 | trans-DDP | KCl | 3.35E−03 |
| 4718 | cyclobutylamine | 1 | trans-DDP | acetate | 3.41E−03 |
| 4719 | cyclobutylamine | 1 | trans-DDP | propionate | 3.15E−03 |
| 4720 | cyclobutylamine | 1 | trans-DDP | butyrate | 3.77E−03 |
| 4721 | cyclobutylamine | 1 | trans-DDP | isobutyrate | 3.10E−03 |
| 4722 | cyclobutylamine | 1 | trans-DDP | oxalate | 1.29E−03 |
| 4723 | cyclobutylamine | 1 | trans-DDP | malonate | 2.03E−03 |
| 4724 | cyclobutylamine | 1 | trans-DDP | succinate | 1.88E−03 |
| 4725 | cyclopentylamine | 1 | trans-DDP | KCl | 1.47E−03 |
| 4726 | cyclopentylamine | 1 | trans-DDP | acetate | 1.43E−03 |
| 4727 | cyclopentylamine | 1 | trans-DDP | propionate | 1.58E−03 |
| 4728 | cyclopentylamine | 1 | trans-DDP | butyrate | 1.86E−03 |
| 4729 | cyclopentylamine | 1 | trans-DDP | isobutyrate | 1.31E−03 |
| 4730 | cyclopentylamine | 1 | trans-DDP | oxalate | 1.22E−03 |
| 4731 | cyclopentylamine | 1 | trans-DDP | malonate | 1.47E−04 |
| 4732 | cyclopentylamine | 1 | trans-DDP | succinate | 8.84E−04 |
| 4733 | cyclohexylamine | 1 | trans-DDP | KCl | 9.27E−04 |
| 4734 | cyclohexylamine | 1 | trans-DDP | acetate | 1.10E−03 |
| 4735 | cyclohexylamine | 1 | trans-DDP | propionate | 2.02E−03 |
| 4736 | cyclohexylamine | 1 | trans-DDP | butyrate | 1.10E−02 |
| 4737 | cyclohexylamine | 1 | trans-DDP | isobutyrate | 1.25E−02 |
| 4738 | cyclohexylamine | 1 | trans-DDP | oxalate | 2.81E−03 |
| 4739 | cyclohexylamine | 1 | trans-DDP | malonate | 4.28E−04 |
| 4740 | cyclohexylamine | 1 | trans-DDP | succinate | 9.42E−04 |
| 4741 | hexylamine | 1 | trans-DDP | KCl | 8.73E−04 |
| 4742 | hexylamine | 1 | trans-DDP | acetate | 9.39E−04 |
| 4743 | hexylamine | 1 | trans-DDP | propionate | 4.03E−04 |
| 4744 | hexylamine | 1 | trans-DDP | butyrate | 3.23E−03 |
| 4745 | hexylamine | 1 | trans-DDP | isobutyrate | 4.41E−03 |
| 4746 | hexylamine | 1 | trans-DDP | oxalate | 7.22E−04 |
| 4747 | hexylamine | 1 | trans-DDP | malonate | 7.03E−04 |
| 4748 | hexylamine | 1 | trans-DDP | succinate | 2.11E−03 |
| 4749 | heptylamine | 1 | trans-DDP | KCl | 1.21E−03 |
| 4750 | heptylamine | 1 | trans-DDP | acetate | 2.35E−03 |
| 4751 | heptylamine | 1 | trans-DDP | propionate | 2.01E−03 |
| 4752 | heptylamine | 1 | trans-DDP | butyrate | 1.49E−03 |
| 4753 | heptylamine | 1 | trans-DDP | isobutyrate | 4.41E−03 |
| 4754 | heptylamine | 1 | trans-DDP | oxalate | 2.73E−03 |
| 4755 | heptylamine | 1 | trans-DDP | malonate | 6.92E−04 |
| 4756 | heptylamine | 1 | trans-DDP | succinate | 7.69E−04 |
| 4757 | octylamine | 1 | trans-DDP | KCl | 1.25E−02 |
| 4758 | octylamine | 1 | trans-DDP | acetate | 4.48E−03 |
| 4759 | octylamine | 1 | trans-DDP | propionate | 6.22E−04 |
| 4760 | octylamine | 1 | trans-DDP | butyrate | 1.06E−03 |
| 4761 | octylamine | 1 | trans-DDP | isobutyrate | 4.12E−03 |
| 4762 | octylamine | 1 | trans-DDP | oxalate | 1.25E−02 |
| 4763 | octylamine | 1 | trans-DDP | malonate | 1.10E−03 |
| 4764 | octylamine | 1 | trans-DDP | succinate | 1.72E−03 |

What is claimed is:

1. A coordination complex, comprising: a structure represented by the formula:

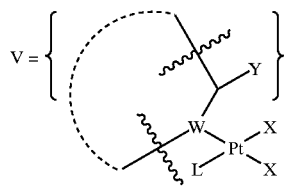

wherein, independently for each occurrence:
X represents halogen or other labile ligand;
W represents S, N, or P;
Y represents —OR7, —SR7, a halogen or —N(R9)R10;
R9 and R10, each independently, represent —H, alkyl, alkenyl, —(CH$_2$)$_n$—R7, or R9 and R10, taken together with the N atom to which they are attached complete a heterocycle having from 4 to about 8 atoms in the ring structure, all optionally substituted;
L represents a non-labile ligand; and
R7 represents —H, alkyl, aryl, cycloalkyl, cycloalkenyl, heterocycle or polycycle; and
the ligand V comprises a heterocycle, optionaly aromatic and optionally substituted, that comprises W and Y and has from 4 to about 8 atoms in the ring structure;
and wherein the symbol represents a single or a double bond.

2. The coordination complex of claim 1, wherein W is N.

3. The coordination complex of claim 1, wherein Pt is Pt(II).

4. A pharmaceutical composition, comprising: a therapeutically effective amount of a coordination complex of claim 1 and a pharmaceutically acceptable carrier.

5. The pharmaceutical composition of claim 4, wherein said coordination complex is ammine (2-amino-3-picoline) dichloroplatinum(II).

6. The coordination complex of claim 1, wherein V is a 6-membered aromatic heterocycle.

7. The coordination complex of claim 6, wherein V is pyridine or a substituted pyridine.

8. The coordination complex of claim 6, wherein V is picoline or a substituted picoline.

9. The coordination complex of claim 1, wherein Pt is Pt(IV) and two additional ligands in the trans axial positions are present.

10. The coordination complex of claim 9, wherein said each of said additional ligands comprise a carboxylate group.

11. A pharmaceutical composition, comprising: a therapeutically effective amount of a coordination complex of claim 9 and a pharmaceutically acceptable carrier.

12. The pharmaceutical composition of claim 11, wherein said coordination complex is ammine(2-amino-3-picoline) dichlorodiacetoplatinum(IV).

13. The coordination complex of claim 1, wherein both X are halogens.

14. The coordination complex of claim 13, wherein said halogen is chlorine.

15. The coordination complex of claim 1, wherein both X comprise a carboxylate group.

16. The coordination complex of claim 15, wherein said carboxylate group is a chelating dicarboxylate.

17. The coordination complex of claim 15, wherein at least one X is acetate.

18. The coordination complex of claim 1, wherein L is an amine having the structure NR2(R3), wherein R2 and R3 each independently represent a hydrogen, an alkyl, an alkenyl, —(CH$_2$)$_m$—R4, or R2 an R3, taken together with the N atom to which they are attached complete a heterocycle having from 4 to 8 atoms in the ring structure; and wherein R2 represents an aryl, a cycloalkyl, a cycloalkenyl, a heterocycle or a polycycle; and m is zero or an integer in the range of 1 to 8.

19. The coordination complex of claim 1, wherein L is an ammine.

20. A coordination complex, comprising: a structure represented by the formula:

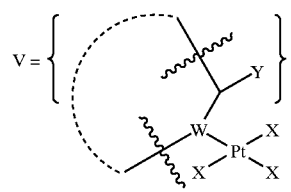

wherein, independently for each occurrence:
X represents halogen or other labile ligand;
W represents S, N, or P;
Y represents —OR7, —SR7, a halogen or —N(R9)R10;
R9 and R10, each independently, represent —H, alkyl, alkenyl, —(CH$_2$)$_m$—R7, or R9 and R10; taken together with the N atom to which they are attached complete a heterocycle having from 4 to about 8 atoms in the ring structure, all optionally substituted;
L represents a non-labile ligand; and
R7 represents —H, alkyl, aryl, cycloalkyl, cycloalkenyl, heterocycle or polycycle; and the ligand V comprises a heterocycle, optionally aromatic and optionally substituted, that comprises W and Y and has from 4 to about 8 atoms in the ring structure;
and wherein the symbol represents a single or a double bond.

21. The coordination complex of claim 20, wherein each of X is a halogen.

22. The coordination complex of claim 21, wherein said halogen is chlorine.

23. A pharmaceutical composition, comprising: a therapeutically effective amount of a coordination complex of claim 20, and a pharmaceutically acceptable carrier.

24. A coordination complex, comprising: a structure represented by the formula:

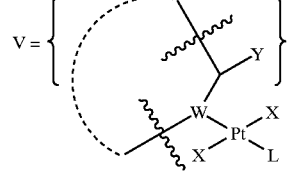

where, in independently for each occurrence:
X represents halogen or other labile ligand;
W represents S, N, or P;
Y represents —OR7, —SR7, a halogen or —N(R9)R10 ;

R9 and R10, each independently, represent —H, alkyl, alkenyl, —(CH$_2$)$_n$—R7, or R9 and R10, taken together with the N atom to which they are attached complete a heterocycle having from 4 to about 8 atoms in the ring structure, all optionally substituted;

L represents a non-labile ligand; and

R7 represents —H, alkyl, aryl, cycloalkyl, cycloalkenyl, heterocycle or polycycle; and the ligand V comprises a heterocycle, optionally aromatic and optionally substituted, that comprises W and Y and has from 4 to about 8 atoms in the ring structure.

and wherein the symbol ⚍ represents a single or a double bond.

25. A pharmaceutical composition, comprising: a therapeutically effective amount of a coordination complex of claim 24, and a pharmaceutically acceptable carrier.

* * * * *